United States Patent
Huang et al.

(10) Patent No.: US 8,492,328 B2
(45) Date of Patent: Jul. 23, 2013

(54) BIOMARKERS AND METHODS FOR DETERMINING SENSITIVITY TO INSULIN GROWTH FACTOR-1 RECEPTOR MODULATORS

(75) Inventors: Fei Huang, Princeton, NJ (US); Xia Han, Pennington, NJ (US); Rameh Hafezi, Franklin Park, NJ (US); Jiwen Chen, Bridgewater, NJ (US); Douglas Michael Robinson, Hanover, MA (US); Gayle M. Wittenberg, Princeton, NJ (US); Ashok Ramesh Dongre, Newtown, PA (US); Joan M. Carboni, Yardley, PA (US); Ricardo M. Attar, Lawrenceville, NJ (US); Warren Hurlburt, Mount Laurel, NJ (US); Marco M. Gottardis, Princeton, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 466 days.

(21) Appl. No.: 12/600,504

(22) PCT Filed: May 15, 2008

(86) PCT No.: PCT/US2008/063621
§ 371 (c)(1),
(2), (4) Date: Nov. 17, 2009

(87) PCT Pub. No.: WO2008/144345
PCT Pub. Date: Nov. 27, 2008

(65) Prior Publication Data
US 2010/0184125 A1    Jul. 22, 2010

Related U.S. Application Data

(60) Provisional application No. 60/938,570, filed on May 17, 2007.

(51) Int. Cl.
*A01N 61/00* (2006.01)
*G01N 33/53* (2006.01)
(52) U.S. Cl.
USPC ............................................... 514/1; 435/7.1
(58) Field of Classification Search
None
See application file for complete search history.

(56) References Cited

U.S. PATENT DOCUMENTS

| | | | |
|---|---|---|---|
| 5,569,588 | A | 10/1996 | Ashby et al. |
| 7,534,792 | B2 | 5/2009 | Wittman et al. |
| 2005/0112630 | A1* | 5/2005 | Shaughnessy et al. ......... 435/6 |
| 2006/0140960 | A1 | 6/2006 | Wang et al. |
| 2008/0089837 | A1 | 4/2008 | Laing et al. |

FOREIGN PATENT DOCUMENTS

| | | |
|---|---|---|
| WO | WO 0034784 | 6/2000 |
| WO | WO 0164942 A1 | 9/2001 |
| WO | WO 0232925 A2 | 4/2002 |
| WO | WO 02053596 A2 | 7/2002 |
| WO | WO 02079192 A1 | 10/2002 |
| WO | WO 03059951 A2 | 7/2003 |
| WO | WO 03100008 A2 | 12/2003 |
| WO | WO 03106621 A2 | 12/2003 |
| WO | WO 2004030620 A2 | 4/2004 |
| WO | WO 2004031401 A2 | 4/2004 |
| WO | WO 2004063151 A2 | 7/2004 |
| WO | WO 2004071529 A2 | 8/2004 |
| WO | WO 2004083248 A1 | 9/2004 |
| WO | WO 2004087756 A2 | 10/2004 |
| WO | WO 2005005635 A2 | 1/2005 |
| WO | WO 2005016967 A2 | 2/2005 |
| WO | WO 2005016970 A2 | 2/2005 |
| WO | WO 2005021510 A2 | 3/2005 |
| WO | WO2005/082415 | 9/2005 |
| WO | WO 2006060419 A2 | 6/2006 |
| WO | WO 2007028005 A2 | 3/2007 |
| WO | WO 2008079873 A2 | 7/2008 |
| WO | WO 2008086128 A2 | 7/2008 |
| WO | WO 2008131050 A1 | 10/2008 |

OTHER PUBLICATIONS

Tockman et al (Cancer Res., 1992, 52:2711s-2718s).*
Hoei-Hansen et al (Mol Hum Reprod, 2004, 10(6): 423-431).*
Sueoka et al (Am J Respir Cell Mol Biol, 2000, 23: 297-303).*
Afonja, et al., "Induction of PDCD4 tumor suppressor gene expression by RAR agonists, antiestrogen and HER-2/neu antagonist in breast cancer cells. Evidence for a role in apoptosis", Oncogene, vol. 23, pp. 8135-8145 (2004).
Almeida, et al., "The Insulin-Like Growth Factor I Receptor Gene is the Target for the 15q26 Amplicon in Breast Cancer", Genes, Chromosomes Cancer, vol. 11, pp. 63-65 (1994).
Alizadeh, et al., "Distinct types of diffuse large B-cell lymphoma identified by gene expression profiling", Nature, vol. 403, pp. 503-511 (2000).
Alon, et al., "Broad patterns of gene expression revealed by clustering analysis of tumor and normal colon tissues probed by oligonucleotide arrays", PNAS, vol. 96, pp. 6745-6750 (1999).

(Continued)

*Primary Examiner* — Sean Aeder
(74) *Attorney, Agent, or Firm* — Stephen C. D'Amico; Paul Golian

(57) ABSTRACT

IGF1R biomarkers useful in a method for identifying and monitoring a mammal that will respond therapeutically to a method of treating cancer comprising administering an IGF1R modulator, wherein the method comprises (a) exposing the mammal to the IGF1R modulator and (b) measuring in the mammal the level of the at least one biomarker, wherein a difference in the level of the at least one biomarker measured in (b) compared to the level of the biomarker in a mammal that has not been exposed to the IGF1R modulator indicates that the mammal will respond therapeutically to the method of treating cancer and (c) wherein the level of the biomarker in a mammal after exposure to a IGF1R modulator indicates that the mammal has responded therapeutically to the method of treating cancer.

7 Claims, No Drawings

OTHER PUBLICATIONS

Andrews, et al., "Results of a Pilot Study Involving the Use of an Antisense Oligodeoxynucleotide Directed Against the Insulin-Like Growth Factor Type I Receptor in Malignant Astrocytomas", J. Clin. Oncol., vol. 19 (8), pp. 2189-2200 (2001).

Arteaga, et al., "Growth Inhibition of Human Breast Cancer Cells in Vitro with an Antibody against the Type I Somatomedin Receptor", Cancer Res., vol. 49, pp. 6237-6241 (1989).

Baer, et al., "Profiling and Functional Annotation of MRNA Gene Expression in Pediatric Rhabdomyosarcoma and Ewing's Sarcoma", Int. J. Cancer, vol. 110, pp. 687-694 (2004).

Baird, et al., "Gene Expression Profiling of Human Sarcomas: Insights into Sarcoma Biology", Cancer Res., vol. 65 (20), pp. 9226-9235 (2005).

Baselga, et al., "Phase II Study of Weekly Intravenous Recombinant Humanized Anti-p185$^{HER2}$ Monoclonal Antibody in Patients with HER2/neu-Overexpressing Metastatic Breast Cancer", J. Clin. Oncology, vol. 14 (3), pp. 737-744 (1996).

Baserga, et al., "The IGF-1 Receptor in Cancer Biology", Int. J. Cancer, vol. 107, pp. 873-877 (2003).

Benini, et al., "Inhibition of Insulin-like Growth Factor I Receptor Increases the Antitumor Activity of Doxorubicin and Vincristine against Ewing's Sarcoma Cells", Clin. Cancer Res., vol. 7, pp. 1790-1797 (2001).

Benjamini, et al., "Controlling the False Discovery Rate: a Practical and Powerful Approach to Multiple Testing", J.R. Statist. Soc. B, vol. 57 (1), pp. 289-300 (1995).

Blanchard, et al., "Sequence to array: Probing the genome's secrets", Nature Biotech., vol. 14, pp. 1649 (1996).

Bittner, et al., "Molecular classification of cutaneous malignant melanoma by gene expression profiling", Nature, vol. 406, pp. 536-540 (2000).

Burrow, et al., "Expression of Insulin-Like Growth Factor Receptor, IGF-1, and IGF-2 in Primary and Metastatic Osteosarcoma", J. Surg. Oncology, vol. 69, pp. 21-27 (1998).

Camirand, et al., "Inhibition of insulin-like growth factor-1 receptor signaling enhances growth-inhibitory and proapoptotic effects of gefitinib (Iressa) in human breast cancer cells", Breast Cancer Res., vol. 7, pp. R570-R579 (2005).

Carter, et al., "Inhibition of drug-resistant mutants of ABL, KIT, and EGF receptor kinases", PNAS, vol. 102 (31), pp. 11011-11016 (2005).

Clemens, et al., Clinical Trials Poster Presentations, "Abstract A101: BMS-754807, an oral dual IGF-1R/IR inhibitor: First-in-human single-dose study of safety, tolerability, pharmacokinetics, and pharmacodynamics in healthy subjects", Molecular Cancer Therapeutics 8 (Meeting Abstract Supplement) A101, Dec. 10, 2009; Abstracts: AACR-NCI-EORTC International Conference: Molecular Targets and Cancer Therapeutics—Nov. 15-19, 2009; Boston, MA.

D'Ambrosio, et al., "A Soluble Insulin-like Growth Factor I Receptor That Induces Apoptosis of Tumor Cells in Vivo and Inhibits Tumorigenesis", Cancer Res., vol. 56, pp. 4013-4020 (1996).

Dressman, et al., "An Integrated Genomic-Based Approach to Individualized Treatment of Patients with Advanced-Stage Ovarian Cancer", J. Clin. Oncol., vol. 25 (5), pp. 517-525 (2007).

Dressman, et al., "Gene Expression Profiles of Multiple Breast Cancer Phenotypes and Response to Neoadjuvant Chemotherapy", Clin. Canc. Res., vol. 12 (3),pp. 819-826 (2006).

Ebadi, et al., "Metallothionein in Carcinogenesis and Cancer Chemotherapy", Gen. Pharmac., vol. 25 (7), pp. 1297-1310 (1994).

Eng, et al., "An Approach to Correlate Tandem Mass Spectral Data of Peptides with Amino Acid Sequences in a Protein Database", J. Am. Soc. Mass Spectrom., vol. 5, pp. 976-989 (1994).

Garcia-Echeverria, et al., "In vivo antitumor of NVP-AEW541—A novel, potent, and selective inhibitor of the IGF-IR kinase", Cancer Cell, vol. 5, pp. 231-239 (2004).

Glinsky, et al., "Gene expression profiling predicts clinical outcome of prostate cancer", J. Clin. Investigation, vol. 113 (6), pp. 913-923 (2004).

Golub, et al., "Molecular Classification of Cancer: Class Discovery and Class Prediction by Gene Expression Monitoring", Science, vol. 286, pp. 531-537 (1999).

Gooch, et al., "Insulin-like growth factor (IGF)-I rescues breast cancer cells from chemotherapy-induced cell death—proliferative and anti-apoptotic effects", Breast Cancer Res. Treatment, vol. 56, pp. 1-10 (1999).

Haluska, et al., [402] Complete IGF Signaling Blockade by the Dual-Kinase Inhibitor, BMS-754807, Is Sufficient to Overcome Tamoxifen and Letrozole Resistance In Vitro and In Vivo, Poster Discussion 4: Dec. 11, 2009; San Antonio Breast Cancer Symposium.

Hess, et al., "Pharmacogenomic Predictor of Sensitivity to Preoperative Chemotherapy with Paclitaxel and Fluorouracil, Doxorubicin, and Cyclophosphmide in Breast Cancer", J. Clin. Oncol., vol. 24 (26), pp. 4236-4244 (2006).

Huang, et al., "Mechanisms of Acquired Resistance to an IGF-1R Inhibitor in Multiple Models", Presented at AACR-NCI-EORTC International Conference, Nov. 15-19, 2009, Boston, MA. (Poster No. A153).

Huang, et al., "The Mechanisms of Differential Sensitivity to an Insulin-like Growth Factor-1 Receptor Inhibitor (BMS-536924) and Rationale for Combining with EGFR/HER2 Inhibitors", Cancer Res., vol. 69 (1), p. 161-170 (2009).

Huang, et al., "Identification of sensitivity markers for BMS-536924, an inhibitor for insulin-like growth factor-1 receptor", Abstract No. 3506, J. Clin. Pharmac., 2007 ASCO Annual Meeting Proceedings Part I, vol. 25, No. 18S (Jun. 20 supplement) 2007:3506.

Huang, et al., "Identification of Candidate Molecular Markers Predicting Sensitivity in Solid Tumors to Dasatanib: Rationale for Patient Selection", Cancer Res., vol. 67 (5), pp. 2226-2238 (2007).

Irizarry, et al., "Exploration, normalization, and summaries of high density oligonucleotide array probe level data", Biostatistics, vol. 4 (2), pp. 249-264 (2003).

Iwao-Koizumi, et al., "Prediction of Docetaxel Response in Human Breast Cancer by Gene Expression Profiling", J. Clin. Oncol., vol. 23 (3), pp. 422-431 (2005).

Jackson, et al., "Regulation of breast cancer cell motility by insulin receptor substrate-2 (IRS-2) in metastic variants of human breast cancer cell lines", Oncogene, vol. 20, pp. 7318-7325 (2001).

Juncker-Jensen, et al., "Insulin-like growth factor binding protein 2 is a marker for antiestrogen resistant human breast cancer cell lines but is not a major growth regulator", Growth Hormone & IGF Research, vol. 16, pp. 224-239 (2006).

Khan, et al., "Classification and diagnostic prediction of cancers using gene expression profiling and artificial neural networks", Nature Medicine, vol. 7 (6), pp. 673-679 (2001).

Khan, et al., "Gene Expression Profiling of Alveolar Rhabdomyosarcoma with cDNA Microarrays", Cancer Res., vol. 58, pp. 5009-5013 (1998).

LeRoith, et al., "The insulin-like growth factor system and cancer", Cancer Ltrs., vol. 195, pp. 127-137 (2003).

Lipton, et al., "Global analysis of the Deinococcus radiodurans proteome by using accurate mass tags", PNAS, vol. 99 (17), pp. 11049-11054 (2002).

Lockhart, et al., "Expression monitoring by hybridization to high-density oligonucleotide arrays", Nature Biol., vol. 14, pp. 1675-1680 (1996).

Lombardo, et al., "Discovery of N-(2-Chloro-6-methyl-phenyl)-2-(6-(4-(2-hydroxyethyl)-piperazin-1-yl)-2-methylpyrimidin-4-ylamino)thiazole-5-carboxamide (BMS-354825), a Dual Src/Abl Kinase Inhibitor with Potent Antitumor Activity in Preclinical Assays", J. Med. Chem., vol. 47, pp. 6658-6661 (2004).

Long, et al., "Loss of the Metastatic Phenotype in Murine Carcinoma Cells Expressing an Antisense RNA to the Insulin-like Growth Factor Receptor", Cancer Res., vol. 55, pp. 1006-1009 (1995).

Lu, et al., "Insulin-Like Growth Factor-I Receptor Signaling and Resistance to Trastuzumab (Herceptin)", J. National Cancer Institute, vol. 93 (24), pp. 1852-1857 (2001).

Lynch, et al., "Activating Mutations in the Epidermal Growth Factor Receptor Underlying Responsiveness of Non-Small-Cell Lung Cancer to Gefitinib", N. Engl. J. Med., vol. 350 (21), pp. 2129-2139 (2004).

Manara, et al., "Preclinical In Vivo Study of New Insulin-Like Growth Factor-I Receptor—Specific Inhibitor in Ewing's Sarcoma", Clin. Cancer Res., vol. 13 (4), pp. 1322-1330 (2007).

Merlino, et al., "Rhabdomyosarcoma—working out the pathways", Oncogen, vol. 18, pp. 5340-5348 (1999).

Nielsen, et al., "Molecular characterisation of soft tissue tumours: a gene expression study", The Lancet, vol. 359, pp. 1301-1307 (2002).

Osmak, et al., "Drug Resistant Tumor Cells have Increased Levels of Tumor Markers for Invasion and Metastasis", Anticancer Research, vol. 19, pp. 3193-3198 (1999).

Osmak, et al., "Drug-Resistant Human Laryngeal Carcinoma Cells have Increased Levels of Cathepsin B", Anticancer Research, vol. 21, pp. 481-484 (2001).

Pietrzkowski, et al., "Inhibition of Growth of Prostatic Cancer Cell Lines by Peptide Analogues of Insulin-like Growth Factor 1", Cancer Res., vol. 53, pp. 1102-1106 (1993).

Potti, et al., "Genomic signatures to guide the use of chemotherapeutics", vol. 12, pp. 1294-1300 (2006).

Prokisch, et al., "Integrative Analysis of the Mitochondrial Proteome in Yeast", vol. 2 (6), pp. 0795-0804 (2004).

Rainier, et al., "Transcribed dinucleotide repeat polymorphism in the IGF2 gene", Human Molecular Genetics, vol. 3 (2), pp. 386 (1994).

Rath, et al., "The C-terminal CD47/IAP-binding domain of thrombospondin-1 prevents camptothecin- and doxorubicin-induced apoptosis in human thyroid carcinoma cells", Biochimica et Biophysica Acta, vol. 1763, pp. 1125-1134 (2006).

Rouzier, et al., "Breast Cancer Molecular Subtypes Respond Differently to Preoperative Chemotherapy", Clin. Cancer Res., vol. 11 (16), pp. 5678-5684 (2005).

Scaddan, et al., "Characterization of Cysteine Proteases and Their Endogenous Inhibitors in MCF-7 and Adriamycin-Resistant MCF-7 Human Breast Cancer Cells", Invasion Metastasis, vol. 13, pp. 301-313 (1993).

Schena, et al., "Quantitative Monitoring of Gene Expression Patterns with a Complementary DNA Microarray", Science, vol. 270, pp. 467-470 (1995).

Scotlandi, et al., "Insulin-like Growth Factor I Receptor-mediated Circuit in Ewing's Sarcoma/Peripheral Neuroectodermal Tumor: A Possible Therapeutic Target", Cancer Res., vol. 56, pp. 4570-4574 (1996).

Scotlandi, et al., "Antitumor Activity of the Insulin-Like Growth Factor-I Receptor Kinase Inhibitor NVP-AEW541 in Musculoskeletal Tumors", Cancer Res., vol. 65 (9), pp. 3868-3876 (2005).

Shipp, et al., "Diffuse large B-cell lymphoma outcome prediction by gene-expression profiling and supervised machine learning", Nature Med., vol. 8 (1), pp. 68-74 (2002).

Sonneveld, P., "Multidrug resistance in haematological malignancies", J. Internal Med., vol. 247, pp. 521-534 (2000).

Steinbach, et al., "Co-inhibition of epidermal growth factor receptor and type 1 insulin-like growth factor receptor synergistically sensitizes human malignant glioma cells to CD95L-induced apoptosis", Biochemical Biophysical Res. Communications, vol. 321, pp. 524-530 (2004).

Turner, et al., "Insulin-like Growth Factor-I Receptor Overexpression Mediates Cellular Radioresistance and Local Breast Cancer Recurrence after Lumpectomy and Radiation", Cancer Res., vol. 57, pp. 3079-3083 (1997).

Van't Veer, et. al., "Gene expression profiling predicts clinical outcome of breast cancer", Nature, vol. 415, pp. 530-536 (2002).

Walker, et al., "Insulin-like Growth Factor Binding Proteins IGFBP3, IGFBP4, and IGFBP5 Predict Endocrine Responsiveness in Patients with Ovarian Cancer", Clin. Cancer Res., vol. 13 (5), pp. 1438-1444 (2007).

Wands, et al., "High Affinity Monoclonal Antibodies to Hepatitis B Surface Antigen ($HB_8AG$) Produced by Somatic Cell Hybrids", Gastroenterology, vol. 80, pp. 225-232 (1981).

Wittman, et al., "Discovery of a 1H-Benzoimidazol-2-yl)-1H-pyridin-2-one (BMS-536924) Inhibitor of Insulin-like Growth Factor I Receptor Kinase with in Vivo Antitumor Activity", J. Med. Chem., vol. 48, pp. 5639-5643 (2005).

Yee, et al., "Insulin-like Growth Factor I Expression by Tumors of Neuroectodermal Origin with the t(11;22) Chromosomal Translocation", J. Clin. Invest., vol. 86, pp. 1806-1814 (1990).

Zhan, et al., "Activation of an Imprinted Allele of the Insulin-like Growth Factor II Gene Implicated in Rhabdomyosarcoma", J. Clin. Investigation, vol. 94, pp. 445-448 (1994).

Cockett, et al., "Applied genomics: integration of the technology within pharmaceutical research and development", Curr. Opin. Biotech., vol. 11, pp. 602-609 (2000).

\* cited by examiner

BIOMARKERS AND METHODS FOR DETERMINING SENSITIVITY TO INSULIN GROWTH FACTOR-1 RECEPTOR MODULATORS

This application claims benefit to International Application No. PCT/US2008/063621, filed May 15, 2008, under 35 U.S.C. §365(a); which claims priority to provisional application U.S. Serial No. 60/938,570, filed May 17, 2007; under 35 U.S.C. §119(e). The entire teachings of the referenced applications are incorporated herein by reference.

FIELD OF THE INVENTION

The present invention relates generally to the field of pharmacogenomics, and more specifically, to methods and procedures used to monitor response or determine sensitivity in patients to allow the identification of individualized genetic profiles which will aid in treating diseases and disorders.

BRIEF DESCRIPTION OF THE SEQUENCE LISTING

Incorporated herein by reference in its entirety is a Sequence Listing entitled, "11082USPCT ST25.txt", comprising SEQ ID NO:1 through SEQ ID NO:286, which include amino acid sequences disclosed herein. The Sequence Listing has been submitted herewith in ASCII text format via EFS, and thus constitutes both the paper and computer readable form thereof. The Sequence Listing was first created using PatentIn on May 7, 2012, and is 52 KB in size.

BACKGROUND OF THE INVENTION

Cancer is a disease with extensive histoclinical heterogeneity. Although conventional histological and clinical features have been correlated to prognosis, the same apparent prognostic type of tumors varies widely in its responsiveness to therapy and consequent survival of the patient.

New prognostic and predictive markers, which would facilitate an individualization of therapy for each patient, are needed to accurately predict patient response to treatments, such as small molecule or biological molecule drugs, in the clinic. The problem may be solved by the identification of new parameters that could better predict the patient's sensitivity to treatment. The classification of patient samples is a crucial aspect of cancer diagnosis and treatment. The association of a patient's response to a treatment with molecular and genetic markers can open up new opportunities for treatment development in non-responding patients, or distinguish a treatment's indication among other treatment choices because of higher confidence in the efficacy. Further, the pre-selection of patients who are likely to respond well to a medicine, drug, or combination therapy may reduce the number of patients needed in a clinical study or accelerate the time needed to complete a clinical development program (M. Cockett et al., Current Opinion in Biotechnology, 11:602-609 (2000)).

The ability to determine which patients are responding to anti-angiogenesis therapies (such as IGF1R modulators) or predict drug sensitivity in patients is particularly challenging because drug responses reflect not only properties intrinsic to the target cells, but also a host's metabolic properties. Efforts to use genetic information to predict or monitor drug response have primarily focused on individual genes that have broad effects, such as the multidrug resistance genes mdr1 and mrp1 (P. Sonneveld, J. Intern. Med., 247:521-534 (2000)).

The development of microarray technologies for large scale characterization of gene mRNA expression pattern has made it possible to systematically search for molecular markers and to categorize cancers into distinct subgroups not evident by traditional histopathological methods (J. Khan et al., Cancer Res., 58:5009-5013 (1998); A. A. Alizadeh et al., Nature, 403:503-511 (2000); M. Bittner et al., Nature, 406:536-540 (2000); J. Khan et al., Nature Medicine, 7(6):673-679 (2001); and T. R. Golub et al., Science, 286:531-537 (1999); U. Alon et al., P.N.A.S. USA, 96:6745-6750 (1999)). Such technologies and molecular tools have made it possible to monitor the expression level of a large number of transcripts within a cell population at any given time (see, e.g., Schena et al., Science, 270:467-470 (1995); Lockhart et al., Nature Biotechnology, 14:1675-1680 (1996); Blanchard et al., Nature Biotechnology, 14:1649 (1996); U.S. Pat. No. 5,569,588 to Ashby et al.).

Recent studies demonstrate that gene expression information generated by microarray analysis of human tumors can predict clinical outcome (L. J. van't Veer et al., Nature, 415:530-536 (2002); M. Shipp et al., Nature Medicine, 8(1):68-74 (2002); G. Glinsky et al., The Journal of Clin. Invest., 113(6):913-923 (2004)). These findings bring hope that cancer treatment will be vastly improved by better predicting and monitoring the response of individual tumors to therapy.

PCT Application No. PCT/US2006/034201 provides biomarkers useful for identifying a mammal that will respond therapeutically to a method of treating cancer comprising administering an IGF1R modulator.

Needed are new and alternative methods and procedures to determine drug sensitivity or monitor response in patients to allow the development of individualized diagnostics which are necessary to treat diseases and disorders based on patient response at a molecular level.

SUMMARY OF THE INVENTION

The invention provides methods and procedures for determining patient sensitivity or monitor response at the molecular level to one or more insulin growth factor 1 receptor (IGF1R) modulators. The invention also provides methods of determining or predicting whether an individual requiring therapy for a disease state such as cancer will or will not respond to treatment, prior to administration of the treatment, wherein the treatment comprises administration of one or more IGF1R modulators. The one or more IGF1R modulators are compounds that can be selected from, for example, one or more IGF1R specific ligands, one or more small molecule IGF1R inhibitors, or one or more IGF1R binding monoclonal antibodies.

In one aspect, the invention provides a method for predicting the likelihood a mammal will respond therapeutically to a method of treating cancer comprising administering an IGF1R modulator, wherein the method comprises: (a) measuring in the mammal the level of at least one biomarker selected from the biomarkers of Tables 2-8; (b) exposing a biological sample from said mammal to the IGF1R modulator; (c) following the exposing of step (b), measuring in said biological sample the level of the at least one biomarker, wherein an increase in the level of the at least one biomarker measured in step (c) compared to the level of the at least one biomarker measured in step (a), indicates an increased likelihood that the mammal will respond therapeutically to said method of treating cancer when said at least one biomarker is a sensitivity biomarker, and indicates an increased likelihood that the mammal will not respond therapeutically to said method of treating cancer when said at least one biomarker is a resistance biomarker.

In another aspect, the invention provides a method for identifying a mammal that will respond therapeutically to a method of treating cancer comprising administering an IGF1R modulator, wherein the method comprises: (a) measuring in the mammal the level of at least one biomarker selected from the biomarkers of Tables 2-8; (b) exposing a biological sample from the mammal to the IGF1R modulator; (c) following the exposing in step (b), measuring in said biological sample the level of the at least one biomarker and using said measurement to determine whether the mammal is likely to respond therapeutically to said method of treating cancer.

A difference in the level of the biomarker that is sufficient to indicate whether the mammal will or will not respond therapeutically to the method of treating cancer can be readily determined by one of skill in the art using known techniques. The increase or decrease in the level of the biomarker can be correlated to determine whether the difference is sufficient to identify a mammal that will respond therapeutically. The difference in the level of the biomarker that is sufficient can, in one aspect, be predetermined prior to determining whether the mammal will respond therapeutically to the treatment. In one aspect, the difference in the level of the biomarker is a difference in the mRNA level (measured, for example, by RT-PCR or a microarray), such as at least a two-fold difference, at least a three-fold difference, or at least a four-fold difference in the level of expression. In another aspect, the difference in the level of the biomarker is determined by IHC. In another aspect, the difference in the level of the biomarker refers to a p-value of <0.05 in Anova analysis. In yet another aspect, the difference is determined in an ELISA assay.

As used herein, respond therapeutically refers to the alleviation or abrogation of the cancer. This means that the life expectancy of an individual affected with the cancer will be increased or that one or more of the symptoms of the cancer will be reduced or ameliorated. The term encompasses a reduction in cancerous cell growth or tumor volume. Whether a mammal responds therapeutically can be measured by many methods well known in the art, such as PET imaging.

The mammal can be, for example, a human, rat, mouse, dog rabbit, pig sheep, cow, horse, cat, primate, or monkey.

The method of the invention can be, for example, an in vitro method wherein the step of measuring in the mammal the level of at least one biomarker comprises taking a biological sample from the mammal and then measuring the level of the biomarker(s) in the biological sample. The biological sample can comprise, for example, at least one of serum, whole fresh blood, peripheral blood mononuclear cells, frozen whole blood, fresh plasma, frozen plasma, urine, saliva, skin, hair follicle, bone marrow, or tumor tissue.

The level of the at least one biomarker can be, for example, the level of protein and/or mRNA transcript of the biomarker(s).

In another aspect, the invention provides a method for identifying a mammal that will respond therapeutically to a method of treating cancer comprising administering an IGF1R modulator, wherein the method comprises: (a) exposing a biological sample from the mammal to the IGF1R modulator; (b) following the exposing of step (a), measuring in said biological sample the level of at least one biomarker selected from the biomarkers of Tables 2-8, wherein a difference in the level of the at least one biomarker measured in step (b), compared to the level of the biomarker in a mammal that has not been exposed to said IGF1R modulator, indicates that the mammal will respond therapeutically to said method of treating cancer.

In yet another aspect, the invention provides a method for testing or predicting whether a mammal will respond therapeutically to a method of treating cancer comprising administering an IGF1R modulator, wherein the method comprises: (a) measuring in the mammal the level of at least one biomarker selected from the biomarkers of Tables 2-8; (b) exposing the mammal to the IGF1R modulator; (c) following the exposing of step (b), measuring in the mammal the level of the at least one biomarker, wherein a difference in the level of the at least one biomarker measured in step (c) compared to the level of the at least one biomarker measured in step (a) indicates that the mammal will respond therapeutically to said method of treating cancer.

In another aspect, the invention provides a method for determining whether a compound inhibits IGF1R activity in a mammal, comprising: (a) exposing the mammal to the compound; and (b) following the exposing of step (a), measuring in the mammal the level of at least one biomarker selected from the biomarkers of Tables 2-8, wherein a difference in the level of said biomarker measured in step (b), compared to the level of the biomarker in a mammal that has not been exposed to said compound, indicates that the compound inhibits IGF1R activity in the mammal In yet another aspect, the invention provides a method for determining whether a mammal has been exposed to a compound that inhibits IGF1R activity, comprising (a) exposing the mammal to the compound; and (b) following the exposing of step (a), measuring in the mammal the level of at least one biomarker selected from the biomarkers of Tables 2-8, wherein a difference in the level of said biomarker measured in step (b), compared to the level of the biomarker in a mammal that has not been exposed to said compound, indicates that the mammal has been exposed to a compound that inhibits IGF1R activity.

In another aspect, the invention provides a method for determining whether a mammal is responding to a compound that inhibits IGF1R activity, comprising (a) exposing the mammal to the compound; and (b) following the exposing of step (a), measuring in the mammal the level of at least one biomarker selected from the biomarkers of Tables 2-8, wherein a difference in the level of the at least one biomarker measured in step (b), compared to the level of the at least one biomarker in a mammal that has not been exposed to said compound, indicates that the mammal is responding to the compound that inhibits IGF1R activity.

As used herein, "responding" encompasses responding by way of a biological and cellular response, as well as a clinical response (such as improved symptoms, a therapeutic effect, or an adverse event), in a mammal The invention also provides an isolated biomarker selected from the biomarkers of Tables 2-8. The biomarkers of the invention comprise sequences selected from the nucleotide and amino acid sequences provided in Tables 2-8 and the Sequence Listing, as well as fragments and variants thereof.

The invention also provides a biomarker set comprising two or more biomarkers selected from the biomarkers of Tables 2-8.

The invention also provides kits for determining or predicting whether a patient would be susceptible or resistant to a treatment that comprises one or more IGF1R modulators. The patient may have a cancer or tumor such as, for example, a colon cancer or tumor.

In one aspect, the kit comprises a suitable container that comprises one or more specialized microarrays of the invention, one or more IGF1R modulators for use in testing cells from patient tissue specimens or patient samples, and instructions for use. The kit may further comprise reagents or materials for monitoring the expression of a biomarker set at the level of mRNA or protein.

In another aspect, the invention provides a kit comprising two or more biomarkers selected from the biomarkers of Tables 2-8.

In yet another aspect, the invention provides a kit comprising at least one of an antibody and a nucleic acid for detecting the presence of at least one of the biomarkers selected from the biomarkers of Tables 2-8. In one aspect, the kit further comprises instructions for determining whether or not a mammal will respond therapeutically to a method of treating cancer comprising administering a compound that inhibits IGF1R activity. In another aspect, the instructions comprise the steps of (a) measuring in the mammal the level of at least one biomarker selected from the biomarkers of Tables 2-8, (b) exposing the mammal to the compound, (c) following the exposing of step (b), measuring in the mammal the level of the at least one biomarker, wherein a difference in the level of the at least one biomarker measured in step (c) compared to the level of the at least one biomarker measured in step (a) indicates that the mammal will respond therapeutically to said method of treating cancer.

The invention also provides screening assays for determining if a patient will be susceptible or resistant to treatment with one or more IGF1R modulators.

The invention also provides a method of monitoring the treatment of a patient having a disease, wherein said disease is treated by a method comprising administering one or more IGF1R modulators.

The invention also provides individualized genetic profiles which are necessary to treat diseases and disorders based on patient response at a molecular level.

The invention also provides specialized microarrays, e.g., oligonucleotide microarrays or cDNA microarrays, comprising one or more biomarkers having expression profiles that correlate with either sensitivity or resistance to one or more IGF1R modulators.

The invention also provides antibodies, including polyclonal or monoclonal, directed against one or more biomarkers of the invention.

The invention will be better understood upon a reading of the detailed description of the invention when considered in connection with any accompanying figures.

DETAILED DESCRIPTION OF THE INVENTION

Identification of biomarkers that provide rapid and accessible readouts of efficacy, drug exposure, or clinical response is increasingly important in the clinical development of drug candidates. Embodiments of the invention include measuring changes in the levels of secreted proteins, or plasma biomarkers, which represent one category of biomarker. In one aspect, plasma samples, which represent a readily accessible source of material, serve as surrogate tissue for biomarker analysis.

The invention provides biomarkers that respond to the modulation of a specific signal transduction pathway and also correlate with IGF1R modulator sensitivity or resistance. These biomarkers can be employed for predicting and monitoring response to one or more IGF1R modulators. In one aspect, the biomarkers of the invention are those provided in Tables 2-8 and the Sequence Listing, including both polynucleotide and polypeptide sequences. In another aspect, the biomarkers of the invention are nucleotide sequences that, due to the degeneracy of the genetic code, encodes for a polypeptide sequence provided in the sequence listing.

The biomarkers serve as useful molecular tools for predicting and monitoring response to IGF1R modulators that affect IGF1R activity or the IGF1R signal transduction pathway.

In addition to playing an important role in normal cell growth, maintenance and development, insulin-like growth factor receptor (IGF1R) and its ligands are also important in the establishment and maintenance of the malignant phenotype. Binding of IGF-1 and IGF-II ligands to the IGF1R initiates a cascade of events leading to activation of mitogenic signaling pathway (Ras/Raf/MAPK) and antiapoptotic/survival pathway (PI3K-Akt/mTor), resulting in proliferation, transformation and survival in tumor cells (D. LeRoith, et al., Cancer Lett., 195(2):127-37 (2003), R. Baserga, et al., Int. J. Cancer;107:873-7 (2003)). IGF1R overexpression and/or enhanced activity have been observed in diverse tumor types suggesting that the potential therapeutic use of agents targeting this pathway is broad. IGF1R provides a critical survival signal in multiple tumor types. The expression of this receptor is an indicator of poor prognosis, thus, it has emerged as an attractive and compelling target for cancer therapy to inhibit the progression of multiple tumor types in cancer patients. Various drug discovery approaches have been explored in recent years to modulate the function of IGF1R. Approaches aimed at the reduction of receptor number or enzymatic activity using a variety of strategies in preclinical models have been shown to reverse the malignant phenotype in tumor cells. These strategies include antisense (L. Long, et al., Cancer Res, 55(5):1006-9 (1995), D. Andrews et al., J. Clin. Oncol., 19(8):2189-200 (2001)), monoclonal antibody (C. Arteaga, et al., Cancer Res., 49(22):6237-41 (1989)), small molecule inhibitors (M. Wittman, et al., J. Med. Chem., September 8;48(18):5639-43 (2005), C. Garcia-Echeverria, et al., Cancer Cell, 5(3):231-9 (2004)), IGF-1 mimetic peptides (Z. Pietrzkowski, et al., Cancer Res., 53(5):1102-6 (1993)) as well as dominant negative mutants that lack enzyme activity (C. D'Ambrosio, et al., Cancer Res, 56(17): 4013-20 (1996)).

However, this targeted therapy may only be successful if the receptor is absolutely necessary for pathogenesis and tumor progression. IGF1R and its ligands have been shown to be important in the mesenchymal originated soft tissue sarcomas and neuroblastoma (G. Merlino, et al., Oncogene;18: 5340-8 (1999), K. Scotlandi, et al., Cancer Res.;56:4570-4 (1996), S. Burrow, et al., J. Surg. Oncol.;69:21-7 (1998), D. Yee, et al., J. Clin. Invest., 86(6) : 1806-14 (1990)). These rare tumors have distinctive biological characteristics including aggressive local behavior and a predilection for metastasis. With multimodal treatments and very aggressive chemotherapeutic regimens, the survival rate is disappointingly low and, thus, there is a high unmet medical need for the treatment of patients with these tumor types. Inhibition of IGF1R by antibody or small molecule either alone or in combination with other chemotherapeutic agents have demonstrated anti-tumor activity in sarcomas (S. Benini, et al., Clinical Cancer Res., 7, 1790-97 (2001), K. Scotlandi, et al., Cancer Res., May 1;65(9):3868-76 (2005), M. Manara, et al., Clinical Cancer Res.; 13(4) 1322-30 (2007)).

One of the integral goals in the development of these targeted cancer therapies is to identify the targeted patients population who are most likely to benefit from the drug treatment. Utilizing biomarkers has successfully guided the development of Herceptin® and EGFR inhibitors (J. Baselga, et al., J Clin Oncol. 14, 737-744 (2005), T. Lynch, et al., N. Engl. J. Med., 350, 2129-2139 (2004)). More recently, gene expression profiling studies have demonstrated the advantages of molecular "signatures" or marker sets generated by microarray analysis in predicting chemotherapeutic response and guiding the targeted therapies (K. Iwao-Koizumi, et al., J. Clin. Oncol.;23:422-31 (2005), H. Dressman, et al., Clin. Cancer Res.;12:819-26 (2006), R. Rouzier, et al., Clin. Cancer Res.;11:5678-85 (2005), K. Hess, et al., J. Clin. Oncol.; 24:4236-44 (2006), H. Dressman, et al., J. Clin. Oncol., February 10;25(5):517-25 (2007), A. Potti, et al., Nat. Med., November;12(11):1294-300 (2006)). These findings provide hope that cancer treatments of the future will be vastly improved by using molecular "signatures" to choose the most effective drug for patient targeting. One of the challenges is to determine the targeted patient population for the drug before clinical data is available.

To overcome this challenge, as described previously (F. Huang F, et al., Cancer Res., March 1;67(5):2226-38 (2007)), cultured cancer cell lines can be used as models to identify biomarkers that correlate with response to a therapy assuming these markers identified in vitro are ultimately applicable in clinical studies to select targeted patient population.

To this end, in this study, the gene and protein profiling by both microarray and LC/MS based "bottom-up" protein profiling (M. Lipton, et al., Proc. Natl. Acad. Sci. USA., August 20;99(17):11049-54 (2002), H. Prokisch et al., PLoS Biol., June;2(6):e160 (2004)) were conduced in parallel using a panel of 29 cell lines to identify genes or proteins whose basal expression levels are correlated with the in vitro sensitivity of cells to compound 1 or compound 2 (as defined below) and potentially could be used as predictive markers. To gain insights of acquired resistance of compound 1, gene expression profiles of a pair of sensitive and acquired resistant cell lines were compared to identify genes correlated with the acquired resistance. These genes were then compared to the genes over expressed in the resistant cell lines at basal level (correlated with the de novo resistance to the drug). Common mechanism of de novo resistance and acquired resistance to IGF1R inhibitor compound 1 was explored. Furthermore, genes/proteins modulated by drug treatment of compound 1 were identified and linked to the possible mechanisms of the drug action. These markers could be useful to monitor the biological effects of the drug and to select the optimal dose in the clinical studies. To explore the relation between these biomarkers and the drug target IGF1R, pathway analyses were performed and cross-talk between the IGF1R and other kinases was evident, this led us to propose the hypothesis for the potential synergistic activity between compound 1 and other agents targeting these kinases. Drug combination studies of compound 1 with other agents, such as EGFR inhibitors, were performed and synergy in tumor growth inhibition in vitro was observed with combined inhibition of multiple pathways. In this study, we identified the biomarkers of potentially predictive the targeted sub-population of patient with sarcomas that would be benefit from the treatment of IGF1R inhibitor.

IGF1R Modulators:

As used herein, the term "IGF1R modulator" is intended to mean a compound or drug that is a biological molecule or a small molecule that directly or indirectly modulates IGF1R activity or the IGF1R signal transduction pathway. Thus, compounds or drugs as used herein is intended to include both small molecules and biological molecules. Direct or indirect modulation includes activation or inhibition of IGF1R activity or the IGF1R signal transduction pathway. In one aspect, inhibition refers to inhibition of the binding of IGF1R to an IGF1R ligand such as, for example, VEGF. In another aspect, inhibition refers to inhibition of the kinase activity of IGF1R.

IGF1R modulators include, for example, IGF1R specific ligands, small molecule IGF1R inhibitors, and IGF1R monoclonal antibodies. In one aspect, the IGF1R modulator inhibits IGF1R activity and/or inhibits the IGF1R signal transduction pathway. In another aspect, the IGF1R modulator is an IGF1R monoclonal antibody that inhibits IGF1R activity and/or inhibits the IGF1R signal transduction pathway.

IGF1R modulators include biological molecules or small molecules.

Biological molecules include all lipids and polymers of monosaccharides, amino acids, and nucleotides having a molecular weight greater than 450. Thus, biological molecules include, for example, oligosaccharides and polysaccharides; oligopeptides, polypeptides, peptides, and proteins; and oligonucleotides and polynucleotides. Oligonucleotides and polynucleotides include, for example, DNA and RNA.

Biological molecules further include derivatives of any of the molecules described above. For example, derivatives of biological molecules include lipid and glycosylation derivatives of oligopeptides, polypeptides, peptides, and proteins.

Derivatives of biological molecules further include lipid derivatives of oligosaccharides and polysaccharides, e.g., lipopolysaccharides. Most typically, biological molecules are antibodies, or functional equivalents of antibodies. Functional equivalents of antibodies have binding characteristics comparable to those of antibodies, and inhibit the growth of cells that express IGF1R. Such functional equivalents include, for example, chimerized, humanized, and single chain antibodies as well as fragments thereof Functional equivalents of antibodies also include polypeptides with amino acid sequences substantially the same as the amino acid sequence of the variable or hypervariable regions of the antibodies. An amino acid sequence that is substantially the same as another sequence, but that differs from the other sequence by means of one or more substitutions, additions, and/or deletions, is considered to be an equivalent sequence. Preferably, less than 50%, more preferably less than 25%, and still more preferably less than 10%, of the number of amino acid residues in a sequence are substituted for, added to, or deleted from the protein.

The functional equivalent of an antibody is preferably a chimerized or humanized antibody. A chimerized antibody comprises the variable region of a non-human antibody and the constant region of a human antibody. A humanized antibody comprises the hypervariable region (CDRs) of a non-human antibody. The variable region other than the hypervariable region, e.g., the framework variable region, and the constant region of a humanized antibody are those of a human antibody.

Suitable variable and hypervariable regions of non-human antibodies may be derived from antibodies produced by any non-human mammal in which monoclonal antibodies are made. Suitable examples of mammals other than humans include, for example, rabbits, rats, mice, horses, goats, or primates.

Functional equivalents further include fragments of antibodies that have binding characteristics that are the same as, or are comparable to, those of the whole antibody. Suitable fragments of the antibody include any fragment that comprises a sufficient portion of the hypervariable (i.e., complementarity determining) region to bind specifically, and with sufficient affinity, to IGF1R tyrosine kinase to inhibit growth of cells that express such receptors.

Such fragments may, for example, contain one or both Fab fragments or the F(ab')2 fragment. Preferably, the antibody fragments contain all six complementarity determining regions of the whole antibody, although functional fragments containing fewer than all of such regions, such as three, four, or five CDRs, are also included.

In one aspect, the fragments are single chain antibodies, or Fv fragments. Single chain antibodies are polypeptides that comprise at least the variable region of the heavy chain of the antibody linked to the variable region of the light chain, with or without an interconnecting linker. Thus, Fv fragment comprises the entire antibody combining site. These chains may be produced in bacteria or in eukaryotic cells.

The antibodies and functional equivalents may be members of any class of immunoglobulins, such as IgG, IgM, IgA, IgD, or IgE, and the subclasses thereof.

In one aspect, the antibodies are members of the IgG1 subclass. The functional equivalents may also be equivalents of combinations of any of the above classes and subclasses.

In one aspect, the IGF1R antibody is provided in PCT publication nos. WO2005/016970, WO02/53596, WO2004/71529, WO2005/16967, WO2004/83248, WO03/106621, WO03/100008, WO03/59951, WO2004/87756, or WO2005/05635.

In another aspect, the IGF1R modulator is derived from fibronectin, such as an AdNectin (Adnexus Therapeutics) (See, PCT publication nos. WO00/34784, WO01/64942, WO02/32925).

In addition to the biological molecules discussed above, the IGF1R modulators useful in the invention may also be small molecules. Any molecule that is not a biological molecule is considered herein to be a small molecule. Some examples of small molecules include organic compounds, organometallic compounds, salts of organic and organometallic compounds, saccharides, amino acids, and nucleotides. Small molecules further include molecules that would otherwise be considered biological molecules, except their molecular weight is not greater than 450. Thus, small molecules may be lipids, oligosaccharides, oligopeptides, and oligonucleotides and their derivatives, having a molecular weight of 450 or less.

It is emphasized that small molecules can have any molecular weight. They are merely called small molecules because they typically have molecular weights less than 450. Small molecules include compounds that are found in nature as well as synthetic compounds. In one embodiment, the IGF1R modulator is a small molecule that inhibits the growth of tumor cells that express IGF1R. In another embodiment, the IGF1R modulator is a small molecule that inhibits the growth of refractory tumor cells that express IGF1R.

Numerous small molecules have been described as being useful to inhibit IGF1R.

In one aspect, the IGF1R modulator is selected from PCT publication nos. WO02/79192, WO2004/30620, WO2004/31401 WO2004/63151, and WO2005/21510, and from U.S. provisional application Nos. 60/819,171, 60/870,872, 60/883,601, and 60/912,446.

In another aspect, the IGF1R modulator is selected from (S)-4-(2-(3-chlorophenyl)-2-hydroxyethylamino)-3-(4-methyl-6-morpholino-1H-benzo[d]imidazol-2-yl)-pyridin-2(1H)-one and (2S)-1-(4-((5-cyclopropyl-1H-pyrazol-3-yl)amino)pyrrolo[2,1-f][1,2,4]triazin-2-yl)-N-(6-fluoro-3-pyridinyl)-2-methyl-2-pyrrolidinecarboxamide.

In another aspect, the IGF1R modulator is selected from XL-228 (Exelixis), AEW-541 (Novartis), and OSI-906 (OSI).

Biomarkers and Biomarker Sets:

The invention includes individual biomarkers and biomarker sets having both diagnostic and prognostic value in disease areas in which signaling through IGF1R or the IGF1R pathway is of importance, e.g., in cancers or tumors, in immunological disorders, conditions or dysfunctions, or in disease states in which cell signaling and/or cellular proliferation controls are abnormal or aberrant. The biomarker sets comprise a plurality of biomarkers such as, for example, a plurality of the biomarkers provided in Tables 2-8 that highly correlate with resistance or sensitivity to one or more IGF1R modulators.

The biomarkers and biomarker sets of the invention enable one to predict or reasonably foretell the likely effect of one or more IGF1R modulators in different biological systems or for cellular responses. The biomarkers and biomarker sets can be used in in vitro assays of IGF1R modulator response by test cells to predict in vivo outcome. In accordance with the invention, the various biomarkers and biomarker sets described herein, or the combination of these biomarker sets with other biomarkers or markers, can be used, for example, to predict and monitor how patients with cancer might respond to therapeutic intervention with one or more IGF1R modulators.

A biomarker and biomarker set of cellular gene expression patterns correlating with sensitivity or resistance of cells following exposure of the cells to one or more IGF1R modulators provides a useful tool for screening one or more tumor samples before treatment with the IGF1R modulator. The screening allows a prediction of cells of a tumor sample exposed to one or more IGF1R modulators, based on the expression results of the biomarker and biomarker set, as to whether or not the tumor, and hence a patient harboring the tumor, will or will not respond to treatment with the IGF1R modulator.

The biomarker or biomarker set can also be used as described herein for monitoring the progress of disease treatment or therapy in those patients undergoing treatment for a disease involving an IGF1R modulator.

The biomarkers also serve as targets for the development of therapies for disease treatment. Such targets may be particularly applicable to treatment of cancer, such as, for example, hepatocellular carcinoma, colorectal cancer (CRC), NSCLC, and metastatic breast cancer.

Indeed, because these biomarkers are differentially expressed in sensitive and resistant cells, their expression patterns are correlated with relative intrinsic sensitivity of cells to treatment with IGF1R modulators. Accordingly, the biomarkers highly expressed in resistant cells may serve as targets for the development of new therapies for the tumors which are resistant to IGF1R modulators, particularly IGF1R inhibitors. The level of biomarker protein and/or mRNA can be determined using methods well known to those skilled in the art. For example, quantification of protein can be carried out using methods such as ELISA, 2-dimensional SDS PAGE, Western blot, immunopreciptation, immunohistochemistry, fluorescence activated cell sorting (FACS), or flow cytometry. Quantification of mRNA can be carried out using methods such as PCR, array hybridization, Northern blot, in-situ hybridization, dot-blot, Taqman, or RNAse protection assay.

Microassays:

The invention also includes specialized microarrays, e.g., oligonucleotide microarrays or cDNA microarrays, comprising one or more biomarkers, showing expression profiles that correlate with either sensitivity or resistance to one or more IGF1R modulators. Such microarrays can be employed in in vitro assays for assessing the expression level of the biomarkers in the test cells from tumor biopsies, and determining whether these test cells are likely to be resistant or sensitive to IGF1R modulators. For example, a specialized microarray can be prepared using all the biomarkers, or subsets thereof, as described herein and shown in Tables 2-8. Cells from a tissue or organ biopsy can be isolated and exposed to one or more of the IGF1R modulators. In one aspect, following application of nucleic acids isolated from both untreated and treated cells to one or more of the specialized microarrays, the pattern of gene expression of the tested cells can be determined and compared with that of the biomarker pattern from the control panel of cells used to create the biomarker set on the microarray. Based upon the gene expression pattern results from the cells that underwent testing, it can be determined if the cells show a resistant or a sensitive profile of gene expression. Whether or not the tested cells from a tissue or organ biopsy will respond to one or more of the IGF1R modulators and the course of treatment or therapy can then be determined or evaluated based on the information gleaned from the results of the specialized microarray analysis.

Antibodies:

The invention also includes antibodies, including polyclonal or monoclonal, directed against one or more of the polypeptide biomarkers. Such antibodies can be used in a variety of ways, for example, to purify, detect, and target the biomarkers of the invention, including both in vitro and in vivo diagnostic, detection, screening, and/or therapeutic methods.

Kits:

The invention also includes kits for determining or predicting whether a patient would be susceptible or resistant to a treatment that comprises one or more IGF1R modulators. The patient may have a cancer or tumor such as, for example, a breast cancer or tumor. Such kits would be useful in a clinical setting for use in testing a patient's biopsied tumor or cancer samples, for example, to determine or predict if the patient's tumor or cancer will be resistant or sensitive to a given treatment or therapy with an IGF1R modulator. The kit comprises a suitable container that comprises: one or more microarrays, e.g., oligonucleotide microarrays or cDNA microarrays, that comprise those biomarkers that correlate with resistance and sensitivity to IGF1R modulators, particularly IGF1R inhibitors; one or more IGF1R modulators for use in testing cells from patient tissue specimens or patient samples; and instructions for use. In addition, kits contemplated by the invention can further include, for example, reagents or materials for monitoring the expression of biomarkers of the invention at the level of mRNA or protein, using other techniques and systems practiced in the art such as, for example, RT-PCR assays, which employ primers designed on the basis of one or more of the biomarkers described herein, immunoassays, such as enzyme linked immunosorbent assays (ELISAs), immunoblotting, e.g., Western blots, or in situ hybridization, and the like, as further described herein.

Application of Biomarkers and Biomarker Sets:

The biomarkers and biomarker sets may be used in different applications. Biomarker sets can be built from any combination of biomarkers listed in Tables 2-8 to make predictions about the likely effect of any IGF1R modulator in different biological systems. The various biomarkers and biomarkers sets described herein can be used, for example, as diagnostic or prognostic indicators in disease management, to predict how patients with cancer might respond to therapeutic intervention with compounds that modulate the IGF1R, and to predict how patients might respond to therapeutic intervention that modulates signaling through the entire IGF1R regulatory pathway.

While the data described herein were generated in cell lines that are routinely used to screen and identify compounds that have potential utility for cancer therapy, the biomarkers have both diagnostic and prognostic value in other diseases areas in which signaling through IGF1R or the IGF1R pathway is of importance, e.g., in immunology, or in cancers or tumors in which cell signaling and/or proliferation controls have gone awry.

In accordance with the invention, cells from a patient tissue sample, e.g., a tumor or cancer biopsy, can be assayed to determine the expression pattern of one or more biomarkers prior to treatment with one or more IGF1R modulators. Success or failure of a treatment can be determined based on the biomarker expression pattern of the cells from the test tissue (test cells), e.g., tumor or cancer biopsy, as being relatively similar or different from the expression pattern of a control set of the one or more biomarkers. Thus, if the test cells show a biomarker expression profile which corresponds to that of the biomarkers in the control panel of cells which are sensitive to the IGF1R modulator, it is highly likely or predicted that the individual's cancer or tumor will respond favorably to treatment with the IGF1R modulator. By contrast, if the test cells show a biomarker expression pattern corresponding to that of the biomarkers of the control panel of cells which are resistant to the IGF1R modulator, it is highly likely or predicted that the individual's cancer or tumor will not respond to treatment with the IGF1R modulator.

The invention also provides a method of monitoring the treatment of a patient having a disease treatable by one or more IGF1R modulators. The isolated test cells from the patient's tissue sample, e.g., a tumor biopsy or blood sample, can be assayed to determine the expression pattern of one or more biomarkers before and after exposure to an IGF1R modulator wherein, preferably, the IGF1R modulator is an IGF1R inhibitor. The resulting biomarker expression profile of the test cells before and after treatment is compared with that of one or more biomarkers as described and shown herein to be highly expressed in the control panel of cells that are either resistant or sensitive to an IGF1R modulator. Thus, if a patient's response is sensitive to treatment by an IGF1R modulator, based on correlation of the expression profile of the one or biomarkers, the patient's treatment prognosis can be qualified as favorable and treatment can continue. Also, if, after treatment with an IGF1R modulator, the test cells don't show a change in the biomarker expression profile corresponding to the control panel of cells that are sensitive to the IGF1R modulator, it can serve as an indicator that the current treatment should be modified, changed, or even discontinued. This monitoring process can indicate success or failure of a patient's treatment with an IGF1R modulator and such monitoring processes can be repeated as necessary or desired.

The biomarkers of the invention can be used to predict an outcome prior to having any knowledge about a biological system. Essentially, a biomarker can be considered to be a statistical tool. Biomarkers are useful primarily in predicting the phenotype that is used to classify the biological system. In an embodiment of the invention, the goal of the prediction is to classify cancer cells as having an active or inactive IGF1R pathway. Cancer cells with an inactive IGF1R pathway can be considered resistant to treatment with an IGF1R modulator.

EXAMPLES

Methods and Samples:

In the following examples, the compound (S)-4-(2-(3-chlorophenyl)-2-hydroxyethylamino)-3-(4-methyl-6-morpholino-1H-benzo[d]imidazol-2-yl)-pyridin-2(1-H)-one was used:

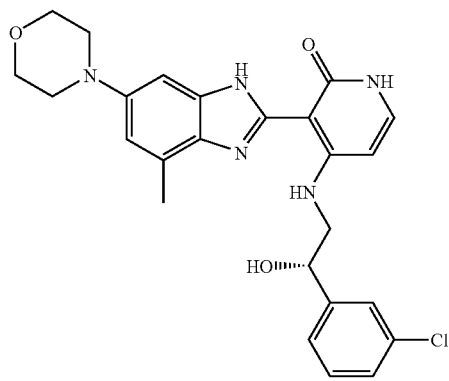 [SMILES: Cc1cc(N2CCOCC2)cc2[nH]c(-c3c(NC[C@@H](O)c4cccc(Cl)c4)cc[nH]c3=O)nc12]

This compound is referred to herein as "compound 1."

In the following examples, the compound (2S)-1-(4-((5-cyclopropyl-1H-pyrazol-3-yl)amino)pyrrolo[2,1-f][1,2,4]triazin-2-yl)-N-(6-fluoro-3-pyridinyl)-2-methyl-2-pyrrolidinecarboxamide was used:

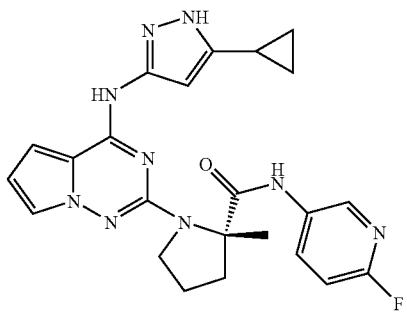 [SMILES: C[C@@]1(C(=O)Nc2ccc(F)nc2)CCCN1c1nc(Nc2cc(C3CC3)[nH]n2)c2cccn2n1]

This compound is referred to herein as "compound 2."

Example 1

Identification of Biomarkers

Methods and Materials
Cell Lines:

All pediatric sarcoma and neuroblastoma cell lines were obtained from Dr. Lee Helman at NIH. All cell lines were grown in RPMI medium supplemented with Glutamax (Gibco/Invitrogen #61870-036), 10% inactivated fetal bovine serum (Gibco/Invitrogen #16140-071), 10 mM Hepes, penicillin and streptomycin. For the baseline profiling study, cells were harvested at 70-80% confluence; and for drug treatment study, two rhabdomyosarcoma (RMS) cell lines Rh36 and Rh41 were treated with 0.35 µM compound 1 for 6, 36 and 72 hours before harvest. To develop the compound 1-resistant RD1, the sensitive RD-1 cells ($IC_{50}$=0.238 µM to compound 1) were first exposed to the dug at the $IC_{50}$ concentration and passed as the cultures reached 70-80% confluence. The concentration of compound 1 was increased gradually every other culture passage and the $IC_{50}$ value for the compound in these cells was measured periodically during this treatment time until the resistance level reached a plateau. The resulted RD1-Resist cells has $IC_{50}$=1.999 µM to compound 1, more than 8 fold of the parental RD1.

In vitro Cellular Proliferation Assays:

Proliferation was evaluated by incorporation of [3H]-thymidine into DNA after exposure to IGF1R inhibitor compound 1 or compound 2 to determine the sensitivity of cell lines to these compounds. Cells were plated at an optimized density for each cell line per well in 96-well microtiter Falcon plates, incubated overnight, and then exposed to a serial dilution of drug. After 72 hours incubation with drug at 37° C., cells were pulsed with 4 µCi/ml [6-3H] thymidine (Amersham Pharmacia Biotech, UK) for 3 hours, trypsinized, harvested onto UniFilter-96, GF/B plates (PerkinElmer, Boston, Mass.) and scintillation was measured on a TopCount NXT (Packard, Conn.). Results were expressed as an $IC_{50}$, which is the drug concentration required to inhibit cell proliferation by 50% to that of untreated control cells. The mean $IC_{50}$ and standard deviation (SD) from multiple tests for each cell line were calculated.

Drug Combination Study:

A Dilution of Ratios Drug Combination method was used in cellular proliferation assays to determine whether there was synergy, additivity or antagonism when two compounds were added simultaneously to a variety of human tumor cells in vitro (R. Tallarida, R. J., Drug Synergism and Dose-Effect Data Analysis. 1st edition ed. Chapman & Hall/CRC (2000)). Drug stock solutions for two compounds, are combined in ratios of 10:1, 5:1, 3:1, 1:1, 1:3, 1:5. These ratios, as well as the individual compound stock solutions, are diluted in a serial manner, using 70% DMSO. These serial dilutions are then mixed with RPMI growth medium, and added to cells to test the IC50 values of single agent as well as two compounds in the cellular proliferation assays. Combination Indexes with 95% confidence intervals were used to determine if the combination results represented synergistic, additive, or antagonistic effect.

Gene Expression Profiling:

RNA was isolated from the cultured cells using the RNeasy™ kits from Qiagen (Valencia, Calif.). 10 µg of total RNA from each cell line was used to prepare biotinylated probe according to the Affymetrix GeneChip® Expression Analysis Technical Manual, 2001. Targets were hybridized to Affymetrix high density oligonucleotide array human HG-U133A 2.0 GeneChip® (Affymetrix, Santa Clara, Calif.). The arrays were then washed and stained using the GeneChip® Fluidics station and quantitated with GeneChip® Operating Software (GCOS) V1.0 according to the manufacture's instructions.

Protein Extraction and Tryptic Digestion:

Total protein content for each cell lysate was determined by the bicinchoninic acid assay (Pierce, Rockford, Ill.). An aliquot from each lysate containing 200 µg total protein was withdrawn for further processing.

The normalized samples were chloroform-methanol precipitated using a protein extraction kit (Calbiochem, San Diego, Calif.). Pellets were solublized in a solution containing 8M urea, 200 mM ammonium bicarbonate, and 40 mM DTT. Samples were diluted 4-fold, trypsin was added at 1:50 enyzme:substrate ratio and incubated overnight at 37° C.

Solid Phase Extraction:

Solid phase extraction was performed using an Empore C18 SPE plate (3M, St Paul, Minn.) on a Quadr3 liquid handling workstation (Tomtec, Hamden, Conn.). Sample sequence on the plate was randomized to minimize systemic bias during processing. After sample loading, the SPE plate was washed with 450 µl water in 0.1% trifluoroacetic acid twice and eluted with 300 µl 95% acetonitrile in 0.1% trifluoroacetic acid twice.

Randomization, Duplication, and Lyophilization:

Samples were then split across two separate 96-well plates (VWR, West Chester, Pa.) in a separate randomized order. This process generated two technical replicates for each sample. Following lyophilization on a SpeedVac (Thermo Savant, Holbrook, N.Y.), samples were stored at −80° C. before analysis.

Liquid Chromatography—Mass Spectrometry:

Samples of tryptic peptides were separated on an Zorbax 300SB-C18 column (0.5×150 mm, 3.5 nm) from Agilent (Santa Clara, Calif.) equipped with a 0.5 µm pre-column filter (Opti-solve). The mobile phases were delivered at a total flow rate of 12 µl/min by an Agilent 1100 Capillary HPLC system. Mobile phase A was water in 0.2% isopropyl alcohol, 0.1% acetic acid and 0.001% trifluoroacetic acid; Mobile B was 95% acetonitrile in 0.2% isopropyl alcohol, 0.1% acetic acid and 0.001% trifluoroacetic acid. The following gradient was used to separate the peptides:

| | Time (min) | | | | | | |
|---|---|---|---|---|---|---|---|
| | 0 | 2 | 4 | 64 | 69 | 71 | 71.1 | 80 |
| % B | 0 | 0 | 10 | 40 | 100 | 100 | 0 | Stop |

Samples were re-dissolved in 40 µl reconstitution solution in 0.2% isopropyl alcohol, 5% acetic acid and 0.001% trifluoroacetic acid. Six microliters of sample was injected for each run using an Agilent 1100 micro well plate sampler chilled at 4° C. To achieve optimum mass accuracy, a peptide standard Glu-Fibrinopeptide B (Sigma, St. Louis, Mo.) was introduced through a Valco-type mixing tee into the flowing system immediately after the HPLC column outlet at 1 µl/min. The HPLC eluent was detected on a Qtof Ultima QqTOF hybrid mass spectrometer (Waters, Manchester, UK) operated in the electrospray positive ionization mode. Mass spectra were acquired for the mass range of 300 to 1800 Da. Each acquisition was 80 minutes long, with 1 second scan time and 0.1 second inter scan delay. Accuracy of the mass measurement was typically within 20 parts per million. A collection of proprietary algorithms (Extractor, Cluster and Time Adjustment) written in-house were applied to extract and quantify peptide peak information, adjust peaks for retention time shifts that may occur during HPLC separation and match peaks across runs. This preprocessing resulted the raw peptide expression measures for each sample.

Peptide Identification:

The peptide ions generated from statistical analyses were sequenced by tandem mass spectrometry (MS/MS). Samples were rerun onto the same LC-MS system in data dependant mode in which the MS survey scan would switch to MSMS product scan when targeted peptide ions were found at the same retention time and mass. MS/MS spectra were generated and submitted to SEQUEST search (J. Eng, et al., J. Am. Soc. Mass. Spectrom., 5: 976-989 (1994)) to yield protein identifications.

Statistical Analysis

Analysis of Baseline Gene and Protein Expression of 29 Cell Lines:

The gene expression raw data were normalized by the Robust Multichip Average (RMA, R. Irizarry, et al., Biostatistics;4(2):249-64 (2003)) method and $\log_2$ transformed, while the protein profiling data was quantile normalized and log2 transformed. To identify genes or proteins whose expression level significantly correlation with the drug sensitivity for the compounds, two separate statistic analyses were performed. First, a two-sample t-test between the resistant and sensitive cell lines (based on a threshold $IC_{50}$ cutoff of 0.35 µM) was performed. Second, Pearson correlation between the normalized expression level of each gene/protein and the $\log2(IC_{50})$ values of the 29 cell lines was calculated to identify genes/proteins correlated with the drug sensitivity ($IC_{50}$).

Analysis of Gene and Protein Expression Data of Cells with Drug Treatment:

Pre-filter was applied to both gene and protein expression data. Lowly expressed probe sets with normalized and $\log_2$ transformed expression values less than 5 cross all samples were removed resulting probe sets of 10,479 for gene expression data. For peptide, it must be found in at least 15 LCMS experimental runs and for subsequent statistical analysis in at least 20 cell lines. This filter reduced the number of overall peptides to 9022 for further analysis. A two-way ANOVA mixed model was applied to each probe set in the gene expression profiling data, as well as each peptide in the protein expression profiling data, separately. The model that was applied to each dataset was nearly identical except for a single term in the model applied to the protein expression data which appropriately accounted for the existence of the technical replicates. The analysis was run using SAS version 9.1 (SAS Institute Inc., Cary, N.C., USA). The general form of the model was as follows: (Intensity~Treatment+Time+Treatment×Time+Error) where Intensity represents the normalized, log2 transformed intensity; Treatment is a term that captures candidates that display significant differential expression upon treatment; Time is a term that captures candidates that display significant differential expression over time; and the Treatment×Time term captures candidates that display significant differential expression upon treatment with compound over time as compared with control. The multiple testing with False Discovery Rate (FDR; Y. Benjamini, et al., J. Roy. Stat. Soc. B.; 57:289-300 (1995)) was apply to each dataset separately, the total of 2056 probe sets with FDR p value<0.05 in either the Treatment effect or Treatment×Time interaction and the fold change between treatment group vs. DMSO control group is greater than 1.2 fold or less than −1.2 fold were selected.

Globaltest Pathway Analysis:

RMA normalized baseline expression data for 28 sarcoma cell lines was first filtered based on following criteria: 1) Maximal expression level across all samples must be greater than 5; 2) Coefficient of Variation (CV) must by greater than 0.03. These resulted a total of 17276 probe sets for further analysis. Globaltest was carried out with Bioconductor (www.bioconductor.org) package (Version 4.4.0) using this filtered dataset and compound 1 resistant/sensitive classification for each cell line against a collection of 183 KEGG pathways. The p value indicating the association between expression values and resistant/sensitive classifications, as well as its multiplicity-adjusted version, FWER (Holm's method), were reported for each pathway. Gene plots were generated for interesting pathways according to user's guide (J. Geoman, et al., Testing association of a pathway with a clinical variable. Package globaltest. Version 4.4.0. (October 2006)) and used to assess the influence of each gene in a specific pathway on the drug sensitivity classification. For Rh41 drug treatment study, expression datasets were first filtered to remove probe sets whose maximal expression level less than 5, which resulted 9269 probe sets. Globaltest was carried out similar as above, with treatment (DMSO control vs. compound 1) as grouping factor. It gives a bar and a reference line for each gene tested. The reference line for each bar gives the expected height under the null hypothesis that the gene is not associated with the sensitivity classification. Marks indicate with how many standard deviations (under the null hypothesis) the bar exceeds the reference line. Bars are colored based on sensitivity classification. The test statistic for a pathway is the average of the bars for all the genes tested.

Ingenuity Pathway Analysis:

497 baseline markers correlated with sensitivity to compound 1 were imported into Ingenuity pathway analysis. Network nodes were colored by the fold change between sensitive and resistant cells. For the drug modulated markers, treatment-induced probe sets in the sensitive cell line Rh41 (FDR adjusted treatment effect less than 0.05, or FDR adjusted treatment-time-interaction less than 0.05) were used for pathway analysis. Genes on canonical pathways were colored based on the fold change between cells with compound 1 treatment and DMSO control.

Results

The Sensitivity Classification of the 29 Pediatric Sarcoma Cell Lines to IGF1R Inhibitors:

The sensitivity to IGF1R inhibitors compound 1 and compound 2 for each of the 29 pediatric sarcoma and neuroblastoma cell lines was determined by cellular proliferation assays and expressed in term of drug concentration required for 50% cell proliferation inhibition ($IC_{50}$). The results are summarized in Table 1, and a wide range of activity in this panel of cancer cell lines was observed for both compound 1 and compound 2 compounds.

TABLE 1

The IC$_{50}$ of each cell line and sensitive/resistant classification to compounds 2 and 1.

| Cell Type | Cell Line | Compound 2 IC$_{50}$ (uM) | Compound 2 Sensitivity Classification | Compound 1 IC$_{50}$ (uM) | Compound 1 Sensitivity Classification |
|---|---|---|---|---|---|
| Ewing | TC32 | 0.0084 | S | 0.055 | S |
| Ewing | RDES | 0.0117 | S | 0.123 | S |
| Ewing | TC71 | 0.0143 | S | 0.119 | S |
| Ewing | VW | 0.019 | S | 0.101 | S |
| Ewing | 5838 | 0.034 | S | 0.172 | S |
| Ewing | LG | 0.0375 | S | 0.063 | S |
| Ewing | JD | 0.391 | R | 0.232 | S |
| Ewing | KAG | 1.665 | R | 2.113 | R |
| Fibrosarcoma | HT1080/S | 0.531 | R | 1.409 | R |
| Fibrosarcoma | SW-684 | 5 | R | 5 | R |
| Leiomyosarcoma | SK-LMS-1 | 0.6866 | R | 0.5 | R |
| Liposarcoma | To184.T | 0.4695 | R | not tested | not tested |
| Liposarcoma | HTB-92 | 1.0199 | R | 0.584 | R |
| Liposarcoma | SA-4 | 1.3007 | R | 0.779 | R |
| Melignant Pleural Mesothelioma | H211 | 0.733 | R | 0.418 | R |
| Melignant Pleural Mesothelioma | H2052 | 1.0502 | R | 0.403 | R |
| Melignant Pleural Mesothelioma | H513 | 4.448 | R | 3.117 | R |
| Melignant Pleural Mesothelioma | H2595 | 4.4752 | R | 5 | R |
| Neuroblastoma | LAN-1 | 0.04 | S | 0.136 | S |
| Neuroblastoma | SHSY5Y | 0.106 | S | 0.149 | S |
| Neuroblastoma | SK-NSH | 0.139 | S | 0.196 | S |
| Neuroblastoma | IMR-32 | 0.261 | S | 0.277 | S |
| Neuroblastoma | SK-NAS | 0.497 | R | 0.192 | S |
| Rhabdomyosarcoma | Rh4 | 0.004 | S | 0.027 | S |
| Rhabdomyosarcoma | Rh41 | 0.0047 | S | 0.069 | S |
| Rhabdomyosarcoma | ME | 0.015 | S | 0.163 | S |
| Rhabdomyosarcoma | Rh1 | 0.0267 | S | 0.135 | S |
| Rhabdomyosarcoma | CTR | 0.2526 | S | 0.37 | R |
| Rhabdomyosarcoma | Rh36 | 1.432 | R | 1.6 | R |

"S" means sensitive and
"R" means resistant to the corresponding compounds.
The cell subtypes are also indicated.

Comparing the IC$_{50}$ data of these two compounds, compound 2 is more potent than compound 1 in most of the cell lines tested. To classify the cell lines as sensitive or resistant to the compounds, the IC$_{50}$ value for each cell line was log-transformed, and the mean of log$_{10}$(IC$_{50}$) across all cell lines was calculated. The sensitivity/resistance phenotype of the cell lines to compound 1 or compound 2 was classified as follows: the cell lines with log$_{10}$(IC$_{50}$) below the mean log$_{10}$(IC$_{50}$) of all cell lines were defined as sensitive to the compound, while those with log$_{10}$(IC$_{50}$) above the mean log$_{10}$(IC$_{50}$) were considered to be resistant to the compound. As shown in Table 1, 16 cell lines were classified as sensitive and 12 cell lines classified as resistant (To184-T was not tested) for compound 1; whereas 15 and 14 cell lines were classified as either sensitive or resistant to compound 2, respectively. Although the sensitivity/resistance demarcation is arbitrary, apparently, the cut off is around 0.35 μM for both compounds. In general, both compounds have a similar sensitivity/resistance profile in this panel of cell lines with the exception of three cell lines that having IC$_{50}$ values around the borderline of the sensitive/resistant demarcation: CTR was defined as sensitive to compound 2 (IC$_{50}$=0.2526 μM) but resistant to compound 1 (IC$_{50}$=0.37 μM), whereas JD and SK-NAS were defined as resistant to compound 2 but resistant to compound 1.

Relation Between the Drug Sensitivity and Cell Subtypes:

The correlation between the sensitive/resistant classification and different subtypes of cell lines was further explored. Interestingly, the sensitivity of these cell lines to IGF1R inhibitor compounds was found to be closely related to specific subtypes. As shown in Table 1, most of Ewing's, RMS and neuroblastoma cells are sensitive to the compounds, whereas all fibrosarcoma, leiomyosarcoma, liposarcoma and malignant pleural mesothelioma cells are resistant. The distribution of cell sub-types is significantly different in sensitive and resistant classes with p-value=0.011 for compound 2 and p-value=0.004 for compound 1, respectively in the chi-square test. Although the sample size for each subtype is not big enough to be conclusive, the results may suggest that certain subtypes of sarcoma are more responsive than others, and these responsive tumor types may represent patient subpopulations to be targeted in clinical studies for IGF1R inhibitors.

Identification of Genes/Proteins with Expression Significantly Correlated with the Sensitivity to IGF1R Inhibitors:

The expression level of the drug target IGF1R was evaluated and apparently did not significantly correlate to the sensitivity of compound 2 and/or compound 1 in the 29 cancer cell lines, so IGF1R level is not useful to predict response to compound 2 and/or compound 1 in cancer cells or in patients. Other predictive biomarkers are needed for selecting the potential targeted patient population.

To identify genes or proteins whose basal expression patterns were strongly correlated with the sensitivity to compounds 1 and 2, gene expression profiling and proteomics were performed in parallel using the 29 pediatric sarcoma and neuroblastoma cancer cell lines (RDES and Rh4 were not included in protein profiling). Two statistical methods were used in analyzing both expression datasets: first, two sample t-test was performed to identify genes differentially expressed between sensitive and resistant cell line groups (p<0.001, 2-fold); second, to avoid the bias of arbitrary cut off for the sensitive/resistant demarcation, the Pearson correlations between the log2(IC$_{50}$) value and the expression level of each gene or protein in all cell lines were calculated to identify genes/proteins significantly correlated with the drug sensitivity (p<0.001). The overlap between these two analyses led to selection of genes/proteins that are significantly correlated with the drug sensitivity/resistance classification for compound 1 or compound 2. For gene expression profiling, there are a total of 497 probe sets with 386 unique genes significantly correlated with the sensitivity to compound 1 (Table 2), and 368 probe sets with 282 unique genes significantly correlated with the sensitivity to compound 2 (Table 3); and. There are 98 or 124 genes highly expressed in the cell lines sensitive to compound 2 or to compound 1, conversely, 184 or 262 genes are highly expressed in the cell lines resistant to compound 2 or compound 1, respectively, with 227 common markers for these two compounds.

TABLE 2

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| \multicolumn{7}{c}{Genes higher expressed in the group of sensitive cell lines} | | | | | | |
| 214451_at | NM_003221 | transcription factor AP-2 beta (activating enhancer binding protein 2 beta) | TFAP2B | 1.3E−05 | 56.6 | 4.3E−04 |
| 212713_at | R72286 | microfibrillar-associated protein 4 | MFAP4 | 1.7E−06 | 14.5 | 9.9E−05 |
| 204915_s_at | AB028641 | SRY (sex determining region Y)-box 11 | SOX11 | 1.7E−07 | 13.4 | 4.3E−05 |
| 216623_x_at | AK025084 | trinucleotide repeat containing 9 | TNRC9 | 3.2E−04 | 13.2 | 5.5E−04 |
| 221011_s_at | NM_030915 | limb bud and heart development homolog (mouse) /// limb bud and heart development homolog (mouse) | LBH | 7.1E−05 | 12.2 | 4.7E−04 |
| 202517_at | NM_001313 | collapsin response mediator protein 1 | CRMP1 | 3.0E−06 | 11.3 | 4.1E−04 |
| 205888_s_at | AI962693 | janus kinase and microtubule interacting protein 2 /// myelin transcription factor 1-like | JAKMIP2 /// MYT1L | 3.1E−08 | 9.3 | 1.1E−05 |
| 207781_s_at | NM_021998 | zinc finger protein 711 | ZNF711 | 9.2E−12 | 8.1 | 3.6E−07 |
| 221748_s_at | AL046979 | tensin 1 /// tensin 1 | TNS1 | 5.4E−05 | 7.8 | 4.3E−04 |
| 213170_at | AA406605 | glutathione peroxidase 7 | GPX7 | 2.0E−05 | 7.4 | 1.6E−04 |
| 205123_s_at | NM_003692 | transmembrane protein with EGF-like and two follistatin-like domains 1 | TMEFF1 | 1.2E−05 | 6.9 | 1.0E−04 |
| 203999_at | AV731490 | — | — | 1.6E−06 | 6.7 | 9.2E−04 |
| 218445_at | NM_018649 | H2A histone family, member Y2 | H2AFY2 | 1.2E−07 | 6.3 | 9.7E−05 |
| 215043_s_at | X83301 | SMA3 /// SMA5 | SMA3 /// SMA5 | 4.0E−07 | 6.2 | 1.5E−05 |
| 209598_at | AB020690 | paraneoplastic antigen MA2 | PNMA2 | 2.5E−05 | 6.1 | 1.4E−04 |
| 212382_at | BF433429 | Transcription factor 4 | TCF4 | 1.3E−06 | 5.8 | 1.0E−04 |
| 212386_at | BF592782 | CDNA FLJ11918 fis, clone HEMBB1000272 | — | 1.6E−06 | 5.7 | 6.0E−06 |
| 205889_s_at | NM_014790 | janus kinase and microtubule interacting protein 2 | JAKMIP2 | 9.6E−08 | 5.5 | 4.5E−06 |
| 205830_at | NM_004362 | calmegin | CLGN | 5.6E−08 | 5.4 | 4.4E−07 |
| 211071_s_at | BC006471 | myeloid/lymphoid or mixed-lineage leukemia (trithorax homolog, *Drosophila*); translocated to, 11 /// myeloid/lymphoid or mixed-lineage leukemia (trithorax homolog, *Drosophila*); translocated to, 11 | MLLT11 | 1.9E−05 | 5.3 | 5.7E−04 |
| 212599_at | AK025298 | autism susceptibility candidate 2 | AUTS2 | 2.1E−05 | 5.3 | 1.8E−05 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 206440_at | NM_004664 | lin-7 homolog A (*C. elegans*) | LIN7A | 9.1E-04 | 4.8 | 3.2E-04 |
| 206565_x_at | NM_006780 | SMA3 | SMA3 | 9.0E-07 | 4.7 | 4.6E-06 |
| 219855_at | NM_018159 | nudix (nucleoside diphosphate linked moiety X)-type motif 11 | NUDT11 | 3.8E-04 | 4.7 | 8.1E-04 |
| 213131_at | R38389 | olfactomedin 1 | OLFM1 | 1.6E-04 | 4.7 | 6.0E-04 |
| 200884_at | NM_001823 | creatine kinase, brain | CKB | 2.8E-07 | 4.6 | 9.8E-07 |
| 206655_s_at | NM_000407 | glycoprotein Ib (platelet), beta polypeptide /// septin 5 | GP1BB /// SEPT5 | 1.2E-05 | 4.5 | 9.1E-04 |
| 214023_x_at | AL533838 | tubulin, beta 2B | TUBB2B | 5.4E-04 | 4.5 | 1.5E-04 |
| 204860_s_at | AI817801 | NLR family, apoptosis inhibitory protein /// similar to Baculoviral IAP repeat-containing protein 1 (Neuronal apoptosis inhibitory protein) | NAIP /// LOC728519 | 3.0E-05 | 4.2 | 1.1E-04 |
| 208998_at | U94592 | uncoupling protein 2 (mitochondrial, proton carrier) | UCP2 | 2.6E-06 | 4.2 | 6.1E-06 |
| 204165_at | NM_003931 | WAS protein family, member 1 | WASF1 | 2.7E-07 | 4.1 | 1.1E-05 |
| 212847_at | AL036840 | Far upstream element (FUSE) binding protein 1 | FUBP1 | 1.0E-07 | 4.1 | 1.2E-04 |
| 213216_at | AL537463 | OTU domain containing 3 | OTUD3 | 9.8E-06 | 3.9 | 1.9E-05 |
| 213547_at | AB014567 | cullin-associated and neddylation-dissociated 2 (putative) | CAND2 | 3.3E-05 | 3.7 | 2.1E-05 |
| 204742_s_at | NM_015032 | androgen-induced proliferation inhibitor | APRIN | 8.9E-06 | 3.5 | 1.5E-05 |
| 213605_s_at | AL049987 | Similar to Beta-glucuronidase precursor | LOC728411 | 1.6E-05 | 3.5 | 3.5E-05 |
| 204457_s_at | NM_002048 | growth arrest-specific 1 | GAS1 | 1.4E-04 | 3.4 | 1.1E-04 |
| 214102_at | AK023737 | centaurin, delta 1 | CENTD1 | 1.9E-06 | 3.4 | 5.6E-06 |
| 201449_at | AL567227 | TIA1 cytotoxic granule-associated RNA binding protein | TIA1 | 1.3E-08 | 3.4 | 2.4E-05 |
| 205347_s_at | NM_021992 | thymosin-like 8 | TMSL8 | 7.6E-05 | 3.3 | 1.2E-04 |
| 212816_s_at | BE613178 | cystathionine-beta-synthase | CBS | 5.8E-05 | 3.2 | 5.6E-04 |
| 214850_at | X75940 | glucuronidase, beta pseudogene 1 | GUSBP1 | 4.9E-06 | 3.2 | 1.4E-04 |
| 212731_at | U79297 | ankyrin repeat domain 46 | ANKRD46 | 1.8E-07 | 3.2 | 2.2E-06 |
| 221965_at | AI990326 | M-phase phosphoprotein 9 | MPHOSPH9 | 1.6E-07 | 3.1 | 8.2E-06 |
| 213283_s_at | BG285616 | sal-like 2 (*Drosophila*) | SALL2 | 2.7E-06 | 3.1 | 2.4E-05 |
| 200644_at | NM_023009 | MARCKS-like 1 | MARCKSL1 | 2.8E-05 | 3.1 | 1.8E-05 |
| 210882_s_at | U04811 | trophinin | TRO | 2.2E-05 | 3.0 | 4.4E-05 |
| 204040_at | NM_014746 | ring finger protein 144 | RNF144 | 1.8E-04 | 3.0 | 1.9E-04 |
| 203069_at | NM_014849 | synaptic vesicle glycoprotein 2A | SV2A | 3.1E-04 | 3.0 | 8.0E-04 |
| 215146_s_at | AB028966 | tetratricopeptide repeat domain 28 | TTC28 | 7.9E-07 | 3.0 | 1.4E-08 |
| 213610_s_at | BE326381 | kelch-like 23 (*Drosophila*) | KLHL23 | 7.0E-06 | 2.9 | 5.1E-05 |
| 202967_at | NM_001512 | glutathione S-transferase A4 | GSTA4 | 1.2E-04 | 2.9 | 3.1E-04 |
| 218223_s_at | NM_016274 | pleckstrin homology domain containing, family O member 1 | PLEKHO1 | 5.9E-07 | 2.9 | 1.2E-07 |
| 221261_x_at | NM_030801 | melanoma antigen family D, 4 /// melanoma antigen family D, 4 | MAGED4 | 1.9E-05 | 2.9 | 9.3E-06 |
| 212624_s_at | BF339445 | chimerin (chimaerin) 1 | CHN1 | 9.7E-05 | 2.9 | 1.5E-04 |
| 215599_at | X83300 | SMA4 /// similar to SMA4 | SMA4 /// LOC730390 | 9.8E-06 | 2.8 | 1.3E-04 |
| 212126_at | BG391282 | CDNA clone IMAGE: 4842353 | — | 1.4E-07 | 2.8 | 7.4E-05 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 209153_s_at | M31523 | transcription factor 3 (E2A immunoglobulin enhancer binding factors E12/E47) | TCF3 | 1.4E−06 | 2.8 | 9.7E−05 |
| 214724_at | AF070621 | DIX domain containing 1 | DIXDC1 | 1.8E−05 | 2.7 | 2.8E−04 |
| 208986_at | AL559478 | transcription factor 12 (HTF4, helix-loop-helix transcription factors 4) | TCF12 | 2.3E−06 | 2.7 | 2.7E−07 |
| 213626_at | AL049442 | carbonyl reductase 4 | CBR4 | 9.6E−06 | 2.7 | 3.3E−04 |
| 218868_at | NM_020445 | ARP3 actin-related protein 3 homolog B (yeast) | ACTR3B | 6.8E−06 | 2.6 | 6.9E−04 |
| 203298_s_at | NM_004973 | jumonji, AT rich interactive domain 2 | JARID2 | 1.3E−07 | 2.6 | 1.6E−04 |
| 37577_at | U79256 | Rho GTPase activating protein 19 | ARHGAP19 | 4.1E−05 | 2.6 | 1.1E−04 |
| 212482_at | BF671894 | required for meiotic nuclear division 5 homolog A (S. cerevisiae) | RMND5A | 1.8E−06 | 2.5 | 1.9E−04 |
| 204173_at | NM_002475 | myosin, light chain 6B, alkali, smooth muscle and non-muscle | MYL6B | 9.9E−04 | 2.5 | 7.4E−04 |
| 203151_at | AW296788 | microtubule-associated protein 1A | MAP1A | 2.3E−04 | 2.5 | 7.7E−04 |
| 212919_at | AV715578 | DCP2 decapping enzyme homolog (S. cerevisiae) | DCP2 | 1.1E−06 | 2.5 | 3.3E−05 |
| 213694_at | AW027347 | round spermatid basic protein 1 | RSBN1 | 9.2E−07 | 2.5 | 2.8E−04 |
| 203625_x_at | BG105365 | melanoma cell adhesion molecule | MCAM | 1.8E−04 | 2.5 | 1.4E−04 |
| 204795_at | NM_025263 | proline rich 3 | PRR3 | 1.0E−05 | 2.5 | 2.0E−04 |
| 212670_at | AA479278 | elastin (supravalvular aortic stenosis, Williams-Beuren syndrome) | ELN | 2.0E−05 | 2.5 | 1.4E−04 |
| 212547_at | N34842 | FLJ35348 | FLJ35348 | 9.4E−07 | 2.5 | 7.2E−05 |
| 210567_s_at | BC001441 | S-phase kinase-associated protein 2 (p45) | SKP2 | 6.7E−04 | 2.4 | 4.1E−04 |
| 209748_at | AB029006 | spastin | SPAST | 4.0E−07 | 2.4 | 3.8E−04 |
| 215128_at | AV704232 | CDNA FLJ11682 fis, clone HEMBA1004880 | — | 4.7E−05 | 2.4 | 4.5E−04 |
| 203825_at | NM_007371 | bromodomain containing 3 | BRD3 | 1.2E−06 | 2.4 | 4.5E−05 |
| 214220_s_at | AW003635 | Alstrom syndrome 1 | ALMS1 | 1.4E−06 | 2.4 | 1.6E−05 |
| 210045_at | AU151428 | isocitrate dehydrogenase 2 (NADP+), mitochondrial | IDH2 | 6.1E−06 | 2.4 | 5.7E−04 |
| 218683_at | NM_021190 | polypyrimidine tract binding protein 2 | PTBP2 | 1.5E−06 | 2.4 | 5.8E−04 |
| 218457_s_at | NM_022552 | DNA (cytosine-5-)-methyltransferase 3 alpha | DNMT3A | 2.2E−06 | 2.4 | 7.2E−05 |
| 204061_at | NM_005044 | protein kinase, X-linked | PRKX | 6.2E−06 | 2.4 | 2.3E−05 |
| 210649_s_at | AF231056 | AT rich interactive domain 1A (SWI-like) | ARID1A | 7.1E−07 | 2.4 | 7.2E−08 |
| 212153_at | AB007930 | pogo transposable element with ZNF domain | POGZ | 8.7E−08 | 2.4 | 6.1E−05 |
| 218265_at | NM_024077 | SECIS binding protein 2 | SECISBP2 | 1.1E−06 | 2.4 | 2.2E−05 |
| 210543_s_at | U34994 | protein kinase, DNA-activated, catalytic polypeptide | PRKDC | 5.0E−04 | 2.3 | 1.3E−04 |
| 220443_s_at | NM_012476 | ventral anterior homeobox 2 | VAX2 | 2.0E−04 | 2.3 | 5.1E−04 |
| 202561_at | AF070613 | tankyrase, TRF1-interacting ankyrin-related ADP-ribose polymerase | TNKS | 1.4E−04 | 2.3 | 4.6E−04 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 203795_s_at | NM_020993 | B-cell CLL/lymphoma 7A | BCL7A | 3.1E−06 | 2.3 | 3.3E−04 |
| 213387_at | AB033066 | ATPase family, AAA domain containing 2B | ATAD2B | 2.5E−06 | 2.3 | 1.0E−04 |
| 203046_s_at | NM_003920 | timeless homolog (*Drosophila*) | TIMELESS | 6.7E−07 | 2.3 | 7.1E−06 |
| 211929_at | AA527502 | heterogeneous nuclear ribonucleoprotein A3 | HNRPA3 | 1.8E−05 | 2.3 | 1.8E−04 |
| 222101_s_at | BF222893 | dachsous 1 (*Drosophila*) | DCHS1 | 5.2E−04 | 2.3 | 2.3E−04 |
| 203940_s_at | NM_014909 | vasohibin 1 | VASH1 | 6.0E−04 | 2.3 | 1.8E−04 |
| 203026_at | NM_014872 | zinc finger and BTB domain containing 5 | ZBTB5 | 3.7E−08 | 2.3 | 5.5E−05 |
| 212164_at | AL522296 | transmembrane protein 183A | TMEM183A | 1.1E−06 | 2.2 | 1.7E−04 |
| 207705_s_at | NM_025176 | KIAA0980 protein | RP4-691N24.1 | 1.4E−04 | 2.2 | 9.6E−05 |
| 210962_s_at | AB019691 | A kinase (PRKA) anchor protein (yotiao) 9 | AKAP9 | 5.2E−08 | 2.2 | 2.0E−05 |
| 210555_s_at | U85430 | nuclear factor of activated T-cells, cytoplasmic, calcineurin-dependent 3 | NFATC3 | 5.4E−07 | 2.2 | 5.1E−05 |
| 220040_x_at | NM_018684 | KIAA1166 | KIAA1166 | 1.8E−05 | 2.2 | 8.6E−04 |
| 220735_s_at | NM_020654 | SUMO1/sentrin specific peptidase 7 | SENP7 | 1.0E−04 | 2.2 | 2.3E−04 |
| 220143_x_at | NM_018032 | LUC7-like (*S. cerevisiae*) | LUC7L | 3.0E−06 | 2.2 | 2.0E−04 |
| 221203_s_at | NM_018023 | YEATS domain containing 2 | YEATS2 | 6.8E−08 | 2.2 | 1.1E−08 |
| 212710_at | AL043774 | calmodulin regulated spectrin-associated protein 1 | CAMSAP1 | 2.0E−05 | 2.2 | 8.7E−04 |
| 208838_at | AB020636 | — | — | 1.4E−04 | 2.2 | 5.7E−06 |
| 218724_s_at | NM_021809 | TGFB-induced factor 2 (TALE family homeobox) | TGIF2 | 3.2E−04 | 2.2 | 7.7E−05 |
| 206554_x_at | NM_006515 | SET domain and mariner transposase fusion gene | SETMAR | 6.6E−04 | 2.2 | 1.7E−04 |
| 202540_s_at | NM_000859 | 3-hydroxy-3-methylglutaryl-Coenzyme A reductase | HMGCR | 4.0E−05 | 2.2 | 4.6E−05 |
| 204060_s_at | NM_005044 | protein kinase, X-linked /// protein kinase, Y-linked | PRKX /// PRKY | 6.8E−05 | 2.2 | 4.9E−05 |
| 203859_s_at | NM_002579 | paralemmin | PALM | 2.4E−05 | 2.1 | 7.1E−04 |
| 209431_s_at | AF254083 | POZ (BTB) and AT hook containing zinc finger 1 | PATZ1 | 5.4E−06 | 2.1 | 4.5E−04 |
| 212704_at | AI049962 | zinc finger, CCHC domain containing 11 | ZCCHC11 | 5.6E−06 | 2.1 | 5.2E−05 |
| 207401_at | NM_002763 | prospero-related homeobox 1 | PROX1 | 3.7E−04 | 2.1 | 5.1E−04 |
| 204557_s_at | NM_014934 | DAZ interacting protein 1 | DZIP1 | 6.7E−04 | 2.1 | 6.8E−06 |
| 212753_at | AI692203 | polycomb group ring finger 3 | PCGF3 | 8.9E−08 | 2.1 | 1.9E−04 |
| 201051_at | BE560202 | acidic (leucine-rich) nuclear phosphoprotein 32 family, member A | ANP32A | 5.9E−05 | 2.1 | 5.0E−04 |
| 212693_at | BE670928 | MDN1, midasin homolog (yeast) | MDN1 | 2.3E−04 | 2.1 | 9.3E−04 |
| 201741_x_at | M69040 | splicing factor, arginine/serine-rich 1 (splicing factor 2, alternate splicing factor) | SFRS1 | 2.4E−07 | 2.1 | 7.8E−05 |
| 208644_at | M32721 | poly (ADP-ribose) polymerase family, member 1 | PARP1 | 2.0E−05 | 2.0 | 1.3E−04 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 218306_s_at | NM_003922 | hect (homologous to the E6-AP (UBE3A) carboxyl terminus) domain and RCC1 (CHC1)-like domain (RLD) 1 | HERC1 | 1.2E−05 | 2.0 | 1.0E−04 |
| 213743_at | BE674119 | cyclin T2 | CCNT2 | 8.7E−07 | 2.0 | 4.2E−04 |
| 208073_x_at | NM_003316 | tetratricopeptide repeat domain 3 | TTC3 | 1.6E−06 | 2.0 | 9.5E−04 |
| 209043_at | AF033026 | 3'-phosphoadenosine 5'-phosphosulfate synthase 1 | PAPSS1 | 6.6E−06 | 2.0 | 3.4E−05 |
| 209715_at | L07515 | chromobox homolog 5 (HP1 alpha homolog, *Drosophila*) | CBX5 | 9.9E−05 | 2.0 | 3.1E−05 |

Genes higher expressed in the group of resistant cell lines

| 209016_s_at | BC002700 | keratin 7 | KRT7 | 8.9E−05 | −81.0 | 3.5E−06 |
|---|---|---|---|---|---|---|
| 222108_at | AC004010 | adhesion molecule with Ig-like domain 2 | AMIGO2 | 1.0E−06 | −46.4 | 1.6E−05 |
| 209008_x_at | U76549 | keratin 8 /// keratin 8 | KRT8 | 1.1E−05 | −45.6 | 2.5E−04 |
| 202858_at | NM_006758 | U2 small nuclear RNA auxiliary factor 1 | U2AF1 | 1.3E−08 | −42.3 | 4.4E−06 |
| 204070_at | NM_004585 | retinoic acid receptor responder (tazarotene induced) 3 | RARRES3 | 4.1E−04 | −40.9 | 3.0E−05 |
| 201324_at | NM_001423 | epithelial membrane protein 1 | EMP1 | 6.9E−12 | −40.0 | 3.4E−06 |
| 211506_s_at | AF043337 | interleukin 8 | IL8 | 1.7E−06 | −39.6 | 3.5E−05 |
| 209835_x_at | BC004372 | CD44 molecule (Indian blood group) | CD44 | 2.5E−11 | −38.7 | 3.3E−06 |
| 201858_s_at | J03223 | proteoglycan 1, secretory granule | PRG1 | 7.6E−07 | −37.9 | 1.5E−04 |
| 202638_s_at | NM_000201 | intercellular adhesion molecule 1 (CD54), human rhinovirus receptor | ICAM1 | 1.8E−04 | −34.2 | 2.6E−04 |
| 201596_x_at | NM_000224 | keratin 18 | KRT18 | 2.3E−07 | −33.3 | 2.0E−05 |
| 204855_at | NM_002639 | serpin peptidase inhibitor, clade B (ovalbumin), member 5 | SERPINB5 | 9.3E−04 | −30.4 | 5.9E−05 |
| 217901_at | BF031829 | Desmoglein 2 | DSG2 | 8.6E−05 | −30.2 | 7.5E−04 |
| 205083_at | NM_001159 | aldehyde oxidase 1 | AOX1 | 7.5E−07 | −28.3 | 3.1E−05 |
| 202855_s_at | AL513917 | solute carrier family 16, member 3 (monocarboxylic acid transporter 4) | SLC16A3 | 6.4E−08 | −25.5 | 3.1E−06 |
| 215034_s_at | AI189753 | transmembrane 4 L six family member 1 | TM4SF1 | 2.5E−06 | −25.1 | 1.1E−04 |
| 221530_s_at | BE857425 | basic helix-loop-helix domain containing, class B, 3 | BHLHB3 | 1.1E−06 | −24.5 | 3.6E−07 |
| 202854_at | NM_000194 | hypoxanthine phosphoribosyltransferase 1 (Lesch-Nyhan syndrome) | HPRT1 | 2.6E−08 | −24.1 | 3.5E−06 |
| 201798_s_at | NM_013451 | fer-1-like 3, myoferlin (*C. elegans*) | FER1L3 | 2.4E−10 | −23.5 | 2.5E−06 |
| 209803_s_at | AF001294 | pleckstrin homology-like domain, family A, member 2 | PHLDA2 | 2.2E−11 | −23.2 | 3.3E−06 |
| 210916_s_at | AF098641 | CD44 molecule (Indian blood group) /// mitogen-activated protein kinase 10 | CD44 /// MAPK10 | 5.1E−11 | −21.7 | 1.1E−05 |
| 203108_at | NM_003979 | G protein-coupled receptor, family C, group 5, member A | GPRC5A | 5.8E−09 | −20.7 | 1.3E−05 |
| 204420_at | BG251266 | FOS-like antigen 1 | FOSL1 | 6.7E−09 | −20.5 | 4.7E−05 |
| 206632_s_at | NM_004900 | apolipoprotein B mRNA editing enzyme, catalytic polypeptide-like 3B | APOBEC3B | 3.2E−09 | −20.3 | 1.5E−05 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 212444_at | AA156240 | cDNA clone IMAGE: 6025865 | — | 1.2E−07 | −18.4 | 1.0E−04 |
| 204470_s_at | NM_001511 | chemokine (C—X—C motif) ligand 1 (melanoma growth stimulating activity, alpha) | CXCL1 | 1.1E−04 | −17.7 | 2.8E−05 |
| 201109_s_at | AV726673 | thrombospondin 1 | THBS1 | 4.0E−04 | −17.5 | 9.9E−04 |
| 205627_at | NM_001785 | cytidine deaminase | CDA | 5.9E−05 | −17.5 | 5.4E−05 |
| 209278_s_at | L27624 | tissue factor pathway inhibitor 2 | TFPI2 | 3.3E−04 | −15.7 | 4.7E−04 |
| 208747_s_at | M18767 | complement component 1, s subcomponent | C1S | 1.5E−04 | −15.3 | 8.1E−04 |
| 201842_s_at | AI826799 | EGF-containing fibulin-like extracellular matrix protein 1 | EFEMP1 | 8.3E−04 | −14.0 | 8.7E−04 |
| 210592_s_at | M55580 | spermidine/spermine N1-acetyltransferase 1 | SAT1 | 1.2E−08 | −13.9 | 6.3E−06 |
| 204222_s_at | NM_006851 | GLI pathogenesis-related 1 (glioma) | GLIPR1 | 2.6E−05 | −13.8 | 5.6E−04 |
| 202627_s_at | AL574210 | serpin peptidase inhibitor, clade E (nexin, plasminogen activator inhibitor type 1), member 1 | SERPINE1 | 1.6E−04 | −13.2 | 6.7E−04 |
| 203851_at | NM_002178 | insulin-like growth factor binding protein 6 | IGFBP6 | 1.8E−06 | −13.2 | 3.0E−04 |
| 208949_s_at | BC001120 | lectin, galactoside-binding, soluble, 3 (galectin 3) | LGALS3 | 2.3E−04 | −13.1 | 6.4E−04 |
| 210042_s_at | AF073890 | cathepsin Z | CTSZ | 3.0E−07 | −12.9 | 2.1E−05 |
| 206513_at | NM_004833 | absent in melanoma 2 | AIM2 | 1.1E−04 | −12.6 | 1.9E−04 |
| 202202_s_at | NM_002290 | laminin, alpha 4 | LAMA4 | 2.5E−05 | −12.2 | 8.0E−04 |
| 204363_at | NM_001993 | coagulation factor III (thromboplastin, tissue factor) | F3 | 3.0E−04 | −11.9 | 5.4E−04 |
| 202832_at | NM_014635 | GRIP and coiled-coil domain containing 2 | GCC2 | 6.1E−04 | −11.9 | 5.5E−05 |
| 202267_at | NM_005562 | laminin, gamma 2 | LAMC2 | 3.7E−04 | −11.7 | 1.6E−04 |
| 219759_at | NM_022350 | leukocyte-derived arginine aminopeptidase | LRAP | 1.2E−06 | −11.6 | 1.5E−05 |
| 217744_s_at | NM_022121 | PERP, TP53 apoptosis effector | PERP | 1.0E−06 | −11.4 | 4.0E−05 |
| 204279_at | NM_002800 | proteasome (prosome, macropain) subunit, beta type, 9 (large multifunctional peptidase 2) | PSMB9 | 1.3E−05 | −11.2 | 8.0E−06 |
| 201474_s_at | NM_002204 | integrin, alpha 3 (antigen CD49C, alpha 3 subunit of VLA-3 receptor) | ITGA3 | 2.2E−08 | −11.1 | 3.3E−07 |
| 201468_s_at | NM_000903 | NAD(P)H dehydrogenase, quinone 1 | NQO1 | 3.8E−05 | −10.8 | 2.4E−05 |
| 205798_at | NM_002185 | interleukin 7 receptor /// interleukin 7 receptor | IL7R | 3.2E−07 | −10.7 | 7.5E−04 |
| 221059_s_at | NM_021615 | coactosin-like 1 (Dictyostelium) | COTL1 | 3.8E−09 | −10.5 | 2.5E−06 |
| 218211_s_at | NM_024101 | melanophilin | MLPH | 6.2E−06 | −10.4 | 6.7E−05 |
| 201042_at | AL031651 | transglutaminase 2 (C polypeptide, protein-glutamine-gamma-glutamyltransferase) | TGM2 | 1.4E−04 | −10.1 | 6.7E−04 |
| 212473_s_at | BE965029 | microtubule associated monoxygenase, calponin and LIM domain containing 2 | MICAL2 | 1.8E−05 | −10.1 | 9.7E−04 |
| 201631_s_at | NM_003897 | immediate early response 3 | IER3 | 1.9E−06 | −9.3 | 4.3E−05 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 210896_s_at | AF306765 | aspartate beta-hydroxylase | ASPH | 9.8E−08 | −9.2 | 1.4E−04 |
| 208581_x_at | NM_005952 | metallothionein 1X | MT1X | 3.8E−06 | −8.9 | 1.9E−04 |
| 214446_at | NM_012081 | elongation factor, RNA polymerase II, 2 | ELL2 | 4.9E−10 | −8.7 | 3.2E−05 |
| 201170_s_at | NM_003670 | basic helix-loop-helix domain containing, class B, 2 | BHLHB2 | 2.5E−07 | −8.5 | 3.5E−06 |
| 202862_at | NM_000137 | fumarylacetoacetate hydrolase (fumarylacetoacetase) | FAH | 4.0E−07 | −8.5 | 1.6E−05 |
| 203234_at | NM_003364 | uridine phosphorylase 1 | UPP1 | 1.7E−06 | −8.5 | 2.2E−05 |
| 218322_s_at | NM_016234 | acyl-CoA synthetase long-chain family member 5 | ACSL5 | 9.4E−05 | −8.3 | 1.9E−06 |
| 206461_x_at | NM_005951 | metallothionein 1H | MT1H | 1.1E−06 | −8.2 | 8.6E−05 |
| 212185_x_at | NM_005953 | metallothionein 2A | MT2A | 1.4E−06 | −8.1 | 1.9E−04 |
| 208790_s_at | AF312393 | polymerase I and transcript release factor | PTRF | 3.4E−05 | −7.8 | 8.7E−04 |
| 36711_at | AL021977 | v-maf musculoaponeurotic fibrosarcoma oncogene homolog F (avian) | MAFF | 7.4E−09 | −7.7 | 9.7E−07 |
| 218084_x_at | NM_014164 | FXYD domain containing ion transport regulator 5 | FXYD5 | 5.2E−06 | −7.6 | 5.1E−06 |
| 217996_at | AA576961 | pleckstrin homology-like domain, family A, member 1 | PHLDA1 | 3.8E−07 | −7.5 | 2.5E−04 |
| 211456_x_at | AF333388 | metallothionein 1H-like protein | LOC645745 | 1.3E−06 | −7.4 | 1.1E−04 |
| 213865_at | AI378788 | discoidin, CUB and LCCL domain containing 2 | DCBLD2 | 2.3E−07 | −7.4 | 5.7E−04 |
| 209514_s_at | BE502030 | RAB27A, member RAS oncogene family | RAB27A | 2.3E−05 | −7.3 | 3.2E−04 |
| 209310_s_at | U25804 | caspase 4, apoptosis-related cysteine peptidase | CASP4 | 1.4E−05 | −7.1 | 1.3E−04 |
| 209040_s_at | U17496 | proteasome (prosome, macropain) subunit, beta type, 8 (large multifunctional peptidase 7) | PSMB8 | 1.8E−05 | −7.1 | 6.9E−06 |
| 205100_at | NM_005110 | glutamine-fructose-6-phosphate transaminase 2 | GFPT2 | 3.3E−06 | −7.1 | 2.1E−04 |
| 213572_s_at | AI554300 | serpin peptidase inhibitor, clade B (ovalbumin), member 1 | SERPINB1 | 1.4E−07 | −7.0 | 1.4E−07 |
| 209679_s_at | BC003379 | small trans-membrane and glycosylated protein | LOC57228 | 2.4E−06 | −7.0 | 1.1E−04 |
| 203821_at | NM_001945 | heparin-binding EGF-like growth factor | HBEGF | 3.8E−05 | −6.9 | 9.8E−05 |
| 220016_at | NM_024060 | AHNAK nucleoprotein (desmoyokin) | AHNAK | 5.1E−05 | −6.9 | 2.4E−05 |
| 212070_at | AL554008 | G protein-coupled receptor 56 | GPR56 | 6.1E−05 | −6.8 | 1.6E−07 |
| 211429_s_at | AF119873 | serpin peptidase inhibitor, clade A (alpha-1 antiproteinase, antitrypsin), member 1 | SERPINA1 | 5.0E−04 | −6.8 | 5.1E−05 |
| 202863_at | NM_003113 | SP100 nuclear antigen | SP100 | 1.7E−07 | −6.7 | 1.4E−05 |
| 216336_x_at | AL031602 | metallothionein 1M | MT1M | 5.3E−06 | −6.6 | 1.3E−05 |
| 217165_x_at | M10943 | metallothionein 1F (functional) | MT1F | 5.6E−06 | −6.6 | 1.9E−04 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 201983_s_at | AW157070 | epidermal growth factor receptor (erythroblastic leukemia viral (v-erb-b) oncogene homolog, avian) | EGFR | 1.6E−06 | −6.5 | 2.8E−04 |
| 210538_s_at | U37546 | baculoviral IAP repeat-containing 3 | BIRC3 | 1.6E−04 | −6.5 | 5.4E−05 |
| 201926_s_at | BC001288 | CD55 molecule, decay accelerating factor for complement (Cromer blood group) | CD55 | 3.6E−06 | −6.5 | 3.4E−04 |
| 208944_at | D50683 | transforming growth factor, beta receptor II (70/80 kDa) | TGFBR2 | 1.2E−06 | −6.5 | 9.7E−04 |
| 208690_s_at | BC000915 | PDZ and LIM domain 1 (elfin) | PDLIM1 | 1.6E−04 | −6.4 | 5.6E−05 |
| 210117_at | AF311312 | sperm associated antigen 1 | SPAG1 | 3.6E−05 | −6.4 | 4.2E−04 |
| 210138_at | AF074979 | regulator of G-protein signalling 20 | RGS20 | 5.9E−06 | −6.3 | 1.4E−05 |
| 217478_s_at | X76775 | major histocompatibility complex, class II, DM alpha | HLA-DMA | 2.9E−04 | −6.2 | 1.3E−04 |
| 202499_s_at | NM_006931 | solute carrier family 2 (facilitated glucose transporter), member 3 | SLC2A3 | 1.1E−06 | −6.2 | 2.0E−04 |
| 214791_at | AK023116 | hypothetical protein BC004921 | LOC93349 | 1.1E−06 | −6.1 | 2.6E−06 |
| 209457_at | U16996 | dual specificity phosphatase 5 | DUSP5 | 1.5E−05 | −6.1 | 1.7E−04 |
| 207574_s_at | NM_015675 | growth arrest and DNA-damage-inducible, beta | GADD45B | 1.2E−06 | −6.0 | 1.6E−04 |
| 214866_at | X74039 | plasminogen activator, urokinase receptor | PLAUR | 8.1E−07 | −5.8 | 3.8E−04 |
| 211612_s_at | U62858 | interleukin 13 receptor, alpha 1 /// interleukin 13 receptor, alpha 1 | IL13RA1 | 1.5E−07 | −5.7 | 1.1E−05 |
| 207265_s_at | NM_016657 | KDEL (Lys-Asp-Glu-Leu) endoplasmic reticulum protein retention receptor 3 | KDELR3 | 1.4E−07 | −5.6 | 5.0E−04 |
| 213274_s_at | AA020826 | cathepsin B | CTSB | 6.6E−05 | −5.6 | 2.2E−04 |
| 200632_s_at | NM_006096 | N-myc downstream regulated gene 1 | NDRG1 | 5.2E−05 | −5.5 | 2.1E−04 |
| 222150_s_at | AK026747 | hypothetical protein LOC54103 | LOC54103 | 8.8E−07 | −5.5 | 1.1E−06 |
| 210136_at | AW070431 | myelin basic protein | MBP | 1.8E−06 | −5.4 | 5.9E−04 |
| 216985_s_at | AJ002077 | syntaxin 3 | STX3 | 1.7E−06 | −5.4 | 3.5E−06 |
| 201412_at | NM_014045 | low density lipoprotein receptor-related protein 10 | LRP10 | 3.9E−06 | −5.3 | 1.2E−04 |
| 205579_at | NM_000861 | histamine receptor H1 | HRH1 | 1.0E−06 | −5.3 | 9.3E−06 |
| 202733_at | NM_004199 | procollagen-proline, 2-oxoglutarate 4-dioxygenase (proline 4-hydroxylase), alpha polypeptide II | P4HA2 | 5.2E−04 | −5.3 | 3.8E−04 |
| 210987_x_at | M19267 | tropomyosin 1 (alpha) | TPM1 | 1.7E−04 | −5.2 | 3.2E−04 |
| 204032_at | NM_003567 | breast cancer anti-estrogen resistance 3 | BCAR3 | 2.8E−06 | −5.1 | 7.4E−04 |
| 209706_at | AF247704 | NK3 transcription factor related, locus 1 (Drosophila) | NKX3-1 | 2.0E−05 | −5.1 | 2.3E−05 |
| 205499_at | NM_014467 | sushi-repeat-containing protein, X-linked 2 | SRPX2 | 6.7E−06 | −5.0 | 1.2E−05 |
| 202085_at | NM_004817 | tight junction protein 2 (zona occludens 2) | TJP2 | 9.4E−04 | −4.9 | 5.0E−04 |
| 219620_x_at | NM_017723 | hypothetical protein FLJ20245 | FLJ20245 | 7.0E−07 | −4.9 | 2.3E−04 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 212923_s_at | AK024828 | chromosome 6 open reading frame 145 | C6orf145 | 2.4E−08 | −4.9 | 6.1E−05 |
| 212463_at | BE379006 | CD59 molecule, complement regulatory protein | CD59 | 1.8E−07 | −4.8 | 2.4E−04 |
| 201506_at | NM_000358 | transforming growth factor, beta-induced, 68 kDa | TGFBI | 1.9E−04 | −4.8 | 6.6E−04 |
| 202180_s_at | NM_017458 | major vault protein | MVP | 6.1E−05 | −4.7 | 9.6E−05 |
| 203726_s_at | NM_000227 | laminin, alpha 3 | LAMA3 | 9.8E−04 | −4.6 | 6.6E−04 |
| 212543_at | U83115 | absent in melanoma 1 | AIM1 | 4.0E−04 | −4.6 | 1.4E−04 |
| 205266_at | NM_002309 | leukemia inhibitory factor (cholinergic differentiation factor) | LIF | 2.5E−07 | −4.6 | 3.7E−06 |
| 203939_at | NM_002526 | 5'-nucleotidase, ecto (CD73) | NT5E | 8.0E−04 | −4.6 | 6.7E−04 |
| 222294_s_at | AW971415 | CDNA clone IMAGE: 5745639 | — | 4.1E−05 | −4.6 | 1.2E−04 |
| 206034_at | NM_002640 | serpin peptidase inhibitor, clade B (ovalbumin), member 8 | SERPINB8 | 5.9E−06 | −4.6 | 5.9E−04 |
| 214459_x_at | M12679 | major histocompatibility complex, class I, C | HLA-C | 9.7E−04 | −4.6 | 1.3E−04 |
| 202990_at | NM_002863 | phosphorylase, glycogen; liver (Hers disease, glycogen storage disease type VI) | PYGL | 1.5E−05 | −4.6 | 8.0E−04 |
| 205896_at | NM_003059 | solute carrier family 22 (organic cation transporter), member 4 | SLC22A4 | 2.3E−05 | −4.5 | 1.8E−04 |
| 203041_s_at | J04183 | lysosomal-associated membrane protein 2 | LAMP2 | 1.2E−04 | −4.5 | 2.7E−05 |
| 201471_s_at | NM_003900 | sequestosome 1 | SQSTM1 | 3.9E−06 | −4.5 | 2.0E−04 |
| 218631_at | NM_021732 | arginine vasopressin-induced 1 | AVPI1 | 2.9E−05 | −4.5 | 3.1E−05 |
| 204981_at | NM_002555 | solute carrier family 22 (organic cation transporter), member 18 | SLC22A18 | 6.9E−06 | −4.5 | 1.1E−04 |
| 203005_at | NM_002342 | lymphotoxin beta receptor (TNFR superfamily, member 3) | LTBR | 2.5E−07 | −4.5 | 2.8E−07 |
| 200766_at | NM_001909 | cathepsin D | CTSD | 3.4E−05 | −4.4 | 9.5E−06 |
| 204745_x_at | NM_005950 | metallothionein 1G | MT1G | 4.0E−06 | −4.4 | 2.8E−04 |
| 219165_at | NM_021630 | PDZ and LIM domain 2 (mystique) | PDLIM2 | 9.2E−06 | −4.3 | 9.7E−04 |
| 201482_at | NM_002826 | quiescin Q6 | QSCN6 | 1.7E−05 | −4.3 | 6.1E−05 |
| 218368_s_at | NM_016639 | tumor necrosis factor receptor superfamily, member 12A | TNFRSF12A | 7.6E−07 | −4.2 | 6.7E−05 |
| 209873_s_at | AF053719 | plakophilin 3 | PKP3 | 3.2E−04 | −4.2 | 7.3E−05 |
| 204254_s_at | NM_000376 | vitamin D (1,25-dihydroxyvitamin D3) receptor | VDR | 3.1E−05 | −4.2 | 5.6E−06 |
| 203430_at | NM_014320 | heme binding protein 2 | HEBP2 | 4.5E−05 | −4.2 | 9.1E−05 |
| 202531_at | NM_002198 | interferon regulatory factor 1 | IRF1 | 4.4E−05 | −4.1 | 3.0E−05 |
| 205398_s_at | NM_005902 | SMAD family member 3 | SMAD3 | 4.4E−06 | −4.1 | 7.5E−04 |
| 203518_at | NM_000081 | lysosomal trafficking regulator | LYST | 5.2E−04 | −4.1 | 2.4E−04 |
| 218273_s_at | NM_018444 | protein phosphatase 2C, magnesium-dependent, catalytic subunit | PPM2C | 8.3E−08 | −4.0 | 2.1E−04 |
| 202087_s_at | NM_001912 | cathepsin L | CTSL | 9.0E−05 | −4.0 | 1.6E−04 |
| 218764_at | NM_024064 | protein kinase C, eta | PRKCH | 7.8E−05 | −3.9 | 1.2E−05 |
| 201422_at | NM_006332 | interferon, gamma-inducible protein 30 | IFI30 | 7.7E−04 | −3.9 | 2.7E−04 |
| 212196_at | AW242916 | Interleukin 6 signal transducer (gp130, oncostatin M receptor) | IL6ST | 4.5E−05 | −3.9 | 8.0E−04 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 202201_at | NM_000713 | biliverdin reductase B (flavin reductase (NADPH)) | BLVRB | 3.3E−05 | −3.8 | 4.3E−06 |
| 209417_s_at | BC001356 | interferon-induced protein 35 | IFI35 | 6.6E−05 | −3.8 | 2.9E−04 |
| 203329_at | NM_002845 | protein tyrosine phosphatase, receptor type, M | PTPRM | 3.9E−06 | −3.8 | 5.8E−05 |
| 200701_at | NM_006432 | Niemann-Pick disease, type C2 | NPC2 | 1.2E−04 | −3.7 | 8.2E−04 |
| 219622_at | NM_017817 | RAB20, member RAS oncogene family | RAB20 | 8.5E−04 | −3.7 | 8.7E−04 |
| 207467_x_at | NM_001750 | calpastatin | CAST | 6.6E−06 | −3.6 | 4.1E−04 |
| 205640_at | NM_000694 | aldehyde dehydrogenase 3 family, member B1 | ALDH3B1 | 7.4E−07 | −3.6 | 1.5E−07 |
| 203215_s_at | AA877789 | myosin VI | MYO6 | 9.1E−04 | −3.5 | 4.0E−05 |
| 217998_at | NM_007350 | pleckstrin homology-like domain, family A, member 1 /// hypothetical LOC652993 | PHLDA1 /// LOC652993 | 4.5E−07 | −3.4 | 2.1E−04 |
| 204158_s_at | NM_006019 | T-cell, immune regulator 1, ATPase, H+ transporting, lysosomal V0 subunit A3 | TCIRG1 | 5.4E−05 | −3.4 | 7.5E−04 |
| 208637_x_at | BC003576 | actinin, alpha 1 | ACTN1 | 1.2E−07 | −3.4 | 4.4E−05 |
| 218844_at | NM_025149 | hypothetical protein FLJ20920 | FLJ20920 | 1.5E−04 | −3.4 | 8.3E−05 |
| 219716_at | NM_030641 | apolipoprotein L, 6 | APOL6 | 1.4E−05 | −3.4 | 2.2E−08 |
| 204747_at | NM_001549 | interferon-induced protein with tetratricopeptide repeats 3 | IFIT3 | 1.7E−06 | −3.4 | 4.2E−04 |
| 202693_s_at | AW194730 | serine/threonine kinase 17a (apoptosis-inducing) | STK17A | 1.6E−04 | −3.3 | 6.4E−04 |
| 210276_s_at | AF281030 | TRIO and F-actin binding protein | TRIOBP | 2.5E−04 | −3.3 | 3.4E−04 |
| 205730_s_at | NM_014945 | actin binding LIM protein family, member 3 | ABLIM3 | 3.2E−05 | −3.3 | 1.2E−04 |
| 202861_at | NM_002616 | period homolog 1 (Drosophila) | PER1 | 4.8E−05 | −3.3 | 5.6E−05 |
| 217739_s_at | NM_005746 | pre-B-cell colony enhancing factor 1 | PBEF1 | 7.8E−06 | −3.3 | 1.4E−04 |
| 221044_s_at | NM_021616 | tripartite motif-containing 34 /// tripartite motif-containing 6 and tripartite motif-containing 34 | TRIM34 /// TRIM6-TRIM34 | 4.7E−06 | −3.3 | 3.1E−04 |
| 207375_s_at | NM_002189 | interleukin 15 receptor, alpha | IL15RA | 1.1E−05 | −3.3 | 1.3E−04 |
| 213816_s_at | AA005141 | met proto-oncogene (hepatocyte growth factor receptor) | MET | 1.8E−06 | −3.2 | 9.9E−04 |
| 221843_s_at | AA195017 | KIAA1609 | KIAA1609 | 4.6E−05 | −3.2 | 3.4E−05 |
| 218983_at | NM_016546 | complement component 1, r subcomponent-like | C1RL | 3.6E−04 | −3.2 | 3.1E−04 |
| 207357_s_at | NM_017540 | UDP-N-acetyl-alpha-D-galactosamine:polypeptide N-acetylgalactosaminyltransferase 10 (GalNAc-T10) | GALNT10 | 3.9E−06 | −3.2 | 7.3E−05 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 218292_s_at | NM_016203 | protein kinase, AMP-activated, gamma 2 non-catalytic subunit | PRKAG2 | 1.2E−06 | −3.2 | 1.4E−04 |
| 207643_s_at | NM_001065 | tumor necrosis factor receptor superfamily, member 1A | TNFRSF1A | 1.5E−05 | −3.2 | 2.6E−04 |
| 204629_at | NM_013327 | parvin, beta | PARVB | 1.1E−04 | −3.1 | 7.5E−04 |
| 212552_at | BE617588 | hippocalcin-like 1 | HPCAL1 | 1.5E−04 | −3.1 | 3.1E−04 |
| 204682_at | NM_000428 | latent transforming growth factor beta binding protein 2 | LTBP2 | 1.1E−05 | −3.1 | 4.0E−06 |
| 219691_at | NM_017654 | sterile alpha motif domain containing 9 | SAMD9 | 6.1E−05 | −3.1 | 3.5E−05 |
| 200885_at | NM_005167 | ras homolog gene family, member C | RHOC | 1.6E−06 | −3.1 | 2.0E−04 |
| 212737_at | AL513583 | GM2 ganglioside activator | GM2A | 1.7E−05 | −3.0 | 7.2E−06 |
| 210514_x_at | AF226990 | HLA-G histocompatibility antigen, class I, G | HLA-G | 7.8E−04 | −3.0 | 7.4E−04 |
| 201944_at | NM_000521 | hexosaminidase B (beta polypeptide) | HEXB | 9.4E−07 | −2.9 | 4.2E−04 |
| 218849_s_at | NM_006663 | protein phosphatase 1, regulatory (inhibitor) subunit 13 like | PPP1R13L | 4.5E−05 | −2.9 | 2.4E−04 |
| 204693_at | NM_007061 | CDC42 effector protein (Rho GTPase binding) 1 | CDC42EP1 | 5.0E−05 | −2.9 | 2.8E−04 |
| 209546_s_at | AF323540 | apolipoprotein L, 1 | APOL1 | 3.7E−06 | −2.9 | 1.2E−05 |
| 204034_at | NM_014297 | ethylmalonic encephalopathy 1 | ETHE1 | 3.8E−06 | −2.9 | 4.2E−05 |
| 202307_s_at | NM_000593 | transporter 1, ATP-binding cassette, sub-family B (MDR/TAP) | TAP1 | 3.3E−04 | −2.9 | 2.4E−04 |
| 210978_s_at | BC002616 | transgelin 2 | TAGLN2 | 2.5E−04 | −2.9 | 8.6E−05 |
| 202275_at | NM_000402 | glucose-6-phosphate dehydrogenase | G6PD | 3.7E−04 | −2.9 | 3.0E−04 |
| 217150_s_at | S73854 | neurofibromin 2 (bilateral acoustic neuroma) | NF2 | 3.3E−05 | −2.9 | 1.2E−04 |
| 202545_at | NM_006254 | protein kinase C, delta | PRKCD | 1.5E−05 | −2.9 | 7.9E−04 |
| 214783_s_at | BG177920 | annexin A11 | ANXA11 | 7.0E−07 | −2.8 | 6.2E−05 |
| 214077_x_at | H15129 | Meis1 homolog 3 (mouse) pseudogene 1 | MEIS3P1 | 7.1E−04 | −2.8 | 9.5E−04 |
| 213083_at | AJ005866 | solute carrier family 35, member D2 | SLC35D2 | 4.3E−04 | −2.8 | 4.9E−04 |
| 220049_s_at | NM_025239 | programmed cell death 1 ligand 2 | PDCD1LG2 | 2.7E−04 | −2.8 | 3.1E−05 |
| 211926_s_at | AI827941 | myosin, heavy chain 9, non-muscle | MYH9 | 1.6E−05 | −2.8 | 6.2E−04 |
| 221291_at | NM_025217 | UL16 binding protein 2 | ULBP2 | 1.6E−04 | −2.8 | 2.4E−04 |
| 208613_s_at | AV712733 | filamin B, beta (actin binding protein 278) | FLNB | 5.2E−04 | −2.7 | 6.0E−04 |
| 218747_s_at | NM_018009 | TAP binding protein-like | TAPBPL | 3.6E−04 | −2.7 | 7.4E−05 |
| 219684_at | NM_022147 | receptor (chemosensory) transporter protein 4 | RTP4 | 1.4E−04 | −2.7 | 8.0E−04 |
| 206284_x_at | NM_001834 | clathrin, light chain (Lcb) | CLTB | 2.0E−04 | −2.6 | 1.5E−06 |
| 201847_at | NM_000235 | lipase A, lysosomal acid, cholesterol esterase (Wolman disease) | LIPA | 3.7E−05 | −2.6 | 9.1E−04 |
| 205192_at | NM_003954 | mitogen-activated protein kinase kinase kinase 14 | MAP3K14 | 3.4E−05 | −2.6 | 2.4E−04 |
| 221473_x_at | U49188 | serine incorporator 3 | SERINC3 | 1.5E−07 | −2.6 | 6.7E−05 |
| 218194_at | NM_015523 | REX2, RNA exonuclease 2 homolog (S. cerevisiae) | REXO2 | 8.9E−06 | −2.6 | 6.6E−04 |
| 205084_at | NM_018844 | B-cell receptor-associated protein 29 | BCAP29 | 2.8E−06 | −2.6 | 4.9E−04 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 202996_at | NM_021173 | polymerase (DNA-directed), delta 4 | POLD4 | 6.3E−05 | −2.6 | 5.3E−04 |
| 208872_s_at | AA814140 | receptor accessory protein 5 | REEP5 | 4.6E−05 | −2.6 | 2.8E−04 |
| 60471_at | AA625133 | Ras and Rab interactor 3 | RIN3 | 1.5E−05 | −2.6 | 6.8E−05 |
| 203925_at | NM_002061 | glutamate-cysteine ligase, modifier subunit | GCLM | 6.8E−05 | −2.5 | 5.9E−06 |
| 201587_s_at | NM_001569 | interleukin-1 receptor-associated kinase 1 | IRAK1 | 1.1E−05 | −2.5 | 8.4E−05 |
| 204769_s_at | M74447 | transporter 2, ATP-binding cassette, sub-family B (MDR/TAP) | TAP2 | 9.5E−06 | −2.5 | 9.6E−06 |
| 201953_at | NM_006384 | calcium and integrin binding 1 (calmyrin) | CIB1 | 2.1E−06 | −2.5 | 5.0E−04 |
| 215723_s_at | AJ276230 | phospholipase D1, phosphatidylcholine-specific | PLD1 | 8.6E−06 | −2.5 | 4.7E−05 |
| 205032_at | NM_002203 | integrin, alpha 2 (CD49B, alpha 2 subunit of VLA-2 receptor) | ITGA2 | 6.5E−04 | −2.5 | 7.1E−04 |
| 203045_at | NM_004148 | ninjurin 1 | NINJ1 | 2.9E−05 | −2.5 | 4.0E−04 |
| 221641_s_at | AF241787 | acyl-CoA thioesterase 9 | ACOT9 | 8.9E−05 | −2.5 | 5.5E−04 |
| 209039_x_at | AF001434 | EH-domain containing 1 | EHD1 | 5.2E−05 | −2.5 | 8.8E−04 |
| 209179_s_at | BC003164 | leukocyte receptor cluster (LRC) member 4 | LENG4 | 3.1E−06 | −2.4 | 1.5E−04 |
| 206670_s_at | NM_013445 | glutamate decarboxylase 1 (brain, 67 kDa) /// LAG1 homolog, ceramide synthase 6 (S. cerevisiae) | GAD1 /// LASS6 | 2.9E−04 | −2.4 | 8.0E−04 |
| 201360_at | NM_000099 | cystatin C (amyloid angiopathy and cerebral hemorrhage) | CST3 | 5.6E−05 | −2.4 | 7.7E−04 |
| 53720_at | AI862559 | hypothetical protein FLJ11286 | FLJ11286 | 3.2E−04 | −2.4 | 4.4E−04 |
| 201975_at | NM_002956 | restin (Reed-Steinberg cell-expressed intermediate filament-associated protein) | RSN | 1.4E−04 | −2.4 | 3.7E−04 |
| 200618_at | NM_006148 | LIM and SH3 protein 1 | LASP1 | 3.8E−05 | −2.4 | 8.0E−04 |
| 209575_at | BC001903 | interleukin 10 receptor, beta | IL10RB | 4.2E−04 | −2.3 | 9.6E−06 |
| 220761_s_at | NM_016281 | TAO kinase 3 | TAOK3 | 3.7E−04 | −2.3 | 5.2E−06 |
| 208659_at | AF034607 | chloride intracellular channel 1 | CLIC1 | 1.9E−08 | −2.3 | 4.1E−05 |
| 213272_s_at | AF070596 | transmembrane protein 159 | TMEM159 | 2.0E−05 | −2.3 | 1.1E−04 |
| 219710_at | NM_024577 | SH3 domain and tetratricopeptide repeats 2 | SH3TC2 | 3.3E−04 | −2.3 | 5.1E−05 |
| 203258_at | NM_006442 | DR1-associated protein 1 (negative cofactor 2 alpha) | DRAP1 | 1.9E−05 | −2.3 | 5.7E−04 |
| 221534_at | AF073483 | chromosome 11 open reading frame 68 | C11orf68 | 2.1E−04 | −2.3 | 1.5E−04 |
| 202122_s_at | NM_005817 | mannose-6-phosphate receptor binding protein 1 | M6PRBP1 | 6.5E−07 | −2.3 | 4.4E−04 |
| 202205_at | NM_003370 | vasodilator-stimulated phosphoprotein | VASP | 7.5E−06 | −2.2 | 1.6E−05 |
| 203920_at | NM_005693 | nuclear receptor subfamily 1, group H, member 3 | NR1H3 | 3.6E−04 | −2.2 | 5.5E−04 |
| 207196_s_at | NM_006058 | TNFAIP3 interacting protein 1 | TNIP1 | 1.1E−05 | −2.2 | 4.1E−04 |
| 218881_s_at | NM_024530 | FOS-like antigen 2 | FOSL2 | 1.1E−07 | −2.2 | 1.8E−06 |
| 204398_s_at | NM_012155 | echinoderm microtubule associated protein like 2 | EML2 | 4.9E−05 | −2.2 | 2.5E−06 |
| 202378_s_at | NM_017526 | leptin receptor overlapping transcript | LEPROT | 3.7E−04 | −2.2 | 1.3E−04 |

TABLE 2-continued

Genes correlated with the sensitivity of 28 sarcoma cell lines to compound 1 as identified by Affymetrix gene array.

| probe | Accession # | Gene Title | Gene Symbol | p-value in t-test | Fold (S/R) | p-value (correlation) |
|---|---|---|---|---|---|---|
| 219332_at | NM_024723 | MICAL-like 2 | MICALL2 | 4.4E−05 | −2.2 | 6.4E−04 |
| 203454_s_at | NM_004045 | ATX1 antioxidant protein 1 homolog (yeast) | ATOX1 | 5.9E−06 | −2.2 | 3.0E−04 |
| 208757_at | BC001123 | transmembrane emp24 protein transport domain containing 9 | TMED9 | 7.9E−07 | −2.2 | 8.7E−05 |
| 209584_x_at | AF165520 | apolipoprotein B mRNA editing enzyme, catalytic polypeptide-like 3C | APOBEC3C | 4.1E−05 | −2.2 | 2.0E−04 |
| 220174_at | NM_025061 | leucine rich repeat containing 8 family, member E | LRRC8E | 9.7E−05 | −2.2 | 6.2E−04 |
| 200709_at | NM_000801 | FK506 binding protein 1A, 12 kDa | FKBP1A | 2.7E−06 | −2.2 | 5.8E−05 |
| 215037_s_at | U72398 | BCL2-like 1 | BCL2L1 | 5.9E−04 | −2.2 | 4.3E−04 |
| 221926_s_at | BF196320 | interleukin 17 receptor C | IL17RC | 2.2E−06 | −2.2 | 5.7E−06 |
| 203279_at | NM_014674 | ER degradation enhancer, mannosidase alpha-like 1 | EDEM1 | 8.4E−06 | −2.2 | 5.7E−04 |
| 218109_s_at | NM_022736 | major facilitator superfamily domain containing 1 | MFSD1 | 1.7E−04 | −2.2 | 1.5E−04 |
| 221561_at | L21934 | sterol O-acyltransferase (acyl-Coenzyme A: cholesterol acyltransferase) 1 | SOAT1 | 5.8E−05 | −2.2 | 8.8E−04 |
| 214703_s_at | AW954107 | mannosidase, alpha, class 2B, member 2 | MAN2B2 | 2.4E−04 | −2.1 | 9.9E−04 |
| 202377_at | AW026535 | — | — | 1.5E−04 | −2.1 | 7.5E−05 |
| 202908_at | NM_006005 | Wolfram syndrome 1 (wolframin) | WFS1 | 7.7E−05 | −2.1 | 5.1E−04 |
| 40420_at | AB015718 | serine/threonine kinase 10 | STK10 | 1.6E−07 | −2.1 | 1.1E−04 |
| 209940_at | AF083068 | poly (ADP-ribose) polymerase family, member 3 | PARP3 | 7.4E−06 | −2.1 | 1.7E−04 |
| 208701_at | BC000373 | Amyloid beta (A4) precursor-like protein 2 | APLP2 | 1.2E−04 | −2.1 | 8.5E−05 |
| 218065_s_at | NM_020644 | TMEM9 domain family, member B | TMEM9B | 6.5E−06 | −2.1 | 1.3E−04 |
| 204458_at | AL110209 | lysophospholipase 3 (lysosomal phospholipase A2) | LYPLA3 | 8.0E−05 | −2.1 | 5.9E−04 |
| 218749_s_at | NM_024959 | solute carrier family 24 (sodium/potassium/calcium exchanger), member 6 | SLC24A6 | 2.0E−07 | −2.1 | 2.1E−05 |
| 220189_s_at | NM_014275 | mannosyl (alpha-1,3-)-glycoprotein beta-1,4-N-acetylglucosaminyltransferase, isozyme B | MGAT4B | 7.0E−05 | −2.1 | 1.4E−04 |
| 218498_s_at | NM_014584 | ERO1-like (S. cerevisiae) | ERO1L | 1.5E−06 | −2.1 | 8.2E−05 |
| 201022_s_at | NM_006870 | destrin (actin depolymerizing factor) | DSTN | 5.2E−06 | −2.1 | 3.3E−06 |
| 208407_s_at | NM_001331 | catenin (cadherin-associated protein), delta 1 | CTNND1 | 4.0E−04 | −2.1 | 7.8E−04 |
| 336_at | D38081 | thromboxane A2 receptor | TBXA2R | 4.7E−04 | −2.0 | 8.4E−05 |
| 221087_s_at | NM_014349 | apolipoprotein L, 3 | APOL3 | 1.5E−04 | −2.0 | 2.1E−05 |
| 218154_at | NM_024736 | gasdermin domain containing 1 | GSDMDC1 | 9.5E−06 | −2.0 | 1.3E−04 |

The genes were selected by two statistic analyses: t-test (p < 0.001 and 2 fold between the groups of 16 sensitive cell lines and 12 resistant cell lines) and the Pearson correlations between the log2 (IC$_{50}$) data and the expression level of each gene in the 28 cell lines (p < 0.001).
The overlapped genes listed here with p values and fold change indicated.
The genes are rank ordered by the fold changes.
The positive fold changes indicate the genes have higher expression level in the sensitive cell lines and the negative fold changes indicate the genes have higher expression level in the resistant cell lines.

TABLE 3

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| | | Genes higher expressed in the group of sensitive cell lines | | | | |
| 214451_at | NM_003221 | transcription factor AP-2 beta (activating enhancer binding protein 2 beta) | TFAP2B | 7.2E−05 | 18.4 | 2.3E−04 |
| 216623_x_at | AK025084 | trinucleotide repeat containing 9 | TNRC9 | 5.3E−04 | 15.1 | 3.0E−05 |
| 219740_at | NM_024749 | vasohibin 2 | VASH2 | 2.8E−04 | 10.4 | 4.7E−04 |
| 211341_at | L20433 | POU domain, class 4, transcription factor 1 | POU4F1 | 6.8E−04 | 9.5 | 3.9E−05 |
| 212713_at | R72286 | microfibrillar-associated protein 4 | MFAP4 | 2.6E−04 | 8.3 | 5.8E−04 |
| 206440_at | NM_004664 | lin-7 homolog A (*C. elegans*) | LIN7A | 4.8E−04 | 5.6 | 3.3E−05 |
| 204914_s_at | AW157202 | SRY (sex determining region Y)-box 11 | SOX11 | 6.9E−05 | 5.5 | 5.5E−04 |
| 218824_at | NM_018215 | hypothetical protein FLJ10781 | FLJ10781 | 5.1E−05 | 5.4 | 7.6E−04 |
| 204457_s_at | NM_002048 | growth arrest-specific 1 | GAS1 | 8.9E−04 | 5.1 | 4.9E−05 |
| 215043_s_at | X83301 | SMA3 /// SMA5 | SMA3 /// SMA5 | 7.9E−05 | 4.8 | 3.9E−05 |
| 203139_at | NM_004938 | death-associated protein kinase 1 | DAPK1 | 6.9E−05 | 4.8 | 9.6E−05 |
| 212599_at | AK025298 | autism susceptibility candidate 2 | AUTS2 | 1.5E−04 | 4.7 | 2.4E−04 |
| 205888_s_at | AI962693 | janus kinase and microtubule interacting protein 2 /// myelin transcription factor 1-like | JAKMIP2 /// MYT1L | 2.6E−04 | 4.7 | 1.6E−06 |
| 206565_x_at | NM_006780 | SMA3 | SMA3 | 6.9E−05 | 4.2 | 1.5E−05 |
| 207781_s_at | NM_021998 | zinc finger protein 711 | ZNF711 | 7.7E−06 | 4.0 | 9.7E−06 |
| 204860_s_at | AI817801 | NLR family, apoptosis inhibitory protein /// similar to Baculoviral IAP repeat-containing protein 1 (Neuronal apoptosis inhibitory protein) | NAIP /// LOC728519 | 9.0E−04 | 4.0 | 2.5E−04 |
| 213657_s_at | BE858194 | Zinc finger protein 710 /// MRNA full length insert cDNA clone EUROIMAGE 375854 /// Dedicator of cytokinesis 4 | ZNF710 /// DOCK4 | 1.7E−05 | 4.0 | 9.2E−04 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 213216_at | AL537463 | OTU domain containing 3 | OTUD3 | 8.5E−04 | 3.9 | 1.4E−05 |
| 204165_at | NM_003931 | WAS protein family, member 1 | WASF1 | 1.6E−04 | 3.8 | 1.6E−04 |
| 200884_at | NM_001823 | creatine kinase, brain | CKB | 9.4E−05 | 3.6 | 1.1E−04 |
| 212847_at | AL036840 | Far upstream element (FUSE) binding protein 1 | FUBP1 | 9.3E−06 | 3.5 | 7.4E−05 |
| 205889_s_at | NM_014790 | janus kinase and microtubule interacting protein 2 | JAKMIP2 | 2.3E−04 | 3.5 | 9.4E−07 |
| 213605_s_at | AL049987 | Similar to Beta-glucuronidase precursor | LOC728411 | 5.5E−04 | 3.4 | 1.2E−04 |
| 208998_at | U94592 | uncoupling protein 2 (mitochondrial, proton carrier) | UCP2 | 7.2E−04 | 3.3 | 6.5E−05 |
| 212731_at | U79297 | ankyrin repeat domain 46 | ANKRD46 | 5.0E−06 | 3.2 | 8.5E−06 |
| 213058_at | AL033538 | tetratricopeptide repeat domain 28 | TTC28 | 4.8E−05 | 3.1 | 5.0E−05 |
| 204742_s_at | NM_015032 | androgen-induced proliferation inhibitor | APRIN | 2.7E−04 | 3.0 | 7.4E−06 |
| 201449_at | AL567227 | TIA1 cytotoxic granule-associated RNA binding protein | TIA1 | 5.5E−06 | 3.0 | 5.6E−05 |
| 203117_s_at | NM_014871 | ubiquitin specific peptidase 52 | USP52 | 8.9E−05 | 2.9 | 6.5E−05 |
| 37577_at | U79256 | Rho GTPase activating protein 19 | ARHGAP19 | 5.0E−04 | 2.9 | 3.0E−04 |
| 213283_s_at | BG285616 | sal-like 2 (Drosophila) | SALL2 | 4.1E−04 | 2.9 | 3.8E−04 |
| 200644_at | NM_023009 | MARCKS-like 1 | MARCKSL1 | 3.4E−04 | 2.9 | 4.3E−04 |
| 210045_at | AU151428 | isocitrate dehydrogenase 2 (NADP+), mitochondrial | IDH2 | 5.7E−07 | 2.8 | 4.8E−05 |
| 218457_s_at | NM_022552 | DNA (cytosine-5-)-methyltransferase 3 alpha | DNMT3A | 2.2E−06 | 2.8 | 1.2E−04 |
| 208986_at | AL559478 | transcription factor 12 (HTF4, helix-loop-helix transcription factors 4) | TCF12 | 1.6E−05 | 2.8 | 7.2E−07 |
| 213891_s_at | AI927067 | CDNA FLJ11918 fis, clone HEMBB1000272 | — | 4.0E−04 | 2.7 | 6.5E−04 |
| 210882_s_at | U04811 | trophinin | TRO | 1.9E−04 | 2.6 | 9.5E−04 |
| 218223_s_at | NM_016274 | pleckstrin homology domain containing, family O member 1 | PLEKHO1 | 1.3E−04 | 2.6 | 3.7E−06 |
| 212547_at | N34842 | FLJ35348 | FLJ35348 | 2.4E−06 | 2.6 | 1.5E−05 |
| 203825_at | NM_007371 | bromodomain containing 3 | BRD3 | 1.7E−06 | 2.6 | 6.7E−06 |
| 212126_at | BG391282 | CDNA clone IMAGE: 4842353 | — | 4.3E−05 | 2.6 | 2.1E−05 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 206554_x_at | NM_006515 | SET domain and mariner transposase fusion gene | SETMAR | 1.3E−04 | 2.6 | 1.9E−04 |
| 221261_x_at | NM_030801 | melanoma antigen family D, 4 /// melanoma antigen family D, 4 | MAGED4 | 1.8E−04 | 2.6 | 6.8E−05 |
| 212386_at | BF592782 | CDNA FLJ11918 fis, clone HEMBB1000272 | — | 4.8E−04 | 2.6 | 4.3E−04 |
| 215599_at | X83300 | SMA4 /// similar to SMA4 | SMA4 /// LOC730390 | 6.5E−04 | 2.6 | 1.5E−04 |
| 209715_at | L07515 | chromobox homolog 5 (HP1 alpha homolog, *Drosophila*) | CBX5 | 1.2E−05 | 2.6 | 1.7E−06 |
| 221260_s_at | NM_030809 | chromosome 12 open reading frame 22 /// chromosome 12 open reading frame 22 | C12orf22 | 9.9E−04 | 2.5 | 1.7E−04 |
| 212966_at | AL043112 | hypermethylated in cancer 2 | HIC2 | 2.4E−04 | 2.5 | 7.4E−04 |
| 215128_at | AV704232 | CDNA FLJ11682 fis, clone HEMBA1004880 | — | 3.2E−04 | 2.5 | 5.8E−05 |
| 212670_at | AA479278 | elastin (supravalvular aortic stenosis, Williams-Beuren syndrome) | ELN | 2.1E−04 | 2.4 | 3.3E−04 |
| 203298_s_at | NM_004973 | jumonji, AT rich interactive domain 2 | JARID2 | 1.5E−04 | 2.4 | 5.3E−05 |
| 220443_s_at | NM_012476 | ventral anterior homeobox 2 | VAX2 | 6.6E−05 | 2.4 | 7.2E−06 |
| 204799_at | NM_014838 | zinc finger, BED-type containing 4 | ZBED4 | 1.6E−06 | 2.4 | 5.0E−04 |
| 209153_s_at | M31523 | transcription factor 3 (E2A immunoglobulin enhancer binding factors E12/E47) | TCF3 | 1.4E−04 | 2.4 | 1.8E−04 |
| 203625_x_at | BG105365 | melanoma cell adhesion molecule | MCAM | 7.4E−04 | 2.4 | 5.6E−05 |
| 213387_at | AB033066 | ATPase family, AAA domain containing 2B | ATAD2B | 2.0E−05 | 2.3 | 3.0E−05 |
| 213694_at | AW027347 | round spermatid basic protein 1 | RSBN1 | 2.8E−04 | 2.3 | 6.5E−04 |
| 203046_s_at | NM_003920 | timeless homolog (*Drosophila*) | TIMELESS | 1.2E−05 | 2.3 | 2.7E−07 |
| 214877_at | BE794663 | CDK5 regulatory subunit associated protein 1-like 1 | CDKAL1 | 5.5E−05 | 2.3 | 9.2E−04 |
| 208838_at | AB020636 | — | — | 2.6E−04 | 2.3 | 8.3E−06 |
| 213610_s_at | BE326381 | kelch-like 23 (*Drosophila*) | KLHL23 | 7.7E−04 | 2.3 | 8.3E−04 |
| 221965_at | AI990326 | M-phase phosphoprotein 9 | MPHOSPH9 | 5.8E−04 | 2.3 | 1.1E−04 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 203026_at | NM_014872 | zinc finger and BTB domain containing 5 | ZBTB5 | 1.6E−06 | 2.3 | 2.9E−05 |
| 210555_s_at | U85430 | nuclear factor of activated T-cells, cytoplasmic, calcineurin-dependent 3 | NFATC3 | 5.7E−07 | 2.3 | 5.8E−06 |
| 211929_at | AA527502 | heterogeneous nuclear ribonucleoprotein A3 | HNRPA3 | 3.5E−04 | 2.2 | 6.2E−04 |
| 212704_at | AI049962 | zinc finger, CCHC domain containing 11 | ZCCHC11 | 2.9E−05 | 2.2 | 7.8E−06 |
| 208664_s_at | AU131711 | tetratricopeptide repeat domain 3 | TTC3 | 1.7E−05 | 2.2 | 4.7E−04 |
| 210649_s_at | AF231056 | AT rich interactive domain 1A (SWI-like) | ARID1A | 9.6E−05 | 2.2 | 4.1E−07 |
| 204060_s_at | NM_005044 | protein kinase, X-linked /// protein kinase, Y-linked | PRKX /// PRKY | 8.2E−04 | 2.2 | 1.4E−04 |
| 212153_at | AB007930 | pogo transposable element with ZNF domain | POGZ | 6.5E−04 | 2.2 | 6.9E−04 |
| 221902_at | AL567940 | G protein-coupled receptor 153 | GPR153 | 5.3E−04 | 2.2 | 4.4E−04 |
| 213302_at | AL044326 | phosphoribosylformylglycinamidine synthase (FGAR amidotransferase) | PFAS | 3.7E−04 | 2.2 | 4.1E−04 |
| 52975_at | AA534894 | family with sequence similarity 125, member B | FAM125B | 7.3E−04 | 2.1 | 1.1E−04 |
| 212164_at | AL522296 | transmembrane protein 183A | TMEM183A | 1.5E−04 | 2.1 | 4.2E−05 |
| 208990_s_at | AF132362 | heterogeneous nuclear ribonucleoprotein H3 (2H9) | HNRPH3 | 5.8E−07 | 2.1 | 7.7E−06 |
| 221883_at | AA133342 | PBX/knotted 1 homeobox 1 | PKNOX1 | 3.0E−05 | 2.1 | 1.2E−04 |
| 202540_s_at | NM_000859 | 3-hydroxy-3-methylglutaryl-Coenzyme A reductase | HMGCR | 1.8E−04 | 2.1 | 3.1E−04 |
| 217025_s_at | AL110225 | drebrin 1 | DBN1 | 2.3E−04 | 2.1 | 4.3E−05 |
| 218683_at | NM_021190 | polypyrimidine tract binding protein 2 | PTBP2 | 1.9E−04 | 2.1 | 8.9E−05 |
| 210962_s_at | AB019691 | A kinase (PRKA) anchor protein (yotiao) 9 | AKAP9 | 5.9E−05 | 2.1 | 2.1E−06 |
| 212482_at | BF671894 | required for meiotic nuclear division 5 homolog A (S. cerevisiae) | RMND5A | 3.8E−04 | 2.1 | 1.5E−04 |
| 212919_at | AV715578 | DCP2 decapping enzyme homolog (S. cerevisiae) | DCP2 | 2.0E−04 | 2.1 | 1.1E−04 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 219800_s_at | NM_024838 | — | — | 5.5E−04 | 2.1 | 3.9E−04 |
| 201741_x_at | M69040 | splicing factor, arginine/serine-rich 1 (splicing factor 2, alternate splicing factor) | SFRS1 | 3.6E−06 | 2.1 | 1.4E−04 |
| 218875_s_at | NM_012177 | F-box protein 5 | FBXO5 | 8.3E−04 | 2.1 | 6.8E−04 |
| 212170_at | BF447705 | RNA binding motif protein 12 | RBM12 | 2.5E−04 | 2.1 | 6.4E−05 |
| 214221_at | AI825212 | Alstrom syndrome 1 | ALMS1 | 5.9E−04 | 2.1 | 4.2E−05 |
| 210473_s_at | M37712 | G protein-coupled receptor 125 | GPR125 | 1.8E−04 | 2.1 | 2.6E−04 |
| 208839_s_at | AL136810 | cullin-associated and neddylation-dissociated 1 | CAND1 | 4.8E−04 | 2.1 | 1.2E−05 |
| 208644_at | M32721 | poly (ADP-ribose) polymerase family, member 1 | PARP1 | 3.3E−04 | 2.0 | 6.2E−05 |
| 205256_at | NM_014830 | zinc finger and BTB domain containing 39 | ZBTB39 | 1.5E−05 | 2.0 | 3.4E−06 |
| 202455_at | NM_005474 | histone deacetylase 5 | HDAC5 | 4.1E−04 | 2.0 | 2.3E−05 |
| 213677_s_at | BG434893 | PMS1 postmeiotic segregation increased 1 (*S. cerevisiae*) | PMS1 | 7.1E−06 | 2.0 | 6.4E−05 |
| 206128_at | AI264306 | adrenergic, alpha-2C-, receptor | ADRA2C | 9.1E−04 | 2.0 | 3.0E−05 |
| 201833_at | NM_001527 | histone deacetylase 2 | HDAC2 | 2.1E−06 | 2.0 | 7.8E−05 |
| 202051_s_at | NM_005095 | zinc finger, MYM-type 4 | ZMYM4 | 2.8E−04 | 2.0 | 3.8E−04 |
| 204520_x_at | NM_014577 | bromodomain containing 1 | BRD1 | 7.5E−06 | 2.0 | 8.3E−04 |
| 201235_s_at | BG339064 | BTG family, member 2 | BTG2 | 9.3E−04 | 2.0 | 5.9E−04 |

Genes higher expressed in the group of resistant cell lines

| 222108_at | AC004010 | adhesion molecule with Ig-like domain 2 | AMIGO2 | 4.8E−05 | −40.9 | 7.8E−05 |
|---|---|---|---|---|---|---|
| 209835_x_at | BC004372 | CD44 molecule (Indian blood group) | CD44 | 1.3E−06 | −33.2 | 5.0E−06 |
| 201858_s_at | J03223 | proteoglycan 1, secretory granule | PRG1 | 3.0E−05 | −30.8 | 2.6E−04 |
| 202638_s_at | NM_000201 | intercellular adhesion molecule 1 (CD54), human rhinovirus receptor | ICAM1 | 3.6E−04 | −30.3 | 4.0E−04 |
| 217901_at | BF031829 | Desmoglein 2 | DSG2 | 9.6E−04 | −25.6 | 5.7E−04 |
| 205083_at | NM_001159 | aldehyde oxidase 1 | AOX1 | 6.5E−05 | −24.1 | 1.7E−04 |
| 213010_at | AI088622 | protein kinase C, delta binding protein | PRKCDBP | 3.8E−04 | −21.8 | 7.5E−04 |
| 202855_s_at | AL513917 | solute carrier family 16, member 3 (monocarboxylic acid transporter 4) | SLC16A3 | 1.5E−05 | −21.5 | 1.2E−05 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 202854_at | NM_000194 | hypoxanthine phosphoribosyltransferase 1 (Lesch-Nyhan syndrome) | HPRT1 | 1.4E−05 | −20.0 | 8.7E−06 |
| 215034_s_at | AI189753 | transmembrane 4 L six family member 1 | TM4SF1 | 2.0E−04 | −20.0 | 1.1E−04 |
| 210916_s_at | AF098641 | CD44 molecule (Indian blood group) /// mitogen-activated protein kinase 10 | CD44 /// MAPK10 | 1.0E−06 | −18.7 | 7.2E−06 |
| 221530_s_at | BE857425 | basic helix-loop-helix domain containing, class B, 3 | BHLHB3 | 3.5E−04 | −18.1 | 4.7E−06 |
| 209803_s_at | AF001294 | pleckstrin homology-like domain, family A, member 2 | PHLDA2 | 1.6E−06 | −17.4 | 2.0E−06 |
| 204420_at | BG251266 | FOS-like antigen 1 | FOSL1 | 1.6E−06 | −17.2 | 9.8E−06 |
| 201596_x_at | NM_000224 | keratin 18 | KRT18 | 2.3E−05 | −16.8 | 1.6E−05 |
| 209278_s_at | L27624 | tissue factor pathway inhibitor 2 | TFPI2 | 3.0E−04 | −16.1 | 7.4E−05 |
| 203108_at | NM_003979 | G protein-coupled receptor, family C, group 5, member A | GPRC5A | 5.0E−05 | −15.9 | 1.2E−04 |
| 211864_s_at | AF207990 | fer-1-like 3, myoferlin (*C. elegans*) | FER1L3 | 1.3E−05 | −15.7 | 3.8E−06 |
| 204470_at | NM_001511 | chemokine (C—X—C motif) ligand 1 (melanoma growth stimulating activity, alpha) | CXCL1 | 9.1E−04 | −15.4 | 2.5E−04 |
| 204279_at | NM_002800 | proteasome (prosome, macropain) subunit, beta type, 9 (large multifunctional peptidase 2) | PSMB9 | 2.4E−07 | −15.0 | 9.1E−07 |
| 205627_at | NM_001785 | cytidine deaminase | CDA | 7.0E−04 | −14.9 | 4.8E−04 |
| 212444_at | AA156240 | CDNA clone IMAGE: 6025865 | — | 7.8E−05 | −14.8 | 3.2E−04 |
| 201842_s_at | AI826799 | EGF-containing fibulin-like extracellular matrix protein 1 | EFEMP1 | 4.2E−04 | −14.3 | 5.7E−04 |
| 208747_s_at | M18767 | complement component 1, s subcomponent | C1S | 4.6E−04 | −14.1 | 6.9E−04 |
| 204602_at | NM_012242 | dickkopf homolog 1 (*Xenopus laevis*) | DKK1 | 2.0E−04 | −13.9 | 6.6E−04 |
| 201468_s_at | NM_000903 | NAD(P)H dehydrogenase, quinone 1 | NQO1 | 5.6E−06 | −13.7 | 5.1E−05 |
| 201631_s_at | NM_003897 | immediate early response 3 | IER3 | 1.1E−06 | −13.7 | 5.8E−05 |
| 204222_s_at | NM_006851 | GLI pathogenesis-related 1 (glioma) | GLIPR1 | 7.3E−05 | −13.0 | 4.2E−04 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 210592_s_at | M55580 | spermidine/spermine N1-acetyltransferase 1 | SAT1 | 5.6E−07 | −12.6 | 3.7E−06 |
| 208949_s_at | BC001120 | lectin, galactoside-binding, soluble, 3 (galectin 3) | LGALS3 | 8.9E−04 | −11.3 | 2.3E−04 |
| 206513_at | NM_004833 | absent in melanoma 2 | AIM2 | 8.3E−04 | −11.0 | 7.4E−04 |
| 203851_at | NM_002178 | insulin-like growth factor binding protein 6 | IGFBP6 | 1.7E−04 | −11.0 | 1.7E−04 |
| 202627_s_at | AL574210 | serpin peptidase inhibitor, clade E (nexin, plasminogen activator inhibitor type 1), member 1 | SERPINE1 | 7.1E−04 | −10.9 | 6.4E−04 |
| 210042_s_at | AF073890 | cathepsin Z | CTSZ | 4.4E−05 | −10.8 | 3.2E−05 |
| 202858_at | NM_006758 | U2 small nuclear RNA auxiliary factor 1 | U2AF1 | 9.2E−04 | −10.7 | 2.2E−04 |
| 208510_s_at | NM_015869 | peroxisome proliferator-activated receptor gamma | PPARG | 8.7E−05 | −10.2 | 1.6E−04 |
| 202202_s_at | NM_002290 | laminin, alpha 4 | LAMA4 | 4.8E−04 | −10.2 | 2.6E−04 |
| 219759_at | NM_022350 | leukocyte-derived arginine aminopeptidase | LRAP | 6.1E−05 | −9.8 | 6.4E−05 |
| 205798_at | NM_002185 | interleukin 7 receptor /// interleukin 7 receptor | IL7R | 1.5E−05 | −9.8 | 2.6E−04 |
| 202862_at | NM_000137 | fumarylacetoacetate hydrolase (fumarylacetoacetase) | FAH | 1.3E−06 | −9.8 | 9.7E−06 |
| 201474_s_at | NM_002204 | integrin, alpha 3 (antigen CD49C, alpha 3 subunit of VLA-3 receptor) | ITGA3 | 3.9E−06 | −9.7 | 6.8E−07 |
| 221059_s_at | NM_021615 | coactosin-like 1 (*Dictyostelium*) | COTL1 | 5.7E−06 | −9.6 | 8.2E−06 |
| 217744_s_at | NM_022121 | PERP, TP53 apoptosis effector | PERP | 3.6E−05 | −9.3 | 2.9E−04 |
| 211367_s_at | U13699 | caspase 1, apoptosis-related cysteine peptidase (interleukin 1, beta, convertase) | CASP1 | 7.1E−05 | −9.1 | 7.4E−04 |
| 209040_s_at | U17496 | proteasome (prosome, macropain) subunit, beta type, 8 (large multifunctional peptidase 7) | PSMB8 | 5.8E−09 | −9.1 | 1.1E−06 |
| 201042_at | AL031651 | transglutaminase 2 (C polypeptide, protein-glutamine-gamma-glutamyltransferase) | TGM2 | 6.7E−04 | −9.1 | 3.7E−04 |
| 212473_s_at | BE965029 | microtubule associated monooxygenase, calponin and LIM domain containing 2 | MICAL2 | 2.3E−04 | −8.9 | 8.0E−04 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 218211_s_at | NM_024101 | melanophilin | MLPH | 2.1E−04 | −8.8 | 2.5E−05 |
| 210896_s_at | AF306765 | aspartate beta-hydroxylase | ASPH | 3.2E−06 | −8.2 | 1.5E−04 |
| 210951_x_at | AF125393 | RAB27A, member RAS oncogene family | RAB27A | 6.0E−06 | −8.1 | 1.7E−05 |
| 203234_at | NM_003364 | uridine phosphorylase 1 | UPP1 | 1.9E−05 | −8.0 | 2.1E−05 |
| 209310_s_at | U25804 | caspase 4, apoptosis-related cysteine peptidase | CASP4 | 1.2E−07 | −7.8 | 8.3E−05 |
| 212268_at | NM_030666 | serpin peptidase inhibitor, clade B (ovalbumin), member 1 | SERPINB1 | 5.6E−06 | −7.6 | 1.2E−07 |
| 201324_at | NM_001423 | epithelial membrane protein 1 | EMP1 | 4.0E−05 | −7.4 | 4.2E−06 |
| 218084_x_at | NM_014164 | FXYD domain containing ion transport regulator 5 | FXYD5 | 6.8E−06 | −7.3 | 2.4E−05 |
| 201170_s_at | NM_003670 | basic helix-loop-helix domain containing, class B, 2 | BHLHB2 | 8.1E−05 | −7.3 | 8.4E−05 |
| 218322_s_at | NM_016234 | acyl-CoA synthetase long-chain family member 5 | ACSL5 | 9.0E−04 | −7.2 | 2.3E−04 |
| 202863_at | NM_003113 | SP100 nuclear antigen | SP100 | 3.4E−06 | −7.1 | 2.0E−05 |
| 214791_at | AK023116 | hypothetical protein BC004921 | LOC93349 | 2.7E−06 | −7.1 | 2.8E−05 |
| 206461_x_at | NM_005951 | metallothionein 1H | MT1H | 6.4E−05 | −7.1 | 6.7E−04 |
| 209679_s_at | BC003379 | small trans-membrane and glycosylated protein | LOC57228 | 2.9E−06 | −6.9 | 1.5E−05 |
| 202510_s_at | NM_006291 | tumor necrosis factor, alpha-induced protein 2 | TNFAIP2 | 9.7E−04 | −6.9 | 3.8E−04 |
| 36711_at | AL021977 | v-maf musculoaponeurotic fibrosarcoma oncogene homolog F (avian) | MAFF | 2.0E−07 | −6.8 | 4.6E−08 |
| 206632_s_at | NM_004900 | apolipoprotein B mRNA editing enzyme, catalytic polypeptide-like 3B | APOBEC3B | 1.6E−04 | −6.6 | 5.0E−05 |
| 211456_x_at | AF333388 | metallothionein 1H-like protein | LOC645745 | 7.3E−05 | −6.4 | 8.8E−04 |
| 214446_at | NM_012081 | elongation factor, RNA polymerase II, 2 | ELL2 | 1.9E−05 | −6.3 | 2.1E−05 |
| 220016_at | NM_024060 | AHNAK nucleoprotein (desmoyokin) | AHNAK | 9.7E−04 | −6.0 | 2.9E−04 |
| 205100_at | NM_005110 | glutamine-fructose-6-phosphate transaminase 2 | GFPT2 | 1.3E−04 | −5.9 | 2.7E−04 |
| 210538_s_at | U37546 | baculoviral IAP repeat-containing 3 | BIRC3 | 8.8E−04 | −5.8 | 2.3E−04 |
| 216336_x_at | AL031602 | metallothionein 1M | MT1M | 1.2E−04 | −5.8 | 1.8E−04 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 210117_at | AF311312 | sperm associated antigen 1 | SPAG1 | 1.2E−04 | −5.7 | 5.8E−04 |
| 216985_s_at | AJ002077 | syntaxin 3 | STX3 | 1.4E−06 | −5.6 | 5.3E−06 |
| 217165_x_at | M10943 | metallothionein 1F (functional) | MT1F | 2.8E−04 | −5.6 | 9.8E−04 |
| 204017_at | NM_006855 | KDEL (Lys-Asp-Glu-Leu) endoplasmic reticulum protein retention receptor 3 | KDELR3 | 1.2E−05 | −5.5 | 3.9E−04 |
| 217996_at | AA576961 | pleckstrin homology-like domain, family A, member 1 | PHLDA1 | 2.2E−04 | −5.3 | 3.8E−04 |
| 202733_at | NM_004199 | procollagen-proline, 2-oxoglutarate 4-dioxygenase (proline 4-hydroxylase), alpha polypeptide II | P4HA2 | 3.7E−05 | −5.3 | 6.9E−05 |
| 209457_at | U16996 | dual specificity phosphatase 5 | DUSP5 | 1.3E−04 | −5.0 | 9.8E−04 |
| 214866_at | X74039 | plasminogen activator, urokinase receptor | PLAUR | 4.5E−05 | −5.0 | 1.2E−04 |
| 211612_s_at | U62858 | interleukin 13 receptor, alpha 1 /// interleukin 13 receptor, alpha 1 | IL13RA1 | 1.5E−04 | −5.0 | 4.3E−04 |
| 210987_x_at | M19267 | tropomyosin 1 (alpha) | TPM1 | 7.4E−04 | −5.0 | 2.3E−05 |
| 213274_s_at | AA020826 | cathepsin B | CTSB | 7.9E−04 | −5.0 | 1.6E−04 |
| 202949_s_at | NM_001450 | four and a half LIM domains 2 | FHL2 | 5.6E−05 | −4.9 | 5.2E−04 |
| 203939_at | NM_002526 | 5'-nucleotidase, ecto (CD73) | NT5E | 9.5E−04 | −4.9 | 6.1E−05 |
| 222294_s_at | AW971415 | CDNA clone IMAGE: 5745639 | — | 8.3E−06 | −4.9 | 1.2E−05 |
| 202085_at | NM_004817 | tight junction protein 2 (zona occludens 2) | TJP2 | 1.4E−04 | −4.9 | 2.8E−04 |
| 209706_at | AF247704 | NK3 transcription factor related, locus 1 (*Drosophila*) | NKX3-1 | 6.0E−05 | −4.9 | 1.8E−04 |
| 222150_s_at | AK026747 | hypothetical protein LOC54103 | LOC54103 | 1.8E−05 | −4.8 | 2.6E−06 |
| 200632_s_at | NM_006096 | N-myc downstream regulated gene 1 | NDRG1 | 6.2E−04 | −4.8 | 4.1E−04 |
| 210136_at | AW070431 | myelin basic protein | MBP | 1.6E−05 | −4.6 | 1.0E−04 |
| 205579_at | NM_000861 | histamine receptor H1 | HRH1 | 6.3E−05 | −4.6 | 1.5E−04 |
| 201412_at | NM_014045 | low density lipoprotein receptor-related protein 10 | LRP10 | 8.4E−05 | −4.6 | 2.8E−04 |
| 211799_x_at | U62824 | major histocompatibility complex, class I, C | HLA-C | 5.4E−04 | −4.6 | 8.6E−04 |
| 203005_at | NM_002342 | lymphotoxin beta receptor (TNFR superfamily, member 3) | LTBR | 1.1E−06 | −4.5 | 4.4E−06 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 209417_s_at | BC001356 | interferon-induced protein 35 | IFI35 | 1.7E−05 | −4.3 | 7.7E−05 |
| 203041_s_at | J04183 | lysosomal-associated membrane protein 2 | LAMP2 | 8.4E−04 | −4.3 | 9.0E−04 |
| 213865_at | AI378788 | discoidin, CUB and LCCL domain containing 2 | DCBLD2 | 8.1E−04 | −4.2 | 3.6E−04 |
| 201649_at | NM_004223 | ubiquitin-conjugating enzyme E2L 6 | UBE2L6 | 2.6E−04 | −4.2 | 6.4E−05 |
| 202180_s_at | NM_017458 | major vault protein | MVP | 3.1E−04 | −4.1 | 2.7E−04 |
| 211000_s_at | AB015706 | interleukin 6 signal transducer (gp 130, oncostatin M receptor) | IL6ST | 1.8E−04 | −4.1 | 8.0E−04 |
| 203518_at | NM_000081 | lysosomal trafficking regulator | LYST | 4.9E−05 | −4.0 | 4.4E−05 |
| 205896_at | NM_003059 | solute carrier family 22 (organic cation transporter), member 4 | SLC22A4 | 3.2E−04 | −4.0 | 6.6E−04 |
| 201482_at | NM_002826 | quiescin Q6 | QSCN6 | 2.1E−05 | −4.0 | 6.0E−05 |
| 218631_at | NM_021732 | arginine vasopressin-induced 1 | AVPI1 | 8.6E−04 | −3.9 | 2.6E−04 |
| 201471_s_at | NM_003900 | sequestosome 1 | SQSTM1 | 1.4E−04 | −3.9 | 4.8E−04 |
| 212463_at | BE379006 | CD59 molecule, complement regulatory protein | CD59 | 2.6E−04 | −3.8 | 3.5E−04 |
| 205266_at | NM_002309 | leukemia inhibitory factor (cholinergic differentiation factor) | LIF | 8.2E−05 | −3.8 | 5.1E−05 |
| 204745_x_at | NM_005950 | metallothionein 1G | MT1G | 1.6E−04 | −3.7 | 4.4E−04 |
| 202087_s_at | NM_001912 | cathepsin L | CTSL | 2.7E−04 | −3.7 | 6.1E−04 |
| 202531_at | NM_002198 | interferon regulatory factor 1 | IRF1 | 2.3E−04 | −3.7 | 3.1E−04 |
| 205398_s_at | NM_005902 | SMAD family member 3 | SMAD3 | 1.9E−05 | −3.7 | 6.4E−04 |
| 202201_at | NM_000713 | biliverdin reductase B (flavin reductase (NADPH)) | BLVRB | 2.5E−05 | −3.6 | 3.6E−05 |
| 202499_s_at | NM_006931 | solute carrier family 2 (facilitated glucose transporter), member 3 | SLC2A3 | 4.8E−04 | −3.6 | 5.9E−05 |
| 203329_at | NM_002845 | protein tyrosine phosphatase, receptor type, M | PTPRM | 2.2E−05 | −3.6 | 8.0E−05 |
| 218273_s_at | NM_018444 | protein phosphatase 2C, magnesium-dependent, catalytic subunit | PPM2C | 1.8E−05 | −3.6 | 2.0E−05 |
| 202948_at | NM_000877 | interleukin 1 receptor, type I | IL1R1 | 4.3E−04 | −3.5 | 6.5E−04 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 204158_s_at | NM_006019 | T-cell, immune regulator 1, ATPase, H+ transporting, lysosomal V0 subunit A3 | TCIRG1 | 3.1E−06 | −3.4 | 1.8E−04 |
| 202861_at | NM_002616 | period homolog 1 (*Drosophila*) | PER1 | 5.6E−05 | −3.4 | 3.8E−05 |
| 219691_at | NM_017654 | sterile alpha motif domain containing 9 | SAMD9 | 1.1E−05 | −3.4 | 8.9E−05 |
| 202074_s_at | NM_021980 | optineurin | OPTN | 9.9E−04 | −3.3 | 6.4E−04 |
| 204981_at | NM_002555 | solute carrier family 22 (organic cation transporter), member 18 | SLC22A18 | 7.4E−04 | −3.3 | 7.4E−06 |
| 202693_s_at | AW194730 | serine/threonine kinase 17a (apoptosis-inducing) | STK17A | 1.6E−04 | −3.3 | 1.0E−04 |
| 207467_x_at | NM_001750 | calpastatin | CAST | 3.4E−05 | −3.2 | 1.6E−04 |
| 218552_at | NM_018281 | enoyl Coenzyme A hydratase domain containing 2 | ECHDC2 | 1.0E−04 | −3.2 | 3.0E−04 |
| 204863_s_at | BE856546 | interleukin 6 signal transducer (gp130, oncostatin M receptor) /// melanoma antigen family A, 4 | IL6ST /// MAGEA4 | 4.3E−04 | −3.2 | 9.8E−04 |
| 218983_at | NM_016546 | complement component 1, r subcomponent-like | C1RL | 5.1E−05 | −3.2 | 6.4E−05 |
| 205640_at | NM_000694 | aldehyde dehydrogenase 3 family, member B1 | ALDH3B1 | 6.0E−05 | −3.1 | 2.3E−05 |
| 212737_at | AL513583 | GM2 ganglioside activator | GM2A | 3.9E−04 | −3.1 | 3.2E−05 |
| 203430_at | NM_014320 | heme binding protein 2 | HEBP2 | 3.5E−04 | −3.1 | 1.9E−05 |
| 210978_s_at | BC002616 | transgelin 2 | TAGLN2 | 3.3E−04 | −3.1 | 3.1E−05 |
| 209304_x_at | AF087853 | growth arrest and DNA-damage-inducible, beta | GADD45B | 5.5E−04 | −3.0 | 9.4E−04 |
| 211528_x_at | M90685 | HLA-G histocompatibility antigen, class I, G | HLA-G | 3.1E−04 | −3.0 | 9.7E−04 |
| 204747_at | NM_001549 | interferon-induced protein with tetratricopeptide repeats 3 | IFIT3 | 3.5E−05 | −3.0 | 4.0E−04 |
| 217739_s_at | NM_005746 | pre-B-cell colony enhancing factor 1 | PBEF1 | 3.6E−05 | −3.0 | 1.2E−04 |
| 202307_s_at | NM_000593 | transporter 1, ATP-binding cassette, sub-family B (MDR/TAP) | TAP1 | 1.2E−05 | −3.0 | 6.1E−04 |
| 207375_s_at | NM_002189 | interleukin 15 receptor, alpha | IL15RA | 1.6E−04 | −3.0 | 8.1E−04 |
| 219716_at | NM_030641 | apolipoprotein L, 6 | APOL6 | 4.1E−04 | −2.9 | 4.2E−05 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 212552_at | BE617588 | hippocalcin-like 1 | HPCAL1 | 2.2E−04 | −2.9 | 1.0E−04 |
| 217998_at | NM_007350 | pleckstrin homology-like domain, family A, member 1 /// hypothetical LOC652993 | PHLDA1 /// LOC652993 | 9.7E−05 | −2.9 | 3.6E−04 |
| 202275_at | NM_000402 | glucose-6-phosphate dehydrogenase | G6PD | 6.9E−05 | −2.9 | 1.2E−04 |
| 201954_at | NM_005720 | actin related protein 2/3 complex, subunit 1B, 41 kDa /// similar to Actin-related protein 2/3 complex subunit 1B (ARP2/3 complex 41 kDa subunit) (p41-ARC) | ARPC1B /// LOC653888 | 7.2E−04 | −2.9 | 5.3E−04 |
| 214447_at | NM_005238 | v-ets erythroblastosis virus E26 oncogene homolog 1 (avian) | ETS1 | 2.5E−04 | −2.8 | 8.3E−04 |
| 221044_s_at | NM_021616 | tripartite motif-containing 34 /// tripartite motif-containing 6 and tripartite motif-containing 34 | TRIM34 /// TRIM6-TRIM34 | 2.7E−04 | −2.8 | 8.1E−04 |
| 221843_s_at | AA195017 | KIAA1609 | KIAA1609 | 6.9E−04 | −2.8 | 7.7E−05 |
| 213083_at | AJ005866 | solute carrier family 35, member D2 | SLC35D2 | 2.0E−04 | −2.7 | 2.2E−05 |
| 208637_x_at | BC003576 | actinin, alpha 1 | ACTN1 | 2.9E−04 | −2.7 | 1.7E−04 |
| 53720_at | AI862559 | hypothetical protein FLJ11286 | FLJ11286 | 2.4E−05 | −2.7 | 6.6E−06 |
| 208829_at | AF029750 | TAP binding protein (tapasin) | TAPBP | 6.8E−04 | −2.6 | 8.3E−04 |
| 204682_at | NM_000428 | latent transforming growth factor beta binding protein 2 | LTBP2 | 5.9E−04 | −2.6 | 2.4E−04 |
| 208613_s_at | AV712733 | filamin B, beta (actin binding protein 278) | FLNB | 2.1E−04 | −2.6 | 2.4E−04 |
| 201944_at | NM_000521 | hexosaminidase B (beta polypeptide) | HEXB | 3.2E−05 | −2.6 | 4.4E−04 |
| 208872_s_at | AA814140 | receptor accessory protein 5 | REEP5 | 1.6E−05 | −2.6 | 2.0E−04 |
| 218747_s_at | NM_018009 | TAP binding protein-like | TAPBPL | 9.1E−04 | −2.6 | 2.7E−04 |
| 209546_s_at | AF323540 | apolipoprotein L, 1 | APOL1 | 2.4E−04 | −2.6 | 7.1E−05 |
| 205032_at | NM_002203 | integrin, alpha 2 (CD49B, alpha 2 subunit of VLA-2 receptor) | ITGA2 | 7.2E−05 | −2.5 | 4.9E−04 |
| 204769_s_at | M74447 | transporter 2, ATP-binding cassette, sub-family B (MDR/TAP) | TAP2 | 1.6E−05 | −2.5 | 1.4E−05 |
| 206284_x_at | NM_001834 | clathrin, light chain (Lcb) | CLTB | 3.9E−04 | −2.4 | 4.3E−05 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 204034_at | NM_014297 | ethylmalonic encephalopathy 1 | ETHE1 | 5.5E−04 | −2.4 | 2.2E−05 |
| 219684_at | NM_022147 | receptor (chemosensory) transporter protein 4 | RTP4 | 7.9E−04 | −2.4 | 5.4E−04 |
| 211769_x_at | BC006088 | serine incorporator 3 /// serine incorporator 3 | SERINC3 | 1.7E−06 | −2.4 | 1.1E−04 |
| 213272_s_at | AF070596 | transmembrane protein 159 | TMEM159 | 5.6E−05 | −2.4 | 7.6E−05 |
| 201587_s_at | NM_001569 | interleukin-1 receptor-associated kinase 1 | IRAK1 | 1.3E−04 | −2.4 | 1.4E−04 |
| 203925_at | NM_002061 | glutamate-cysteine ligase, modifier subunit | GCLM | 2.3E−04 | −2.4 | 4.2E−04 |
| 220761_s_at | NM_016281 | TAO kinase 3 | TAOK3 | 8.4E−05 | −2.3 | 2.0E−07 |
| 214783_s_at | BG177920 | annexin A11 | ANXA11 | 2.4E−04 | −2.3 | 8.6E−04 |
| 217751_at | NM_015917 | glutathione S-transferase kappa 1 | GSTK1 | 7.3E−04 | −2.3 | 5.4E−04 |
| 203045_at | NM_004148 | ninjurin 1 | NINJ1 | 3.8E−05 | −2.3 | 2.7E−04 |
| 203167_at | NM_003255 | TIMP metallopeptidase inhibitor 2 | TIMP2 | 9.0E−04 | −2.3 | 5.5E−04 |
| 60471_at | AA625133 | Ras and Rab interactor 3 | RIN3 | 5.9E−05 | −2.2 | 2.7E−04 |
| 209179_s_at | BC003164 | leukocyte receptor cluster (LRC) member 4 | LENG4 | 7.8E−06 | −2.2 | 1.8E−04 |
| 202013_s_at | NM_000401 | exostoses (multiple) 2 | EXT2 | 4.7E−05 | −2.2 | 4.2E−04 |
| 218739_at | NM_016006 | abhydrolase domain containing 5 | ABHD5 | 3.0E−04 | −2.2 | 9.1E−04 |
| 219677_at | NM_025106 | splA/ryanodine receptor domain and SOCS box containing 1 | SPSB1 | 3.9E−06 | −2.2 | 1.1E−04 |
| 209575_at | BC001903 | interleukin 10 receptor, beta | IL10RB | 2.8E−04 | −2.2 | 2.9E−05 |
| 218154_at | NM_024736 | gasdermin domain containing 1 | GSDMDC1 | 5.0E−09 | −2.2 | 7.2E−06 |
| 201847_at | NM_000235 | lipase A, lysosomal acid, cholesterol esterase (Wolman disease) | LIPA | 3.3E−04 | −2.2 | 2.2E−05 |
| 201953_at | NM_006384 | calcium and integrin binding 1 (calmyrin) | CIB1 | 1.2E−04 | −2.2 | 6.5E−04 |
| 200752_s_at | NM_005186 | calpain 1, (mu/I) large subunit | CAPN1 | 3.3E−04 | −2.2 | 4.9E−04 |
| 205084_at | NM_018844 | B-cell receptor-associated protein 29 | BCAP29 | 8.0E−04 | −2.1 | 6.6E−04 |
| 221827_at | BE788439 | RanBP-type and C3HC4-type zinc finger containing 1 | RBCK1 | 2.6E−06 | −2.1 | 1.9E−04 |
| 203258_at | NM_006442 | DR1-associated protein 1 (negative cofactor 2 alpha) | DRAP1 | 1.6E−04 | −2.1 | 5.1E−04 |
| 201360_at | NM_000099 | cystatin C (amyloid angiopathy and cerebral hemorrhage) | CST3 | 6.0E−04 | −2.1 | 4.6E−04 |

TABLE 3-continued

Genes correlated with the sensitivity of 29 sarcoma cell lines to compound 2 as identified by Affymetrix gene array.

| probe | Accession # | Gene Title | Gene Symbol | p-value in t-test | Fold (S/R) | p-value (correlation) |
|---|---|---|---|---|---|---|
| 200709_at | NM_000801 | FK506 binding protein 1A, 12 kDa | FKBP1A | 8.6E−06 | −2.0 | 9.5E−05 |
| 218109_s_at | NM_022736 | major facilitator superfamily domain containing 1 | MFSD1 | 2.9E−04 | −2.0 | 4.0E−04 |
| 203454_s_at | NM_004045 | ATX1 antioxidant protein 1 homolog (yeast) | ATOX1 | 6.3E−05 | −2.0 | 3.3E−04 |

The genes were selected by two statistic analyses: t-test ($p < 0.001$ and 2 fold between the groups of 15 sensitive cell lines and 14 resistant cell lines) and the Pearson correlations between the log2 ($IC_{50}$) data and the expression level of each gene in the 29 cell lines ($p < 0.001$).
The overlapped genes listed here with p values and fold change indicated.
The genes are rank ordered by the fold changes.
The positive fold changes indicate the genes have higher expression level in the sensitive cell lines and the negative fold changes indicate the genes have higher expression level in the resistant cell lines.

The same two statistical methods were applied to protein profiling data to identify proteins that correlated with the sensitivity of the cell lines to IGF1R inhibitors. This yielded 251 unique peptide ions for compound 1, and 228 unique peptide ions for compound 2, 153 of which overlap between the two compounds. These unique peptide ions were then sequenced by tandem mass spectrometry to obtain the identity of the corresponding protein markers. As shown in Table 4, 76 peptides were identified to represent 46 proteins that were differentially expressed between the sensitive and resistant cell line groups for compound 1; and 70 peptides representing 45 proteins (Table 5) for compound 2, with 39 proteins common for both compounds.

TABLE 4

Proteins correlated with the sensitivity of 26 sarcoma cell lines to compound 1 as identified by LC/MS based protein profiling.

| Protein name | Swiss-protein ID | Identified by microarray | Gene name | Peptide sequence |
|---|---|---|---|---|
| actinin, alpha | P12814 | Yes | ACTN1 | VGWEQLLTTIAR (SEQ ID NO: 1) |
| | | | | FAIQDISVEETSAK (SEQ ID NO: 2) |
| | | | | TINEVENQILTR (SEQ ID NO: 3) |
| actinin, alpha | O43707 | Yes | ACTN4 | DYETATLSDIK (SEQ ID NO: 4) |
| AHNAK nucleoprotein | Q09666 | Yes | AHNAK | VPGIDATTK (SEQ ID NO: 5) |
| | | | | GEGPEVDVNLPK (SEQ ID NO: 6) |
| | | | | FSMPGFK (SEQ ID NO: 7) |
| | | | | IGFSGPKLEGGEVDLKGPK (SEQ ID NO: 8) |
| | | | | ISMPDFDLHLK (SEQ ID NO: 9) |
| | | | | ISMPDIDLNLK: (SEQ ID NO: 10) |
| | | | | GEGPDVHMTLPKGDISISGPK (SEQ ID NO: 11) |
| Plasma membrane calcium-transporting ATPase 4 | P23634 | | ATP2B4 | SMSTVIRNPNGGFR (SEQ ID NO: 12) |
| | | | | TSPVEGLSGNPADLEK (SEQ ID NO: 13) |
| | | | | PADGILIQGNDLK (SEQ ID NO: 14) |
| ATP synthase, H+ transporting, mitochondrial F1 complex | Q9Y653 | Yes | ATP5G | TIAMDGTEGLVR (SEQ ID NO: 15) |
| calpain | | | CAPN2 | SMVAVMDSDTTGK (SEQ ID NO: 16) |
| Creatine Kinase, brain | | Yes | CKB | FCTGLTQIETLFK (SEQ ID NO: 17) |
| chloride intracelluar protein 1 | O00299 | Yes | CLIC1 | GVTFNVTTVDTK (SEQ ID NO: 18) |
| heat shock protein 60 | | | CPN60 | VGEVIVTK (SEQ ID NO: 19) |
| catenin | | Yes | CTNNA1 | TLAVER (SEQ ID NO: 20) |
| | | | | HVNPVQALSEFK (SEQ ID NO: 21) |

TABLE 4-continued

Proteins correlated with the sensitivity of 26 sarcoma cell lines to compound 1 as identified by LC/MS based protein profiling.

| Protein name | Swiss-protein ID | Identified by microarray | Gene name | Peptide sequence |
|---|---|---|---|---|
| destrin | P60981 | Yes | DSTN | YALYDASFETK (SEQ ID NO: 22) |
| myoferlin | Q9NZM1 | Yes | FER1L3 | VGETIIDLENR (SEQ ID NO: 23) |
| filamin B | | Yes | FLNB | GDYVLAVK (SEQ ID NO: 24) |
| G protein-coupled receptor 56 | | Yes | GPR56 | SSLHYKPTPDLR (SEQ ID NO: 25) |
| histone 2 | | Yes | H2AFY2 | EIQTAVR (SEQ ID NO: 26) |
| histone 3 | | Yes | H3F3B | EIAQDFK (SEQ ID NO: 27) |
| histone 1 | | | HIST1H4I | TLYGFGG (SEQ ID NO: 28) |
| | | | | DAVTYTEHAK (SEQ ID NO: 29) |
| histone 3 | | Yes | HIST3H3 | YRPGTVALR (SEQ ID NO: 30) |
| high mobility protein 1 | | | HMGB1 | KHPDASVNFSEFSK (SEQ ID NO: 31) |
| high mobility protein 2 | P26583 | Yes | HMGB2 | LGEMWSEQSAK (SEQ ID NO: 32) |
| heterogeneous nuclear ribonucleoprotein | | Yes | HNRPA2 | MSSYAFFVQTCR (SEQ ID NO: 33)<br>IDTIEIITDR (SEQ ID NO: 34) |
| heterogeneous nuclear ribonucleoprotein | | Yes | HNRPA3 | LTDCVVMR (SEQ ID NO: 35) |
| heterogeneous nuclear ribonucleoprotein | Q14103 | Yes | HNRPD | IFVGGLSPDTPEEK (SEQ ID NO: 36) |
| heterogeneous nuclear ribonucleoprotein | P09651 | Yes | HRNPA1 | NQGGYGGSSSSSSYGSGR (SEQ ID NO: 37) |
| heterogeneous nuclear ribonucleoprotein | P22626 | Yes | HRNPA2 | EDSQRPGAHLTVK (SEQ ID NO: 38)<br>GFGFVTFDDHDPVDK (SEQ ID NO: 39) |
| heterogeneous nuclear ribonucleoprotein | Q14103 | Yes | HNRPD | MFIGGLSWDTTK (SEQ ID NO: 40) |
| heterogeneous nuclear ribonucleoprotein | | Yes | HRNPK | GFGFVLFK (SEQ ID NO: 41)<br>IILDLISESPIK (SEQ ID NO: 42) |
| heterogeneous nuclear ribonucleoprotein | | Yes | HRNPM | AFITNIPFDVK (SEQ ID NO: 43) |
| KH domain containing, RNA binding, signal transduction associated 1 | Q07666 | Yes | KHDRBS1 | DSLDPSFTHAMQLLTAEIEK (SEQ ID NO: 44) |
| LIM domain and actin binding | Q9UHB6 | | LIMA1 | YPHIKDGEDLK (SEQ ID NO: 45) |
| matrin 3 | | Yes | MATR3 | SNTENLSQHFR (SEQ ID NO: 46)<br>MKSQAFIEMETR (SEQ ID NO: 47)<br>YQLLQLVEPFGVISNHLILNK (SEQ ID NO: 48)<br>DLSAAGIGLLAAATQSLSMPASLGR (SEQ ID NO: 49) |
| myosin heavy chain | | Yes | MYH9 | VVFQEFR (SEQ ID NO: 50)<br>LQQELDDLLVDLDHQR (SEQ ID NO: 51)<br>VISGVLQLGNIVFK (SEQ ID NO: 52)<br>LDPHLVLDQLR (SEQ ID NO: 53) |
| myosin light chain | O00159 | Yes | MYL6 | HVLVTLGEK (SEQ ID NO: 54)<br>ELLTTMGDR (SEQ ID NO: 55)<br>EAFQLFDR (SEQ ID NO: 56)<br>DGFIDKEDLHDMLASLGK (SEQ ID NO: 57)<br>IAEFTTNLTEEEEK (SEQ ID NO: 58)<br>VLDFEHFLPMLQTVAK (SEQ ID NO: 59) |

TABLE 4-continued

Proteins correlated with the sensitivity of 26 sarcoma cell lines to compound 1 as identified by LC/MS based protein profiling.

| Protein name | Swiss-protein ID | Identified by microarray | Gene name | Peptide sequence |
|---|---|---|---|---|
| lactate dehydrogenase | | | LDHB | IVVVTAGVR (SEQ ID NO: 60) |
| histone H2B | | Yes | NP_00351 | AMGIMNSFVNDIFER (SEQ ID NO: 61) |
| tublin, alpha | | | NP_006073 | FDLMYAK (SEQ ID NO: 62) |
| cleavage and polyadenylation specific factor 1 | Q10570 | Yes | CPSF1 | MYAVYK (SEQ ID NO: 63) |
| poly rC binding protein | | Yes | PCBP2 | IITLTGPTNAIFK (SEQ ID NO: 64) |
| peroxiredoxin | | Yes | PRDX6 | LPFPIIDDR (SEQ ID NO: 65) |
| protein tyrosine phosphatase, receptor type, F | | | PTPRF | TFALHK (SEQ ID NO: 66) |
| Radixin | P35241 | | RDX | YANVIAYDHSR (SEQ ID NO: 67)<br>KALELDQER (SEQ ID NO: 68)<br>KENPLQFKFR (SEQ ID NO: 69) |
| splicing factor proline/glutamine rich | | | SFPQ | LFVGNLPADITEDEFKR (SEQ ID NO: 70) |
| spectrin, beta | | | SPTBN2 | ALAVEGK (SEQ ID NO: 71)<br>AAMRETWLSENQR (SEQ ID NO: 72) |
| Stathmin | P16949 | Yes | STMN1 | DLSLEEIQK (SEQ ID NO: 73) |
| Syntaxin | O15400 | Yes | STX7 | TLNQLGTPQDSPELR (SEQ ID NO: 74) |
| thymoprotein | | | TMPO | YGVNPGPIVGTTR (SEQ ID NO: 75) |

The peptide ions were selected by the overlaps between the two statistic analyses: t-test ($p < 0.001$ and 2 fold between the groups of 14 sensitive cell lines and 12 resistant cell lines) and the Pearson correlations between the $\log2(IC_{50})$ data and the expression level of each peptide ion in the 26 cell lines ($p < 0.001$).
The peptide ions generated from statistical analyses were sequenced by tandem mass spectrometry to get the identification of the proteins which are listed in this Table.
The name of protein and gene, the sequence of each peptide ion associated with identified protein are listed.
The overlap with Affymetrix gene expression results also indicated.

TABLE 5

Proteins correlated with the sensitivity of 27 sarcoma cell lines to compound 2 as identified by LC/MS based protein profiling.

| Protein name | Swiss-protein ID | Identified by microarray | Gene name | Peptide sequence |
|---|---|---|---|---|
| Septin 7 | Q16181 | | SEPT7 | IKIYEFPETDDEEENKLVK (SEQ ID NO: 76) |
| actinin, alpha | P12814 | Yes | ACTN1 | VGWEQLLTTIAR (SEQ ID NO: 77)<br>FAIQDISVEETSAK (SEQ ID NO: 78)<br>TINEVENQILTR (SEQ ID NO: 79)<br>RDQALTEEHAR (SEQ ID NO: 80) |
| actinin, alpha | O43707 | Yes | ACTN4 | DYETATLSDIK (SEQ ID NO: 81)<br>ISNRPAFMPSEGK (SEQ ID NO: 82) |
| AHNAK nucleoprotein | Q09666 | Yes | AHNAK | VPGIDATTK (SEQ ID NO: 83)<br>GEGPEVDVNLPK (SEQ ID NO: 84)<br>FSMPGFK (SEQ ID NO: 85)<br>IGFSGPKLEGGEVDLKGPK (SEQ ID NO: 86)<br>ISMPDFDLHLK (SEQ ID NO: 87)<br>ISMPDIDLNLK (SEQ ID NO: 88)<br>GEGPDVHMTLPKGDISISGPK (SEQ ID NO: 89)<br>GDLDASVPSMK (SEQ ID NO: 90) |

TABLE 5-continued

Proteins correlated with the sensitivity of 27 sarcoma cell lines to compound 2 as identified by LC/MS based protein profiling.

| Protein name | Swiss-protein ID | Identified by microarray | Gene name | Peptide sequence |
|---|---|---|---|---|
| Plasma membrane calcium-transporting ATPase 4 | P23634 | | ATP2B4 | TSPVEGLSGNPADLEK (SEQ ID NO: 91) |
| ATP synthase, H+ transporting, mitochondrial F1 complex | Q9Y653 | Yes | ATP5G | PADGILIQGNDLK (SEQ ID NO: 92) TIAMDGTEGLVR (SEQ ID NO: 93) |
| Creatine Kinase, brain | | Yes | CKB | FCTGLTQIETLFK (SEQ ID NO: 94) |
| chloride intracelluar protein 1 | O00299 | Yes | CLIC1 | GVTFNVTTVDTK (SEQ ID NO: 95) |
| catenin | | Yes | CTNNA1 | HVNPVQALSEFK (SEQ ID NO: 96) |
| destrin | P60981 | Yes | DSTN | YALYDASFETK (SEQ ID NO: 97) |
| myoferlin | Q9NZM1 | Yes | FER1L3 | VGETIIDLENR (SEQ ID NO: 98) |
| filamin B | | Yes | FLNB | GDYVLAVK (SEQ ID NO: 99) |
| G protein-coupled receptor 56 | | Yes | GPR56 | SSLHYKPTPDLR (SEQ ID NO: 100) |
| histone 2 | Q99877 | Yes | H2AFY2 | ESYSVYVYK (SEQ ID NO: 101) |
| histone 3 | | Yes | HIST3H3 | YRPGTVALR (SEQ ID NO: 102) |
| high mobility protein 1 | | | HMGB1 | KHPDASVNFSEFSK (SEQ ID NO: 103) |
| high mobility protein 2 | | Yes | HMGB2 | MSSYAFFVQTCR (SEQ ID NO: 104) |
| heterogeneous nuclear ribonucleoprotein | | Yes | HNRPA3 | LTDCVVMR (SEQ ID NO: 105) |
| heterogeneous nuclear ribonucleoprotein | P09651 | Yes | HRNPA1 | NQGGYGGSSSSSSYGSGR (SEQ ID NO: 106) |
| heterogeneous nuclear ribonucleoprotein | | Yes | HRNPA2 | EDSQRPGAHLTVK (SEQ ID NO: 107) GFGFVTFDDHDPVDK (SEQ ID NO: 108) |
| heterogeneous nuclear ribonucleoprotein | Q14103 | Yes | HRNPD | GFGFVLFK (SEQ ID NO: 109) |
| heterogeneous nuclear ribonucleoprotein | | Yes | HRNPK | IILDLISESPIK (SEQ ID NO: 110) |
| heterogeneous nuclear ribonucleoprotein | | Yes | HRNPM | AFITNIPFDVK (SEQ ID NO: 111) |
| KH domain containing, RNA binding, signal transduction associated 1 | Q07666 | Yes | KHDRBS1 | DSLDPSFTHAMQLLTAEIEK (SEQ ID NO: 112) |
| LIM domain and actin binding | Q9UHB6 | | LIMA1 | YPHIKDGEDLK (SEQ ID NO: 113) SNTENLSQHFR (SEQ ID NO: 114) |

TABLE 5-continued

Proteins correlated with the sensitivity of 27 sarcoma cell lines to compound 2 as identified by LC/MS based protein profiling.

| Protein name | Swiss-protein ID | Identified by microarray | Gene name | Peptide sequence |
|---|---|---|---|---|
| matrin 3 | | Yes | MATR3 | MKSQAFIEMETR (SEQ ID NO: 115) YQLLQLVEPFGVISNHLILNK (SEQ ID NO: 116) DLSAAGIGLLAAATQSLSMPASLGR (SEQ ID NO: 117) |
| myosin heavy chain | | Yes | MYH9 | VVFQEFR (SEQ ID NO: 118) |
| | | | | LQQELDDLLVDLDHQR (SEQ ID NO: 119) VISGVLQLGNIVFK (SEQ ID NO: 120) LDPHLVLDQLR (SEQ ID NO: 121) IVGLDQVTGMTETAFGSAYK (SEQ ID NO: 122) |
| myosin light chain | O00159 | Yes | MYL6 | HVLVTLGEK (SEQ ID NO: 123) |
| | | | | EAFQLFDR (SEQ ID NO: 124) |
| lactate dehydrogenase | P07195 | | LDHB | IVVVTAGVR (SEQ ID NO: 125) |
| histone H2B | | Yes | NP_00351 | AMGIMNSFVNDIFER (SEQ ID NO: 126) |
| Annexin A2 | P07355 | Yes | ANXA2 | TPAQYDASELK (SEQ ID NO: 127) |
| Clathrin heavy chain 1 | Q00610 | Yes | CLTC | IVLDNSVFSEHR (SEQ ID NO: 128) |
| tublin, alpha | P68363 | | NP_006073 | FDLMYAK (SEQ ID NO: 129) LDHKFDLMYAK (SEQ ID NO: 130) |
| calcium binding protein P22 | Q99653 | | NP_009167 | ETGFSHSQITR (SEQ ID NO: 131) |
| | | | | ISRDELLQVLR (SEQ ID NO: 132) |
| cleavage and polyadenylation specific factor 1 | Q10570 | Yes | CPSF1 | MYAVYK (SEQ ID NO: 133) |
| poly rC binding protein | | Yes | PCBP2 | IITLTGPTNAIFK (SEQ ID NO: 134) |
| peroxiredoxin | P30041 | Yes | PRDX6 | LPFPIIDDR (SEQ ID NO: 135) |
| protein tyrosine phosphatase, receptor type, F | | | PTPRF | YANVIAYDHSR (SEQ ID NO: 136) |
| Radixin | P35241 | | RDX | KALELDQER (SEQ ID NO: 137) KENPLQFK (SEQ ID NO: 138) |
| splicing factor proline/glutamine rich | | | SFPQ | LFVGNLPADITEDEFKR (SEQ ID NO: 139) |
| spectrin, beta | O15020 | | SPTBN2 | VGDLYSDLRDGR (SEQ ID NO: 140) AAMRETWLSENQR (SEQ ID NO: 141) |
| Stathmin | P16949 | Yes | STMN1 | DLSLEEIQK (SEQ ID NO: 142) |
| Syntaxin | O15400 | Yes | STX7 | TLNQLGTPQDSPELR (SEQ ID NO: 143) |
| thymoprotein | | | TMPO | YGVNPGPIVGTTR (SEQ ID NO: 144) |
| Tubulin beta-2 chain | P05217 | Yes | TUBB2C | EIVHIQAGQCGNQIGAK (SEQ ID NO: 145) |

The peptide ions were selected by the overlaps between the two statistic analyses: t-test (p < 0.001 and 2 fold between the groups of 13 sensitive cell lines and 14 resistant cell lines) and the Pearson correlations between the log2($IC_{50}$) data and the expression level of each peptide ion in the 27 cell lines (p < 0.001).
The peptide ions generated from statistical analyses were sequenced by tandem mass spectrometry to get the identification of the proteins which are listed in this Table.
The name of protein and gene, the sequence of each peptide ion associated with identified protein are listed.
The overlap with Affymetrix gene expression results also indicated.

In general, a higher number of genes than proteins was identified using the same statistic analyses due to the complicity of the protein profiling technology. Cross comparing the gene and protein profiling results, the overlaps between identified genes and proteins are significantly large as indicated in Tables 4 and 5. 71.7% (33 out 46) proteins for compound 1 and 73.3% (33 out 45) proteins for compound 2 also identified in gene expression profiling, respectively, suggesting good concordance between the results detected by the two technologies. For some of the markers identified by the protein profiling, for example, ATP2B4, it was also detected as significantly differentially expressed between the sensitive and resistant cell lines (−2.3 fold and p values are 0.0043 and 0.0016 for t-test and correlation test, respectively) by gene profiling, yet did not meet the stringent statistical cutoff of p values of 0.001.

Genes/Proteins Modulated by IGF1R Inhibitor Compound 1 Treatment:

There is differential sensitivity of compound 1 in a pair of human RMS cell lines, Rh36 (resistant, $IC_{50}$=1.6 μM) and Rh41 (sensitive, $IC_{50}$=0.069 μM). In order to understand the mechanism of the differential sensitivity, both cell lines were evaluated using gene expression profiling and proteomics analyses to search at genomics scale for genes or proteins that are differentially modulated by IGF1R inhibitor compound 1 in a time course study with the drug treatment for 6, 30 and 72 hours. Cell lysates were subjected in parallel to microarray and LC/MS based "bottom-up" protein profiling analyses. A two-way ANOVA mixed model was utilized to identify drug treatment effect as well as treatment and time interaction on the expression of genes and protein. Overall, there were some mRNA transcripts or peptides with expression change upon the drug treatment in Rh36 cell line at 6 hr, and these changes mainly reflected the initial stress response to the stimuli the cell encountered. However, the drug had little to no effect at later time points, 36 and 72 hrs in Rh36 cells. This makes sense for the given concentration of compound 1 cell treated, Rh36 is highly resistant, so the drug had little effect on cell growth compared to the sensitive cell Rh41, which had dramatic changes in gene/protein expression. The genes and protein that were modulated by compound 1 in the sensitive RH41 cell line are listed in Table 6 and Table 7, respectively.

TABLE 6

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 213880_at | AL524520 | LGR5 | leucine-rich repeat-containing G protein-coupled receptor 5 | 0.0007 | 0.9280 | 3.5 |
| 203131_at | NM_006206 | PDGFRA | platelet-derived growth factor receptor, alpha polypeptide | 0.0011 | 0.6916 | 3.3 |
| 219106_s_at | NM_006063 | KBTBD10 | kelch repeat and BTB (POZ) domain containing 10 | 0.0007 | 0.0666 | 2.6 |
| 207558_s_at | NM_000325 | PITX2 | paired-like homeodomain transcription factor 2 | 0.0130 | 0.8149 | 2.3 |
| 212614_at | BG285011 | ARID5B | AT rich interactive domain 5B (MRF1-like) | 0.0005 | 0.2446 | 2.3 |
| 214375_at | AI962377 | PPFIBP1 /// LOC440091 /// LOC729222 | PTPRF interacting protein, binding protein 1 (liprin beta 1) /// similar to Liprin-beta 1 (Protein tyrosine phosphatase receptor type f polypeptide-interacting protein binding protein 1) (PTPRF-interacting protein binding protein 1) (hSGT2) /// similar to PTPRF interacting protein binding protein 1 isoform 1 | 0.0030 | 0.0721 | 2.2 |
| 209102_s_at | AF019214 | HBP1 | HMG-box transcription factor 1 | 0.0004 | 0.0424 | 2.2 |
| 216321_s_at | X03348 | NR3C1 | nuclear receptor subfamily 3, group C, member 1 (glucocorticoid receptor) | 0.0059 | 0.2261 | 2.1 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 209199_s_at | N22468 | MEF2C | MADS box transcription enhancer factor 2, polypeptide C (myocyte enhancer factor 2C) | 0.0022 | 0.2701 | 2.1 |
| 202364_at | NM_005962 | MXI1 | MAX interactor 1 /// MAX interactor 1 | 0.0014 | 0.4787 | 2.0 |
| 213624_at | AA873600 | SMPDL3A | sphingomyelin phosphodiesterase, acid-like 3A | 0.0027 | 0.5082 | 2.0 |
| 218258_at | NM_015972 | POLR1D | polymerase (RNA) I polypeptide D, 16 kDa | 0.0006 | 0.0546 | 2.0 |
| 220416_at | NM_024837 | ATP8B4 | ATPase, Class I, type 8B, member 4 | 0.0056 | 0.4286 | 2.0 |
| 212148_at | AL049381 | PBX1 | Pre-B-cell leukemia transcription factor 1 | 0.0024 | 0.5563 | 2.0 |
| 205923_at | NM_005045 | RELN | reelin | 0.0020 | 0.3396 | 2.0 |
| 213891_s_at | AI927067 | — | CDNA FLJ11918 fis, clone HEMBB1000272 | 0.0029 | 0.3970 | 2.0 |
| 206306_at | NM_001036 | RYR3 | ryanodine receptor 3 | 0.0014 | 0.2488 | 1.9 |
| 214608_s_at | AJ000098 | EYA1 | eyes absent homolog 1 (*Drosophila*) | 0.0007 | 0.0714 | 1.9 |
| 221217_s_at | NM_018723 | A2BP1 | ataxin 2-binding protein 1 | 0.0015 | 0.0721 | 1.9 |
| 213593_s_at | AW978896 | TRA2A | transformer-2 alpha | 0.0153 | 0.4675 | 1.9 |
| 203628_at | H05812 | IGF1R | insulin-like growth factor 1 receptor | 0.0017 | 0.0401 | 1.9 |
| 212406_s_at | AB028973 | PCMTD2 | protein-L-isoaspartate (D-aspartate) O-methyltransferase domain containing 2 | 0.0007 | 0.5279 | 1.9 |
| 213139_at | AI572079 | SNAI2 | snail homolog 2 (*Drosophila*) | 0.0064 | 0.3069 | 1.9 |
| 215123_at | AL049250 | LOC23117 /// LOC339047 /// LOC642778 /// LOC642799 /// LOC728888 | KIAA0220-like protein /// hypothetical protein LOC339047 /// similar to nuclear pore complex interacting protein /// similar to nuclear pore complex interacting protein /// similar to Protein KIAA0220 | 0.0116 | 0.4345 | 1.9 |
| 220751_s_at | NM_016348 | C5orf4 | chromosome 5 open reading frame 4 | 0.0038 | 0.3618 | 1.9 |
| 205619_s_at | NM_004527 | MEOX1 | mesenchyme homeobox 1 | 0.0072 | 0.1300 | 1.8 |
| 218694_at | NM_016608 | ARMCX1 | armadillo repeat containing, X-linked 1 | 0.0021 | 0.2291 | 1.8 |
| 201739_at | NM_005627 | SGK | serum/glucocorticoid regulated kinase | 0.0025 | 0.3263 | 1.8 |
| 221899_at | AI809961 | PFAAP5 | Phosphonoformate immuno-associated protein 5 | 0.0076 | 0.5328 | 1.8 |
| 217989_at | NM_016245 | HSD17B11 | hydroxysteroid (17-beta) dehydrogenase 11 | 0.0010 | 0.2141 | 1.8 |
| 204030_s_at | NM_014575 | SCHIP1 | schwannomin interacting protein 1 | 0.0019 | 0.5363 | 1.8 |
| 205741_s_at | NM_001392 | DTNA | dystrobrevin, alpha | 0.0038 | 0.5200 | 1.8 |
| 203753_at | NM_003199 | TCF4 | transcription factor 4 | 0.0034 | 0.0971 | 1.8 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 219961_s_at | NM_018474 | C20orf19 | chromosome 20 open reading frame 19 | 0.0043 | 0.7121 | 1.8 |
| 201384_s_at | NM_005899 | NBR1 /// LOC727732 | neighbor of BRCA1 gene 1 /// similar to neighbor of BRCA1 gene 1 | 0.0015 | 0.8006 | 1.8 |
| 211341_at | L20433 | POU4F1 | POU domain, class 4, transcription factor 1 | 0.0030 | 0.0990 | 1.8 |
| 203408_s_at | NM_002971 | SATB1 | special AT-rich sequence binding protein 1 (binds to nuclear matrix/scaffold-associating DNA's) | 0.0011 | 0.0695 | 1.8 |
| 200632_s_at | NM_006096 | NDRG1 | N-myc downstream regulated gene 1 | 0.0057 | 0.0839 | 1.7 |
| 204019_s_at | NM_015677 | SH3YL1 | SH3 domain containing, Ysc84-like 1 (*S. cerevisiae*) | 0.0079 | 0.1130 | 1.7 |
| 207327_at | NM_004100 | EYA4 | eyes absent homolog 4 (*Drosophila*) | 0.0058 | 0.1761 | 1.7 |
| 213435_at | AB028957 | SATB2 | SATB family member 2 | 0.0081 | 0.5816 | 1.7 |
| 219935_at | NM_007038 | ADAMTS5 | ADAM metallopeptidase with thrombospondin type 1 motif, 5 (aggrecanase-2) | 0.0030 | 0.0441 | 1.7 |
| 209112_at | BC001971 | CDKN1B | cyclin-dependent kinase inhibitor 1B (p27, Kip1) | 0.0044 | 0.2948 | 1.7 |
| 201294_s_at | N24643 | WSB1 | WD repeat and SOCS box-containing 1 | 0.0100 | 0.1315 | 1.7 |
| 221589_s_at | AW612403 | ALDH6A1 | aldehyde dehydrogenase 6 family, member A1 | 0.0135 | 0.6528 | 1.7 |
| 209479_at | BC000758 | CCDC28A | coiled-coil domain containing 28A | 0.0071 | 0.2439 | 1.7 |
| 200921_s_at | NM_001731 | BTG1 | B-cell translocation gene 1, anti-proliferative | 0.0085 | 0.7445 | 1.7 |
| 212179_at | AW157501 | C6orf111 | chromosome 6 open reading frame 111 | 0.0238 | 0.4713 | 1.7 |
| 203824_at | NM_004616 | TSPAN8 | tetraspanin 8 | 0.0167 | 0.6494 | 1.7 |
| 204297_at | NM_002647 | PIK3C3 | phosphoinositide-3-kinase, class 3 | 0.0051 | 0.5000 | 1.7 |
| 209185_s_at | AF073310 | IRS2 | insulin receptor substrate 2 | 0.0021 | 0.8649 | 1.7 |
| 202551_s_at | BG546884 | CRIM1 | cysteine rich transmembrane BMP regulator 1 (chordin-like) | 0.0111 | 0.1974 | 1.7 |
| 213782_s_at | BF939176 | MYOZ2 | myozenin 2 | 0.0121 | 0.8529 | 1.7 |
| 212761_at | AI949687 | TCF7L2 | transcription factor 7-like 2 (T-cell specific, HMG-box) | 0.0012 | 0.1631 | 1.7 |
| 202028_s_at | BC000603 | RPL38 | ribosomal protein L38 | 0.0118 | 0.1143 | 1.7 |
| 207401_at | NM_002763 | PROX1 | prospero-related homeobox 1 | 0.0305 | 0.2292 | 1.7 |
| 204851_s_at | AF040254 | DCX | doublecortex; lissencephaly, X-linked (doublecortin) | 0.0302 | 0.0565 | 1.7 |
| 202553_s_at | NM_015484 | SYF2 | SYF2 homolog, RNA splicing factor (*S. cerevisiae*) | 0.0015 | 0.2787 | 1.7 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 209034_at | AF279899 | PNRC1 | proline-rich nuclear receptor coactivator 1 | 0.0093 | 0.6717 | 1.7 |
| 217906_at | NM_014315 | KLHDC2 | kelch domain containing 2 | 0.0017 | 0.6814 | 1.7 |
| 208671_at | AF164794 | SERINC1 | serine incorporator 1 | 0.0044 | 0.3841 | 1.7 |
| 206854_s_at | NM_003188 | MAP3K7 | mitogen-activated protein kinase kinase kinase 7 | 0.0007 | 0.0592 | 1.6 |
| 221841_s_at | BF514079 | KLF4 | Kruppel-like factor 4 (gut) | 0.0068 | 0.1692 | 1.6 |
| 203810_at | BG252490 | DNAJB4 | DnaJ (Hsp40) homolog, subfamily B, member 4 | 0.0037 | 0.2405 | 1.6 |
| 210858_x_at | U26455 | ATM | ataxia telangiectasia mutated (includes complementation groups A, C and D) | 0.0045 | 0.0493 | 1.6 |
| 218645_at | NM_021994 | ZNF277P | zinc finger protein 277 pseudogene | 0.0030 | 0.1008 | 1.6 |
| 218142_s_at | NM_016302 | CRBN | cereblon | 0.0012 | 0.1954 | 1.6 |
| 206363_at | NM_005360 | MAF | v-maf musculoaponeurotic fibrosarcoma oncogene homolog (avian) | 0.0089 | 0.5222 | 1.6 |
| 220917_s_at | NM_025132 | WDR19 | WD repeat domain 19 | 0.0010 | 0.2438 | 1.6 |
| 213413_at | BG434174 | STON1 | stonin 1 | 0.0079 | 0.7123 | 1.6 |
| 203227_s_at | NM_005981 | TSPAN31 | tetraspanin 31 | 0.0079 | 0.3100 | 1.6 |
| 222273_at | AI419423 | PAPOLG | poly(A) polymerase gamma | 0.0365 | 0.6023 | 1.6 |
| 202160_at | NM_004380 | CREBBP | CREB binding protein (Rubinstein-Taybi syndrome) | 0.0026 | 0.3771 | 1.6 |
| 202105_at | NM_001551 | IGBP1 | immunoglobulin (CD79A) binding protein 1 | 0.0004 | 0.0261 | 1.6 |
| 215450_at | W87901 | — | — | 0.0185 | 0.1143 | 1.6 |
| 217988_at | NM_021178 | CCNB1IP1 | cyclin B1 interacting protein 1 | 0.0005 | 0.0571 | 1.6 |
| 212956_at | AI348094 | TBC1D9 | TBC1 domain family, member 9 (with GRAM domain) | 0.0005 | 0.0274 | 1.6 |
| 212448_at | AB007899 | NEDD4L | neural precursor cell expressed, developmentally down-regulated 4-like | 0.0043 | 0.4684 | 1.6 |
| 203789_s_at | NM_006379 | SEMA3C | sema domain, immunoglobulin domain (Ig), short basic domain, secreted, (semaphorin) 3C | 0.0051 | 0.3375 | 1.6 |
| 214683_s_at | AI251890 | CLK1 | CDC-like kinase 1 | 0.0358 | 0.7292 | 1.6 |
| 201008_s_at | AA812232 | TXNIP | thioredoxin interacting protein | 0.0060 | 0.3503 | 1.6 |
| 209212_s_at | AB030824 | KLF5 | Kruppel-like factor 5 (intestinal) | 0.0074 | 0.4147 | 1.6 |
| 215043_s_at | X83301 | SMA3 /// SMA5 | SMA3 /// SMA5 | 0.0240 | 0.8101 | 1.6 |
| 218603_at | NM_016217 | HECA | headcase homolog (Drosophila) | 0.0026 | 0.3544 | 1.6 |
| 219599_at | NM_018507 | PRO1843 | hypothetical protein PRO1843 | 0.0213 | 0.5078 | 1.6 |
| 212616_at | BF668950 | CHD9 | chromodomain helicase DNA binding protein 9 | 0.0061 | 0.6115 | 1.6 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 210111_s_at | AF277175 | KIAA0265 | KIAA0265 protein | 0.0024 | 0.5594 | 1.6 |
| 213258_at | BF511231 | TFPI | tissue factor pathway inhibitor (lipoprotein-associated coagulation inhibitor) | 0.0050 | 0.2677 | 1.6 |
| 217627_at | BE515346 | ZNF573 | zinc finger protein 573 | 0.0188 | 0.3191 | 1.6 |
| 213032_at | AI186739 | NFIB | nuclear factor I/B | 0.0041 | 0.0563 | 1.6 |
| 215071_s_at | AL353759 | HIST1H2AC | histone cluster 1, H2ac | 0.0021 | 0.1437 | 1.6 |
| 206059_at | NM_003430 | ZNF91 | zinc finger protein 91 | 0.0109 | 0.0953 | 1.6 |
| 218168_s_at | NM_020247 | CABC1 | chaperone, ABC1 activity of bc1 complex homolog (*S. pombe*) | 0.0046 | 0.3869 | 1.6 |
| 201465_s_at | BC002646 | JUN | jun oncogene | 0.0055 | 0.0800 | 1.6 |
| 218643_s_at | NM_014171 | CRIPT | cysteine-rich PDZ-binding protein | 0.0078 | 0.7762 | 1.6 |
| 213655_at | AA502643 | PAFAH1B1 | Platelet-activating factor acetylhydrolase, isoform Ib, alpha subunit 45 kDa | 0.0017 | 0.0157 | 1.6 |
| 206565_x_at | NM_006780 | SMA3 | SMA3 | 0.0055 | 0.8548 | 1.6 |
| 203298_s_at | NM_004973 | JARID2 | jumonji, AT rich interactive domain 2 | 0.0007 | 0.0705 | 1.6 |
| 216623_x_at | AK025084 | TNRC9 | trinucleotide repeat containing 9 | 0.0255 | 0.7718 | 1.6 |
| 204485_s_at | NM_005486 | TOM1L1 | target of myb1-like 1 (chicken) | 0.0016 | 0.3551 | 1.6 |
| 205431_s_at | NM_021073 | BMP5 | bone morphogenetic protein 5 | 0.0075 | 0.3673 | 1.6 |
| 205054_at | NM_004543 | NEB | nebulin | 0.0015 | 0.2275 | 1.6 |
| 209750_at | N32859 | NR1D2 | nuclear receptor subfamily 1, group D, member 2 | 0.0270 | 0.0803 | 1.6 |
| 208131_s_at | NM_000961 | PTGIS | prostaglandin I2 (prostacyclin) synthase /// prostaglandin I2 (prostacyclin) synthase | 0.0025 | 0.0783 | 1.6 |
| 219679_s_at | NM_018604 | WAC | WW domain containing adaptor with coiled-coil | 0.0129 | 0.1806 | 1.6 |
| 221763_at | AI694023 | JMJD1C | jumonji domain containing 1C | 0.0007 | 0.0389 | 1.6 |
| 203420_at | NM_016255 | FAM8A1 | family with sequence similarity 8, member A1 | 0.0043 | 0.1789 | 1.6 |
| 210102_at | BC001234 | LOH11CR2A | loss of heterozygosity, 11, chromosomal region 2, gene A | 0.0183 | 0.4585 | 1.5 |
| 212936_at | AI927701 | C5orf21 | chromosome 5 open reading frame 21 | 0.0020 | 0.1531 | 1.5 |
| 204726_at | NM_001257 | CDH13 | cadherin 13, H-cadherin (heart) | 0.0388 | 0.7671 | 1.5 |
| 202832_at | NM_014635 | GCC2 | GRIP and coiled-coil domain containing 2 | 0.0047 | 0.2332 | 1.5 |
| 203510_at | BG170541 | MET | met proto-oncogene (hepatocyte growth factor receptor) | 0.0049 | 0.3651 | 1.5 |
| 207186_s_at | NM_004459 | BPTF | bromodomain PHD finger transcription factor | 0.0135 | 0.2421 | 1.5 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 212593_s_at | N92498 | PDCD4 | programmed cell death 4 (neoplastic transformation inhibitor) | 0.0059 | 0.7650 | 1.5 |
| 203491_s_at | AI123527 | CEP57 | centrosomal protein 57 kDa | 0.0149 | 0.1552 | 1.5 |
| 217100_s_at | AK026451 | UBXD7 | UBX domain containing 7 | 0.0069 | 0.2624 | 1.5 |
| 210346_s_at | AF212224 | CLK4 | CDC-like kinase 4 | 0.0007 | 0.0252 | 1.5 |
| 218277_s_at | NM_024612 | DHX40 | DEAH (Asp-Glu-Ala-His) box polypeptide 40 | 0.0049 | 0.6421 | 1.5 |
| 212764_at | AI806174 | — | — | 0.0031 | 0.1646 | 1.5 |
| 207170_s_at | NM_015416 | LETMD1 | LETM1 domain containing 1 | 0.0020 | 0.4216 | 1.5 |
| 213939_s_at | AI871641 | RUFY3 | RUN and FYVE domain containing 3 | 0.0143 | 0.7780 | 1.5 |
| 210962_s_at | AB019691 | AKAP9 | A kinase (PRKA) anchor protein (yotiao) 9 | 0.0062 | 0.7228 | 1.5 |
| 201637_s_at | NM_005087 | FXR1 | fragile X mental retardation, autosomal homolog 1 | 0.0100 | 0.6502 | 1.5 |
| 200965_s_at | NM_006720 | ABLIM1 | actin binding LIM protein 1 | 0.0017 | 0.0274 | 1.5 |
| 203139_at | NM_004938 | DAPK1 | death-associated protein kinase 1 | 0.0051 | 0.8963 | 1.5 |
| 201737_s_at | NM_005885 | 6-Mar | membrane-associated ring finger (C3HC4) 6 | 0.0112 | 0.5449 | 1.5 |
| 221190_s_at | NM_013326 | C18orf8 | chromosome 18 open reading frame 8 | 0.0095 | 0.4956 | 1.5 |
| 218330_s_at | NM_018162 | NAV2 | neuron navigator 2 | 0.0163 | 0.7871 | 1.5 |
| 217783_s_at | NM_016061 | YPEL5 | yippee-like 5 (Drosophila) | 0.0033 | 0.1201 | 1.5 |
| 205824_at | NM_001541 | HSPB2 | heat shock 27 kDa protein 2 | 0.0139 | 0.6070 | 1.5 |
| 211675_s_at | AF054589 | MDFIC | MyoD family inhibitor domain containing /// MyoD family inhibitor domain containing | 0.0029 | 0.1408 | 1.5 |
| 218625_at | NM_016588 | NRN1 | neuritin 1 | 0.0465 | 0.5695 | 1.5 |
| 214016_s_at | AL558875 | SFPQ | splicing factor proline/glutamine-rich (polypyrimidine tract binding protein associated) | 0.0146 | 0.5232 | 1.5 |
| 212634_at | AW298092 | KIAA0776 | KIAA0776 | 0.0198 | 0.0537 | 1.5 |
| 213002_at | AA770596 | MARCKS | Myristoylated alanine-rich protein kinase C substrate | 0.0105 | 0.1001 | 1.5 |
| 212654_at | AL566786 | TPM2 /// PPIL5 | tropomyosin 2 (beta) /// peptidylprolyl isomerase (cyclophilin)-like 5 | 0.0166 | 0.6932 | 1.5 |
| 200962_at | AI348010 | RPL31 /// LOC285260 /// RPL31P4 /// RPL31P10 /// LOC641790 /// LOC646841 /// LOC648737 /// | ribosomal protein L31 /// similar to ribosomal protein L31 /// ribosomal protein L31 pseudogene 4 /// ribosomal protein L31 pseudogene 10 /// similar to ribosomal protein L31 /// similar to ribosomal protein L31 /// similar to | 0.0047 | 0.3069 | 1.5 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| | | LOC653773 /// LOC727792 /// LOC729646 /// LOC732015 | ribosomal protein L31 /// similar to ribosomal protein L31 /// similar to ribosomal protein L31 /// hypothetical protein LOC729646 /// similar to ribosomal protein L31 | | | |
| 217591_at | BF725121 | SKIL | SKI-like oncogene | 0.0284 | 0.1213 | 1.5 |
| 211161_s_at | AF130082 | COL3A1 | collagen, type III, alpha 1 (Ehlers-Danlos syndrome type IV, autosomal dominant) | 0.0016 | 0.4548 | 1.5 |
| 208796_s_at | BC000196 | CCNG1 | cyclin G1 | 0.0018 | 0.2131 | 1.5 |
| 214042_s_at | AW071997 | RPL22 | ribosomal protein L22 | 0.0007 | 0.0592 | 1.5 |
| 220755_s_at | NM_016947 | C6orf48 | chromosome 6 open reading frame 48 | 0.0005 | 0.1746 | 1.5 |
| 212665_at | AL556438 | TIPARP | TCDD-inducible poly(ADP-ribose) polymerase | 0.0025 | 0.2295 | 1.5 |
| 212773_s_at | BG165094 | TOMM20 | translocase of outer mitochondrial membrane 20 homolog (yeast) | 0.0188 | 0.1173 | 1.5 |
| 212455_at | N36997 | YTHDC1 | YTH domain containing 1 | 0.0010 | 0.0732 | 1.5 |
| 201285_at | NM_013446 | MKRN1 | makorin, ring finger protein, 1 /// makorin, ring finger protein, 1 | 0.0045 | 0.9558 | 1.5 |
| 203140_at | NM_001706 | BCL6 | B-cell CLL/lymphoma 6 (zinc finger protein 51) /// B-cell CLL/lymphoma 6 (zinc finger protein 51) | 0.0135 | 0.6753 | 1.5 |
| 212451_at | N52532 | KIAA0256 | KIAA0256 gene product | 0.0190 | 0.0968 | 1.5 |
| 203002_at | NM_016201 | AMOTL2 | angiomotin like 2 | 0.0311 | 0.1937 | 1.5 |
| 208886_at | BC000145 | H1F0 | H1 histone family, member 0 | 0.0008 | 0.2034 | 1.5 |
| 204094_s_at | NM_014779 | TSC22D2 | TSC22 domain family, member 2 | 0.0034 | 0.5023 | 1.5 |
| 204822_at | NM_003318 | TTK | TTK protein kinase | 0.0086 | 0.1596 | 1.5 |
| 213241_at | AF035307 | PLXNC1 | plexin C1 | 0.0283 | 0.9168 | 1.5 |
| 209286_at | AI754416 | CDC42EP3 | CDC42 effector protein (Rho GTPase binding) 3 | 0.0050 | 0.2353 | 1.5 |
| 206572_x_at | NM_003429 | ZNF85 | zinc finger protein 85 | 0.0206 | 0.6963 | 1.5 |
| 222288_at | AI004009 | — | Transcribed locus, weakly similar to NP_001013658.1 protein LOC387873 [*Homo sapiens*] | 0.0045 | 0.2761 | 1.5 |
| 206829_x_at | NM_025189 | ZNF430 | zinc finger protein 430 | 0.0074 | 0.4605 | 1.5 |
| 214280_x_at | X79536 | HNRPA1 | heterogeneous nuclear ribonucleoprotein A1 | 0.0029 | 0.1967 | 1.5 |
| 217936_at | AW044631 | ARHGAP5 | Rho GTPase activating protein 5 | 0.0214 | 0.5528 | 1.5 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 212463_at | BE379006 | CD59 | CD59 molecule, complement regulatory protein | 0.0012 | 0.1864 | 1.5 |
| 208835_s_at | AW089673 | CROP | cisplatin resistance-associated overexpressed protein | 0.0311 | 0.1778 | 1.5 |
| 203640_at | BE328496 | MBNL2 | muscleblind-like 2 (*Drosophila*) | 0.0030 | 0.0670 | 1.4 |
| 218316_at | NM_012460 | TIMM9 | translocase of inner mitochondrial membrane 9 homolog (yeast) | 0.0042 | 0.1350 | 1.4 |
| 204920_at | AF154830 | CPS1 | carbamoyl-phosphate synthetase 1, mitochondrial | 0.0095 | 0.7685 | 1.4 |
| 205022_s_at | NM_005197 | CHES1 | checkpoint suppressor 1 | 0.0085 | 0.2652 | 1.4 |
| 205443_at | NM_003082 | SNAPC1 | small nuclear RNA activating complex, polypeptide 1, 43 kDa | 0.0038 | 0.0942 | 1.4 |
| 204215_at | NM_024315 | C7orf23 | chromosome 7 open reading frame 23 | 0.0100 | 0.3811 | 1.4 |
| 202023_at | NM_004428 | EFNA1 | ephrin-A1 | 0.0135 | 0.5642 | 1.4 |
| 203538_at | NM_001745 | CAMLG /// FAM39DP | calcium modulating ligand /// family with sequence similarity 39, member D pseudogene | 0.0082 | 0.0804 | 1.4 |
| 202976_s_at | NM_014899 | RHOBTB3 | Rho-related BTB domain containing 3 | 0.0039 | 0.1116 | 1.4 |
| 205811_at | NM_007215 | POLG2 | polymerase (DNA directed), gamma 2, accessory subunit | 0.0160 | 0.7714 | 1.4 |
| 218253_s_at | NM_006893 | LGTN | ligatin | 0.0064 | 0.2044 | 1.4 |
| 210312_s_at | BC002640 | IFT20 | intraflagellar transport 20 homolog (*Chlamydomonas*) | 0.0087 | 0.2350 | 1.4 |
| 217990_at | NM_016576 | GMPR2 | guanosine monophosphate reductase 2 | 0.0035 | 0.2297 | 1.4 |
| 204633_s_at | AF074393 | RPS6KA5 | ribosomal protein S6 kinase, 90 kDa, polypeptide 5 | 0.0232 | 0.5765 | 1.4 |
| 221499_s_at | AK026970 | STX16 | syntaxin 16 | 0.0114 | 0.1455 | 1.4 |
| 205954_at | NM_006917 | RXRG | retinoid X receptor, gamma | 0.0050 | 0.0389 | 1.4 |
| 202956_at | NM_006421 | ARFGEF1 | ADP-ribosylation factor guanine nucleotide-exchange factor 1(brefeldin A-inhibited) | 0.0270 | 0.6102 | 1.4 |
| 213844_at | NM_019102 | HOXA5 | homeobox A5 | 0.0046 | 0.1113 | 1.4 |
| 220924_s_at | NM_018976 | SLC38A2 | solute carrier family 38, member 2 | 0.0060 | 0.6814 | 1.4 |
| 209656_s_at | AL136550 | TMEM47 | transmembrane protein 47 | 0.0015 | 0.3325 | 1.4 |
| 208204_s_at | NM_001234 | CAV3 | caveolin 3 | 0.0078 | 0.9326 | 1.4 |
| 205872_x_at | NM_022359 | PDE4DIP | phosphodiesterase 4D interacting protein (myomegalin) | 0.0299 | 0.0719 | 1.4 |
| 213605_s_at | AL049987 | LOC728411 | Similar to Beta-glucuronidase precursor | 0.0399 | 0.3946 | 1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 201417_at | AL136179 | SOX4 | SRY (sex determining region Y)-box 4 | 0.0121 | 0.4154 | 1.4 |
| 200912_s_at | NM_001967 | EIF4A2 | eukaryotic translation initiation factor 4A, isoform 2 | 0.0005 | 0.0721 | 1.4 |
| 217987_at | NM_019048 | ASNSD1 | asparagine synthetase domain containing 1 | 0.0226 | 0.2254 | 1.4 |
| 212689_s_at | AA524505 | JMJD1A | jumonji domain containing 1A | 0.0012 | 0.1485 | 1.4 |
| 218268_at | NM_022771 | TBC1D15 | TBC1 domain family, member 15 | 0.0245 | 0.3320 | 1.4 |
| 201616_s_at | AL577531 | CALD1 | caldesmon 1 | 0.0442 | 0.2187 | 1.4 |
| 212675_s_at | AB011154 | — | — | 0.0149 | 0.7153 | 1.4 |
| 218397_at | NM_018062 | FANCL | Fanconi anemia, complementation group L | 0.0064 | 0.1684 | 1.4 |
| 209181_s_at | U49245 | RABGGTB | Rab geranylgeranyltransferase, beta subunit | 0.0031 | 0.1108 | 1.4 |
| 215983_s_at | D83768 | UBXD6 | UBX domain containing 6 | 0.0214 | 0.2921 | 1.4 |
| 209781_s_at | AF069681 | KHDRBS3 | KH domain containing, RNA binding, signal transduction associated 3 | 0.0013 | 0.3269 | 1.4 |
| 201200_at | NM_003851 | CREG1 | cellular repressor of E1A-stimulated genes 1 | 0.0121 | 0.2634 | 1.4 |
| 213619_at | AV753392 | HNRPH1 | Heterogeneous nuclear ribonucleoprotein H1 (H) | 0.0052 | 0.0417 | 1.4 |
| 201549_x_at | NM_006618 | JARID1B | jumonji, AT rich interactive domain 1B | 0.0176 | 0.5037 | 1.4 |
| 200899_s_at | NM_012215 | MGEA5 | meningioma expressed antigen 5 (hyaluronidase) | 0.0261 | 0.5721 | 1.4 |
| 218718_at | NM_016205 | PDGFC | platelet derived growth factor C | 0.0007 | 0.0280 | 1.4 |
| 201289_at | NM_001554 | CYR61 | cysteine-rich, angiogenic inducer, 61 | 0.0154 | 0.4485 | 1.4 |
| 202118_s_at | AA541758 | CPNE3 | copine III | 0.0079 | 0.0589 | 1.4 |
| 200620_at | NM_004872 | TMEM59 | transmembrane protein 59 | 0.0007 | 0.2260 | 1.4 |
| 213645_at | AF305057 | ENOSF1 | enolase superfamily member 1 | 0.0273 | 0.6899 | 1.4 |
| 202906_s_at | AF049895 | NBN | nibrin | 0.0383 | 0.0964 | 1.4 |
| 209205_s_at | BC003600 | LMO4 | LIM domain only 4 | 0.0029 | 0.1916 | 1.4 |
| 205361_s_at | AI718295 | PFDN4 | prefoldin subunit 4 | 0.0037 | 0.0482 | 1.4 |
| 208697_s_at | BC000734 | EIF3S6 | eukaryotic translation initiation factor 3, subunit 6 48 kDa | 0.0012 | 0.0582 | 1.4 |
| 203881_s_at | NM_004010 | DMD | dystrophin (muscular dystrophy, Duchenne and Becker types) | 0.0152 | 0.0504 | 1.4 |
| 202227_s_at | NM_006696 | BRD8 | bromodomain containing 8 | 0.0046 | 0.0774 | 1.4 |
| 201166_s_at | NM_014676 | PUM1 | pumilio homolog 1 (Drosophila) | 0.0007 | 0.5211 | 1.4 |
| 213967_at | AI634532 | LOC138046 | hypothetical protein LOC138046 | 0.0337 | 0.4178 | 1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 203117_s_at | NM_014871 | USP52 | ubiquitin specific peptidase 52 | 0.0177 | 0.5403 | 1.4 |
| 212209_at | AL133033 | THRAP2 | thyroid hormone receptor associated protein 2 | 0.0041 | 0.6494 | 1.4 |
| 204588_s_at | NM_003982 | SLC7A7 | solute carrier family 7 (cationic amino acid transporter, y+ system), member 7 | 0.0051 | 0.1846 | 1.4 |
| 214451_at | NM_003221 | TFAP2B | transcription factor AP-2 beta (activating enhancer binding protein 2 beta) | 0.0190 | 0.1948 | 1.4 |
| 215096_s_at | AU145746 | ESD | esterase D/formylglutathione hydrolase | 0.0032 | 0.1013 | 1.4 |
| 213224_s_at | AK025724 | LOC92482 | hypothetical protein LOC92482 | 0.0079 | 0.0654 | 1.4 |
| 201174_s_at | NM_018975 | TERF2IP | telomeric repeat binding factor 2, interacting protein | 0.0222 | 0.3358 | 1.4 |
| 201735_s_at | NM_001829 | CLCN3 | chloride channel 3 | 0.0415 | 0.3570 | 1.4 |
| 209130_at | BC003686 | SNAP23 | synaptosomal-associated protein, 23 kDa | 0.0124 | 0.1309 | 1.4 |
| 207992_s_at | NM_000480 | AMPD3 | adenosine monophosphate deaminase (isoform E) | 0.0015 | 0.0645 | 1.4 |
| 200091_s_at | AA888388 | RPS25 | ribosomal protein S25 /// ribosomal protein S25 | 0.0010 | 0.0877 | 1.4 |
| 221471_at | AW173623 | SERINC3 | serine incorporator 3 | 0.0041 | 0.1925 | 1.4 |
| 206132_at | NM_002387 | MCC | mutated in colorectal cancers | 0.0154 | 0.2417 | 1.4 |
| 207598_x_at | NM_005431 | XRCC2 | X-ray repair complementing defective repair in Chinese hamster cells 2 | 0.0088 | 0.0663 | 1.4 |
| 212530_at | AL080111 | NEK7 | NIMA (never in mitosis gene a)-related kinase 7 | 0.0110 | 0.9827 | 1.4 |
| 218343_s_at | NM_012086 | GTF3C3 | general transcription factor IIIC, polypeptide 3, 102 kDa | 0.0404 | 0.7847 | 1.4 |
| 217731_s_at | NM_021999 | ITM2B | integral membrane protein 2B | 0.0189 | 0.3784 | 1.4 |
| 218181_s_at | NM_017792 | MAP4K4 | mitogen-activated protein kinase kinase kinase kinase 4 | 0.0042 | 0.1923 | 1.4 |
| 209285_s_at | N38985 | C3orf63 | chromosome 3 open reading frame 63 | 0.0020 | 0.1860 | 1.4 |
| 215245_x_at | AA830884 | FMR1 | fragile X mental retardation 1 | 0.0393 | 0.5658 | 1.4 |
| 201922_at | NM_014886 | TINP1 | TGF beta-inducible nuclear protein 1 | 0.0004 | 0.0197 | 1.4 |
| 214800_x_at | R83000 | BTF3 | basic transcription factor 3 | 0.0015 | 0.0280 | 1.4 |
| 212498_at | AF056433 | — | Full-length cDNA clone CS0DM001YA04 of Fetal liver of *Homo sapiens* (human) | 0.0047 | 0.7550 | 1.4 |
| 209004_s_at | AF142481 | FBXL5 | F-box and leucine-rich repeat protein 5 | 0.0030 | 0.0800 | 1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 204568_at | NM_014924 | KIAA0831 | KIAA0831 | 0.0129 | 0.9702 | 1.4 |
| 216060_s_at | AK021890 | DAAM1 | dishevelled associated activator of morphogenesis 1 | 0.0055 | 0.0785 | 1.4 |
| 201877_s_at | NM_002719 | PPP2R5C | protein phosphatase 2, regulatory subunit B (B56), gamma isoform | 0.0049 | 0.1367 | 1.4 |
| 203155_at | NM_012432 | SETDB1 | SET domain, bifurcated 1 | 0.0110 | 0.2112 | 1.4 |
| 213762_x_at | AI452524 | RBMX | RNA binding motif protein, X-linked | 0.0029 | 0.2264 | 1.4 |
| 203638_s_at | NM_022969 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | 0.0029 | 0.1774 | 1.4 |
| 213186_at | BG502305 | DZIP3 | zinc finger DAZ interacting protein 3 | 0.0125 | 0.4348 | 1.4 |
| 218491_s_at | NM_014174 | THYN1 | thymocyte nuclear protein 1 | 0.0107 | 0.3964 | 1.4 |
| 218508_at | NM_018403 | DCP1A | DCP1 decapping enzyme homolog A (*S. cerevisiae*) | 0.0066 | 0.7693 | 1.4 |
| 204528_s_at | NM_004537 | NAP1L1 | nucleosome assembly protein 1-like 1 | 0.0015 | 0.0941 | 1.4 |
| 218919_at | NM_024699 | ZFAND1 | zinc finger, AN1-type domain 1 | 0.0024 | 0.0684 | 1.4 |
| 57715_at | W72694 | FAM26B | family with sequence similarity 26, member B | 0.0080 | 0.1016 | 1.4 |
| 217550_at | AA576497 | ATF6 | Activating transcription factor 6 | 0.0217 | 0.2505 | 1.4 |
| 212943_at | AB011100 | KIAA0528 | KIAA0528 | 0.0051 | 0.2420 | 1.4 |
| 219767_s_at | NM_005111 | CRYZL1 | crystallin, zeta (quinone reductase)-like 1 | 0.0048 | 0.8085 | 1.4 |
| 209861_s_at | U13261 | METAP2 | methionyl aminopeptidase 2 | 0.0166 | 0.2431 | 1.4 |
| 201779_s_at | AF070558 | RNF13 | ring finger protein 13 | 0.0009 | 0.0227 | 1.4 |
| 214749_s_at | AK000818 | ARMCX6 | armadillo repeat containing, X-linked 6 | 0.0125 | 0.1875 | 1.4 |
| 217266_at | Z97353 | RPL15 /// LOC402694 /// LOC646672 /// LOC653232 /// LOC728002 /// LOC728088 /// LOC728576 /// LOC730925 /// LOC731527 /// LOC731822 | ribosomal protein L15 /// similar to ribosomal protein L15 /// similar to ribosomal protein L15 /// similar to ribosomal protein L15 /// similar to ribosomal protein L15 /// similar to ribosomal protein L15 /// similar to ribosomal protein L15 /// similar to ribosomal protein L15 /// similar to ribosomal protein L15 /// similar to ribosomal protein L15 | 0.0072 | 0.5812 | 1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 221954_at | AA160474 | C20orf111 | Chromosome 20 open reading frame 111 | 0.0035 | 0.1674 | 1.4 |
| 212074_at | BE972774 | UNC84A | unc-84 homolog A (*C. elegans*) | 0.0051 | 0.2261 | 1.4 |
| 204131_s_at | N25732 | FOXO3A | forkhead box O3A | 0.0007 | 0.0981 | 1.4 |
| 222182_s_at | BG105204 | CNOT2 | CCR4-NOT transcription complex, subunit 2 | 0.0043 | 0.1023 | 1.4 |
| 205935_at | NM_001451 | FOXF1 | forkhead box F1 | 0.0102 | 0.5190 | 1.4 |
| 212812_at | AI700633 | SERINC5 | Serine incorporator 5 | 0.0069 | 0.3193 | 1.4 |
| 221580_s_at | BC001972 | JOSD3 | Josephin domain containing 3 | 0.0323 | 0.4333 | 1.4 |
| 217862_at | N24868 | PIAS1 | protein inhibitor of activated STAT, 1 | 0.0247 | 0.1807 | 1.4 |
| 201133_s_at | AA142966 | PJA2 | praja 2, RING-H2 motif containing | 0.0189 | 0.0968 | 1.4 |
| 208771_s_at | J02959 | LTA4H | leukotriene A4 hydrolase | 0.0004 | 0.0344 | 1.4 |
| 200074_s_at | U16738 | RPL14 /// RPL14L /// LOC649821 | ribosomal protein L14 /// ribosomal protein L14 /// ribosomal protein L14-like /// ribosomal protein L14-like /// similar to 60S ribosomal protein L14 (CAG-ISL 7) /// similar to 60S ribosomal protein L14 (CAG-ISL 7) | 0.0025 | 0.0963 | 1.4 |
| 212629_s_at | AI633689 | PKN2 | protein kinase N2 | 0.0106 | 0.0285 | 1.4 |
| 209786_at | BC001282 | HMGN4 | high mobility group nucleosomal binding domain 4 | 0.0124 | 0.1345 | 1.4 |
| 201738_at | NM_005875 | EIF1B | eukaryotic translation initiation factor 1B | 0.0100 | 0.1022 | 1.4 |
| 206114_at | NM_004438 | EPHA4 | EPH receptor A4 | 0.0198 | 0.1139 | 1.4 |
| 218361_at | NM_018178 | GOLPH3L | golgi phosphoprotein 3-like | 0.0087 | 0.5276 | 1.4 |
| 202467_s_at | NM_004236 | COPS2 | COP9 constitutive photomorphogenic homolog subunit 2 (*Arabidopsis*) | 0.0052 | 0.0436 | 1.4 |
| 219658_at | NM_024754 | PTCD2 | pentatricopeptide repeat domain 2 | 0.0065 | 0.4391 | 1.4 |
| 217971_at | NM_021970 | MAP2K1IP1 | mitogen-activated protein kinase kinase 1 interacting protein 1 | 0.0183 | 0.3561 | 1.4 |
| 212408_at | AK023204 | TOR1AIP1 | torsin A interacting protein 1 | 0.0299 | 0.1539 | 1.4 |
| 212795_at | AL137753 | KIAA1033 | KIAA1033 | 0.0500 | 0.9390 | 1.4 |
| 218004_at | NM_018045 | BSDC1 | BSD domain containing 1 | 0.0161 | 0.1788 | 1.4 |
| 205052_at | NM_001698 | AUH | AU RNA binding protein/enoyl-Coenzyme A hydratase | 0.0042 | 0.1537 | 1.4 |
| 203097_s_at | NM_014247 | RAPGEF2 | Rap guanine nucleotide exchange factor (GEF) 2 | 0.0399 | 0.3291 | 1.4 |
| 219077_s_at | NM_016373 | WWOX | WW domain containing oxidoreductase | 0.0069 | 0.1782 | 1.4 |
| 201917_s_at | AI694452 | SLC25A36 | solute carrier family 25, member 36 | 0.0420 | 0.0719 | 1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 203630_s_at | NM_006348 | COG5 | component of oligomeric golgi complex 5 | 0.0160 | 0.5887 | 1.4 |
| 216348_at | AL049693 | RPS17 /// LOC402057 | ribosomal protein S17 /// similar to 40S ribosomal protein S17 | 0.0045 | 0.2251 | 1.4 |
| 212111_at | AA628051 | STX12 | syntaxin 12 | 0.0054 | 0.2425 | 1.4 |
| 202214_s_at | NM_003588 | CUL4B | cullin 4B | 0.0074 | 0.4189 | 1.4 |
| 217807_s_at | NM_015710 | GLTSCR2 | glioma tumor suppressor candidate region gene 2 | 0.0015 | 0.0474 | 1.4 |
| 219138_at | BC000606 | RPL14 | ribosomal protein L14 | 0.0084 | 0.2776 | 1.4 |
| 212358_at | AL117468 | CLIPR-59 | CLIP-170-related protein | 0.0131 | 0.3968 | 1.4 |
| 221476_s_at | AF279903 | RPL15 | ribosomal protein L15 | 0.0016 | 0.0696 | 1.4 |
| 203781_at | NM_004891 | MRPL33 | mitochondrial ribosomal protein L33 | 0.0126 | 0.0635 | 1.4 |
| 221582_at | BC001193 | HIST3H2A | histone cluster 3, H2a | 0.0043 | 0.3642 | 1.4 |
| 208667_s_at | U17714 | ST13 | suppression of tumorigenicity 13 (colon carcinoma) (Hsp70 interacting protein) | 0.0140 | 0.0995 | 1.4 |
| 201358_s_at | NM_016451 | COPB1 | coatomer protein complex, subunit beta 1 | 0.0100 | 0.1582 | 1.4 |
| 211938_at | BF247371 | EIF4B | eukaryotic translation initiation factor 4B | 0.0050 | 0.1793 | 1.4 |
| 212044_s_at | BE737027 | RPL27A | Ribosomal protein L27a | 0.0457 | 0.5986 | 1.4 |
| 215978_x_at | AK021514 | LOC152719 | hypothetical protein LOC152719 | 0.0135 | 0.1439 | 1.4 |
| 203910_at | NM_004815 | ARHGAP29 | Rho GTPase activating protein 29 | 0.0201 | 0.5119 | 1.4 |
| 209682_at | U26710 | CBLB | Cas-Br-M (murine) ecotropic retroviral transforming sequence b | 0.0128 | 0.0489 | 1.3 |
| 202644_s_at | NM_006290 | TNFAIP3 | tumor necrosis factor, alpha-induced protein 3 | 0.0322 | 0.0856 | 1.3 |
| 212215_at | AB007896 | PREPL | prolyl endopeptidase-like | 0.0076 | 0.5632 | 1.3 |
| 218428_s_at | NM_016316 | REV1 | REV1 homolog (*S. cerevisiae*) | 0.0211 | 0.1542 | 1.3 |
| 217954_s_at | NM_015153 | PHF3 | PHD finger protein 3 | 0.0066 | 0.2171 | 1.3 |
| 212232_at | AB023231 | FNBP4 | formin binding protein 4 | 0.0204 | 0.5785 | 1.3 |
| 202231_at | NM_006360 | PCID1 | PCI domain containing 1 (herpesvirus entry mediator) | 0.0048 | 0.0923 | 1.3 |
| 202769_at | AW134535 | CCNG2 | cyclin G2 | 0.0230 | 0.3482 | 1.3 |
| 216221_s_at | D87078 | PUM2 | pumilio homolog 2 (*Drosophila*) | 0.0020 | 0.5905 | 1.3 |
| 213093_at | AI471375 | PRKCA | protein kinase C, alpha | 0.0006 | 0.0721 | 1.3 |
| 201926_s_at | BC001288 | CD55 | CD55 molecule, decay accelerating factor for complement (Cromer blood group) | 0.0261 | 0.3374 | 1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 218450_at | NM_015987 | HEBP1 | heme binding protein 1 | 0.0057 | 0.0971 | 1.3 |
| 218379_at | NM_016090 | RBM7 | RNA binding motif protein 7 | 0.0013 | 0.0274 | 1.3 |
| 212609_s_at | U79271 | AKT3 | V-akt murine thymoma viral oncogene homolog 3 (protein kinase B, gamma) | 0.0054 | 0.0969 | 1.3 |
| 215001_s_at | AL161952 | GLUL | glutamate-ammonia ligase (glutamine synthetase) | 0.0245 | 0.9178 | 1.3 |
| 209120_at | AL037401 | NR2F2 | nuclear receptor subfamily 2, group F, member 2 | 0.0147 | 0.5417 | 1.3 |
| 221593_s_at | BC001663 | RPL31 | ribosomal protein L31 | 0.0170 | 0.1235 | 1.3 |
| 212591_at | AA887480 | RBM34 | RNA binding motif protein 34 | 0.0130 | 0.1604 | 1.3 |
| 207719_x_at | NM_014812 | CEP170 | centrosomal protein 170 kDa | 0.0293 | 0.3400 | 1.3 |
| 205163_at | NM_013292 | MYLPF | fast skeletal myosin light chain 2 | 0.0118 | 0.1064 | 1.3 |
| 213136_at | AI828880 | PTPN2 | protein tyrosine phosphatase, non-receptor type 2 | 0.0039 | 0.2891 | 1.3 |
| 213750_at | AA928506 | — | Full length insert cDNA YH77E09 | 0.0015 | 0.0274 | 1.3 |
| 201682_at | NM_004279 | PMPCB | peptidase (mitochondrial processing) beta | 0.0022 | 0.4599 | 1.3 |
| 201448_at | AL046419 | TIA1 | TIA1 cytotoxic granule-associated RNA binding protein | 0.0430 | 0.4300 | 1.3 |
| 211962_s_at | BG250310 | ZFP36L1 | zinc finger protein 36, C3H type-like 1 | 0.0471 | 0.1958 | 1.3 |
| 214722_at | AW516297 | NOTCH2NL | Notch homolog 2 (*Drosophila*) N-terminal like | 0.0049 | 0.2858 | 1.3 |
| 202723_s_at | AW117498 | FOXO1A | forkhead box O1A (rhabdomyosarcoma) | 0.0019 | 0.3257 | 1.3 |
| 217993_s_at | NM_013283 | MAT2B | methionine adenosyltransferase II, beta | 0.0018 | 0.0583 | 1.3 |
| 216342_x_at | AL121916 | LOC390183 /// LOC442162 | similar to 40S ribosomal protein S4, X isoform /// similar to 40S ribosomal protein S4, X isoform | 0.0037 | 0.5394 | 1.3 |
| 217747_s_at | NM_001013 | RPS9 | ribosomal protein S9 | 0.0004 | 0.0280 | 1.3 |
| 222229_x_at | AL121871 | LOC392501 | similar to 60S ribosomal protein L26 | 0.0007 | 0.0664 | 1.3 |
| 201812_s_at | NM_019059 | TOMM7 /// LOC201725 | translocase of outer mitochondrial membrane 7 homolog (yeast) /// hypothetical protein LOC201725 | 0.0077 | 0.1777 | 1.3 |
| 206506_s_at | NM_003599 | SUPT3H | suppressor of Ty 3 homolog (*S. cerevisiae*) | 0.0013 | 0.0389 | 1.3 |
| 204093_at | NM_001239 | CCNH | cyclin H | 0.0011 | 0.0264 | 1.3 |
| 211967_at | BG538627 | TMEM123 | transmembrane protein 123 | 0.0049 | 0.2276 | 1.3 |
| 212533_at | X62048 | WEE1 | WEE1 homolog (*S. pombe*) | 0.0014 | 0.0990 | 1.3 |
| 211713_x_at | BC005832 | KIAA0101 | KIAA0101 /// KIAA0101 | 0.0035 | 0.0344 | 1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 206169_x_at | NM_025013 | ZC3H7B | zinc finger CCCH-type containing 7B | 0.0199 | 0.1897 | 1.3 |
| 221827_at | BE788439 | RBCK1 | RanBP-type and C3HC4-type zinc finger containing 1 | 0.0033 | 0.1180 | 1.3 |
| 212462_at | AU144267 | MYST4 | MYST histone acetyltransferase (monocytic leukemia) 4 | 0.0491 | 0.9450 | 1.3 |
| 204369_at | NM_006218 | PIK3CA | phosphoinositide-3-kinase, catalytic, alpha polypeptide | 0.0136 | 0.1909 | 1.3 |
| 213438_at | AA995925 | NFASC | neurofascin homolog (chicken) | 0.0177 | 0.0582 | 1.3 |
| 219001_s_at | NM_024345 | WDR32 | WD repeat domain 32 | 0.0159 | 0.7542 | 1.3 |
| 200023_s_at | NM_003754 | EIF3S5 | eukaryotic translation initiation factor 3, subunit 5 epsilon, 47 kDa /// eukaryotic translation initiation factor 3, subunit 5 epsilon, 47 kDa | 0.0004 | 0.0285 | 1.3 |
| 202679_at | NM_000271 | NPC1 | Niemann-Pick disease, type C1 | 0.0280 | 0.5043 | 1.3 |
| 221735_at | H04342 | WDR48 | WD repeat domain 48 | 0.0214 | 0.1303 | 1.3 |
| 205917_at | NM_003417 | ZNF264 | zinc finger protein 264 | 0.0289 | 0.3938 | 1.3 |
| 213483_at | AK025679 | PPWD1 | peptidylprolyl isomerase domain and WD repeat containing 1 | 0.0081 | 0.3358 | 1.3 |
| 203255_at | NM_018693 | FBXO11 | F-box protein 11 | 0.0497 | 0.1031 | 1.3 |
| 201652_at | NM_006837 | COPS5 | COP9 constitutive photomorphogenic homolog subunit 5 (Arabidopsis) | 0.0376 | 0.1262 | 1.3 |
| 218499_at | NM_016542 | RP6-213H19.1 | serine/threonine protein kinase MST4 | 0.0373 | 0.3857 | 1.3 |
| 216570_x_at | AL096829 | LOC646417 | similar to 60S ribosomal protein L29 (P23) | 0.0055 | 0.4385 | 1.3 |
| 212265_at | AL031781 | QKI | quaking homolog, KH domain RNA binding (mouse) | 0.0235 | 0.2288 | 1.3 |
| 213275_x_at | W47179 | CTSB | cathepsin B | 0.0154 | 0.1777 | 1.3 |
| 208655_at | BG530368 | CCNI | Cyclin I | 0.0029 | 0.1777 | 1.3 |
| 212416_at | AV745949 | SCAMP1 | secretory carrier membrane protein 1 | 0.0035 | 0.8372 | 1.3 |
| 202026_at | NM_003002 | SDHD | succinate dehydrogenase complex, subunit D, integral membrane protein | 0.0181 | 0.2574 | 1.3 |
| 212897_at | AI738802 | CDC2L6 | cell division cycle 2-like 6 (CDK8-like) | 0.0031 | 0.3399 | 1.3 |
| 201592_at | NM_003756 | EIF3S3 | eukaryotic translation initiation factor 3, subunit 3 gamma, 40 kDa | 0.0016 | 0.0564 | 1.3 |
| 202076_at | NM_001166 | BIRC2 | baculoviral IAP repeat-containing 2 | 0.0033 | 0.0770 | 1.3 |
| 217799_x_at | NM_003344 | UBE2H | ubiquitin-conjugating enzyme E2H (UBC8 homolog, yeast) | 0.0304 | 0.2586 | 1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 200771_at | NM_002293 | LAMC1 | laminin, gamma 1 (formerly LAMB2) | 0.0012 | 0.2016 | 1.3 |
| 202172_at | BG035116 | VEZF1 | vascular endothelial zinc finger 1 | 0.0037 | 0.2438 | 1.3 |
| 213853_at | AL050199 | DPH4 | DPH4, JJJ3 homolog (*S. cerevisiae*) | 0.0136 | 0.0763 | 1.3 |
| 209242_at | AL042588 | PEG3 | paternally expressed 3 | 0.0184 | 0.8421 | 1.3 |
| 212604_at | AI937794 | MRPS31 | mitochondrial ribosomal protein S31 | 0.0044 | 0.0424 | 1.3 |
| 209422_at | AL109965 | PHF20 | PHD finger protein 20 | 0.0173 | 0.0571 | 1.3 |
| 216380_x_at | AC005011 | LOC728453 /// LOC730288 /// LOC730819 | similar to 40S ribosomal protein S28 /// similar to 40S ribosomal protein S28 /// similar to 40S ribosomal protein S28 | 0.0032 | 0.7942 | 1.3 |
| 213236_at | AK025495 | SASH1 | SAM and SH3 domain containing 1 | 0.0035 | 0.2189 | 1.3 |
| 213322_at | AL031778 | C6orf130 | chromosome 6 open reading frame 130 | 0.0449 | 0.5982 | 1.3 |
| 205070_at | NM_019071 | ING3 | inhibitor of growth family, member 3 | 0.0079 | 0.0885 | 1.3 |
| 204700_x_at | NM_014388 | C1orf107 | chromosome 1 open reading frame 107 | 0.0355 | 0.5585 | 1.3 |
| 210095_s_at | M31159 | IGFBP3 | insulin-like growth factor binding protein 3 | 0.0091 | 0.6408 | 1.3 |
| 222368_at | AW972351 | — | CDNA FLJ37098 fis, clone BRACE2019004 | 0.0041 | 0.0383 | 1.3 |
| 219492_at | NM_012110 | CHIC2 | cysteine-rich hydrophobic domain 2 | 0.0254 | 0.4819 | 1.3 |
| 200017_at | NM_002954 | RPS27A | ribosomal protein S27a /// ribosomal protein S27a | 0.0019 | 0.0719 | 1.3 |
| 214176_s_at | AI348545 | PBXIP1 | Pre-B-cell leukemia transcription factor interacting protein 1 | 0.0039 | 0.1142 | 1.3 |
| 218972_at | NM_018259 | TTC17 | tetratricopeptide repeat domain 17 | 0.0366 | 0.5363 | 1.3 |
| 211337_s_at | BC000966 | 76P | gamma tubulin ring complex protein (76p gene) | 0.0225 | 0.2023 | 1.3 |
| 202668_at | BF001670 | EFNB2 | ephrin-B2 | 0.0059 | 0.0951 | 1.3 |
| 209620_s_at | AB005289 | ABCB7 | ATP-binding cassette, sub-family B (MDR/TAP), member 7 | 0.0129 | 0.2027 | 1.3 |
| 212519_at | AL518159 | UBE2E1 | ubiquitin-conjugating enzyme E2E 1 (UBC4/5 homolog, yeast) | 0.0098 | 0.0900 | 1.3 |
| 203067_at | NM_003477 | PDHX | pyruvate dehydrogenase complex, component X | 0.0135 | 0.3222 | 1.3 |
| 219641_at | NM_017996 | DET1 | de-etiolated homolog 1 (*Arabidopsis*) | 0.0133 | 0.8629 | 1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 206090_s_at | NM_018662 | DISC1 | disrupted in schizophrenia 1 | 0.0429 | 0.7391 | 1.3 |
| 200741_s_at | NM_001030 | RPS27 | ribosomal protein S27 (metallopanstimulin 1) | 0.0020 | 0.0582 | 1.3 |
| 204587_at | NM_003951 | SLC25A14 | solute carrier family 25 (mitochondrial carrier, brain), member 14 | 0.0055 | 0.5404 | 1.3 |
| 202220_at | NM_014949 | KIAA0907 | KIAA0907 | 0.0018 | 0.0746 | 1.3 |
| 213269_at | N21541 | ZNF248 | zinc finger protein 248 | 0.0112 | 0.9344 | 1.3 |
| 211257_x_at | AF273049 | ZNF638 | zinc finger protein 638 | 0.0157 | 0.1090 | 1.3 |
| 219147_s_at | NM_017881 | C9orf95 | chromosome 9 open reading frame 95 | 0.0147 | 0.0770 | 1.3 |
| 202973_x_at | NM_014883 | FAM13A1 | family with sequence similarity 13, member A1 | 0.0169 | 0.6932 | 1.3 |
| 213883_s_at | AA012917 | TM2D1 | TM2 domain containing 1 | 0.0148 | 0.1709 | 1.3 |
| 205370_x_at | NM_001918 | DBT | dihydrolipoamide branched chain transacylase E2 | 0.0034 | 0.1235 | 1.3 |
| 219571_s_at | NM_016265 | ZNF12 | zinc finger protein 12 | 0.0223 | 0.0935 | 1.3 |
| 219133_at | NM_017897 | OXSM | 3-oxoacyl-ACP synthase, mitochondrial | 0.0183 | 0.5794 | 1.3 |
| 220988_s_at | NM_030945 | C1QTNF3 | C1q and tumor necrosis factor related protein 3 /// C1q and tumor necrosis factor related protein 3 | 0.0079 | 0.2302 | 1.3 |
| 202454_s_at | NM_001982 | ERBB3 | v-erb-b2 erythroblastic leukemia viral oncogene homolog 3 (avian) | 0.0180 | 0.5119 | 1.3 |
| 203831_at | NM_014925 | R3HDM2 | R3H domain containing 2 | 0.0183 | 0.7758 | 1.3 |
| 210028_s_at | AF125507 | ORC3L | origin recognition complex, subunit 3-like (yeast) | 0.0029 | 0.2383 | 1.3 |
| 202386_s_at | NM_019081 | KIAA0430 | KIAA0430 | 0.0377 | 0.3255 | 1.3 |
| 215628_x_at | AL049285 | PPP2CA | Protein phosphatase 2 (formerly 2A), catalytic subunit, alpha isoform | 0.0079 | 0.4496 | 1.3 |
| 212018_s_at | AK000822 | RSL1D1 | ribosomal L1 domain containing 1 | 0.0054 | 0.3191 | 1.3 |
| 203667_at | NM_004607 | TBCA | tubulin folding cofactor A | 0.0025 | 0.0280 | 1.3 |
| 212327_at | AK026815 | DKFZP686A01247 | hypothetical protein | 0.0038 | 0.4265 | 1.3 |
| 212334_at | BE880245 | GNS | glucosamine (N-acetyl)-6-sulfatase (Sanfilippo disease IIID) | 0.0218 | 0.1233 | 1.3 |
| 201164_s_at | BG474429 | RNF6 /// PUM1 | ring finger protein (C3H2C3 type) 6 /// pumilio homolog 1 (*Drosophila*) | 0.0026 | 0.2690 | 1.3 |
| 200010_at | NM_000975 | RPL11 | Ribosomal protein L11 /// Ribosomal protein L11 | 0.0019 | 0.0441 | 1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 222034_at | AA443762 | GNB2L1 | Guanine nucleotide binding protein (G protein), beta polypeptide 2-like 1 | 0.0167 | 0.1744 | 1.3 |
| 221207_s_at | NM_015678 | NBEA | neurobeachin | 0.0076 | 0.1564 | 1.3 |
| 222122_s_at | BG403671 | THOC2 | THO complex 2 | 0.0494 | 0.2813 | 1.3 |
| 213168_at | AU145005 | SP3 | Sp3 transcription factor | 0.0257 | 0.4889 | 1.3 |
| 221112_at | NM_017416 | IL1RAPL2 | interleukin 1 receptor accessory protein-like 2 | 0.0483 | 0.9794 | 1.3 |
| 213229_at | BF590131 | DICER1 | Dicer1, Dcr-1 homolog (*Drosophila*) | 0.0454 | 0.0372 | 1.3 |
| 221702_s_at | AF353992 | TM2D3 | TM2 domain containing 3 /// TM2 domain containing 3 | 0.0049 | 0.1787 | 1.3 |
| 200897_s_at | NM_016081 | PALLD | palladin, cytoskeletal associated protein | 0.0042 | 0.0476 | 1.3 |
| 203704_s_at | AW118862 | — | — | 0.0495 | 0.2054 | 1.3 |
| 213065_at | AB011118 | CCDC131 | coiled-coil domain containing 131 | 0.0233 | 0.9011 | 1.3 |
| 207283_at | NM_020217 | RPL23AP13 | ribosomal protein L23a pseudogene 13 | 0.0489 | 0.6649 | 1.3 |
| 202960_s_at | NM_000255 | MUT | methylmalonyl Coenzyme A mutase | 0.0361 | 0.1791 | 1.3 |
| 221486_at | AF067170 | ENSA | endosulfine alpha | 0.0113 | 0.1876 | 1.3 |
| 212558_at | BF508662 | SPRY1 | sprouty homolog 1, antagonist of FGF signaling (*Drosophila*) | 0.0376 | 0.8925 | 1.3 |
| 203481_at | AI655902 | C10orf6 | chromosome 10 open reading frame 6 | 0.0137 | 0.0636 | 1.3 |
| 214281_s_at | AA524525 | RCHY1 | ring finger and CHY zinc finger domain containing 1 | 0.0048 | 0.0861 | 1.3 |
| 200062_at | L05095 | RPL30 | ribosomal protein L30 /// ribosomal protein L30 | 0.0011 | 0.0383 | 1.3 |
| 203221_at | AI758763 | TLE1 | transducin-like enhancer of split 1 (E(sp1) homolog, *Drosophila*) | 0.0020 | 0.0387 | 1.3 |
| 218628_at | NM_016053 | CCDC53 | coiled-coil domain containing 53 | 0.0257 | 0.0506 | 1.3 |
| 214707_x_at | AB002326 | ALMS1 | Alstrom syndrome 1 | 0.0021 | 0.0329 | 1.3 |
| 212758_s_at | AI373166 | TCF8 | transcription factor 8 (represses interleukin 2 expression) | 0.0166 | 0.0274 | 1.3 |
| 202557_at | AI718418 | STCH | stress 70 protein chaperone, microsome-associated, 60 kDa | 0.0144 | 0.1063 | 1.3 |
| 208246_x_at | NM_017618 | — | CDNA FLJ20006 fis, clone ADKA02694 | 0.0043 | 0.1221 | 1.3 |
| 202766_s_at | NM_000138 | FBN1 | fibrillin 1 | 0.0129 | 0.6308 | 1.3 |
| 201830_s_at | NM_005863 | NET1 | neuroepithelial cell transforming gene 1 | 0.0180 | 0.0835 | 1.3 |
| 212805_at | AB002365 | KIAA0367 | KIAA0367 | 0.0344 | 0.3786 | 1.3 |
| 207467_x_at | NM_001750 | CAST | calpastatin | 0.0122 | 0.0990 | 1.3 |
| 201502_s_at | AI078167 | NFKBIA | nuclear factor of kappa light polypeptide gene enhancer in B-cells inhibitor, alpha | 0.0044 | 0.0499 | 1.3 |
| 209111_at | BC004155 | RNF5 | ring finger protein 5 | 0.0072 | 0.9883 | 1.3 |
| 211971_s_at | AI653608 | LRPPRC | leucine-rich PPR-motif containing | 0.0080 | 0.1196 | 1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 210389_x_at | BC000258 | TUBD1 | tubulin, delta 1 | 0.0199 | 0.6862 | 1.3 |
| 212982_at | AI621223 | ZDHHC17 | zinc finger, DHHC-type containing 17 | 0.0496 | 0.4017 | 1.3 |
| 210946_at | AF014403 | PPAP2A | phosphatidic acid phosphatase type 2A | 0.0123 | 0.2350 | 1.3 |
| 203095_at | NM_002453 | MTIF2 | mitochondrial translational initiation factor 2 | 0.0312 | 0.2324 | 1.3 |
| 201857_at | NM_016107 | ZFR | zinc finger RNA binding protein | 0.0069 | 0.0656 | 1.3 |
| 209390_at | AF013168 | TSC1 | tuberous sclerosis 1 | 0.0005 | 0.0554 | 1.3 |
| 213313_at | AI922519 | RABGAP1 | RAB GTPase activating protein 1 | 0.0129 | 0.2904 | 1.3 |
| 209065_at | BC005230 | UQCRB | ubiquinol-cytochrome c reductase binding protein | 0.0314 | 0.1143 | 1.3 |
| 212244_at | AL050091 | GRINL1A /// Gcom1 | glutamate receptor, ionotropic, N-methyl D-aspartate-like 1A /// GRINL1A combined protein | 0.0198 | 0.4925 | 1.3 |
| 208021_s_at | NM_002913 | RFC1 | replication factor C (activator 1) 1, 145 kDa /// replication factor C (activator 1) 1, 145 kDa | 0.0224 | 0.4152 | 1.3 |
| 212542_s_at | BF224151 | PHIP | pleckstrin homology domain interacting protein | 0.0244 | 0.3957 | 1.3 |
| 213657_s_at | BE858194 | ZNF710 /// DOCK4 | Zinc finger protein 710 /// MRNA full length insert cDNA clone EUROIMAGE 375854 /// Dedicator of cytokinesis 4 | 0.0202 | 0.5147 | 1.3 |
| 212226_s_at | AA628586 | PPAP2B | phosphatidic acid phosphatase type 2B | 0.0253 | 0.1768 | 1.3 |
| 203038_at | NM_002844 | PTPRK | protein tyrosine phosphatase, receptor type, K | 0.0050 | 0.1699 | 1.3 |
| 201648_at | AL039831 | JAK1 | Janus kinase 1 (a protein tyrosine kinase) | 0.0364 | 0.4317 | 1.3 |
| 213542_at | AI246730 | ZNF710 | zinc finger protein 710 | 0.0146 | 0.3325 | 1.3 |
| 209684_at | AL136924 | RIN2 | Ras and Rab interactor 2 | 0.0097 | 0.1105 | 1.3 |
| 214003_x_at | BF184532 | RPS20 | ribosomal protein S20 | 0.0009 | 0.0252 | 1.3 |
| 218852_at | NM_017917 | C14orf10 | chromosome 14 open reading frame 10 | 0.0433 | 0.1844 | 1.3 |
| 212893_at | AL080063 | ZZZ3 | zinc finger, ZZ-type containing 3 | 0.0186 | 0.1134 | 1.3 |
| 218263_s_at | NM_021211 | ZBED5 | zinc finger, BED-type containing 5 | 0.0016 | 0.0395 | 1.3 |
| 203301_s_at | NM_021145 | DMTF1 | cyclin D binding myb-like transcription factor 1 | 0.0400 | 0.4154 | 1.3 |
| 207730_x_at | NM_017932 | HDGF2 | Hepatoma-derived growth factor-related protein 2 | 0.0045 | 0.0473 | 1.3 |
| 202302_s_at | NM_023012 | FLJ11021 | similar to splicing factor, arginine/serine-rich 4 | 0.0085 | 0.1061 | 1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 203020_at | NM_014857 | RABGAP1L | RAB GTPase activating protein 1-like | 0.0038 | 0.2687 | 1.3 |
| 220352_x_at | NM_024305 | — | — | 0.0021 | 0.1437 | 1.3 |
| 211452_x_at | AF130054 | LRRFIP1 | leucine rich repeat (in FLII) interacting protein 1 | 0.0066 | 0.0547 | 1.3 |
| 200810_s_at | NM_001280 | CIRBP | cold inducible RNA binding protein | 0.0036 | 0.0793 | 1.3 |
| 212104_s_at | N95026 | RBM9 | RNA binding motif protein 9 | 0.0045 | 0.1200 | 1.3 |
| 213839_at | AW028110 | KIAA0500 | KIAA0500 protein | 0.0297 | 0.2545 | 1.3 |
| 202968_s_at | Y09216 | DYRK2 | dual-specificity tyrosine-(Y)-phosphorylation regulated kinase 2 | 0.0395 | 0.1646 | 1.3 |
| 213074_at | BG545769 | IRAK1BP1 | Interleukin-1 receptor-associated kinase 1 binding protein 1 | 0.0314 | 0.6649 | 1.3 |
| 202623_at | NM_018453 | C14orf11 | chromosome 14 open reading frame 11 | 0.0073 | 0.1164 | 1.3 |
| 213048_s_at | W26593 | SET | SET translocation (myeloid leukemia-associated) | 0.0024 | 0.0197 | 1.3 |
| 219392_x_at | NM_018304 | PRR11 | proline rich 11 | 0.0058 | 0.1864 | 1.3 |
| 201588_at | NM_004786 | TXNL1 | thioredoxin-like 1 | 0.0047 | 0.0284 | 1.3 |
| 200026_at | NM_000995 | RPL34 /// LOC342994 /// LOC651249 /// LOC729536 /// LOC731916 | ribosomal protein L34 /// ribosomal protein L34 /// similar to ribosomal protein L34 /// similar to ribosomal protein L34 /// similar to ribosomal protein L34 /// similar to ribosomal protein L34 /// hypothetical protein LOC729536 /// hypothetical protein LOC729536 /// similar to ribosomal protein L34 /// similar to ribosomal protein L34 | 0.0044 | 0.0681 | 1.3 |
| 213328_at | AI936517 | NEK1 | NIMA (never in mitosis gene a)-related kinase 1 | 0.0285 | 0.0844 | 1.3 |
| 207616_s_at | NM_004180 | TANK | TRAF family member-associated NFKB activator | 0.0256 | 0.2643 | 1.3 |
| 217797_at | NM_016406 | UFC1 | ubiquitin-fold modifier conjugating enzyme 1 | 0.0025 | 0.0646 | 1.3 |
| 222244_s_at | AK000749 | TUG1 | taurine upregulated gene 1 | 0.0055 | 0.1914 | 1.3 |
| 202673_at | NM_003859 | DPM1 | dolichyl-phosphate mannosyltransferase polypeptide 1, catalytic subunit | 0.0116 | 0.0642 | 1.3 |
| 204688_at | NM_003919 | SGCE | sarcoglycan, epsilon | 0.0027 | 0.1571 | 1.3 |
| 207943_x_at | NM_006718 | PLAGL1 | pleiomorphic adenoma gene-like 1 | 0.0133 | 0.6838 | 1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 203044_at | NM_014918 | CHSY1 | carbohydrate (chondroitin) synthase 1 | 0.0272 | 0.0951 | 1.3 |
| 201758_at | NM_006292 | TSG101 | tumor susceptibility gene 101 | 0.0088 | 0.1664 | 1.3 |
| 213531_s_at | AI040009 | RAB3GAP1 | RAB3 GTPase activating protein subunit 1 (catalytic) | 0.0046 | 0.7605 | 1.3 |
| 218598_at | NM_021930 | RINT1 | RAD50 interactor 1 | 0.0193 | 0.2781 | 1.3 |
| 214670_at | AA653300 | ZKSCAN1 | zinc finger with KRAB and SCAN domains 1 | 0.0302 | 0.3630 | 1.3 |
| 218989_x_at | NM_022902 | SLC30A5 | solute carrier family 30 (zinc transporter), member 5 | 0.0118 | 0.0958 | 1.3 |
| 200937_s_at | NM_000969 | RPL5 | ribosomal protein L5 | 0.0011 | 0.0539 | 1.3 |
| 213015_at | BF448315 | — | ARTC1 mRNA, complete sequence | 0.0072 | 0.0197 | 1.3 |
| 211228_s_at | AF085736 | RAD17 | RAD17 homolog (*S. pombe*) | 0.0082 | 0.2369 | 1.3 |
| 209505_at | AI951185 | NR2F1 | Nuclear receptor subfamily 2, group F, member 1 | 0.0237 | 0.7005 | 1.3 |
| 204457_s_at | NM_002048 | GAS1 | growth arrest-specific 1 | 0.0055 | 0.1142 | 1.3 |
| 212596_s_at | AJ010070 | HMG2L1 | high-mobility group protein 2-like 1 | 0.0205 | 0.2332 | 1.3 |
| 201256_at | NM_004718 | COX7A2L | cytochrome c oxidase subunit VIIa polypeptide 2 like | 0.0015 | 0.0271 | 1.3 |
| 205051_s_at | NM_000222 | KIT | v-kit Hardy-Zuckerman 4 feline sarcoma viral oncogene homolog | 0.0500 | 0.3862 | 1.3 |
| 214739_at | AI357539 | LRCH3 | leucine-rich repeats and calponin homology (CH) domain containing 3 | 0.0255 | 0.3342 | 1.3 |
| 201406_at | NM_021029 | RPL36A /// LOC729362 | ribosomal protein L36a /// similar to large subunit ribosomal protein L36a | 0.0039 | 0.1666 | 1.3 |
| 208986_at | AL559478 | TCF12 | transcription factor 12 (HTF4, helix-loop-helix transcription factors 4) | 0.0085 | 0.1013 | 1.3 |
| 200743_s_at | NM_000391 | TPP1 | tripeptidyl peptidase I | 0.0024 | 0.3558 | 1.3 |
| 204725_s_at | NM_006153 | NCK1 | NCK adaptor protein 1 | 0.0084 | 0.2949 | 1.3 |
| 220760_x_at | NM_024733 | ZNF665 | zinc finger protein 665 | 0.0279 | 0.2927 | 1.3 |
| 200888_s_at | NM_000978 | RPL23 | ribosomal protein L23 | 0.0031 | 0.1288 | 1.3 |
| 214257_s_at | AA890010 | SEC22B | SEC22 vesicle trafficking protein homolog B (*S. cerevisiae*) | 0.0340 | 0.0759 | 1.3 |
| 202811_at | NM_006463 | STAMBP | STAM binding protein | 0.0479 | 0.1820 | 1.3 |
| 213685_at | AA830143 | — | Gene from PAC 886K2, chromosome 1 | 0.0170 | 0.2067 | 1.3 |
| 208936_x_at | AF074000 | LGALS8 | lectin, galactoside-binding, soluble, 8 (galectin 8) | 0.0267 | 0.5425 | 1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 201831_s_at | BE875592 | PAK1 /// VDP | p21/Cdc42/Rac1-activated kinase 1 (STE20 homolog, yeast) /// vesicle docking protein p115 | 0.0222 | 0.2437 | 1.3 |
| 209835_x_at | BC004372 | CD44 | CD44 molecule (Indian blood group) | 0.0124 | 0.2180 | 1.3 |
| 220176_at | NM_025152 | NUBPL | nucleotide binding protein-like | 0.0495 | 0.9762 | 1.3 |
| 200038_s_at | NM_000985 | RPL17 | ribosomal protein L17 /// ribosomal protein L17 | 0.0019 | 0.0400 | 1.3 |
| 201989_s_at | AL529409 | CREBL2 | cAMP responsive element binding protein-like 2 | 0.0147 | 0.9018 | 1.3 |
| 207513_s_at | NM_003452 | ZNF189 | zinc finger protein 189 | 0.0252 | 0.1180 | 1.3 |
| 217313_at | AC004692 | — | — | 0.0166 | 0.8256 | 1.3 |
| 218549_s_at | NM_016033 | FAM82B | family with sequence similarity 82, member B | 0.0235 | 0.0666 | 1.3 |
| 217579_x_at | AW301806 | ARL6IP2 | ADP-ribosylation factor-like 6 interacting protein 2 | 0.0069 | 0.0770 | 1.3 |
| 203240_at | NM_003890 | FCGBP | Fc fragment of IgG binding protein | 0.0085 | 0.1142 | 1.3 |
| 217833_at | AL520908 | SYNCRIP | synaptotagmin binding, cytoplasmic RNA interacting protein | 0.0054 | 0.0968 | 1.3 |
| 215529_x_at | AI590053 | DIP2A | DIP2 disco-interacting protein 2 homolog A (*Drosophila*) | 0.0146 | 0.1925 | 1.3 |
| 210774_s_at | AL162047 | NCOA4 | nuclear receptor coactivator 4 | 0.0057 | 0.0763 | 1.3 |
| 200090_at | BG168896 | FNTA | farnesyltransferase, CAAX box, alpha /// farnesyltransferase, CAAX box, alpha | 0.0047 | 0.4557 | 1.3 |
| 215504_x_at | AF131777 | ANKRD10 | Ankyrin repeat domain 10 | 0.0117 | 0.7025 | 1.3 |
| 217379_at | AL121934 | LOC442171 | similar to ribosomal protein L10 | 0.0014 | 0.1820 | 1.3 |
| 204454_at | NM_012317 | LDOC1 | leucine zipper, down-regulated in cancer 1 | 0.0026 | 0.0631 | 1.3 |
| 205888_s_at | AI962693 | JAKMIP2 /// MYT1L | janus kinase and microtubule interacting protein 2 /// myelin transcription factor 1-like | 0.0374 | 0.4240 | 1.3 |
| 212042_x_at | BG389744 | RPL7 | ribosomal protein L7 | 0.0010 | 0.0421 | 1.3 |
| 203306_s_at | NM_006416 | SLC35A1 | solute carrier family 35 (CMP-sialic acid transporter), member A1 | 0.0322 | 0.8372 | 1.3 |
| 214731_at | AB037854 | CTTNBP2NL | CTTNBP2 N-terminal like | 0.0329 | 0.3513 | 1.3 |
| 208943_s_at | U93239 | TLOC1 | translocation protein 1 | 0.0015 | 0.0274 | 1.3 |
| 203966_s_at | NM_021003 | PPM1A | protein phosphatase 1A (formerly 2C), magnesium-dependent, alpha isoform /// protein | 0.0080 | 0.3222 | 1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| | | | phosphatase 1A (formerly 2C), magnesium-dependent, alpha isoform | | | |
| 206323_x_at | NM_002547 | OPHN1 | oligophrenin 1 | 0.0339 | 0.2763 | 1.3 |
| 202372_at | BF240652 | — | Full-length cDNA clone CS0DC007YG11 of Neuroblastoma Cot 25-normalized of Homo sapiens (human) | 0.0040 | 0.0880 | 1.3 |
| 204641_at | NM_002497 | NEK2 | NIMA (never in mitosis gene a)-related kinase 2 | 0.0060 | 0.1598 | 1.3 |
| 218127_at | AI804118 | NFYB | nuclear transcription factor Y, beta | 0.0298 | 0.1675 | 1.3 |
| 202629_at | AV681579 | APPBP2 | amyloid beta precursor protein (cytoplasmic tail) binding protein 2 | 0.0023 | 0.4904 | 1.3 |
| 210817_s_at | BC004130 | CALCOCO2 | calcium binding and coiled-coil domain 2 | 0.0082 | 0.1515 | 1.3 |
| 208195_at | NM_003319 | TTN | titin | 0.0265 | 0.1949 | 1.3 |
| 205126_at | NM_006296 | VRK2 | vaccinia related kinase 2 | 0.0033 | 0.0365 | 1.2 |
| 219356_s_at | NM_016410 | CHMP5 | chromatin modifying protein 5 | 0.0190 | 0.1778 | 1.2 |
| 200686_s_at | NM_004768 | SFRS11 | splicing factor, arginine/serine-rich 11 | 0.0064 | 0.0719 | 1.2 |
| 204630_s_at | NM_004871 | GOSR1 | golgi SNAP receptor complex member 1 | 0.0098 | 0.3668 | 1.2 |
| 221641_s_at | AF241787 | ACOT9 | acyl-CoA thioesterase 9 | 0.0253 | 0.1581 | 1.2 |
| 217317_s_at | AB002391 | HERC2P3 /// HERC2P2 /// LOC440248 | hect domain and RLD 2 pseudogene 3 /// hect domain and RLD 2 pseudogene 2 /// hypothetical LOC440248 | 0.0403 | 0.4707 | 1.2 |
| 213794_s_at | AI269117 | NGDN | neuroguidin, EIF4E binding protein | 0.0074 | 0.1963 | 1.2 |
| 203621_at | NM_002492 | NDUFB5 | NADH dehydrogenase (ubiquinone) 1 beta subcomplex, 5, 16 kDa | 0.0297 | 0.1554 | 1.2 |
| 219940_s_at | NM_018386 | PCID2 | PCI domain containing 2 | 0.0102 | 0.3122 | 1.2 |
| 214715_x_at | AK024789 | ZNF160 | zinc finger protein 160 | 0.0117 | 0.1338 | 1.2 |
| 205452_at | NM_004855 | PIGB | phosphatidylinositol glycan anchor biosynthesis, class B | 0.0061 | 0.2509 | 1.2 |
| 221064_s_at | NM_023076 | C16orf28 | chromosome 16 open reading frame 28 | 0.0198 | 0.9418 | 1.2 |
| 220071_x_at | NM_018097 | CEP27 | centrosomal protein 27 kDa | 0.0116 | 0.1564 | 1.2 |
| 215588_x_at | AK024958 | RIOK3 | RIO kinase 3 (yeast) | 0.0028 | 0.4594 | 1.2 |
| 208717_at | BC001669 | OXA1L | oxidase (cytochrome c) assembly 1-like | 0.0197 | 0.7795 | 1.2 |
| 203883_s_at | BG249608 | RAB11FIP2 | RAB11 family interacting protein 2 (class I) | 0.0049 | 0.1190 | 1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 218766_s_at | NM_015836 | WARS2 | tryptophanyl tRNA synthetase 2 (mitochondrial) | 0.0147 | 0.1269 | 1.2 |
| 221527_s_at | AF196185 | PARD3 | par-3 partitioning defective 3 homolog (C. elegans) | 0.0232 | 0.1408 | 1.2 |
| 200994_at | BG291787 | IPO7 | Importin 7 | 0.0388 | 0.6843 | 1.2 |
| 221923_s_at | AA191576 | NPM1 | nucleophosmin (nucleolar phosphoprotein B23, numatrin) | 0.0071 | 0.0636 | 1.2 |
| 201253_s_at | NM_006319 | CDIPT | CDP-diacylglycerol--inositol 3-phosphatidyltransferase (phosphatidylinositol synthase) | 0.0133 | 0.1470 | 1.2 |
| 213687_s_at | BE968801 | RPL35A | ribosomal protein L35a | 0.0012 | 0.0344 | 1.2 |
| 221419_s_at | NM_013307 | — | — | 0.0174 | 0.1039 | 1.2 |
| 212153_at | AB007930 | POGZ | pogo transposable element with ZNF domain | 0.0024 | 0.4615 | 1.2 |
| 202021_x_at | AF083441 | EIF1 | eukaryotic translation initiation factor 1 | 0.0012 | 0.1070 | 1.2 |
| 213896_x_at | BE856549 | KIAA0974 | KIAA0974 | 0.0118 | 0.1469 | 1.2 |
| 200823_x_at | NM_000992 | RPL29 | ribosomal protein L29 | 0.0061 | 0.2552 | 1.2 |
| 215179_x_at | AK023843 | PGF | Placental growth factor, vascular endothelial growth factor-related protein | 0.0085 | 0.1642 | 1.2 |
| 203351_s_at | AF047598 | ORC4L | origin recognition complex, subunit 4-like (yeast) | 0.0199 | 0.3619 | 1.2 |
| 200905_x_at | NM_005516 | HLA-E | major histocompatibility complex, class I, E | 0.0053 | 0.1334 | 1.2 |
| 219119_at | NM_016200 | LSM8 | LSM8 homolog, U6 small nuclear RNA associated (S. cerevisiae) | 0.0447 | 0.2301 | 1.2 |
| 214305_s_at | AW003030 | SF3B1 | splicing factor 3b, subunit 1, 155 kDa | 0.0061 | 0.0197 | 1.2 |
| 200099_s_at | AL356115 | RPS3A /// LOC439992 | ribosomal protein S3A /// ribosomal protein S3A /// similar to ribosomal protein S3a /// similar to ribosomal protein S3a | 0.0040 | 0.0558 | 1.2 |
| 218007_s_at | NM_015920 | RPS27L | ribosomal protein S27-like | 0.0046 | 0.0971 | 1.2 |
| 203445_s_at | NM_005730 | CTDSP2 | CTD (carboxy-terminal domain, RNA polymerase II, polypeptide A) small phosphatase 2 | 0.0057 | 0.1941 | 1.2 |
| 220796_x_at | NM_024881 | SLC35E1 | solute carrier family 35, member E1 | 0.0136 | 0.2093 | 1.2 |
| 203261_at | NM_006571 | DCTN6 | dynactin 6 | 0.0322 | 0.2746 | 1.2 |
| 204362_at | NM_003930 | SKAP2 | src kinase associated phosphoprotein 2 | 0.0267 | 0.5442 | 1.2 |
| 200858_s_at | NM_001012 | RPS8 | ribosomal protein S8 | 0.0024 | 0.0843 | 1.2 |
| 212229_s_at | AK001699 | FBXO21 | F-box protein 21 | 0.0336 | 0.1148 | 1.2 |
| 216187_x_at | AF222691 | KNS2 | Kinesin 2 | 0.0161 | 0.8431 | 1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 201483_s_at | BC002802 | SUPT4H1 | suppressor of Ty 4 homolog 1 (*S. cerevisiae*) | 0.0079 | 0.9595 | 1.2 |
| 208855_s_at | AF083420 | STK24 | serine/threonine kinase 24 (STE20 homolog, yeast) | 0.0136 | 0.0721 | 1.2 |
| 207180_s_at | NM_006410 | HTATIP2 | HIV-1 Tat interactive protein 2, 30 kDa | 0.0359 | 0.8053 | 1.2 |
| 219590_x_at | NM_015958 | DPH5 | DPH5 homolog (*S. cerevisiae*) | 0.0029 | 0.1068 | 1.2 |
| 218630_at | NM_017777 | MKS1 | Meckel syndrome, type 1 | 0.0224 | 0.5271 | 1.2 |
| 202279_at | NM_004894 | C14orf2 | chromosome 14 open reading frame 2 | 0.0155 | 0.0721 | 1.2 |
| 217122_s_at | AL031282 | SLC35E2 /// LOC728661 | solute carrier family 35, member E2 /// similar to solute carrier family 35, member E2 | 0.0178 | 0.3398 | 1.2 |
| 208933_s_at | AI659005 | — | — | 0.0027 | 0.0803 | 1.2 |
| 205327_s_at | NM_001616 | ACVR2A | activin A receptor, type IIA | 0.0357 | 0.5733 | 1.2 |
| 203448_s_at | AI347136 | TERF1 | telomeric repeat binding factor (NIMA-interacting) 1 | 0.0112 | 0.0284 | 1.2 |
| 218250_s_at | NM_013354 | CNOT7 | CCR4-NOT transcription complex, subunit 7 | 0.0049 | 0.0564 | 1.2 |
| 214097_at | AW024383 | RPS21 | ribosomal protein S21 | 0.0345 | 0.3691 | 1.2 |
| 214802_at | AK022397 | EXOC7 | exocyst complex component 7 | 0.0299 | 0.4976 | 1.2 |
| 202970_at | AI192838 | — | MRNA; cDNA DKFZp667B0924 (from clone DKFZp667B0924) | 0.0404 | 0.1580 | 1.2 |
| 202317_s_at | NM_006048 | UBE4B | ubiquitination factor E4B (UFD2 homolog, yeast) | 0.0069 | 0.5881 | 1.2 |
| 209329_x_at | BC000587 | HIGD2A | HIG1 domain family, member 2A | 0.0186 | 0.5037 | 1.2 |
| 214686_at | AA868898 | ZNF266 | zinc finger protein 266 | 0.0199 | 0.6239 | 1.2 |
| 214143_x_at | AI560573 | RPL24 /// ACSM3 /// SLC36A2 | ribosomal protein L24 /// acyl-CoA synthetase medium-chain family member 3 /// solute carrier family 36 (proton/amino acid symporter), member 2 | 0.0022 | 0.0284 | 1.2 |
| 203316_s_at | NM_003094 | SNRPE | small nuclear ribonucleoprotein polypeptide E | 0.0241 | 0.1629 | 1.2 |
| 221934_s_at | BF941492 | DALRD3 | DALR anticodon binding domain containing 3 | 0.0322 | 0.8698 | 1.2 |
| 221540_x_at | AF078847 | GTF2H2 /// DKFZP686M0199 /// LOC653866 /// LOC728340 /// LOC730394 | general transcription factor IIH, polypeptide 2, 44 kDa /// similar to TFIIH basal transcription factor complex p44 subunit (Basic transcription factor 2 44 kDa subunit) (BTF2-p44) (General transcription factor IIH polypeptide 2) | 0.0289 | 0.1892 | 1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| | | | /// similar to TFIIH basal transcription factor complex p44 subunit (Basic transcription factor 2 44 kDa subunit) (BTF2-p44) (General transcription factor IIH polypeptide 2) /// similar to TFIIH basal transcription factor complex p44 subunit (Basic transcription factor 2 44 kDa subunit) (BTF2-p44) (General transcription factor IIH polypeptide 2) /// region containing general transcription factor IIH, polypeptide 2, 44 kDa; similar to TFIIH basal transcription factor complex p44 subunit (Basic transcription factor 2 44 kDa subunit) (BTF2-p44) (General transcription factor IIH polypeptide 2) | | | |
| 202054_s_at | NM_000382 | ALDH3A2 | aldehyde dehydrogenase 3 family, member A2 | 0.0264 | 0.2941 | 1.2 |
| 35436_at | L06147 | GOLGA2 | golgi autoantigen, golgin subfamily a, 2 | 0.0143 | 0.2075 | 1.2 |
| 218988_at | NM_018656 | SLC35E3 | solute carrier family 35, member E3 | 0.0332 | 0.4575 | 1.2 |
| 212632_at | N32035 | STX7 | Syntaxin 7 | 0.0264 | 0.4759 | 1.2 |
| 209472_at | BC000819 | RP11-82K18.3 | kynurenine aminotransferase III | 0.0347 | 0.1281 | 1.2 |
| 204020_at | BF739943 | PURA | purine-rich element binding protein A | 0.0149 | 0.0874 | 1.2 |
| 208113_x_at | NM_030979 | PABPC3 | poly(A) binding protein, cytoplasmic 3 /// poly(A) binding protein, cytoplasmic 3 | 0.0330 | 0.2927 | 1.2 |
| 214394_x_at | AI613383 | EEF1D /// LOC126037 | eukaryotic translation elongation factor 1 delta (guanine nucleotide exchange protein) /// similar to Elongation factor 1-delta (EF-1-delta) (Antigen NY-CO-4) | 0.0013 | 0.0326 | 1.2 |
| 213292_s_at | AA908770 | SNX13 | sorting nexin 13 | 0.0283 | 0.1715 | 1.2 |
| 220046_s_at | NM_020307 | CCNL1 | cyclin L1 | 0.0054 | 0.1498 | 1.2 |
| 202379_s_at | AI361805 | NKTR | natural killer-tumor recognition sequence | 0.0226 | 0.0758 | 1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 221787_at | BF431618 | C6orf120 | chromosome 6 open reading frame 120 | 0.0087 | 0.0877 | 1.2 |
| 210296_s_at | BC005375 | PXMP3 | peroxisomal membrane protein 3, 35 kDa (Zellweger syndrome) | 0.0152 | 0.5465 | 1.2 |
| 209678_s_at | L18964 | PRKCI | protein kinase C, iota | 0.0298 | 0.0441 | 1.2 |
| 219926_at | NM_022361 | POPDC3 | popeye domain containing 3 | 0.0062 | 0.0307 | 1.2 |
| 212474_at | D87682 | KIAA0241 | KIAA0241 | 0.0221 | 0.3172 | 1.2 |
| 217820_s_at | NM_018212 | ENAH | enabled homolog (Drosophila) | 0.0366 | 0.1120 | 1.2 |
| 212447_at | AF161402 | KBTBD2 | kelch repeat and BTB (POZ) domain containing 2 | 0.0089 | 0.4481 | 1.2 |
| 212368_at | AA972711 | ZNF292 | zinc finger protein 292 | 0.0176 | 0.0861 | 1.2 |
| 202829_s_at | NM_005638 | SYBL1 | synaptobrevin-like 1 | 0.0160 | 0.1131 | 1.2 |
| 216310_at | AK024376 | TAOK1 | TAO kinase 1 | 0.0075 | 0.5594 | 1.2 |
| 211297_s_at | L20320 | CDK7 | cyclin-dependent kinase 7 (MO15 homolog, Xenopus laevis, cdk-activating kinase) | 0.0359 | 0.0916 | 1.2 |
| 210686_x_at | BC001407 | SLC25A16 | solute carrier family 25 (mitochondrial carrier; Graves disease autoantigen), member 16 | 0.0079 | 0.2001 | 1.2 |
| 201032_at | NM_006698 | BLCAP | bladder cancer associated protein | 0.0011 | 0.1159 | 1.2 |
| 218467_at | NM_020232 | TNFSF5IP1 | tumor necrosis factor superfamily, member 5-induced protein 1 | 0.0055 | 0.1200 | 1.2 |
| 205526_s_at | NM_007044 | KATNA1 | katanin p60 (ATPase-containing) subunit A 1 | 0.0142 | 0.0800 | 1.2 |
| 208066_s_at | NM_001514 | GTF2B | general transcription factor IIB /// general transcription factor IIB | 0.0333 | 0.3117 | 1.2 |
| 209069_s_at | BC001124 | H3F3B | H3 histone, family 3B (H3.3B) | 0.0174 | 0.0958 | 1.2 |
| 210908_s_at | AB055804 | PFDN5 | prefoldin subunit 5 | 0.0045 | 0.0424 | 1.2 |
| 218098_at | AL121903 | — | — | 0.0396 | 0.3857 | 1.2 |
| 208904_s_at | BC000354 | RPS28 /// LOC645899 /// LOC646195 | ribosomal protein S28 /// similar to 40S ribosomal protein S28 /// similar to 40S ribosomal protein S28 | 0.0019 | 0.1381 | 1.2 |
| 201371_s_at | AF062537 | CUL3 | cullin 3 | 0.0109 | 0.0933 | 1.2 |
| 219703_at | NM_018365 | MNS1 | meiosis-specific nuclear structural 1 | 0.0184 | 0.0703 | 1.2 |
| 205788_s_at | NM_014827 | ZC3H11A | zinc finger CCCH-type containing 11A | 0.0255 | 0.7984 | 1.2 |
| 221829_s_at | AI307759 | TNPO1 | transportin 1 | 0.0043 | 0.0185 | 1.2 |
| 212600_s_at | AV727381 | UQCRC2 | ubiquinol-cytochrome c reductase core protein II | 0.0050 | 0.0383 | 1.2 |
| 200034_s_at | NM_000970 | RPL6 | ribosomal protein L6 /// ribosomal protein L6 | 0.0060 | 0.2152 | 1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 200036_s_at | NM_007104 | RPL10A | ribosomal protein L10a /// ribosomal protein L10a | 0.0020 | 0.0971 | 1.2 |
| 216858_x_at | AL080112 | — | — | 0.0298 | 0.1388 | 1.2 |
| 203034_s_at | NM_000990 | RPL27A /// LOC389435 | ribosomal protein L27a /// similar to 60S ribosomal protein L27a | 0.0010 | 0.0274 | 1.2 |
| 200726_at | NM_002710 | PPP1CC | protein phosphatase 1, catalytic subunit, gamma isoform | 0.0326 | 0.5063 | 1.2 |
| 217941_s_at | NM_018695 | ERBB2IP | erbb2 interacting protein | 0.0195 | 0.6001 | 1.2 |
| 200018_at | NM_001017 | RPS13 | ribosomal protein S13 /// ribosomal protein S13 | 0.0006 | 0.0252 | 1.2 |
| 200705_s_at | NM_001959 | EEF1B2 | eukaryotic translation elongation factor 1 beta 2 | 0.0007 | 0.0157 | 1.2 |
| 205042_at | NM_005476 | GNE | glucosamine (UDP-N-acetyl)-2-epimerase/N-acetylmannosamine kinase | 0.0294 | 0.2075 | 1.2 |
| 218654_s_at | NM_016071 | MRPS33 | mitochondrial ribosomal protein S33 | 0.0011 | 0.0282 | 1.2 |
| 212345_s_at | BE675139 | CREB3L2 | cAMP responsive element binding protein 3-like 2 | 0.0168 | 0.1160 | 1.2 |
| 207700_s_at | NM_006534 | NCOA3 | nuclear receptor coactivator 3 | 0.0380 | 0.0932 | 1.2 |
| 202378_s_at | NM_017526 | LEPROT | leptin receptor overlapping transcript | 0.0092 | 0.0747 | 1.2 |
| 215823_x_at | U64661 | PABPC3 /// PABPC1 /// LOC341315 /// LOC652607 | poly(A) binding protein, cytoplasmic 3 /// poly(A) binding protein, cytoplasmic 1 /// hypothetical LOC341315 /// similar to Polyadenylate-binding protein 1 (Poly(A)-binding protein 1) (PABP 1) | 0.0081 | 0.0893 | 1.2 |
| 205176_s_at | NM_014288 | ITGB3BP | integrin beta 3 binding protein (beta3-endonexin) | 0.0354 | 0.3312 | 1.2 |
| 217491_x_at | AF042165 | COX7C | cytochrome c oxidase subunit VIIc | 0.0007 | 0.0452 | 1.2 |
| 209007_s_at | AF267856 | C1orf63 | chromosome 1 open reading frame 63 | 0.0468 | 0.9308 | 1.2 |
| 208993_s_at | AW340788 | PPIG | peptidylprolyl isomerase G (cyclophilin G) | 0.0404 | 0.0424 | 1.2 |
| 212440_at | X76302 | RY1 | putative nucleic acid binding protein RY-1 | 0.0038 | 0.0285 | 1.2 |
| 213179_at | BG289914 | — | — | 0.0149 | 0.7695 | 1.2 |
| 200092_s_at | BF216701 | RPL37 | ribosomal protein L37 /// ribosomal protein L37 | 0.0007 | 0.0197 | 1.2 |
| 208695_s_at | BC001019 | RPL39 | ribosomal protein L39 | 0.0035 | 0.0984 | 1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 202265_at | NM_005180 | BMI1 | B lymphoma Mo-MLV insertion region (mouse) | 0.0159 | 0.0499 | 1.2 |
| 208610_s_at | AI655799 | SRRM2 | serine/arginine repetitive matrix 2 | 0.0301 | 0.0441 | 1.2 |
| 218146_at | NM_018446 | GLT8D1 | glycosyltransferase 8 domain containing 1 | 0.0261 | 0.3313 | 1.2 |
| 215424_s_at | AV689564 | SNW1 | SNW domain containing 1 | 0.0168 | 0.2988 | 1.2 |
| 206089_at | NM_006157 | NELL1 | NEL-like 1 (chicken) | 0.0451 | 0.1134 | 1.2 |
| 201041_s_at | NM_004417 | DUSP1 | dual specificity phosphatase 1 | 0.0237 | 0.9234 | 1.2 |
| 204576_s_at | AA207013 | CLUAP1 | clusterin associated protein 1 | 0.0329 | 0.9377 | 1.2 |
| 202710_at | BC000899 | BET1 | BET1 homolog (*S. cerevisiae*) | 0.0267 | 0.2967 | 1.2 |
| 201653_at | NM_005776 | CNIH | cornichon homolog (*Drosophila*) | 0.0011 | 0.0185 | 1.2 |
| 203858_s_at | NM_001303 | COX10 | COX10 homolog, cytochrome c oxidase assembly protein, heme A: farnesyltransferase (yeast) | 0.0030 | 0.0383 | 1.2 |
| 213049_at | BG436400 | GARNL1 | GTPase activating Rap/RanGAP domain-like 1 | 0.0416 | 0.1940 | 1.2 |
| 217975_at | NM_016303 | WBP5 | WW domain binding protein 5 | 0.0129 | 0.0467 | 1.2 |
| 209760_at | AL136932 | KIAA0922 | KIAA0922 | 0.0378 | 0.7343 | 1.2 |
| 217256_x_at | Z98950 | LOC641903 /// LOC643505 /// LOC646175 /// LOC649299 /// LOC651209 /// LOC728202 /// LOC732102 | similar to large subunit ribosomal protein L36a /// similar to large subunit ribosomal protein L36a /// similar to large subunit ribosomal protein L36a /// similar to large subunit ribosomal protein L36a /// similar to large subunit ribosomal protein L36a /// similar to large subunit ribosomal protein L36a /// similar to large subunit ribosomal protein L36a | 0.0029 | 0.2079 | 1.2 |
| 200847_s_at | NM_016127 | TMEM66 | transmembrane protein 66 | 0.0402 | 0.3313 | 1.2 |
| 203011_at | NM_005536 | IMPA1 | inositol(myo)-1(or 4)-monophosphatase 1 | 0.0121 | 0.0452 | 1.2 |
| 209447_at | AF043290 | SYNE1 | spectrin repeat containing, nuclear envelope 1 | 0.0367 | 0.1023 | 1.2 |
| 217846_at | NM_005051 | QARS | glutaminyl-tRNA synthetase | 0.0008 | 0.0841 | 1.2 |
| 218341_at | NM_024664 | PPCS | phosphopantothenoylcysteine synthetase | 0.0369 | 0.0576 | 1.2 |
| 219762_s_at | NM_015414 | RPL36 | ribosomal protein L36 | 0.0060 | 0.1247 | 1.2 |
| 215907_at | AK027193 | BACH2 | BTB and CNC homology 1, basic leucine zipper transcription factor 2 | 0.0197 | 0.2184 | 1.2 |
| 202336_s_at | NM_000919 | PAM | peptidylglycine alpha-amidating monooxygenase | 0.0451 | 0.2016 | 1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 219220_x_at | NM_020191 | MRPS22 | mitochondrial ribosomal protein S22 | 0.0016 | 0.0383 | 1.2 |
| 203292_s_at | NM_021729 | VPS11 | vacuolar protein sorting 11 homolog (*S. cerevisiae*) | 0.0249 | 0.4069 | 1.2 |
| 201290_at | NM_014300 | SEC11A | SEC11 homolog A (*S. cerevisiae*) | 0.0025 | 0.0417 | 1.2 |
| 219711_at | NM_017652 | ZNF586 | zinc finger protein 586 | 0.0476 | 0.8054 | 1.2 |
| 219030_at | NM_016058 | TPRKB | TP53RK binding protein | 0.0354 | 0.1017 | 1.2 |
| 210139_s_at | L03203 | PMP22 | peripheral myelin protein 22 | 0.0029 | 0.4411 | 1.2 |
| 218991_at | NM_022070 | ABC1 | amplified in breast cancer 1 | 0.0406 | 0.4662 | 1.2 |
| 219563_at | NM_024633 | C14orf139 | chromosome 14 open reading frame 139 | 0.0212 | 0.4167 | 1.2 |
| 216960_s_at | AL049646 | ZNF133 | zinc finger protein 133 | 0.0140 | 0.0798 | 1.2 |
| 216505_x_at | AL118502 | RPS10 /// LOC133569 /// RPS10P3 /// LOC649303 /// LOC654029 /// LOC728791 /// LOC730965 /// LOC732348 | ribosomal protein S10 /// similar to ribosomal protein S10 /// ribosomal protein S10 pseudogene 3 /// similar to ribosomal protein S10 /// similar to 40S ribosomal protein S10 /// similar to 40S ribosomal protein S10 /// similar to 40S ribosomal protein S10 /// similar to ribosomal protein S10 | 0.0045 | 0.0853 | 1.2 |
| 221959_at | BE672313 | C8orf72 | chromosome 8 open reading frame 72 | 0.0176 | 0.3838 | 1.2 |
| 216499_at | AL137590 | — | MRNA; cDNA DKFZp434K0610 (from clone DKFZp434K0610) | 0.0238 | 0.4595 | 1.2 |
| 204274_at | AA812215 | EBAG9 | estrogen receptor binding site associated, antigen, 9 | 0.0258 | 0.1645 | 1.2 |
| 203098_at | AL050164 | CDYL | chromodomain protein, Y-like | 0.0029 | 0.1514 | 1.2 |
| 221868_at | AB032981 | KIAA1155 | KIAA1155 protein | 0.0078 | 0.3685 | 1.2 |
| 201606_s_at | BE796924 | PWP1 | PWP1 homolog (*S. cerevisiae*) | 0.0206 | 0.0351 | 1.2 |
| 219740_at | NM_024749 | VASH2 | vasohibin 2 | 0.0467 | 0.0197 | 1.2 |
| 209510_at | AF064801 | RNF139 | ring finger protein 139 | 0.0064 | 0.0383 | 1.2 |
| 32259_at | AB002386 | EZH1 | enhancer of zeste homolog 1 (*Drosophila*) | 0.0294 | 0.6894 | 1.2 |
| 203180_at | NM_000693 | ALDH1A3 | aldehyde dehydrogenase 1 family, member A3 | 0.0234 | 0.0537 | 1.2 |
| 215582_x_at | AK022303 | MCM3AP | MCM3 minichromosome maintenance deficient 3 (*S. cerevisiae*) associated protein | 0.0261 | 0.6795 | 1.2 |
| 202920_at | BF726212 | ANK2 | ankyrin 2, neuronal | 0.0055 | 0.0418 | 1.2 |
| 221423_s_at | NM_030799 | YIPF5 | Yip1 domain family, member 5 /// Yip1 domain family, member 5 | 0.0284 | 0.2018 | 1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 211935_at | D31885 | ARL6IP1 | ADP-ribosylation factor-like 6 interacting protein 1 | 0.0025 | 0.1564 | 1.2 |
| 214129_at | AI821791 | LOC727942 | similar to phosphodiesterase 4D interacting protein isoform 2 | 0.0262 | 0.0645 | 1.2 |
| 202542_s_at | NM_004757 | SCYE1 | small inducible cytokine subfamily E, member 1 (endothelial monocyte-activating) | 0.0473 | 0.3700 | 1.2 |
| 212505_s_at | AL110250 | KIAA0892 | KIAA0892 | 0.0415 | 0.3689 | 1.2 |
| 202495_at | NM_003192 | TBCC | tubulin folding cofactor C | 0.0288 | 0.1796 | 1.2 |
| 201630_s_at | NM_004300 | ACP1 | acid phosphatase 1, soluble | 0.0049 | 0.7714 | 1.2 |
| 210027_s_at | M80261 | APEX1 | APEX nuclease (multifunctional DNA repair enzyme) 1 | 0.0015 | 0.0441 | 1.2 |
| 219442_at | NM_024048 | C16orf67 | chromosome 16 open reading frame 67 | 0.0205 | 0.1694 | 1.2 |
| 202798_at | NM_006323 | SEC24B | SEC24 related gene family, member B (*S. cerevisiae*) | 0.0149 | 0.4001 | 1.2 |
| 200595_s_at | NM_003750 | EIF3S10 | eukaryotic translation initiation factor 3, subunit 10 theta, 150/170 kDa | 0.0423 | 0.3400 | 1.2 |
| 215373_x_at | AK022213 | FLJ12151 | hypothetical protein FLJ12151 | 0.0344 | 0.2990 | 1.2 |
| 214150_x_at | BE043477 | ATP6V0E1 | ATPase, H+ transporting, lysosomal 9 kDa, V0 subunit e1 | 0.0097 | 0.0385 | 1.2 |
| 213223_at | AK025866 | RPL28 | ribosomal protein L28 | 0.0186 | 0.2522 | 1.2 |
| 206770_s_at | NM_012243 | SLC35A3 | solute carrier family 35 (UDP-N-acetylglucosamine (UDP-GlcNAc) transporter), member A3 | 0.0385 | 0.1965 | 1.2 |
| 200032_s_at | NM_000661 | RPL9 | ribosomal protein L9 /// ribosomal protein L9 | 0.0064 | 0.1269 | 1.2 |
| 200089_s_at | AI953886 | RPL4 | ribosomal protein L4 /// ribosomal protein L4 | 0.0011 | 0.1019 | 1.2 |
| 218936_s_at | NM_014167 | CCDC59 | coiled-coil domain containing 59 | 0.0401 | 0.1497 | 1.2 |
| 200013_at | NM_000986 | RPL24 | ribosomal protein L24 /// ribosomal protein L24 | 0.0012 | 0.0506 | 1.2 |
| 206551_x_at | NM_017644 | KLHL24 | kelch-like 24 (*Drosophila*) | 0.0102 | 0.0791 | 1.2 |
| 205125_at | NM_006225 | PLCD1 | phospholipase C, delta 1 | 0.0415 | 0.4391 | 1.2 |
| 201352_at | NM_014263 | YME1L1 | YME1-like 1 (*S. cerevisiae*) | 0.0080 | 0.0645 | 1.2 |
| 209049_s_at | BC001004 | PRKCBP1 | protein kinase C binding protein 1 | 0.0193 | 0.1143 | 1.2 |
| 200781_s_at | NM_001019 | RPS15A | ribosomal protein S15a | 0.0012 | 0.0252 | 1.2 |
| 208759_at | AF240468 | IKBKB /// NCSTN | inhibitor of kappa light polypeptide gene enhancer in B-cells, kinase beta /// nicastrin | 0.0459 | 0.9106 | 1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 202536_at | AK002165 | CHMP2B | chromatin modifying protein 2B | 0.0369 | 0.0552 | 1.2 |
| 208025_s_at | NM_003483 | HMGA2 | high mobility group AT-hook 2 /// high mobility group AT-hook 2 | 0.0144 | 0.0506 | 1.2 |
| 208137_x_at | NM_030972 | ZNF611 /// LOC731901 | zinc finger protein 611 /// zinc finger protein 611 /// similar to zinc finger protein 160 /// similar to zinc finger protein 160 | 0.0034 | 0.0383 | 1.2 |
| 200081_s_at | BE741754 | RPS6 | ribosomal protein S6 /// ribosomal protein S6 | 0.0029 | 0.0971 | 1.2 |
| 200862_at | NM_014762 | DHCR24 | 24-dehydrocholesterol reductase | 0.0001 | 0.0261 | −3.1 |
| 201287_s_at | NM_002997 | SDC1 | syndecan 1 | 0.0011 | 0.1550 | −2.2 |
| 209146_at | AV704962 | SC4MOL | sterol-C4-methyl oxidase-like | 0.0013 | 0.3139 | −2.1 |
| 209218_at | AF098865 | SQLE | squalene epoxidase | 0.0012 | 0.6633 | −2.1 |
| 202613_at | NM_001905 | CTPS | CTP synthase | 0.0012 | 0.3142 | −2.0 |
| 212218_s_at | AI954041 | FASN | fatty acid synthase | 0.0006 | 0.0369 | −2.0 |
| 201609_x_at | AL578502 | ICMT | isoprenylcysteine carboxyl methyltransferase | 0.0024 | 0.8332 | −1.9 |
| 210950_s_at | BC003573 | FDFT1 | farnesyl-diphosphate farnesyltransferase 1 | 0.0002 | 0.0274 | −1.9 |
| 201790_s_at | AW150953 | DHCR7 | 7-dehydrocholesterol reductase | 0.0036 | 0.9588 | −1.9 |
| 201475_x_at | NM_004990 | MARS | methionine-tRNA synthetase | 0.0005 | 0.2911 | −1.9 |
| 221750_at | BG035985 | HMGCS1 | 3-hydroxy-3-methylglutaryl-Coenzyme A synthase 1 (soluble) | 0.0030 | 0.4659 | −1.9 |
| 200832_s_at | AB032261 | SCD | stearoyl-CoA desaturase (delta-9-desaturase) | 0.0012 | 0.1157 | −1.8 |
| 202580_x_at | NM_021953 | FOXM1 | forkhead box M1 | 0.0019 | 0.0660 | −1.8 |
| 205534_at | NM_002589 | PCDH7 | BH-protocadherin (brain-heart) | 0.0012 | 0.0452 | −1.8 |
| 208002_s_at | NM_007274 | ACOT7 | acyl-CoA thioesterase 7 | 0.0043 | 0.1221 | −1.8 |
| 208881_x_at | BC005247 | IDI1 | isopentenyl-diphosphate delta isomerase 1 | 0.0012 | 0.2090 | −1.8 |
| 210793_s_at | U41815 | NUP98 | nucleoporin 98 kDa | 0.0014 | 0.5809 | −1.8 |
| 211136_s_at | BC004865 | CLPTM1 | cleft lip and palate associated transmembrane protein 1 | 0.0007 | 0.0264 | −1.8 |
| 201490_s_at | NM_005729 | PPIF | peptidylprolyl isomerase F (cyclophilin F) | 0.0015 | 0.6082 | −1.8 |
| 200987_x_at | AA758755 | PSME3 | proteasome (prosome, macropain) activator subunit 3 (PA28 gamma; Ki) | 0.0015 | 0.8757 | −1.8 |
| 212009_s_at | AL553320 | STIP1 | stress-induced-phosphoprotein 1 (Hsp70/Hsp90-organizing protein) | 0.0011 | 0.5636 | −1.8 |
| 202587_s_at | BC001116 | AK1 | adenylate kinase 1 | 0.0014 | 0.8539 | −1.8 |
| 217943_s_at | NM_018067 | RPRC1 | arginine/proline rich coiled-coil 1 | 0.0036 | 0.7553 | −1.8 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 201564_s_at | NM_003088 | FSCN1 | fascin homolog 1, actin-bundling protein (*Strongylocentrotus purpuratus*) | 0.0007 | 0.0411 | −1.8 |
| 210337_s_at | U18197 | ACLY | ATP citrate lyase | 0.0009 | 0.2586 | −1.8 |
| 201679_at | BE646076 | ARS2 | ARS2 protein | 0.0019 | 0.2538 | −1.7 |
| 217992_s_at | NM_024329 | EFHD2 | EF-hand domain family, member D2 | 0.0015 | 0.2671 | −1.7 |
| 202052_s_at | NM_015577 | RAI14 | retinoic acid induced 14 | 0.0160 | 0.7493 | −1.7 |
| 201626_at | BG292233 | INSIG1 | insulin induced gene 1 | 0.0071 | 0.5750 | −1.7 |
| 202743_at | BE622627 | PIK3R3 | phosphoinositide-3-kinase, regulatory subunit 3 (p55, gamma) | 0.0007 | 0.2808 | −1.7 |
| 207622_s_at | NM_005692 | ABCF2 | ATP-binding cassette, sub-family F (GCN20), member 2 | 0.0007 | 0.5505 | −1.7 |
| 210973_s_at | M63889 | FGFR1 | fibroblast growth factor receptor 1 (fms-related tyrosine kinase 2, Pfeiffer syndrome) | 0.0017 | 0.0348 | −1.7 |
| 201281_at | NM_007002 | ADRM1 | adhesion regulating molecule 1 | 0.0004 | 0.7557 | −1.7 |
| 207945_s_at | NM_001893 | CSNK1D | casein kinase 1, delta | 0.0008 | 0.0981 | −1.7 |
| 208637_x_at | BC003576 | ACTN1 | actinin, alpha 1 | 0.0010 | 0.3106 | −1.7 |
| 212563_at | BG491842 | BOP1 /// LOC727967 | block of proliferation 1 /// similar to block of proliferation 1 | 0.0025 | 0.1767 | −1.7 |
| 219894_at | NM_019066 | MAGEL2 | MAGE-like 2 | 0.0033 | 0.8372 | −1.7 |
| 205483_s_at | NM_005101 | ISG15 | ISG15 ubiquitin-like modifier | 0.0296 | 0.9106 | −1.7 |
| 218494_s_at | NM_020062 | SLC2A4RG | SLC2A4 regulator | 0.0007 | 0.0645 | −1.7 |
| 213986_s_at | AI805266 | C19orf6 | chromosome 19 open reading frame 6 | 0.0074 | 0.0807 | −1.7 |
| 212983_at | NM_005343 | HRAS | v-Ha-ras Harvey rat sarcoma viral oncogene homolog | 0.0011 | 0.7695 | −1.7 |
| 204285_s_at | AI857639 | PMAIP1 | phorbol-12-myristate-13-acetate-induced protein 1 | 0.0041 | 0.0964 | −1.7 |
| 201516_at | NM_003132 | SRM | spermidine synthase | 0.0005 | 0.2652 | −1.7 |
| 219099_at | NM_020375 | C12orf5 | chromosome 12 open reading frame 5 | 0.0099 | 0.3265 | −1.7 |
| 201695_s_at | NM_000270 | NP | nucleoside phosphorylase | 0.0031 | 0.2128 | −1.7 |
| 222155_s_at | AK021918 | GPR172A | G protein-coupled receptor 172A | 0.0061 | 0.3703 | −1.7 |
| 217025_s_at | AL110225 | DBN1 | drebrin 1 | 0.0015 | 0.5175 | −1.6 |
| 200720_s_at | AL532341 | ACTR1A | ARP1 actin-related protein 1 homolog A, centractin alpha (yeast) | 0.0024 | 0.3563 | −1.6 |
| 205858_at | NM_002507 | NGFR | nerve growth factor receptor (TNFR superfamily, member 16) | 0.0361 | 0.7526 | −1.6 |
| 218051_s_at | NM_022908 | NT5DC2 | 5'-nucleotidase domain containing 2 | 0.0007 | 0.0532 | −1.6 |
| 202539_s_at | AL518627 | HMGCR | 3-hydroxy-3-methylglutaryl-Coenzyme A reductase | 0.0047 | 0.7250 | −1.6 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 207824_s_at | NM_002383 | MAZ | MYC-associated zinc finger protein (purine-binding transcription factor) | 0.0012 | 0.0274 | −1.6 |
| 208962_s_at | BE540552 | FADS1 | fatty acid desaturase 1 | 0.0007 | 0.0663 | −1.6 |
| 212048_s_at | AW245400 | YARS | tyrosyl-tRNA synthetase | 0.0007 | 0.0642 | −1.6 |
| 201277_s_at | NM_004499 | HNRPAB | heterogeneous nuclear ribonucleoprotein A/B | 0.0007 | 0.0504 | −1.6 |
| 209608_s_at | BC000408 | ACAT2 | acetyl-Coenzyme A acetyltransferase 2 (acetoacetyl Coenzyme A thiolase) | 0.0015 | 0.2423 | −1.6 |
| 212907_at | AI972416 | SLC30A1 | Solute carrier family 30 (zinc transporter), member 1 | 0.0161 | 0.3563 | −1.6 |
| 202852_s_at | NM_024666 | FLJ11506 | hypothetical protein FLJ11506 | 0.0069 | 0.2746 | −1.6 |
| 200664_s_at | BG537255 | DNAJB1 | DnaJ (Hsp40) homolog, subfamily B, member 1 | 0.0008 | 0.2350 | −1.6 |
| 213492_at | X06268 | COL2A1 | collagen, type II, alpha 1 (primary osteoarthritis, spondyloepiphyseal dysplasia, congenital) | 0.0143 | 0.1963 | −1.6 |
| 201874_at | BF978611 | MPZL1 | myelin protein zero-like 1 | 0.0061 | 0.3437 | −1.6 |
| 200825_s_at | NM_006389 | HYOU1 | hypoxia up-regulated 1 | 0.0013 | 0.0376 | −1.6 |
| 212125_at | NM_002883 | RANGAP1 | Ran GTPase activating protein 1 | 0.0124 | 0.2690 | −1.6 |
| 203499_at | NM_004431 | EPHA2 | EPH receptor A2 | 0.0048 | 0.7012 | −1.6 |
| 220892_s_at | NM_021154 | PSAT1 | phosphoserine aminotransferase 1 | 0.0130 | 0.3662 | −1.6 |
| 201005_at | NM_001769 | CD9 | CD9 molecule | 0.0012 | 0.0733 | −1.6 |
| 213523_at | AI671049 | CCNE1 | cyclin E1 | 0.0007 | 0.1144 | −1.6 |
| 221503_s_at | AF034756 | KPNA3 | karyopherin alpha 3 (importin alpha 4) | 0.0042 | 0.0834 | −1.6 |
| 217762_s_at | BE789881 | RAB31 | RAB31, member RAS oncogene family | 0.0068 | 0.3313 | −1.6 |
| 206491_s_at | NM_003827 | NAPA | N-ethylmaleimide-sensitive factor attachment protein, alpha | 0.0043 | 0.1666 | −1.6 |
| 222231_s_at | AK025328 | LRRC59 | leucine rich repeat containing 59 | 0.0012 | 0.2297 | −1.6 |
| 201167_x_at | D13989 | ARHGDIA | Rho GDP dissociation inhibitor (GDI) alpha | 0.0069 | 0.0544 | −1.6 |
| 204141_at | NM_001069 | TUBB2A | tubulin, beta 2A | 0.0031 | 0.7289 | −1.6 |
| 200800_s_at | NM_005345 | HSPA1A /// HSPA1B | heat shock 70 kDa protein 1A /// heat shock 70 kDa protein 1B | 0.0047 | 0.0547 | −1.6 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 213030_s_at | AI688418 | PLXNA2 | plexin A2 | 0.0019 | 0.1469 | −1.6 |
| 200078_s_at | BC005876 | ATP6V0B | ATPase, H+ transporting, lysosomal 21 kDa, V0 subunit b /// ATPase, H+ transporting, lysosomal 21 kDa, V0 subunit b | 0.0007 | 0.1997 | −1.6 |
| 212501_at | AL564683 | CEBPB | CCAAT/enhancer binding protein (C/EBP), beta | 0.0168 | 0.7928 | −1.6 |
| 201248_s_at | NM_004599 | SREBF2 | sterol regulatory element binding transcription factor 2 | 0.0036 | 0.0990 | −1.6 |
| 217717_s_at | BF246499 | YWHAB | tyrosine 3-monooxygenase/tryptophan 5-monooxygenase activation protein, beta polypeptide | 0.0274 | 0.9884 | −1.6 |
| 205417_s_at | NM_004393 | DAG1 | dystroglycan 1 (dystrophin-associated glycoprotein 1) | 0.0024 | 0.1175 | −1.6 |
| 208625_s_at | AF104913 | EIF4G1 | eukaryotic translation initiation factor 4 gamma, 1 | 0.0040 | 0.5095 | −1.6 |
| 205047_s_at | NM_001673 | ASNS | asparagine synthetase | 0.0034 | 0.4312 | −1.6 |
| 211899_s_at | AF082185 | TRAF4 | TNF receptor-associated factor 4 | 0.0152 | 0.4299 | −1.6 |
| 200753_x_at | BE866585 | SFRS2 | splicing factor, arginine/serine-rich 2 | 0.0027 | 0.6707 | −1.5 |
| 211066_x_at | BC006439 | PCDHGC3 /// PCDHGB4 /// PCDHGA8 /// PCDHGA12 /// PCDHGC5 /// PCDHGC4 /// PCDHGB7 /// PCDHGB6 /// PCDHGB5 /// PCDHGB3 /// PCDHGB2 /// PCDHGB1 /// PCDHGA11 /// PCDHGA10 /// PCDHGA9 /// PCDHGA7 /// PCDHGA6 /// PCDHGA5 /// PCDHGA4 /// | protocadherin gamma subfamily C, 3 /// protocadherin gamma subfamily C, 3 /// protocadherin gamma subfamily B, 4 /// protocadherin gamma subfamily B, 4 /// protocadherin gamma subfamily A, 8 /// protocadherin gamma subfamily A, 8 /// protocadherin gamma subfamily A, 12 /// protocadherin gamma subfamily A, 12 /// protocadherin gamma subfamily C, 5 /// protocadherin gamma subfamily C, 5 /// protocadherin gamma subfamily C, 4 /// protocadherin gamma subfamily C, 4 /// protocadherin gamma subfamily | 0.0100 | 0.7921 | −1.5 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| | | PCDHGA3 /// PCDHGA2 /// PCDHGA1 | B, 7 /// protocadherin gamma subfamily B, 7 /// protocadherin gamma subfamily B, 6 /// protocadherin gamma subfamily B, 6 /// protocadherin gamma subfamily B, 5 /// protocadherin gamma subfamily B, 5 /// protocadherin gamma subfamily B, 3 /// protocadherin gamma subfamily B, 3 /// protocadherin gamma subfamily B, 2 /// protocadherin gamma subfamily B, 2 /// protocadherin gamma subfamily B, 1 /// protocadherin gamma subfamily B, 1 /// protocadherin gamma subfamily A, 11 /// protocadherin gamma subfamily A, 11 /// protoc | | | |
| 221539_at | AB044548 | EIF4EBP1 | eukaryotic translation initiation factor 4E binding protein 1 | 0.0005 | 0.1625 | −1.5 |
| 212020_s_at | AU152107 | MKI67 | antigen identified by monoclonal antibody Ki-67 | 0.0100 | 0.3569 | −1.5 |
| 212186_at | BE855983 | ACACA | acetyl-Coenzyme A carboxylase alpha | 0.0046 | 0.7009 | −1.5 |
| 200736_s_at | NM_000581 | GPX1 | glutathione peroxidase 1 | 0.0005 | 0.0958 | −1.5 |
| 212110_at | D31887 | SLC39A14 | solute carrier family 39 (zinc transporter), member 14 | 0.0039 | 0.1774 | −1.5 |
| 221269_s_at | NM_031286 | SH3BGRL3 | SH3 domain binding glutamic acid-rich protein like 3 /// SH3 domain binding glutamic acid-rich protein like 3 | 0.0022 | 0.1530 | −1.5 |
| 218866_s_at | NM_016310 | POLR3K | polymerase (RNA) III (DNA directed) polypeptide K, 12.3 kDa | 0.0006 | 0.0499 | −1.5 |
| 208998_at | U94592 | UCP2 | uncoupling protein 2 (mitochondrial, proton carrier) | 0.0064 | 0.2296 | −1.5 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 201920_at | NM_005415 | SLC20A1 | solute carrier family 20 (phosphate transporter), member 1 | 0.0127 | 0.2383 | −1.5 |
| 217140_s_at | AJ002428 | VDAC1 | voltage-dependent anion channel 1 | 0.0011 | 0.2544 | −1.5 |
| 204178_s_at | NM_006328 | RBM14 | RNA binding motif protein 14 | 0.0012 | 0.0244 | −1.5 |
| 208977_x_at | BC004188 | TUBB2C | tubulin, beta 2C | 0.0007 | 0.1351 | −1.5 |
| 55692_at | W22924 | ELMO2 | engulfment and cell motility 2 | 0.0193 | 0.7394 | −1.5 |
| 201954_at | NM_005720 | ARPC1B /// LOC653888 | actin related protein 2/3 complex, subunit 1B, 41 kDa /// similar to Actin-related protein 2/3 complex subunit 1B (ARP2/3 complex 41 kDa subunit) (p41-ARC) | 0.0090 | 0.6520 | −1.5 |
| 52164_at | AA065185 | C11orf24 | chromosome 11 open reading frame 24 | 0.0012 | 0.3796 | −1.5 |
| 200884_at | NM_001823 | CKB | creatine kinase, brain | 0.0141 | 0.1787 | −1.5 |
| 200744_s_at | AI741124 | GNB1 | guanine nucleotide binding protein (G protein), beta polypeptide 1 | 0.0006 | 0.0653 | −1.5 |
| 200617_at | NM_014730 | KIAA0152 | KIAA0152 | 0.0042 | 0.6385 | −1.5 |
| 203085_s_at | BC000125 | TGFB1 | transforming growth factor, beta 1 (Camurati-Engelmann disease) | 0.0122 | 0.2679 | −1.5 |
| 222278_at | AW969655 | — | Transcribed locus, moderately similar to XP_001002661.1 hypothetical protein [Mus musculus] | 0.0420 | 0.6056 | −1.5 |
| 212300_at | AL049795 | TXLNA | taxilin alpha | 0.0028 | 0.2423 | −1.5 |
| 211237_s_at | AF202063 | FGFR4 | fibroblast growth factor receptor 4 | 0.0018 | 0.0648 | −1.5 |
| 201700_at | NM_001760 | CCND3 | cyclin D3 | 0.0018 | 0.3480 | −1.5 |
| 214677_x_at | X57812 | IGL@ /// IGLV4-3 /// IGLV3-25 /// IGLV2-14 /// IGLJ3 | immunoglobulin lambda locus /// immunoglobulin lambda variable 4-3 /// immunoglobulin lambda variable 3-25 /// immunoglobulin lambda variable 2-14 /// immunoglobulin lambda joining 3 | 0.0075 | 0.3646 | −1.5 |
| 214845_s_at | AF257659 | CALU | calumenin | 0.0069 | 0.6021 | −1.5 |
| 206463_s_at | NM_005794 | DHRS2 | dehydrogenase/reductase (SDR family) member 2 | 0.0135 | 0.4760 | −1.5 |
| 204768_s_at | NM_004111 | FEN1 | flap structure-specific endonuclease 1 | 0.0007 | 0.1484 | −1.5 |
| 213547_at | AB014567 | CAND2 | cullin-associated and neddylation-dissociated 2 (putative) | 0.0025 | 0.0807 | −1.5 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 217861_s_at | NM_013388 | PREB | prolactin regulatory element binding | 0.0012 | 0.8030 | −1.5 |
| 209361_s_at | BC004153 | PCBP4 | poly(rC) binding protein 4 | 0.0022 | 0.1080 | −1.5 |
| 210317_s_at | U28936 | YWHAE | tyrosine 3-monooxygenase/tryptophan 5-monooxygenase activation protein, epsilon polypeptide | 0.0050 | 0.0441 | −1.5 |
| 203968_s_at | NM_001254 | CDC6 | cell division cycle 6 homolog (*S. cerevisiae*) | 0.0012 | 0.1235 | −1.5 |
| 218888_s_at | NM_018092 | NETO2 | neuropilin (NRP) and tolloid (TLL)-like 2 | 0.0044 | 0.3076 | −1.5 |
| 209336_at | U56085 | PWP2 | PWP2 periodic tryptophan protein homolog (yeast) | 0.0065 | 0.9234 | −1.5 |
| 203737_s_at | NM_015062 | PPRC1 | peroxisome proliferator-activated receptor gamma, coactivator-related 1 | 0.0136 | 0.5419 | −1.5 |
| 202478_at | NM_021643 | TRIB2 | tribbles homolog 2 (*Drosophila*) | 0.0026 | 0.2666 | −1.5 |
| 208891_at | BC003143 | DUSP6 | dual specificity phosphatase 6 | 0.0069 | 0.0576 | −1.5 |
| 208815_x_at | AB023420 | HSPA4 | heat shock 70 kDa protein 4 | 0.0025 | 0.0549 | −1.5 |
| 204087_s_at | NM_021095 | SLC5A6 | solute carrier family 5 (sodium-dependent vitamin transporter), member 6 | 0.0035 | 0.7493 | −1.5 |
| 203109_at | NM_003969 | UBE2M | ubiquitin-conjugating enzyme E2M (UBC12 homolog, yeast) | 0.0020 | 0.7428 | −1.5 |
| 208693_s_at | D30658 | GARS | glycyl-tRNA synthetase | 0.0016 | 0.4086 | −1.5 |
| 220651_s_at | NM_018518 | MCM10 | MCM10 minichromosome maintenance deficient 10 (*S. cerevisiae*) | 0.0017 | 0.1151 | −1.5 |
| 217808_s_at | NM_024117 | MAPKAP1 | mitogen-activated protein kinase associated protein 1 | 0.0007 | 0.2075 | −1.5 |
| 201198_s_at | AI860431 | PSMD1 | proteasome (prosome, macropain) 26S subunit, non-ATPase, 1 | 0.0009 | 0.2829 | −1.5 |
| 201193_at | NM_005896 | IDH1 | isocitrate dehydrogenase 1 (NADP+), soluble | 0.0049 | 0.4382 | −1.5 |
| 201551_s_at | J03263 | LAMP1 | lysosomal-associated membrane protein 1 | 0.0031 | 0.0506 | −1.5 |
| 212680_x_at | BE305165 | PPP1R14B | protein phosphatase 1, regulatory (inhibitor) subunit 14B | 0.0006 | 0.2726 | −1.5 |
| 201618_x_at | NM_003801 | GPAA1 | glycosylphosphatidylinositol anchor attachment protein 1 homolog (yeast) | 0.0100 | 0.0923 | −1.5 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 200886_s_at | NM_002629 | PGAM1 /// LOC642969 /// LOC643576 | phosphoglycerate mutase 1 (brain) /// similar to Phosphoglycerate mutase 1 (Phosphoglycerate mutase isozyme B) (PGAM-B) (BPG-dependent PGAM 1) /// similar to Phosphoglycerate mutase 1 (Phosphoglycerate mutase isozyme B) (PGAM-B) (BPG-dependent PGAM 1) | 0.0007 | 0.4197 | −1.5 |
| 212419_at | AA131324 | C10orf56 | chromosome 10 open reading frame 56 | 0.0016 | 0.3823 | −1.5 |
| 212242_at | AL565074 | TUBA1 | tubulin, alpha 1 | 0.0007 | 0.1083 | −1.5 |
| 221640_s_at | AF274972 | LRDD | leucine-rich repeats and death domain containing | 0.0071 | 0.0995 | −1.5 |
| 209035_at | M69148 | MDK | midkine (neurite growth-promoting factor 2) | 0.0009 | 0.0727 | −1.5 |
| 200787_s_at | BC002426 | PEA15 | phosphoprotein enriched in astrocytes 15 | 0.0016 | 0.4992 | −1.5 |
| 212041_at | AL566172 | ATP6V0D1 | ATPase, H+ transporting, lysosomal 38 kDa, V0 subunit d1 | 0.0078 | 0.7937 | −1.5 |
| 218115_at | NM_018154 | ASF1B | ASF1 anti-silencing function 1 homolog B (*S. cerevisiae*) | 0.0066 | 0.2165 | −1.5 |
| 201710_at | NM_002466 | MYBL2 | v-myb myeloblastosis viral oncogene homolog (avian)-like 2 | 0.0036 | 0.1147 | −1.5 |
| 205748_s_at | NM_017876 | RNF126 | ring finger protein 126 | 0.0056 | 0.6038 | −1.5 |
| 203359_s_at | AL525412 | MYCBP | c-myc binding protein | 0.0071 | 0.2121 | −1.5 |
| 212174_at | W02312 | AK2 | adenylate kinase 2 | 0.0014 | 0.2498 | −1.5 |
| 212441_at | D86985 | KIAA0232 | KIAA0232 gene product | 0.0039 | 0.0993 | −1.5 |
| 221972_s_at | AL571362 | SDF4 | stromal cell derived factor 4 | 0.0020 | 0.0645 | −1.5 |
| 207088_s_at | NM_003562 | SLC25A11 | solute carrier family 25 (mitochondrial carrier; oxoglutarate carrier), member 11 | 0.0056 | 0.6504 | −1.5 |
| 202556_s_at | NM_006337 | MCRS1 | microspherule protein 1 | 0.0042 | 0.1233 | −1.5 |
| 205512_s_at | NM_004208 | AIFM1 | apoptosis-inducing factor, mitochondrion-associated, 1 | 0.0035 | 0.7462 | −1.5 |
| 206510_at | AF332197 | SIX2 | sine oculis homeobox homolog 2 (*Drosophila*) | 0.0060 | 0.4870 | −1.5 |
| 210574_s_at | AF241788 | NUDC | nuclear distribution gene C homolog (*A. nidulans*) | 0.0006 | 0.1606 | −1.5 |
| 204695_at | AI343459 | CDC25A | cell division cycle 25 homolog A (*S. cerevisiae*) | 0.0011 | 0.1847 | −1.5 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 200655_s_at | NM_006888 | CALM1 | calmodulin 1 (phosphorylase kinase, delta) | 0.0008 | 0.0712 | −1.5 |
| 202939_at | NM_005857 | ZMPSTE24 | zinc metallopeptidase (STE24 homolog, yeast) | 0.0088 | 0.1153 | −1.5 |
| 203606_at | NM_004553 | NDUFS6 | NADH dehydrogenase (ubiquinone) Fe—S protein 6, 13 kDa (NADH-coenzyme Q reductase) | 0.0014 | 0.0990 | −1.5 |
| 218803_at | NM_018223 | CHFR | checkpoint with forkhead and ring finger domains | 0.0040 | 0.2666 | −1.5 |
| 209645_s_at | NM_000692 | ALDH1B1 | aldehyde dehydrogenase 1 family, member B1 | 0.0026 | 0.6355 | −1.5 |
| 218893_at | NM_024710 | ISOC2 | isochorismatase domain containing 2 | 0.0057 | 0.1709 | −1.5 |
| 201192_s_at | NM_006224 | PITPNA | phosphatidylinositol transfer protein, alpha | 0.0249 | 0.9184 | −1.5 |
| 201478_s_at | U59151 | DKC1 | dyskeratosis congenita 1, dyskerin | 0.0035 | 0.5159 | −1.5 |
| 201020_at | NM_003405 | YWHAH | tyrosine 3-monooxygenase/tryptophan 5-monooxygenase activation protein, eta polypeptide | 0.0119 | 0.2666 | −1.5 |
| 217785_s_at | NM_006555 | YKT6 | YKT6 v-SNARE homolog (S. cerevisiae) | 0.0025 | 0.4852 | −1.5 |
| 203239_s_at | NM_014516 | CNOT3 | CCR4-NOT transcription complex, subunit 3 | 0.0144 | 0.0832 | −1.5 |
| 208091_s_at | NM_030796 | ECOP | EGFR-coamplified and overexpressed protein /// EGFR-coamplified and overexpressed protein | 0.0009 | 0.0746 | −1.5 |
| 202854_at | NM_000194 | HPRT1 | hypoxanthine phosphoribosyltransferase 1 (Lesch-Nyhan syndrome) | 0.0096 | 0.1663 | −1.5 |
| 200611_s_at | AB010427 | WDR1 | WD repeat domain 1 | 0.0024 | 0.7179 | −1.5 |
| 200634_at | NM_005022 | PFN1 | profilin 1 | 0.0007 | 0.0539 | −1.5 |
| 209039_x_at | AF001434 | EHD1 | EH-domain containing 1 | 0.0057 | 0.9870 | −1.5 |
| 221731_x_at | BF218922 | CSPG2 | chondroitin sulfate proteoglycan 2 (versican) | 0.0043 | 0.0878 | −1.5 |
| 204364_s_at | BE535746 | REEP1 | receptor accessory protein 1 | 0.0072 | 0.1344 | −1.5 |
| 216952_s_at | M94363 | LMNB2 | lamin B2 | 0.0011 | 0.0274 | −1.5 |
| 201360_at | NM_000099 | CST3 | cystatin C (amyloid angiopathy and cerebral hemorrhage) | 0.0010 | 0.0252 | −1.5 |
| 201420_s_at | BF975273 | WDR77 | WD repeat domain 77 | 0.0011 | 0.9108 | −1.5 |
| 218214_at | NM_021934 | C12orf44 | chromosome 12 open reading frame 44 | 0.0095 | 0.9055 | −1.5 |
| 202581_at | NM_005346 | HSPA1B | heat shock 70 kDa protein 1B | 0.0185 | 0.1596 | −1.5 |
| 216733_s_at | X86401 | GATM | glycine amidinotransferase (L-arginine:glycine amidinotransferase) | 0.0199 | 0.5609 | −1.5 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 201801_s_at | AF079117 | SLC29A1 | solute carrier family 29 (nucleoside transporters), member 1 | 0.0140 | 0.5393 | −1.5 |
| 202138_x_at | NM_006303 | JTV1 | JTV1 gene | 0.0023 | 0.2414 | −1.5 |
| 217791_s_at | NM_002860 | ALDH18A1 | aldehyde dehydrogenase 18 family, member A1 | 0.0064 | 0.7660 | −1.5 |
| 208677_s_at | AL550657 | BSG | basigin (Ok blood group) | 0.0007 | 0.0428 | −1.5 |
| 203064_s_at | NM_004514 | FOXK2 | forkhead box K2 | 0.0090 | 0.6618 | −1.5 |
| 204042_at | AB020707 | WASF3 | WAS protein family, member 3 | 0.0300 | 0.4120 | −1.5 |
| 201377_at | NM_014847 | UBAP2L | ubiquitin associated protein 2-like | 0.0077 | 0.3919 | −1.5 |
| 217977_at | NM_016332 | SEPX1 | selenoprotein X, 1 | 0.0012 | 0.5433 | −1.4 |
| 218119_at | NM_006327 | TIMM23 /// LOC653252 | translocase of inner mitochondrial membrane 23 homolog (yeast) /// similar to Mitochondrial import inner membrane translocase subunit Tim23 | 0.0054 | 0.4659 | −1.4 |
| 214121_x_at | AA086229 | PDLIM7 | PDZ and LIM domain 7 (enigma) | 0.0029 | 0.0807 | −1.4 |
| 200895_s_at | NM_002014 | FKBP4 | FK506 binding protein 4, 59 kDa | 0.0037 | 0.8039 | −1.4 |
| 205436_s_at | NM_002105 | H2AFX | H2A histone family, member X | 0.0004 | 0.0252 | −1.4 |
| 217899_at | NM_017727 | FLJ20254 | hypothetical protein FLJ20254 | 0.0129 | 0.3602 | −1.4 |
| 204488_at | NM_014908 | TMEM15 | transmembrane protein 15 | 0.0075 | 0.6853 | −1.4 |
| 217903_at | NM_013403 | STRN4 | striatin, calmodulin binding protein 4 | 0.0218 | 0.1914 | −1.4 |
| 201645_at | NM_002160 | TNC | tenascin C (hexabrachion) | 0.0395 | 0.3472 | −1.4 |
| 212739_s_at | AL523860 | NME4 | non-metastatic cells 4, protein expressed in | 0.0015 | 0.3553 | −1.4 |
| 213867_x_at | AA809056 | ACTB | actin, beta | 0.0010 | 0.8642 | −1.4 |
| 201195_s_at | AB018009 | SLC7A5 | solute carrier family 7 (cationic amino acid transporter, y+ system), member 5 | 0.0028 | 0.1293 | −1.4 |
| 209100_at | BC001327 | IFRD2 | interferon-related developmental regulator 2 | 0.0050 | 0.2084 | −1.4 |
| 202771_at | NM_014745 | FAM38A | family with sequence similarity 38, member A | 0.0031 | 0.0541 | −1.4 |
| 201523_x_at | BE262760 | UBE2N | ubiquitin-conjugating enzyme E2N (UBC13 homolog, yeast) | 0.0012 | 0.5131 | −1.4 |
| 200846_s_at | NM_002708 | PPP1CA | protein phosphatase 1, catalytic subunit, alpha isoform | 0.0010 | 0.0395 | −1.4 |
| 210010_s_at | U25147 | SLC25A1 | solute carrier family 25 (mitochondrial carrier; citrate transporter), member 1 | 0.0001 | 0.0157 | −1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 209202_s_at | AF001690 | EXTL3 | exostoses (multiple)-like 3 | 0.0264 | 0.4576 | −1.4 |
| 201043_s_at | NM_006305 | ANP32A | acidic (leucine-rich) nuclear phosphoprotein 32 family, member A | 0.0079 | 0.2051 | −1.4 |
| 210378_s_at | BC004118 | SSNA1 | Sjogren's syndrome nuclear autoantigen 1 | 0.0007 | 0.2575 | −1.4 |
| 200824_at | NM_000852 | GSTP1 | glutathione S-transferase pi | 0.0019 | 0.0537 | −1.4 |
| 212155_at | AA085748 | RNF187 | ring finger protein 187 | 0.0016 | 0.1231 | −1.4 |
| 213011_s_at | BF116254 | TPI1 | triosephosphate isomerase 1 | 0.0039 | 0.3558 | −1.4 |
| 209482_at | BC001430 | POP7 | processing of precursor 7, ribonuclease P subunit (S. cerevisiae) | 0.0014 | 0.3306 | −1.4 |
| 203258_at | NM_006442 | DRAP1 | DR1-associated protein 1 (negative cofactor 2 alpha) | 0.0012 | 0.3362 | −1.4 |
| 221637_s_at | BC001434 | C11orf48 | chromosome 11 open reading frame 48 | 0.0173 | 0.3011 | −1.4 |
| 200646_s_at | NM_006148 | NUCB1 | nucleobindin 1 | 0.0039 | 0.0452 | −1.4 |
| 218308_at | NM_006342 | TACC3 | transforming, acidic coiled-coil containing protein 3 | 0.0011 | 0.4338 | −1.4 |
| 204616_at | NM_006002 | UCHL3 | ubiquitin carboxyl-terminal esterase L3 (ubiquitin thiolesterase) | 0.0045 | 0.0432 | −1.4 |
| 205479_s_at | NM_002658 | PLAU | plasminogen activator, urokinase | 0.0244 | 0.5956 | −1.4 |
| 212432_at | AL542571 | GRPEL1 | GrpE-like 1, mitochondrial (E. coli) | 0.0015 | 0.4084 | −1.4 |
| 208649_s_at | AF100752 | VCP | valosin-containing protein | 0.0035 | 0.5192 | −1.4 |
| 200952_s_at | AI635187 | CCND2 | cyclin D2 | 0.0317 | 0.1578 | −1.4 |
| 208478_s_at | NM_004324 | BAX | BCL2-associated X protein | 0.0479 | 0.9784 | −1.4 |
| 206703_at | NM_000747 | CHRNB1 | cholinergic receptor, nicotinic, beta 1 (muscle) | 0.0146 | 0.9472 | −1.4 |
| 209825_s_at | BC002906 | UCK2 | uridine-cytidine kinase 2 | 0.0010 | 0.0941 | −1.4 |
| 216251_s_at | BF965437 | TTLL12 | tubulin tyrosine ligase-like family, member 12 | 0.0022 | 0.7692 | −1.4 |
| 208622_s_at | AA670344 | VIL2 | villin 2 (ezrin) | 0.0323 | 0.6566 | −1.4 |
| 208941_s_at | BC000941 | SEPHS1 | selenophosphate synthetase 1 | 0.0013 | 0.3793 | −1.4 |
| 209262_s_at | BC002669 | NR2F6 | nuclear receptor subfamily 2, group F, member 6 | 0.0060 | 0.3291 | −1.4 |
| 200600_at | NM_002444 | MSN | moesin | 0.0025 | 0.0666 | −1.4 |
| 200776_s_at | AL518328 | BZW1 /// LOC151579 | basic leucine zipper and W2 domains 1 /// similar to basic leucine zipper and W2 domains 1 | 0.0085 | 0.1920 | −1.4 |
| 201818_at | NM_024830 | AYTL2 | acyltransferase like 2 | 0.0071 | 0.1235 | −1.4 |
| 201082_s_at | NM_004082 | DCTN1 | dynactin 1 (p150, glued homolog, Drosophila) | 0.0118 | 0.0783 | −1.4 |
| 55081_at | W46406 | MICALL1 | MICAL-like 1 | 0.0054 | 0.9766 | −1.4 |
| 216088_s_at | AL078633 | PSMA7 | proteasome (prosome, macropain) subunit, alpha type, 7 | 0.0014 | 0.6547 | −1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 209231_s_at | AI038068 | DCTN5 | dynactin 5 (p25) | 0.0124 | 0.9715 | −1.4 |
| 200827_at | NM_000302 | PLOD1 | procollagen-lysine 1,2-oxoglutarate 5-dioxygenase 1 | 0.0048 | 0.0510 | −1.4 |
| 213746_s_at | AW051856 | FLNA | filamin A, alpha (actin binding protein 280) | 0.0207 | 0.5615 | −1.4 |
| 220949_s_at | NM_024033 | C7orf49 | chromosome 7 open reading frame 49 | 0.0047 | 0.3132 | −1.4 |
| 202908_at | NM_006005 | WFS1 | Wolfram syndrome 1 (wolframin) | 0.0099 | 0.2926 | −1.4 |
| 207714_s_at | NM_004353 | SERPINH1 | serpin peptidase inhibitor, clade H (heat shock protein 47), member 1, (collagen binding protein 1) | 0.0012 | 0.0512 | −1.4 |
| 217752_s_at | NM_018235 | CNDP2 | CNDP dipeptidase 2 (metallopeptidase M20 family) | 0.0082 | 0.5146 | −1.4 |
| 208744_x_at | BG403660 | HSPH1 | heat shock 105 kDa/110 kDa protein 1 | 0.0104 | 0.0536 | −1.4 |
| 202111_at | NM_003040 | SLC4A2 | solute carrier family 4, anion exchanger, member 2 (erythrocyte membrane protein band 3-like 1) | 0.0037 | 0.0681 | −1.4 |
| 212691_at | AW131863 | NUP188 | nucleoporin 188 kDa | 0.0061 | 0.3316 | −1.4 |
| 210338_s_at | AB034951 | HSPA8 | heat shock 70 kDa protein 8 | 0.0019 | 0.1113 | −1.4 |
| 202245_at | AW084510 | LSS | lanosterol synthase (2,3-oxidosqualene-lanosterol cyclase) | 0.0219 | 0.2846 | −1.4 |
| 201762_s_at | NM_002818 | PSME2 | proteasome (prosome, macropain) activator subunit 2 (PA28 beta) | 0.0018 | 0.1893 | −1.4 |
| 218815_s_at | NM_018022 | TMEM51 | transmembrane protein 51 | 0.0079 | 0.6437 | −1.4 |
| 204147_s_at | NM_007111 | TFDP1 | transcription factor Dp-1 | 0.0247 | 0.6619 | −1.4 |
| 201204_s_at | AA706065 | RRBP1 | ribosome binding protein 1 homolog 180 kDa (dog) | 0.0340 | 0.7216 | −1.4 |
| 50314_i_at | AI761506 | C20orf27 | chromosome 20 open reading frame 27 | 0.0025 | 0.1143 | −1.4 |
| 201584_s_at | NM_005804 | DDX39 | DEAD (Asp-Glu-Ala-Asp) box polypeptide 39 | 0.0024 | 0.2953 | −1.4 |
| 208928_at | AF258341 | POR | P450 (cytochrome) oxidoreductase | 0.0269 | 0.3414 | −1.4 |
| 220326_s_at | NM_018071 | FLJ10357 | hypothetical protein FLJ10357 | 0.0005 | 0.0252 | −1.4 |
| 201654_s_at | AI991033 | HSPG2 | heparan sulfate proteoglycan 2 (perlecan) | 0.0045 | 0.0396 | −1.4 |
| 202737_s_at | NM_012321 | LSM4 | LSM4 homolog, U6 small nuclear RNA associated (S. cerevisiae) | 0.0066 | 0.6417 | −1.4 |
| 202528_at | NM_000403 | GALE | UDP-galactose-4-epimerase | 0.0114 | 0.5096 | −1.4 |
| 209652_s_at | BC001422 | PGF | placental growth factor, vascular endothelial growth factor-related protein | 0.0012 | 0.0452 | −1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 203270_at | NM_012145 | DTYMK /// LOC727761 | deoxythymidylate kinase (thymidylate kinase) /// similar to deoxythymidylate kinase (thymidylate kinase) | 0.0049 | 0.2176 | −1.4 |
| 218695_at | NM_019037 | EXOSC4 | exosome component 4 | 0.0046 | 0.3295 | −1.4 |
| 202894_at | NM_004444 | EPHB4 | EPH receptor B4 | 0.0057 | 0.6685 | −1.4 |
| 200700_s_at | NM_006854 | KDELR2 | KDEL (Lys-Asp-Glu-Leu) endoplasmic reticulum protein retention receptor 2 | 0.0021 | 0.3528 | −1.4 |
| 219526_at | NM_024644 | C14orf169 | chromosome 14 open reading frame 169 | 0.0075 | 0.3181 | −1.4 |
| 209052_s_at | BF111870 | WHSC1 | Wolf-Hirschhorn syndrome candidate 1 | 0.0039 | 0.0436 | −1.4 |
| 201282_at | NM_002541 | OGDH | oxoglutarate (alpha-ketoglutarate) dehydrogenase (lipoamide) | 0.0117 | 0.0916 | −1.4 |
| 221484_at | BF691447 | B4GALT5 | UDP-Gal:betaGlcNAc beta 1,4-galactosyltransferase, polypeptide 5 | 0.0078 | 0.4685 | −1.4 |
| 200911_s_at | NM_006283 | TACC1 | transforming, acidic coiled-coil containing protein 1 | 0.0036 | 0.1542 | −1.4 |
| 203039_s_at | NM_005006 | NDUFS1 | NAPH dehydrogenase (ubiquinone) Fe—S protein 1, 75 kDa (NADH-coenzyme Q reductase) | 0.0159 | 0.2193 | −1.4 |
| 201168_x_at | NM_004309 | ARHGDIA /// LOC728908 | Rho GDP dissociation inhibitor (GDI) alpha /// similar to Rho GDP dissociation inhibitor (GDI) alpha | 0.0007 | 0.0451 | −1.4 |
| 201537_s_at | BC002682 | DUSP3 | dual specificity phosphatase 3 (vaccinia virus phosphatase VH1-related) | 0.0061 | 0.1488 | −1.4 |
| 209773_s_at | BC001886 | RRM2 | ribonucleotide reductase M2 polypeptide | 0.0007 | 0.2822 | −1.4 |
| 210986_s_at | Z24727 | TPM1 | tropomyosin 1 (alpha) | 0.0436 | 0.6520 | −1.4 |
| 218493_at | NM_024571 | C16orf33 | chromosome 16 open reading frame 33 | 0.0022 | 0.5112 | −1.4 |
| 202887_s_at | NM_019058 | DDIT4 | DNA-damage-inducible transcript 4 | 0.0039 | 0.1757 | −1.4 |
| 218857_s_at | NM_025080 | ASRGL1 | asparaginase like 1 | 0.0047 | 0.6967 | −1.4 |
| 209190_s_at | AF051782 | DIAPH1 | diaphanous homolog 1 (*Drosophila*) | 0.0057 | 0.6058 | −1.4 |
| 200650_s_at | NM_005566 | LDHA | lactate dehydrogenase A | 0.0004 | 0.0344 | −1.4 |
| 200948_at | NM_005439 | MLF2 | myeloid leukemia factor 2 | 0.0078 | 0.3850 | −1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 200623_s_at | NM_005184 | CALM3 | calmodulin 3 (phosphorylase kinase, delta) | 0.0079 | 0.0721 | −1.4 |
| 204849_at | NM_006602 | TCFL5 | transcription factor-like 5 (basic helix-loop-helix) | 0.0088 | 0.7035 | −1.4 |
| 204331_s_at | NM_021107 | MRPS12 | mitochondrial ribosomal protein S12 | 0.0060 | 0.5066 | −1.4 |
| 213476_x_at | AL565749 | TUBB3 | tubulin beta 3 | 0.0076 | 0.7836 | −1.4 |
| 209321_s_at | AF033861 | ADCY3 | adenylate cyclase 3 | 0.0034 | 0.0856 | −1.4 |
| 200808_s_at | NM_003461 | ZYX | zyxin | 0.0061 | 0.4333 | −1.4 |
| 219212_at | NM_016299 | HSPA14 | heat shock 70 kDa protein 14 | 0.0027 | 0.1403 | −1.4 |
| 206593_s_at | NM_006752 | SURF5 | surfeit 5 | 0.0363 | 0.2712 | −1.4 |
| 201797_s_at | NM_006295 | VARS | valyl-tRNA synthetase | 0.0159 | 0.9226 | −1.4 |
| 203190_at | NM_002496 | NDUFS8 | NADH dehydrogenase (ubiquinone) Fe—S protein 8, 23 kDa (NADH-coenzyme Q reductase) | 0.0019 | 0.8311 | −1.4 |
| 2028_s_at | M96577 | E2F1 | E2F transcription factor 1 | 0.0227 | 0.5305 | −1.4 |
| 203392_s_at | NM_001328 | CTBP1 | C-terminal binding protein 1 | 0.0091 | 0.7822 | −1.4 |
| 217818_s_at | NM_005718 | ARPC4 | actin related protein 2/3 complex, subunit 4, 20 kDa | 0.0112 | 0.4886 | −1.4 |
| 208657_s_at | AF142408 | 9-Sep | septin 9 | 0.0041 | 0.0721 | −1.4 |
| 201252_at | NM_006503 | PSMC4 /// LOC652826 | proteasome (prosome, macropain) 26S subunit, ATPase, 4 /// similar to 26S protease regulatory subunit 6B (MIP224) (MB67-interacting protein) (TAT-binding protein 7) (TBP-7) | 0.0034 | 0.2890 | −1.4 |
| 200880_at | AL534104 | DNAJA1 | DnaJ (Hsp40) homolog, subfamily A, member 1 | 0.0122 | 0.1190 | −1.4 |
| 201573_s_at | M75715 | ETF1 | eukaryotic translation termination factor 1 | 0.0065 | 0.4236 | −1.4 |
| 218131_s_at | NM_017660 | GATAD2A | GATA zinc finger domain containing 2A | 0.0045 | 0.1527 | −1.4 |
| 207740_s_at | NM_012346 | NUP62 | nucleoporin 62 kDa | 0.0302 | 0.2490 | −1.4 |
| 217777_s_at | NM_016395 | PTPLAD1 /// LOC732402 | protein tyrosine phosphatase-like A domain containing 1 /// similar to butyrate-induced transcript 1 | 0.0237 | 0.3399 | −1.4 |
| 218474_s_at | NM_018992 | KCTD5 | potassium channel tetramerisation domain containing 5 | 0.0314 | 0.5788 | −1.4 |
| 200621_at | NM_004078 | CSRP1 | cysteine and glycine-rich protein 1 | 0.0007 | 0.1464 | −1.4 |
| 219438_at | NM_024522 | FAM77C | family with sequence similarity 77, member C | 0.0279 | 0.9563 | −1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 211070_x_at | BC006466 | DBI | diazepam binding inhibitor (GABA receptor modulator, acyl-Coenzyme A binding protein) /// diazepam binding inhibitor (GABA receptor modulator, acyl-Coenzyme A binding protein) | 0.0029 | 0.0800 | −1.4 |
| 212378_at | NM_000819 | GART | phosphoribosylglycinamide formyltransferase, phosphoribosylglycinamide synthetase, phosphoribosylaminoimidazole synthetase | 0.0046 | 0.4656 | −1.4 |
| 208453_s_at | NM_006523 | XPNPEP1 | X-prolyl aminopeptidase (aminopeptidase P) 1, soluble | 0.0102 | 0.6642 | −1.4 |
| 203489_at | NM_006427 | SIVA1 | SIVA1, apoptosis-inducing factor | 0.0054 | 0.3864 | −1.4 |
| 209834_at | AB017915 | CHST3 | carbohydrate (chondroitin 6) sulfotransferase 3 | 0.0107 | 0.4595 | −1.4 |
| 208700_s_at | L12711 | TKT | transketolase (Wernicke-Korsakoff syndrome) | 0.0008 | 0.0502 | −1.4 |
| 202595_s_at | AF161461 | LEPROTL1 | leptin receptor overlapping transcript-like 1 | 0.0451 | 0.8984 | −1.4 |
| 203252_at | NM_005851 | CDK2AP2 | CDK2-associated protein 2 | 0.0302 | 0.6607 | −1.4 |
| 205895_s_at | NM_004741 | NOLC1 | nucleolar and coiled-body phosphoprotein 1 | 0.0243 | 0.5497 | −1.4 |
| 201979_s_at | NM_006247 | PPP5C | protein phosphatase 5, catalytic subunit | 0.0271 | 0.1164 | −1.4 |
| 208313_s_at | NM_004630 | SF1 | splicing factor 1 | 0.0012 | 0.0284 | −1.4 |
| 203814_s_at | NM_000904 | NQO2 | NAD(P)H dehydrogenase, quinone 2 | 0.0332 | 0.6539 | −1.4 |
| 217294_s_at | U88968 | ENO1 | enolase 1, (alpha) | 0.0080 | 0.5283 | −1.4 |
| 201714_at | NM_001070 | TUBG1 | tubulin, gamma 1 | 0.0049 | 0.9428 | −1.4 |
| 212116_at | NM_006510 | TRIM27 | tripartite motif-containing 27 | 0.0042 | 0.3418 | −1.4 |
| 218744_s_at | NM_016223 | PACSIN3 | protein kinase C and casein kinase substrate in neurons 3 | 0.0054 | 0.8147 | −1.4 |
| 201090_x_at | NM_006082 | K-ALPHA-1 | alpha tubulin | 0.0014 | 0.1096 | −1.4 |
| 219361_s_at | NM_022767 | ISG20L1 | interferon stimulated exonuclease gene 20 kDa-like 1 | 0.0012 | 0.0579 | −1.4 |
| 211126_s_at | U46006 | CSRP2 | cysteine and glycine-rich protein 2 | 0.0007 | 0.0582 | −1.4 |
| 202329_at | NM_004383 | CSK | c-src tyrosine kinase | 0.0222 | 0.8338 | −1.4 |
| 212712_at | BE222901 | CAMSAP1 | calmodulin regulated spectrin-associated protein 1 | 0.0064 | 0.4040 | −1.4 |
| 202483_s_at | NM_002882 | RANBP1 | RAN binding protein 1 | 0.0020 | 0.0727 | −1.4 |
| 201368_at | U07802 | ZFP36L2 | zinc finger protein 36, C3H type-like 2 | 0.0165 | 0.2538 | −1.4 |
| 209526_s_at | AB029156 | HDGFRP3 | hepatoma-derived growth factor, related protein 3 | 0.0034 | 0.2976 | −1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 202407_s_at | BF342707 | PRPF31 | PRP31 pre-mRNA processing factor 31 homolog (S. cerevisiae) | 0.0144 | 0.1019 | −1.4 |
| 212126_at | BG391282 | — | CDNA clone IMAGE: 4842353 | 0.0066 | 0.0714 | −1.4 |
| 202779_s_at | NM_014501 | UBE2S /// LOC731049 | ubiquitin-conjugating enzyme E2S /// similar to Ubiquitin-conjugating enzyme E2S (Ubiquitin-conjugating enzyme E2-24 kDa) (Ubiquitin-protein ligase) (Ubiquitin carrier protein) (E2-EPF5) | 0.0007 | 0.0841 | −1.4 |
| 211593_s_at | AB047005 | MAST2 | microtubule associated serine/threonine kinase 2 /// microtubule associated serine/threonine kinase 2 | 0.0061 | 0.1211 | −1.4 |
| 213787_s_at | AV702405 | EBP | emopamil binding protein (sterol isomerase) | 0.0414 | 0.3058 | −1.4 |
| 217796_s_at | NM_017921 | NPLOC4 | nuclear protein localization 4 homolog (S. cerevisiae) | 0.0069 | 0.2545 | −1.4 |
| 214507_s_at | NM_014285 | EXOSC2 | exosome component 2 | 0.0023 | 0.4634 | −1.4 |
| 209233_at | U72514 | EMG1 | EMG1 nucleolar protein homolog (S. cerevisiae) | 0.0052 | 0.4127 | −1.4 |
| 221759_at | AL583123 | G6PC3 | glucose 6 phosphatase, catalytic, 3 | 0.0069 | 0.0941 | −1.4 |
| 215121_x_at | AA680302 | IGL@ /// IGLV4-3 /// IGLV3-25 /// IGLV2-14 | immunoglobulin lambda locus /// immunoglobulin lambda variable 4-3 /// immunoglobulin lambda variable 3-25 /// immunoglobulin lambda variable 2-14 | 0.0302 | 0.3171 | −1.4 |
| 210026_s_at | AY028896 | CARD10 | caspase recruitment domain family, member 10 | 0.0193 | 0.7762 | −1.4 |
| 211762_s_at | BC005978 | KPNA2 /// LOC728860 | karyopherin alpha 2 (RAG cohort 1, importin alpha 1) /// karyopherin alpha 2 (RAG cohort 1, importin alpha 1) /// similar to Importin alpha-2 subunit (Karyopherin alpha-2 subunit) (SRP1-alpha) (RAG cohort protein 1) /// similar to Importin alpha-2 subunit | 0.0066 | 0.4069 | −1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| | | | (Karyopherin alpha-2 subunit) (SRP1-alpha) (RAG cohort protein 1) | | | |
| 218678_at | NM_024609 | NES | nestin | 0.0043 | 0.1063 | −1.4 |
| 201275_at | NM_002004 | FDPS | farnesyl diphosphate synthase (farnesyl pyrophosphate synthetase, dimethylallyltranstransferase, geranyltranstransferase) | 0.0014 | 0.9609 | −1.4 |
| 220011_at | NM_024037 | C1orf135 | chromosome 1 open reading frame 135 | 0.0050 | 0.1904 | −1.4 |
| 201000_at | NM_001605 | AARS | alanyl-tRNA synthetase | 0.0076 | 0.6685 | −1.4 |
| 217835_x_at | NM_018840 | C20orf24 | chromosome 20 open reading frame 24 | 0.0011 | 0.0271 | −1.4 |
| 217755_at | NM_016185 | HN1 | hematological and neurological expressed 1 | 0.0007 | 0.0336 | −1.4 |
| 200734_s_at | BG341906 | ARF3 | ADP-ribosylation factor 3 | 0.0093 | 0.2784 | −1.4 |
| 203411_s_at | NM_005572 | LMNA | lamin A/C | 0.0007 | 0.1514 | −1.4 |
| 218661_at | NM_024845 | FLJ14154 | hypothetical protein FLJ14154 | 0.0066 | 0.3772 | −1.4 |
| 214439_x_at | AF043899 | BIN1 | bridging integrator 1 | 0.0130 | 0.4300 | −1.4 |
| 201953_at | NM_006384 | CIB1 | calcium and integrin binding 1 (calmyrin) | 0.0078 | 0.1914 | −1.4 |
| 208540_x_at | NM_021039 | LOC729659 /// LOC730278 /// LOC730558 | similar to Putative S100 calcium-binding protein A11 pseudogene /// similar to Putative S100 calcium-binding protein A11 pseudogene /// similar to Putative S100 calcium-binding protein A11 pseudogene | 0.0057 | 0.3193 | −1.4 |
| 202718_at | NM_000597 | IGFBP2 | insulin-like growth factor binding protein 2, 36 kDa | 0.0007 | 0.0157 | −1.4 |
| 209567_at | BC001811 | RRS1 | RRS1 ribosome biogenesis regulator homolog (*S. cerevisiae*) | 0.0265 | 0.1269 | −1.4 |
| 212540_at | BG476661 | CDC34 | cell division cycle 34 homolog (*S. cerevisiae*) | 0.0110 | 0.9118 | −1.4 |
| 213470_s_at | BF983406 | HNRPH1 | heterogeneous nuclear ribonucleoprotein H1 (H) | 0.0175 | 0.5096 | −1.4 |
| 200964_at | NM_003334 | UBE1 | ubiquitin-activating enzyme E1 (A1S9T and BN75 temperature sensitivity complementing) | 0.0009 | 0.0599 | −1.4 |
| 221571_at | AI721219 | TRAF3 | TNF receptor-associated factor 3 | 0.0065 | 0.1689 | −1.4 |
| 201096_s_at | AL537042 | ARF4 | ADP-ribosylation factor 4 | 0.0093 | 0.3651 | −1.4 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 215714_s_at | AF254822 | SMARCA4 | SWI/SNF related, matrix associated, actin dependent regulator of chromatin, subfamily a, member 4 | 0.0135 | 0.1898 | −1.4 |
| 202469_s_at | AU149367 | CPSF6 | cleavage and polyadenylation specific factor 6, 68 kDa | 0.0399 | 0.2918 | −1.4 |
| 65585_at | AA527515 | FAM86B1 | family with sequence similarity 86, member B1 | 0.0044 | 0.0891 | −1.4 |
| 213334_x_at | BE676218 | UCHL5IP | UCHL5 interacting protein | 0.0136 | 0.5765 | −1.4 |
| 209213_at | BC002511 | CBR1 | carbonyl reductase 1 | 0.0080 | 0.9371 | −1.4 |
| 206441_s_at | NM_017828 | COMMD4 | COMM domain containing 4 | 0.0069 | 0.0965 | −1.4 |
| 218650_at | NM_022775 | DGCR8 | DiGeorge syndrome critical region gene 8 | 0.0166 | 0.0645 | −1.4 |
| 218200_s_at | NM_004546 | NDUFB2 | NADH dehydrogenase (ubiquinone) 1 beta subcomplex, 2, 8 kDa | 0.0026 | 0.3329 | −1.4 |
| 202692_s_at | NM_014233 | UBTF | upstream binding transcription factor, RNA polymerase I | 0.0074 | 0.4143 | −1.4 |
| 201247_at | BE513151 | — | — | 0.0042 | 0.0441 | −1.4 |
| 208308_s_at | NM_000175 | GPI | glucose phosphate isomerase | 0.0014 | 0.0589 | −1.4 |
| 218028_at | NM_016031 | ELOVL1 | elongation of very long chain fatty acids (FEN1/Elo2, SUR4/Elo3, yeast)-like 1 | 0.0052 | 0.1335 | −1.4 |
| 204955_at | NM_006307 | SRPX | sushi-repeat-containing protein, X-linked | 0.0149 | 0.0681 | −1.4 |
| 201543_s_at | NM_020150 | SAR1A | SAR1 gene homolog A (S. cerevisiae) | 0.0017 | 0.1483 | −1.4 |
| 209093_s_at | K02920 | GBA /// GBAP | glucosidase, beta; acid (includes glucosylceramidase) /// glucosidase, beta; acid, pseudogene | 0.0066 | 0.1233 | −1.4 |
| 201251_at | NM_002654 | PKM2 | pyruvate kinase, muscle | 0.0060 | 0.0966 | −1.3 |
| 209372_x_at | BF971587 | TUBB2A /// TUBB2B | tubulin, beta 2A /// tubulin, beta 2B | 0.0382 | 0.3610 | −1.3 |
| 218305_at | NM_024658 | IPO4 | importin 4 | 0.0192 | 0.5264 | −1.3 |
| 202418_at | NM_020470 | YIF1A | Yip1 interacting factor homolog A (S. cerevisiae) | 0.0156 | 0.7400 | −1.3 |
| 220966_x_at | NM_030978 | ARPC5L | actin related protein 2/3 complex, subunit 5-like /// actin related protein 2/3 complex, subunit 5-like | 0.0059 | 0.2710 | −1.3 |
| 209186_at | M23114 | ATP2A2 | ATPase, Ca++ transporting, cardiac muscle, slow twitch 2 | 0.0041 | 0.0664 | −1.3 |
| 219646_at | NM_017702 | FLJ20186 | hypothetical protein FLJ20186 | 0.0012 | 0.0732 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 213887_s_at | AI554759 | POLR2E | polymerase (RNA) II (DNA directed) polypeptide E, 25 kDa | 0.0006 | 0.0629 | −1.3 |
| 219556_at | NM_025108 | C16orf59 | chromosome 16 open reading frame 59 | 0.0047 | 0.7714 | −1.3 |
| 204975_at | NM_001424 | EMP2 | epithelial membrane protein 2 | 0.0129 | 0.1233 | −1.3 |
| 200628_s_at | M61715 | WARS | tryptophanyl-tRNA synthetase | 0.0060 | 0.5095 | −1.3 |
| 221790_s_at | AL545035 | LDLRAP1 | low density lipoprotein receptor adaptor protein 1 | 0.0220 | 0.1822 | −1.3 |
| 37996_s_at | L08835 | DMPK | dystrophia myotonica-protein kinase | 0.0037 | 0.0582 | −1.3 |
| 208793_x_at | AI744900 | SMARCA4 /// MRPL43 | SWI/SNF related, matrix associated, actin dependent regulator of chromatin, subfamily a, member 4 /// mitochondrial ribosomal protein L43 | 0.0195 | 0.3604 | −1.3 |
| 202262_x_at | NM_013974 | DDAH2 | dimethylarginine dimethylaminohydrolase 2 | 0.0016 | 0.2933 | −1.3 |
| 215489_x_at | AI871287 | HOMER3 | homer homolog 3 (*Drosophila*) | 0.0462 | 0.6112 | −1.3 |
| 210334_x_at | AB028869 | BIRC5 | baculoviral IAP repeat-containing 5 (survivin) | 0.0111 | 0.0735 | −1.3 |
| 213897_s_at | AI832239 | MRPL23 | mitochondrial ribosomal protein L23 | 0.0054 | 0.6849 | −1.3 |
| 212702_s_at | N45111 | BICD2 | bicaudal D homolog 2 (*Drosophila*) | 0.0304 | 0.4187 | −1.3 |
| 217772_s_at | NM_014342 | MTCH2 | mitochondrial carrier homolog 2 (*C. elegans*) | 0.0040 | 0.6337 | −1.3 |
| 204441_s_at | NM_002689 | POLA2 | polymerase (DNA directed), alpha 2 (70 kD subunit) | 0.0049 | 0.1015 | −1.3 |
| 202275_at | NM_000402 | G6PD | glucose-6-phosphate dehydrogenase | 0.0248 | 0.1383 | −1.3 |
| 200045_at | NM_001090 | ABCF1 | ATP-binding cassette, sub-family F (GCN20), member 1 /// ATP-binding cassette, sub-family F (GCN20), member 1 | 0.0051 | 0.9326 | −1.3 |
| 209899_s_at | AF217197 | SIAHBP1 | fuse-binding protein-interacting repressor | 0.0015 | 0.4831 | −1.3 |
| 202041_s_at | NM_004214 | FIBP | fibroblast growth factor (acidic) intracellular binding protein | 0.0044 | 0.2432 | −1.3 |
| 221853_s_at | N39536 | NOMO1 /// NOMO2 /// NOMO3 | NODAL modulator 1 /// NODAL modulator 2 /// NODAL modulator 3 | 0.0018 | 0.2079 | −1.3 |
| 208836_at | U51478 | ATP1B3 | ATPase, Na+/K+ transporting, beta 3 polypeptide | 0.0048 | 0.9938 | −1.3 |
| 214500_at | AF044286 | H2AFY | H2A histone family, member Y | 0.0050 | 0.5729 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 203025_at | NM_003491 | ARD1A | ARD1 homolog A, N-acetyltransferase (S. cerevisiae) | 0.0376 | 0.7352 | −1.3 |
| 206452_x_at | NM_021131 | PPP2R4 | protein phosphatase 2A, regulatory subunit B' (PR 53) | 0.0127 | 0.2664 | −1.3 |
| 202326_at | NM_006709 | EHMT2 | euchromatic histone-lysine N-methyltransferase 2 | 0.0261 | 0.4234 | −1.3 |
| 218708_at | NM_013248 | NXT1 | NTF2-dike export factor 1 | 0.0016 | 0.0699 | −1.3 |
| 208353_x_at | NM_020480 | ANK1 | ankyrin 1, erythrocytic | 0.0036 | 0.5544 | −1.3 |
| 218497_s_at | NM_002936 | RNASEH1 | ribonuclease H1 | 0.0043 | 0.2176 | −1.3 |
| 220864_s_at | NM_015965 | NDUFA13 | NADH dehydrogenase (ubiquinone) 1 alpha subcomplex, 13 | 0.0101 | 0.8591 | −1.3 |
| 212708_at | AV721987 | MSL-1 | male-specific lethal-1 homolog | 0.0026 | 0.2235 | −1.3 |
| 218223_s_at | NM_016274 | PLEKHO1 | pleckstrin homology domain containing, family O member 1 | 0.0247 | 0.8246 | −1.3 |
| 203119_at | NM_024098 | CCDC86 | coiled-coil domain containing 86 | 0.0040 | 0.1268 | −1.3 |
| 200660_at | NM_005620 | S100A11 | S100 calcium binding protein A11 | 0.0007 | 0.1105 | −1.3 |
| 218918_at | NM_020379 | MAN1C1 | mannosidase, alpha, class 1C, member 1 | 0.0076 | 0.6532 | −1.3 |
| 222065_s_at | AI830227 | FLII | flightless I homolog (Drosophila) | 0.0066 | 0.2358 | −1.3 |
| 217946_s_at | NM_016402 | SAE1 | SUMO1 activating enzyme subunit 1 | 0.0007 | 0.1017 | −1.3 |
| 211799_x_at | U62824 | HLA-C | major histocompatibility complex, class I, C | 0.0098 | 0.7199 | −1.3 |
| 200055_at | NM_006284 | TAF10 | TAF10 RNA polymerase II, TATA box binding protein (TBP)-associated factor, 30 kDa /// TAF10 RNA polymerase II, TATA box binding protein (TBP)-associated factor, 30 kDa | 0.0029 | 0.2192 | −1.3 |
| 209478_at | U95006 | PCDHGC3 | Protocadherin gamma subfamily C, 3 | 0.0036 | 0.4002 | −1.3 |
| 218897_at | NM_030577 | TMEM177 | transmembrane protein 177 | 0.0063 | 0.9572 | −1.3 |
| 39835_at | U93181 | SBF1 | SET binding factor 1 | 0.0015 | 0.0290 | −1.3 |
| 212437_at | AL109804 | CENPB | centromere protein B, 80 kDa | 0.0286 | 0.3415 | −1.3 |
| 203871_at | NM_015670 | SENP3 | SUMO1/sentrin/SMT3 specific peptidase 3 | 0.0190 | 0.2427 | −1.3 |
| 218358_at | NM_024324 | CCNK | Cyclin K | 0.0044 | 0.3329 | −1.3 |
| 213892_s_at | AA927724 | APRT | adenine phosphoribosyltransferase | 0.0040 | 0.8086 | −1.3 |
| 220789_s_at | NM_004749 | TBRG4 | transforming growth factor beta regulator 4 | 0.0323 | 0.4333 | −1.3 |
| 202758_s_at | NM_003721 | RFXANK | regulatory factor X-associated ankyrin-containing protein | 0.0032 | 0.3094 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 208620_at | U24223 | PCBP1 | poly(rC) binding protein 1 | 0.0021 | 0.1368 | −1.3 |
| 200768_s_at | BC001686 | MAT2A | methionine adenosyltransferase II, alpha | 0.0073 | 0.0436 | −1.3 |
| 201937_s_at | NM_012100 | DNPEP | aspartyl aminopeptidase | 0.0117 | 0.4038 | −1.3 |
| 209536_s_at | AF320070 | EHD4 | EH-domain containing 4 | 0.0246 | 0.4627 | −1.3 |
| 201727_s_at | NM_001419 | ELAVL1 | ELAV (embryonic lethal, abnormal vision, *Drosophila*)-like 1 (Hu antigen R) | 0.0184 | 0.5267 | −1.3 |
| 202715_at | NM_004341 | CAD /// ARHGEF5 /// LOC653691 | carbamoyl-phosphate synthetase 2, aspartate transcarbamylase, and dihydroorotase /// Rho guanine nucleotide exchange factor (GEF) 5 /// FLJ40722-like | 0.0029 | 0.1198 | −1.3 |
| 202330_s_at | NM_003362 | UNG | uracil-DNA glycosylase | 0.0046 | 0.1330 | −1.3 |
| 215464_s_at | AK001327 | TAX1BP3 | Tax1 (human T-cell leukemia virus type I) binding protein 3 | 0.0038 | 0.2644 | −1.3 |
| 204099_at | NM_003078 | SMARCD3 | SWI/SNF related, matrix associated, actin dependent regulator of chromatin, subfamily d, member 3 | 0.0047 | 0.4707 | −1.3 |
| 203622_s_at | NM_020143 | PNO1 | partner of NOB1 homolog (*S. cerevisiae*) | 0.0066 | 0.0727 | −1.3 |
| 203940_s_at | NM_014909 | VASH1 | vasohibin 1 | 0.0107 | 0.7646 | −1.3 |
| 203349_s_at | NM_004454 | ETV5 | ets variant gene 5 (ets-related molecule) | 0.0074 | 0.5793 | −1.3 |
| 200739_s_at | BG338532 | SUMO3 | SMT3 suppressor of mif two 3 homolog 3 (*S. cerevisiae*) | 0.0146 | 0.1657 | −1.3 |
| 209765_at | Y13786 | ADAM19 | ADAM metallopeptidase domain 19 (meltrin beta) | 0.0079 | 0.4707 | −1.3 |
| 200601_at | U48734 | ACTN4 | actinin, alpha 4 | 0.0062 | 0.0990 | −1.3 |
| 208433_s_at | NM_017522 | LRP8 | low density lipoprotein receptor-related protein 8, apolipoprotein e receptor | 0.0212 | 0.7888 | −1.3 |
| 200913_at | NM_002707 | PPM1G | protein phosphatase 1G (formerly 2C), magnesium-dependent, gamma isoform | 0.0107 | 0.3412 | −1.3 |
| 212185_x_at | NM_005953 | MT2A | metallothionein 2A | 0.0015 | 0.0280 | −1.3 |
| 212624_s_at | BF339445 | CHN1 | chimerin (chimaerin) 1 | 0.0259 | 0.8804 | −1.3 |
| 202756_s_at | NM_002081 | GPC1 | glypican 1 | 0.0074 | 0.7875 | −1.3 |
| 201246_s_at | NM_017670 | OTUB1 | OTU domain, ubiquitin aldehyde binding 1 | 0.0481 | 0.7828 | −1.3 |
| 202761_s_at | NM_015180 | SYNE2 | spectrin repeat containing, nuclear envelope 2 | 0.0415 | 0.0995 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 204317_at | BF305380 | GTSE1 | G-2 and S-phase expressed 1 | 0.0250 | 0.1113 | −1.3 |
| 217913_at | NM_013245 | VPS4A | vacuolar protein sorting 4 homolog A (S. cerevisiae) | 0.0007 | 0.1899 | −1.3 |
| 212005_at | AL582808 | — | — | 0.0086 | 0.1735 | −1.3 |
| 200075_s_at | BC006249 | GUK1 | guanylate kinase 1 /// guanylate kinase 1 | 0.0214 | 0.6352 | −1.3 |
| 221848_at | AL121845 | ZGPAT | zinc finger, CCCH-type with G patch domain | 0.0015 | 0.0424 | −1.3 |
| 218083_at | NM_025072 | PTGES2 | prostaglandin E synthase 2 | 0.0123 | 0.5372 | −1.3 |
| 206050_s_at | NM_002939 | RNH1 | ribonuclease/angiogenin inhibitor 1 | 0.0018 | 0.8628 | −1.3 |
| 209468_at | AB017498 | LRP5 | low density lipoprotein receptor-related protein 5 | 0.0212 | 0.8184 | −1.3 |
| 209103_s_at | BC001049 | UFD1L | ubiquitin fusion degradation 1 like (yeast) | 0.0034 | 0.2084 | −1.3 |
| 218070_s_at | NM_013335 | GMPPA | GDP-mannose pyrophosphorylase A | 0.0192 | 0.1434 | −1.3 |
| 201389_at | NM_002205 | ITGA5 | integrin, alpha 5 (fibronectin receptor, alpha polypeptide) | 0.0122 | 0.1383 | −1.3 |
| 215084_s_at | AL031427 | LRRC42 | leucine rich repeat containing 42 | 0.0036 | 0.4075 | −1.3 |
| 218388_at | NM_012088 | PGLS | 6-phosphogluconolactonase | 0.0008 | 0.0332 | −1.3 |
| 201126_s_at | NM_002406 | MGAT1 | mannosyl (alpha-1,3-)-glycoprotein beta-1,2-N-acetylglucosaminyl transferase | 0.0185 | 0.7484 | −1.3 |
| 210519_s_at | BC000906 | NQO1 | NAD(P)H dehydrogenase, quinone 1 | 0.0128 | 0.4020 | −1.3 |
| 218238_at | NM_012341 | GTPBP4 | GTP binding protein 4 | 0.0378 | 0.1778 | −1.3 |
| 208905_at | BC005299 | CYCS | cytochrome c, somatic | 0.0052 | 0.0872 | −1.3 |
| 207332_s_at | NM_003234 | TFRC | transferrin receptor (p90, CD71) | 0.0035 | 0.4831 | −1.3 |
| 218069_at | NM_024096 | XTP3TPA | XTP3-transactivated protein A | 0.0040 | 0.1290 | −1.3 |
| 211982_x_at | AL546600 | XPO6 | exportin 6 | 0.0049 | 0.9166 | −1.3 |
| 202024_at | NM_004317 | ASNA1 | arsA arsenite transporter, ATP-binding, homolog 1 (bacterial) | 0.0058 | 0.1066 | −1.3 |
| 221657_s_at | BC001719 | ASB6 | ankyrin repeat and SOCS box-containing 6 | 0.0233 | 0.7801 | −1.3 |
| 220964_s_at | NM_030981 | RAB1B | RAB1B, member RAS oncogene family /// RAB1B, member RAS oncogene family | 0.0162 | 0.2294 | −1.3 |
| 203931_s_at | NM_002949 | MRPL12 | mitochondrial ribosomal protein L12 | 0.0045 | 0.5499 | −1.3 |
| 208842_s_at | W93787 | GORASP2 | golgi reassembly stacking protein 2, 55 kDa | 0.0042 | 0.8638 | −1.3 |
| 215905_s_at | AL157420 | WDR57 | WD repeat domain 57 (U5 snRNP specific) | 0.0023 | 0.4162 | −1.3 |
| 212422_at | AL547263 | PDCD11 | programmed cell death 11 | 0.0197 | 0.3396 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 211730_s_at | BC005903 | POLR2L | polymerase (RNA) II (DNA directed) polypeptide L, 7.6 kDa /// polymerase (RNA) II (DNA directed) polypeptide L, 7.6 kDa | 0.0030 | 0.5416 | −1.3 |
| 202264_s_at | NM_006114 | TOMM40 | translocase of outer mitochondrial membrane 40 homolog (yeast) | 0.0150 | 0.7824 | −1.3 |
| 209731_at | U79718 | NTHL1 | nth endonuclease III-like 1 (E. coli) | 0.0137 | 0.6042 | −1.3 |
| 217897_at | NM_022003 | FXYD6 | FXYD domain containing ion transport regulator 6 | 0.0017 | 0.0447 | −1.3 |
| 211564_s_at | BC003096 | PDLIM4 | PDZ and LIM domain 4 | 0.0124 | 0.6209 | −1.3 |
| 203545_at | NM_024079 | ALG8 | asparagine-linked glycosylation 8 homolog (S. cerevisiae, alpha-1,3-glucosyltransferase) | 0.0125 | 0.2016 | −1.3 |
| 217099_s_at | AF258545 | GEMIN4 | gem (nuclear organelle) associated protein 4 | 0.0117 | 0.5238 | −1.3 |
| 218641_at | NM_023941 | MGC3032 | hypothetical protein MGC3032 | 0.0135 | 0.6803 | −1.3 |
| 212411_at | BE747342 | IMP4 | IMP4, U3 small nucleolar ribonucleoprotein, homolog (yeast) | 0.0178 | 0.5931 | −1.3 |
| 214794_at | BF669264 | DLST | dihydrolipoamide S-succinyltransferase (E2 component of 2-oxo-glutarate complex) | 0.0235 | 0.9380 | −1.3 |
| 203311_s_at | M57763 | ARF6 | ADP-ribosylation factor 6 | 0.0425 | 0.3117 | −1.3 |
| 221676_s_at | BC002342 | CORO1C | coronin, actin binding protein, 1C | 0.0093 | 0.5425 | −1.3 |
| 218670_at | NM_025215 | PUS1 | pseudouridylate synthase 1 | 0.0305 | 0.2781 | −1.3 |
| 212003_at | BG171020 | C1orf144 | chromosome 1 open reading frame 144 | 0.0349 | 0.4840 | −1.3 |
| 211576_s_at | BC003068 | SLC19A1 | solute carrier family 19 (folate transporter), member 1 | 0.0047 | 0.1028 | −1.3 |
| 201817_at | NM_014671 | UBE3C | ubiquitin protein ligase E3C | 0.0429 | 0.6649 | −1.3 |
| 220956_s_at | NM_017555 | EGLN2 | egl nine homolog 2 (C. elegans) | 0.0078 | 0.7604 | −1.3 |
| 208910_s_at | L04636 | C1QBP | complement component 1, q subcomponent binding protein | 0.0329 | 0.3231 | −1.3 |
| 203462_x_at | NM_003751 | EIF3S9 | eukaryotic translation initiation factor 3, subunit 9 eta, 116 kDa | 0.0017 | 0.1620 | −1.3 |
| 218834_s_at | NM_017870 | TMEM132A | transmembrane protein 132A | 0.0106 | 0.1838 | −1.3 |
| 208932_at | BC001416 | PPP4C | protein phosphatase 4 (formerly X), catalytic subunit | 0.0040 | 0.1494 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 203228_at | NM_002573 | PAFAH1B3 | platelet-activating factor acetylhydrolase, isoform Ib, gamma subunit 29 kDa | 0.0041 | 0.2248 | −1.3 |
| 203031_s_at | NM_000375 | UROS | uroporphyrinogen III synthase (congenital erythropoietic porphyria) | 0.0130 | 0.8462 | −1.3 |
| 203647_s_at | M18003 | FDX1 | ferredoxin 1 | 0.0430 | 0.8149 | −1.3 |
| 217225_x_at | AL512687 | NOMO2 | NODAL modulator 2 | 0.0042 | 0.2518 | −1.3 |
| 201095_at | NM_004394 | DAP | death-associated protein | 0.0166 | 0.2794 | −1.3 |
| 202128_at | NM_014821 | KIAA0317 | KIAA0317 | 0.0446 | 0.9567 | −1.3 |
| 212129_at | AI589507 | NIPA2 | non imprinted in Prader-Willi/Angelman syndrome 2 | 0.0163 | 0.7517 | −1.3 |
| 204610_s_at | NM_006848 | CCDC85B | coiled-coil domain containing 85B | 0.0377 | 0.4333 | −1.3 |
| 215093_at | U82671 | NSDHL | NAD(P) dependent steroid dehydrogenase-like | 0.0159 | 0.7567 | −1.3 |
| 200950_at | NM_006409 | ARPC1A | actin related protein 2/3 complex, subunit 1A, 41 kDa | 0.0115 | 0.7012 | −1.3 |
| 217716_s_at | NM_013336 | SEC61A1 | Sec61 alpha 1 subunit (*S. cerevisiae*) | 0.0045 | 0.0475 | −1.3 |
| 208132_x_at | NM_004638 | BAT2 | HLA-B associated transcript 2 | 0.0051 | 0.1305 | −1.3 |
| 203960_s_at | NM_016126 | C1orf41 /// IL17RB | chromosome 1 open reading frame 41 /// interleukin 17 receptor B | 0.0053 | 0.0645 | −1.3 |
| 201950_x_at | NM_004930 | CAPZB | capping protein (actin filament) muscle Z-line, beta | 0.0107 | 0.4512 | −1.3 |
| 210966_x_at | BC001460 | LARP1 | La ribonucleoprotein domain family, member 1 | 0.0155 | 0.1383 | −1.3 |
| 210983_s_at | AF279900 | MCM7 | MCM7 minichromosome maintenance deficient 7 (*S. cerevisiae*) | 0.0031 | 0.0832 | −1.3 |
| 200803_s_at | AF033095 | TEGT | testis enhanced gene transcript (BAX inhibitor 1) | 0.0061 | 0.0745 | −1.3 |
| 201554_x_at | NM_004130 | GYG1 | glycogenin 1 | 0.0267 | 0.7594 | −1.3 |
| 205462_s_at | NM_002149 | HPCAL1 | hippocalcin-like 1 | 0.0193 | 0.2490 | −1.3 |
| 211934_x_at | W87689 | GANAB | glucosidase, alpha; neutral AB | 0.0072 | 0.0476 | −1.3 |
| 209344_at | BC002827 | TPM4 | tropomyosin 4 | 0.0239 | 0.8829 | −1.3 |
| 217753_s_at | NM_001029 | RPS26 /// LOC644166 /// LOC644191 /// LOC728937 | ribosomal protein S26 /// similar to 40S ribosomal protein S26 /// similar to 40S ribosomal protein S26 /// similar to 40S ribosomal protein S26 | 0.0010 | 0.1482 | −1.3 |
| 219575_s_at | NM_022341 | PDF /// COG8 | peptide deformylase (mitochondrial) /// component of oligomeric golgi complex 8 | 0.0154 | 0.7836 | −1.3 |
| 203683_s_at | NM_003377 | VEGFB | vascular endothelial growth factor B | 0.0305 | 0.4504 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 204608_at | NM_000048 | ASL | argininosuccinate lyase | 0.0071 | 0.2170 | −1.3 |
| 202085_at | NM_004817 | TJP2 | tight junction protein 2 (zona occludens 2) | 0.0110 | 0.3198 | −1.3 |
| 204275_at | AI796687 | SOLH | small optic lobes homolog (*Drosophila*) | 0.0350 | 0.2001 | −1.3 |
| 212120_at | BE897886 | RHOQ | ras homolog gene family, member Q | 0.0062 | 0.0571 | −1.3 |
| 200737_at | NM_000291 | PGK1 | phosphoglycerate kinase 1 | 0.0017 | 0.3518 | −1.3 |
| 219675_s_at | NM_025076 | UXS1 | UDP-glucuronate decarboxylase 1 | 0.0279 | 0.7782 | −1.3 |
| 209409_at | D86962 | GRB10 | growth factor receptor-bound protein 10 | 0.0104 | 0.0935 | −1.3 |
| 200806_s_at | BE256479 | HSPD1 | heat shock 60 kDa protein 1 (chaperonin) | 0.0042 | 0.1925 | −1.3 |
| 201614_s_at | NM_003707 | RUVBL1 | RuvB-like 1 (*E. coli*) | 0.0029 | 0.0941 | −1.3 |
| 222116_s_at | AL157485 | TBC1D16 | TBC1 domain family, member 16 | 0.0107 | 0.3474 | −1.3 |
| 203806_s_at | NM_000135 | FANCA | Fanconi anemia, complementation group A /// Fanconianemia, complementation group A | 0.0370 | 0.5381 | −1.3 |
| 213180_s_at | BE895285 | GOSR2 | golgi SNAP receptor complex member 2 | 0.0408 | 0.2254 | −1.3 |
| 203184_at | NM_001999 | FBN2 | fibrillin 2 (congenital contractural arachnodactyly) | 0.0227 | 0.1383 | −1.3 |
| 201911_s_at | NM_005766 | FARP1 | FERM, RhoGEF (ARHGEF) and pleckstrin domain protein 1 (chondrocyte-derived) | 0.0107 | 0.6444 | −1.3 |
| 218057_x_at | NM_006067 | COX4NB | COX4 neighbor | 0.0136 | 0.1344 | −1.3 |
| 44783_s_at | R61374 | HEY1 | hairy/enhancer-of-split related with YRPW motif 1 | 0.0156 | 0.0964 | −1.3 |
| 200644_at | NM_023009 | MARCKSL1 | MARCKS-like 1 | 0.0011 | 0.4243 | −1.3 |
| 203276_at | NM_005573 | LMNB1 | lamin B1 | 0.0156 | 0.5237 | −1.3 |
| 212159_x_at | AI125280 | AP2A2 | adaptor-related protein complex 2, alpha 2 subunit | 0.0342 | 0.5742 | −1.3 |
| 204839_at | NM_015918 | POP5 | processing of precursor 5, ribonuclease P/MRP subunit (*S. cerevisiae*) | 0.0121 | 0.4107 | −1.3 |
| 201522_x_at | NM_003097 | SNRPN /// SNURF | small nuclear ribonucleoprotein polypeptide N /// SNRPN upstream reading frame | 0.0035 | 0.4870 | −1.3 |
| 200727_s_at | AA699583 | ACTR2 | ARP2 actin-related protein 2 homolog (yeast) | 0.0170 | 0.1805 | −1.3 |
| 200021_at | NM_005507 | CFL1 | cofilin 1 (non-muscle) /// cofilin 1 (non-muscle) | 0.0039 | 0.1498 | −1.3 |
| 201968_s_at | NM_002633 | PGM1 | phosphoglucomutase 1 | 0.0049 | 0.2714 | −1.3 |
| 202593_s_at | NM_016641 | MIR16 | membrane interacting protein of RGS16 | 0.0177 | 0.1789 | −1.3 |
| 200918_s_at | NM_003139 | SRPR | signal recognition particle receptor ('docking protein') | 0.0112 | 0.3210 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 204238_s_at | NM_006443 | C6orf108 | chromosome 6 open reading frame 108 | 0.0494 | 0.8953 | −1.3 |
| 201704_at | NM_001247 | ENTPD6 | ectonucleoside triphosphate diphosphohydrolase 6 (putative function) | 0.0358 | 0.5222 | −1.3 |
| 201267_s_at | AL545523 | PSMC3 | proteasome (prosome, macropain) 26S subunit, ATPase, 3 | 0.0010 | 0.7722 | −1.3 |
| 201923_at | NM_006406 | PRDX4 | peroxiredoxin 4 | 0.0044 | 0.0475 | −1.3 |
| 211065_x_at | BC006422 | PFKL | phosphofructokinase, liver /// phosphofructokinase, liver | 0.0056 | 0.1200 | −1.3 |
| 205002_at | NM_015699 | AHDC1 | AT hook, DNA binding motif, containing 1 | 0.0301 | 0.6324 | −1.3 |
| 218529_at | NM_016579 | CD320 | CD320 molecule | 0.0027 | 0.2776 | −1.3 |
| 200640_at | NM_003406 | YWHAZ | tyrosine 3-monooxygenase/tryptophan 5-monooxygenase activation protein, zeta polypeptide | 0.0023 | 0.1580 | −1.3 |
| 37384_at | D86995 | PPM1F | protein phosphatase 1F (PP2C domain containing) | 0.0244 | 0.7220 | −1.3 |
| 210678_s_at | U56418 | AGPAT2 | 1-acylglycerol-3-phosphate O-acyltransferase 2 (lysophosphatidic acid acyltransferase, beta) | 0.0380 | 0.8549 | −1.3 |
| 218399_s_at | NM_017955 | CDCA4 | cell division cycle associated 4 | 0.0012 | 0.5384 | −1.3 |
| 203201_at | NM_000303 | PMM2 | phosphomannomutase 2 | 0.0020 | 0.4099 | −1.3 |
| 212829_at | BE878277 | — | CDNA FLJ13267 fis, clone OVARC1000964 /// CDNA FLJ13267 fis, clone OVARC1000964 | 0.0007 | 0.0383 | −1.3 |
| 214119_s_at | AI936769 | FKBP1A | FK506 binding protein 1A, 12 kDa | 0.0045 | 0.0911 | −1.3 |
| 215696_s_at | BC001404 | KIAA0310 | KIAA0310 | 0.0039 | 0.2613 | −1.3 |
| 200020_at | NM_007375 | TARDBP | TAR DNA binding protein /// TAR DNA binding protein | 0.0031 | 0.1467 | −1.3 |
| 212723_at | AK021780 | PTDSR | phosphatidylserine receptor | 0.0091 | 0.1709 | −1.3 |
| 218890_x_at | NM_016622 | MRPL35 | mitochondrial ribosomal protein L35 | 0.0170 | 0.7931 | −1.3 |
| 201577_at | NM_000269 | NME1 | non-metastatic cells 1, protein (NM23A) expressed in | 0.0007 | 0.0699 | −1.3 |
| 205740_s_at | NM_024321 | MGC10433 | hypothetical protein MGC10433 | 0.0094 | 0.3321 | −1.3 |
| 221807_s_at | BG399562 | TRABD | TraB domain containing | 0.0359 | 0.5498 | −1.3 |
| 217947_at | NM_017801 | CMTM6 | CKLF-like MARVEL transmembrane domain containing 6 | 0.0187 | 0.1774 | −1.3 |
| 202934_at | AI761561 | HK2 | hexokinase 2 | 0.0265 | 0.1646 | −1.3 |
| 214726_x_at | AL556041 | ADD1 | adducin 1 (alpha) | 0.0175 | 0.0771 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 204328_at | NM_007267 | TMC6 | transmembrane channel-like 6 | 0.0245 | 0.6147 | −1.3 |
| 47069_at | AA533284 | PRR5 | proline rich 5 (renal) | 0.0045 | 0.0714 | −1.3 |
| 200830_at | NM_002808 | PSMD2 | proteasome (prosome, macropain) 26S subunit, non-ATPase, 2 | 0.0024 | 0.1174 | −1.3 |
| 208858_s_at | BC004998 | FAM62A | family with sequence similarity 62 (C2 domain containing), member A | 0.0154 | 0.5500 | −1.3 |
| 218596_at | NM_018201 | TBC1D13 | TBC1 domain family, member 13 | 0.0433 | 0.2850 | −1.3 |
| 212016_s_at | AA679988 | PTBP1 | polypyrimidine tract binding protein 1 | 0.0124 | 0.0659 | −1.3 |
| 202870_s_at | NM_001255 | CDC20 | cell division cycle 20 homolog (*S. cerevisiae*) | 0.0117 | 0.1758 | −1.3 |
| 209714_s_at | AF213033 | CDKN3 | cyclin-dependent kinase inhibitor 3 (CDK2-associated dual specificity phosphatase) | 0.0069 | 0.7689 | −1.3 |
| 219051_x_at | NM_024042 | METRN | meteorin, glial cell differentiation regulator | 0.0107 | 0.9563 | −1.3 |
| 209365_s_at | U65932 | ECM1 | extracellular matrix protein 1 | 0.0232 | 0.1288 | −1.3 |
| 202535_at | NM_003824 | FADD | Fas (TNFRSF6)-associated via death domain | 0.0366 | 0.8980 | −1.3 |
| 202836_s_at | NM_006701 | TXNL4A | thioredoxin-like 4A | 0.0069 | 0.3942 | −1.3 |
| 217811_at | NM_016275 | SELT | selenoprotein T | 0.0314 | 0.2573 | −1.3 |
| 211505_s_at | AL136601 | STAU1 | staufen, RNA binding protein, homolog 1 (*Drosophila*) | 0.0378 | 0.6525 | −1.3 |
| 203664_s_at | NM_004805 | POLR2D | polymerase (RNA) II (DNA directed) polypeptide D | 0.0204 | 0.3117 | −1.3 |
| 218291_at | NM_014017 | MAPBPIP | mitogen-activated protein-binding protein-interacting protein | 0.0034 | 0.3392 | −1.3 |
| 212858_at | AL520675 | PAQR4 | progestin and adipoQ receptor family member IV | 0.0060 | 0.2961 | −1.3 |
| 218391_at | NM_007241 | SNF8 | SNF8, ESCRT-II complex subunit, homolog (*S. cerevisiae*) | 0.0056 | 0.3662 | −1.3 |
| 201724_s_at | NM_020474 | GALNT1 | UDP-N-acetyl-alpha-D-galactosamine:polypeptide N-acetylgalactosaminyltransferase 1 (GalNAc-T1) | 0.0073 | 0.0441 | −1.3 |
| 200699_at | BE962456 | — | Full-length cDNA clone CS0DC014YA20 of Neuroblastoma Cot 25-normalized of *Homo sapiens* (human) | 0.0042 | 0.6171 | −1.3 |
| 221436_s_at | NM_031299 | CDCA3 | cell division cycle associated 3 /// cell division cycle associated 3 | 0.0140 | 0.1080 | −1.3 |
| 204174_at | NM_001629 | ALOX5AP | arachidonate 5-lipoxygenase-activating protein | 0.0219 | 0.4380 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 212170_at | BF447705 | RBM12 | RNA binding motif protein 12 | 0.0244 | 0.1083 | −1.3 |
| 217911_s_at | NM_004281 | BAG3 | BCL2-associated athanogene 3 | 0.0428 | 0.7171 | −1.3 |
| 208445_s_at | NM_023005 | BAZ1B | bromodomain adjacent to zinc finger domain, 1B | 0.0085 | 0.7292 | −1.3 |
| 221692_s_at | AB049652 | MRPL34 | mitochondrial ribosomal protein L34 /// mitochondrial ribosomal protein L34 | 0.0399 | 0.4826 | −1.3 |
| 218555_at | NM_013366 | ANAPC2 | anaphase promoting complex subunit 2 | 0.0039 | 0.0274 | −1.3 |
| 219203_at | NM_016049 | C14orf122 | chromosome 14 open reading frame 122 | 0.0005 | 0.0911 | −1.3 |
| 220948_s_at | NM_000701 | ATP1A1 | ATPase, Na+/K+ transporting, alpha 1 polypeptide | 0.0107 | 0.3441 | −1.3 |
| 201376_s_at | AI591354 | HNRPF | heterogeneous nuclear ribonucleoprotein F | 0.0101 | 0.3926 | −1.3 |
| 204133_at | NM_004704 | RRP9 | RRP9, small subunit (SSU) processome component, homolog (yeast) | 0.0445 | 0.6616 | −1.3 |
| 201903_at | NM_003365 | UQCRC1 | ubiquinol-cytochrome c reductase core protein I | 0.0085 | 0.2404 | −1.3 |
| 205241_at | NM_005138 | SCO2 | SCO cytochrome oxidase deficient homolog 2 (yeast) | 0.0071 | 0.3412 | −1.3 |
| 200799_at | NM_005345 | HSPA1A | heat shock 70 kDa protein 1A | 0.0253 | 0.0476 | −1.3 |
| 218317_x_at | NM_024044 | GIYD2 /// GIYD1 | GIY-YIG domain containing 2 /// GIY-YIG domain containing 1 | 0.0033 | 0.0441 | −1.3 |
| 209836_x_at | AF060511 | BOLA2 /// BOLA2B | bolA homolog 2 (E. coli) /// bolA homolog 2B (E. coli) | 0.0027 | 0.0592 | −1.3 |
| 213244_at | AI207792 | SCAMP4 | secretory carrier membrane protein 4 | 0.0242 | 0.1143 | −1.3 |
| 201662_s_at | D89053 | ACSL3 | acyl-CoA synthetase long-chain family member 3 | 0.0245 | 0.9280 | −1.3 |
| 206554_x_at | NM_006515 | SETMAR | SET domain and mariner transposase fusion gene | 0.0298 | 0.4143 | −1.3 |
| 203925_at | NM_002061 | GCLM | glutamate-cysteine ligase, modifier subunit | 0.0146 | 0.1594 | −1.3 |
| 200707_at | NM_002743 | PRKCSH | protein kinase C substrate 80K-H | 0.0194 | 0.0567 | −1.3 |
| 201963_at | NM_021122 | ACSL1 | acyl-CoA synthetase long-chain family member 1 | 0.0149 | 0.3605 | −1.3 |
| 207856_s_at | NM_017951 | SMPD4 /// FLJ41352 | sphingomyelin phosphodiesterase 4, neutral membrane (neutral sphingomyelinase-3) /// FLJ41352 protein | 0.0201 | 0.6155 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 200875_s_at | NM_006392 | NOL5A | nucleolar protein 5A (56 kDa with KKE/D repeat) | 0.0031 | 0.4776 | −1.3 |
| 202382_s_at | NM_005471 | GNPDA1 | glucosamine-6-phosphate deaminase 1 | 0.0070 | 0.7544 | −1.3 |
| 203017_s_at | R52678 | SSX2IP | synovial sarcoma, X breakpoint 2 interacting protein | 0.0205 | 0.5419 | −1.3 |
| 208702_x_at | AI525212 | APLP2 | amyloid beta (A4) precursor-like protein 2 | 0.0122 | 0.2960 | −1.3 |
| 201764_at | NM_024056 | TMEM106C | transmembrane protein 106C | 0.0019 | 0.0834 | −1.3 |
| 221521_s_at | BC003186 | GINS2 | GINS complex subunit 2 (Psf2 homolog) | 0.0045 | 0.2979 | −1.3 |
| 216971_s_at | Z54367 | PLEC1 | plectin 1, intermediate filament binding protein 500 kDa | 0.0037 | 0.0894 | −1.3 |
| 217893_s_at | NM_024595 | C1orf108 | chromosome 1 open reading frame 108 | 0.0435 | 0.0434 | −1.3 |
| 219709_x_at | NM_023933 | C16orf24 | chromosome 16 open reading frame 24 | 0.0166 | 0.3879 | −1.3 |
| 205401_at | NM_003659 | AGPS | alkylglycerone phosphate synthase | 0.0355 | 0.3570 | −1.3 |
| 209017_s_at | U02389 | LONP1 | lon peptidase 1, mitochondrial | 0.0368 | 0.7567 | −1.3 |
| 221815_at | BE671816 | ABHD2 | abhydrolase domain containing 2 | 0.0233 | 0.7423 | −1.3 |
| 208972_s_at | AL080089 | ATP5G1 | ATP synthase, H+ transporting, mitochondrial F0 complex, subunit C1 (subunit 9) | 0.0066 | 0.4128 | −1.3 |
| 213052_at | BF246917 | PRKAR2A | Protein kinase, cAMP-dependent, regulatory, type II, alpha | 0.0180 | 0.8806 | −1.3 |
| 208676_s_at | U87954 | DLST /// PA2G4 | dihydrolipoamide S-succinyltransferase (E2 component of 2-oxo-glutarate complex) /// proliferation-associated 2G4, 38 kDa | 0.0016 | 0.3528 | −1.3 |
| 210672_s_at | BC004185 | C16orf35 | chromosome 16 open reading frame 35 | 0.0151 | 0.2049 | −1.3 |
| 204766_s_at | NM_002452 | NUDT1 | nudix (nucleoside diphosphate linked moiety X)-type motif 1 | 0.0048 | 0.3257 | −1.3 |
| 208270_s_at | NM_020216 | RNPEP | arginyl aminopeptidase (aminopeptidase B) | 0.0183 | 0.2672 | −1.3 |
| 213937_s_at | AV723177 | FTSJ1 | FtsJ homolog 1 (*E. coli*) | 0.0436 | 0.9574 | −1.3 |
| 209444_at | BC001851 | RAP1GDS1 | RAP1, GTP-GDP dissociation stimulator 1 | 0.0280 | 0.4171 | −1.3 |
| 211071_s_at | BC006471 | MLLT11 | myeloid/lymphoid or mixed-lineage leukemia (trithorax homolog, *Drosophila*); translocated to, 11 /// myeloid/lymphoid or mixed-lineage | 0.0021 | 0.0418 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 200637_s_at | AI762627 | PTPRF | leukemia (trithorax homolog, *Drosophila*); translocated to, 11 protein tyrosine phosphatase, receptor type, F | 0.0406 | 0.2980 | −1.3 |
| 202475_at | NM_006326 | TMEM147 | transmembrane protein 147 | 0.0016 | 0.4204 | −1.3 |
| 221647_s_at | AL136935 | RIC8A | resistance to inhibitors of cholinesterase 8 homolog A (*C. elegans*) | 0.0132 | 0.5700 | −1.3 |
| 204169_at | NM_000883 | IMPDH1 | IMP (inosine monophosphate) dehydrogenase 1 | 0.0287 | 0.3633 | −1.3 |
| 216969_s_at | AC002301 | KIF22 /// LOC728037 | kinesin family member 22 /// similar to Kinesin-like protein KIF22 (Kinesin-like DNA-binding protein) (Kinesin-like protein 4) | 0.0355 | 0.0578 | −1.3 |
| 202459_s_at | U55968 | LPIN2 | lipin 2 | 0.0083 | 0.3844 | −1.3 |
| 204306_s_at | NM_004357 | CD151 | CD151 molecule (Raph blood group) | 0.0015 | 0.0558 | −1.3 |
| 218550_s_at | NM_018205 | LRRC20 | leucine rich repeat containing 20 | 0.0145 | 0.3547 | −1.3 |
| 201388_at | NM_002809 | PSMD3 | proteasome (prosome, macropain) 26S subunit, non-ATPase, 3 | 0.0015 | 0.0524 | −1.3 |
| 212971_at | AI769685 | CARS | cysteinyl-tRNA synthetase | 0.0007 | 0.0665 | −1.3 |
| 200072_s_at | AF061832 | HNRPM | heterogeneous nuclear ribonucleoprotein M /// heterogeneous nuclear ribonucleoprotein M | 0.0049 | 0.2084 | −1.3 |
| 218420_s_at | NM_025138 | C13orf23 | chromosome 13 open reading frame 23 | 0.0134 | 0.2363 | −1.3 |
| 218408_at | NM_012456 | TIMM10 | translocase of inner mitochondrial membrane 10 homolog (yeast) | 0.0149 | 0.4352 | −1.3 |
| 217973_at | NM_016286 | DCXR | dicarbonyl/L-xylulose reductase | 0.0025 | 0.0732 | −1.3 |
| 204033_at | NM_004237 | TRIP13 | thyroid hormone receptor interactor 13 | 0.0084 | 0.7000 | −1.3 |
| 217871_s_at | NM_002415 | MIF | macrophage migration inhibitory factor (glycosylation-inhibiting factor) | 0.0050 | 0.1736 | −1.3 |
| 201932_at | NM_006369 | LRRC41 | leucine rich repeat containing 41 | 0.0294 | 0.5384 | −1.3 |
| 217923_at | NM_012392 | PEF1 | penta-EF-hand domain containing 1 | 0.0170 | 0.2047 | −1.3 |
| 211595_s_at | AB049944 | MRPS11 | mitochondrial ribosomal protein S11 /// mitochondrial ribosomal protein S11 | 0.0027 | 0.2091 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 213041_s_at | BE798517 | ATP5D | ATP synthase, H+ transporting, mitochondrial F1 complex, delta subunit | 0.0053 | 0.2420 | −1.3 |
| 212219_at | D38521 | PSME4 | proteasome (prosome, macropain) activator subunit 4 | 0.0245 | 0.5016 | −1.3 |
| 200654_at | J02783 | P4HB /// LOC728900 | procollagen-proline, 2-oxoglutarate 4-dioxygenase (proline 4-hydroxylase), beta polypeptide /// similar to prolyl 4-hydroxylase, beta subunit | 0.0151 | 0.0856 | −1.3 |
| 219997_s_at | NM_022730 | COPS7B | COP9 constitutive photomorphogenic homolog subunit 7B (*Arabidopsis*) | 0.0166 | 0.3902 | −1.3 |
| 201014_s_at | NM_006452 | PAICS | phosphoribosylaminoimidazole carboxylase, phosphoribosylaminoimidazole succinocarboxamide synthetase | 0.0484 | 0.3181 | −1.3 |
| 200954_at | NM_001694 | ATP6V0C | ATPase, H+ transporting, lysosomal 16 kDa, V0 subunit c | 0.0248 | 0.1232 | −1.3 |
| 219047_s_at | NM_024706 | ZNF668 | zinc finger protein 668 | 0.0026 | 0.5284 | −1.3 |
| 210125_s_at | AF044773 | BANF1 | barrier to autointegration factor 1 | 0.0006 | 0.0721 | −1.3 |
| 205439_at | NM_000854 | GSTT2 | glutathione S-transferase theta 2 | 0.0203 | 0.3127 | −1.3 |
| 218394_at | NM_024589 | ROGDI | rogdi homolog (*Drosophila*) | 0.0020 | 0.0424 | −1.3 |
| 217934_x_at | NM_005861 | STUB1 | STIP1 homology and U-box containing protein 1 | 0.0049 | 0.2833 | −1.3 |
| 218141_at | NM_022066 | UBE2O | ubiquitin-conjugating enzyme E2O | 0.0077 | 0.0895 | −1.3 |
| 221575_at | BC000586 | SCLY | selenocysteine lyase | 0.0435 | 0.4733 | −1.3 |
| 218447_at | NM_020188 | C16orf61 | chromosome 16 open reading frame 61 | 0.0336 | 0.1746 | −1.3 |
| 212456_at | AB014564 | KIAA0664 | KIAA0664 | 0.0143 | 0.8617 | −1.3 |
| 202308_at | NM_004176 | SREBF1 | sterol regulatory element binding transcription factor 1 | 0.0441 | 0.3563 | −1.3 |
| 217782_s_at | NM_004127 | GPS1 | G protein pathway suppressor 1 | 0.0186 | 0.1542 | −1.3 |
| 208978_at | U36190 | CRIP2 | cysteine-rich protein 2 | 0.0014 | 0.0604 | −1.3 |
| 212767_at | BC004409 | MTG1 | mitochondrial GTPase 1 homolog (*S. cerevisiae*) | 0.0015 | 0.0547 | −1.3 |
| 202236_s_at | NM_003051 | SLC16A1 | solute carrier family 16, member 1 (monocarboxylic acid transporter 1) | 0.0046 | 0.1925 | −1.3 |
| 222118_at | AK023669 | CENPN | centromere protein N | 0.0487 | 0.5572 | −1.3 |
| 204027_s_at | NM_005371 | METTL1 | methyltransferase like 1 | 0.0329 | 0.3662 | −1.3 |
| 204514_at | NM_001384 | DPH2 | DPH2 homolog (*S. cerevisiae*) | 0.0114 | 0.1875 | −1.3 |
| 218565_at | BG223334 | C9orf114 | chromosome 9 open reading frame 114 | 0.0037 | 0.0721 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 202860_at | NM_014856 | DENND4B | DENN/MADD domain containing 4B | 0.0043 | 0.0285 | −1.3 |
| 205085_at | NM_004153 | ORC1L | origin recognition complex, subunit 1-like (yeast) | 0.0423 | 0.8149 | −1.3 |
| 209191_at | BC002654 | TUBB6 | tubulin, beta 6 | 0.0018 | 0.6584 | −1.3 |
| 213730_x_at | BE962186 | TCF3 | transcription factor 3 (E2A immunoglobulin enhancer binding factors E12/E47) | 0.0021 | 0.5366 | −1.3 |
| 203612_at | NM_004053 | BYSL | bystin-like | 0.0126 | 0.6728 | −1.3 |
| 219068_x_at | NM_018188 | ATAD3A | ATPase family, AAA domain containing 3A | 0.0127 | 0.3312 | −1.3 |
| 205444_at | NM_004320 | ATP2A1 | ATPase, Ca++ transporting, cardiac muscle, fast twitch 1 | 0.0427 | 0.1270 | −1.3 |
| 204817_at | NM_012291 | ESPL1 | extra spindle pole bodies homolog 1 (S. cerevisiae) | 0.0293 | 0.0418 | −1.3 |
| 208973_at | BC001072 | PRNPIP | prion protein interacting protein | 0.0077 | 0.3586 | −1.3 |
| 202055_at | AA652173 | KPNA1 | karyopherin alpha 1 (importin alpha 5) | 0.0380 | 0.6914 | −1.3 |
| 201853_s_at | NM_021873 | CDC25B | cell division cycle 25 homolog B (S. cerevisiae) | 0.0043 | 0.1229 | −1.3 |
| 206200_s_at | NM_001157 | ANXA11 | annexin A11 | 0.0055 | 0.2452 | −1.3 |
| 209427_at | AF064238 | SMTN | smoothelin | 0.0020 | 0.0645 | −1.3 |
| 216591_s_at | AF080579 | SDHC /// LOC642502 | succinate dehydrogenase complex, subunit C, integral membrane protein, 15 kDa /// similar to succinate dehydrogenase complex, subunit C isoform 3 precursor | 0.0270 | 0.4786 | −1.3 |
| 208827_at | BC000835 | PSMB6 | proteasome (prosome, macropain) subunit, beta type, 6 | 0.0049 | 0.3860 | −1.3 |
| 201387_s_at | NM_004181 | UCHL1 | ubiquitin carboxyl-terminal esterase L1 (ubiquitin thiolesterase) | 0.0307 | 0.1309 | −1.3 |
| 203536_s_at | NM_004804 | CIAO1 | cytosolic iron-sulfur protein assembly 1 homolog (S. cerevisiae) | 0.0491 | 0.4019 | −1.3 |
| 218580_x_at | NM_017900 | AURKAIP1 /// LOC727877 | aurora kinase A interacting protein 1 /// similar to Cyclin-L2 (Paneth cell-enhanced expression protein) | 0.0027 | 0.4766 | −1.3 |
| 212178_s_at | AK022555 | POM121 /// LOC340318 /// LOC729316 | POM121 membrane glycoprotein (rat) /// nuclear envelope pore membrane LOC340318 /// similar to Nuclear envelope pore membrane protein POM 121 (Pore membrane protein of 121 kDa) (P145) | 0.0119 | 0.0807 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 212285_s_at | AW008051 | AGRIN | agrin | 0.0401 | 0.4488 | −1.3 |
| 218902_at | NM_017617 | NOTCH1 | Notch homolog 1, translocation-associated (*Drosophila*) | 0.0314 | 0.1325 | −1.3 |
| 220547_s_at | NM_019054 | FAM35A | family with sequence similarity 35, member A | 0.0297 | 0.1633 | −1.3 |
| 216602_s_at | AD000092 | FARSLA | phenylalanine-tRNA synthetase-like, alpha subunit | 0.0210 | 0.1596 | −1.3 |
| 213358_at | AB018345 | KIAA0802 /// C21orf57 | KIAA0802 /// chromosome 21 open reading frame 57 | 0.0039 | 0.2086 | −1.3 |
| 202370_s_at | NM_001755 | CBFB | core-binding factor, beta subunit | 0.0351 | 0.2187 | −1.3 |
| 200656_s_at | NM_000918 | P4HB | procollagen-proline, 2-oxoglutarate 4-dioxygenase (proline 4-hydroxylase), beta polypeptide | 0.0037 | 0.0558 | −1.3 |
| 212512_s_at | AA551784 | CARM1 | coactivator-associated arginine methyltransferase 1 | 0.0246 | 0.2430 | −1.3 |
| 212796_s_at | BF195608 | TBC1D2B | TBC1 domain family, member 2B | 0.0233 | 0.4904 | −1.3 |
| 221434_s_at | NM_031210 | C14orf156 | chromosome 14 open reading frame 156 /// chromosome 14 open reading frame 156 | 0.0342 | 0.4605 | −1.3 |
| 220358_at | NM_018664 | SNFT | Jun dimerization protein p21SNFT | 0.0209 | 0.4938 | −1.3 |
| 203040_s_at | NM_000190 | HMBS | hydroxymethylbilane synthase | 0.0077 | 0.4143 | −1.3 |
| 221764_at | AL574186 | C19orf22 | chromosome 19 open reading frame 22 | 0.0051 | 0.0735 | −1.3 |
| 201155_s_at | NM_014874 | MFN2 | mitofusin 2 | 0.0078 | 0.5620 | −1.3 |
| 218492_at | NM_030573 | THAP7 | THAP domain containing 7 | 0.0114 | 0.2235 | −1.3 |
| 208968_s_at | BC002568 | CIAPIN1 | cytokine induced apoptosis inhibitor 1 | 0.0060 | 0.3329 | −1.3 |
| 211752_s_at | BC005954 | NDUFS7 | NAPH dehydrogenase (ubiquinone) Fe—S protein 7, 20 kDa (NADH-coenzyme Q reductase) /// NAPH dehydrogenase (ubiquinone) Fe—S protein 7, 20 kDa (NADH-coenzyme Q reductase) | 0.0491 | 0.3169 | −1.3 |
| 203423_at | NM_002899 | RBP1 | retinol binding protein 1, cellular | 0.0483 | 0.5702 | −1.3 |
| 219084_at | NM_022455 | NSD1 | nuclear receptor binding SET domain protein 1 | 0.0310 | 0.2817 | −1.3 |
| 215159_s_at | AI239732 | NADK | NAD kinase | 0.0266 | 0.3031 | −1.3 |
| 209413_at | BC002431 | B4GALT2 | UDP-Gal:betaGlcNAc beta 1,4-galactosyltransferase, polypeptide 2 | 0.0309 | 0.5550 | −1.3 |
| 205293_x_at | AB017120 | BAIAP2 | BAI1-associated protein 2 | 0.0123 | 0.2614 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 202484_s_at | AF072242 | MBD2 | methyl-CpG binding domain protein 2 | 0.0457 | 0.3651 | −1.3 |
| 214170_x_at | AA669797 | FH | fumarate hydratase | 0.0248 | 0.3513 | −1.3 |
| 222216_s_at | AK026857 | MRPL17 | mitochondrial ribosomal protein L17 | 0.0011 | 0.0990 | −1.3 |
| 209461_x_at | BC001648 | WDR18 | WD repeat domain 18 | 0.0196 | 0.1327 | −1.3 |
| 214141_x_at | BF033354 | SFRS7 | splicing factor, arginine/serine-rich 7, 35 kDa | 0.0046 | 0.0350 | −1.3 |
| 202927_at | NM_006221 | PIN1 | protein (peptidylprolyl cis/trans isomerase) NIMA-interacting 1 | 0.0059 | 0.2652 | −1.3 |
| 201400_at | NM_002795 | PSMB3 | proteasome (prosome, macropain) subunit, beta type, 3 | 0.0045 | 0.1367 | −1.3 |
| 202691_at | NM_006938 | SNRPD1 | small nuclear ribonucleoprotein D1 polypeptide 16 kDa | 0.0014 | 0.0839 | −1.3 |
| 205449_at | NM_013299 | SAC3D1 | SAC3 domain containing 1 | 0.0253 | 0.3329 | −1.3 |
| 208679_s_at | AF279893 | ARPC2 | actin related protein 2/3 complex, subunit 2, 34 kDa | 0.0015 | 0.0811 | −1.3 |
| 36936_at | U58766 | TSTA3 | tissue specific transplantation antigen P35B | 0.0081 | 0.6356 | −1.3 |
| 209860_s_at | J04543 | ANXA7 | annexin A7 | 0.0133 | 0.1925 | −1.3 |
| 200730_s_at | BF576710 | PTP4A1 | protein tyrosine phosphatase type IVA, member 1 | 0.0038 | 0.0899 | −1.3 |
| 217118_s_at | AK025608 | C22orf9 | chromosome 22 open reading frame 9 | 0.0147 | 0.2509 | −1.3 |
| 211926_s_at | AI827941 | MYH9 | myosin, heavy chain 9, non-muscle | 0.0177 | 0.1399 | −1.3 |
| 202578_s_at | NM_018332 | DDX19A | DEAD (Asp-Glu-Ala-As) box polypeptide 19A | 0.0307 | 0.5964 | −1.3 |
| 33307_at | AL022316 | CTA-126B4.3 | CGI-96 protein | 0.0138 | 0.4373 | −1.3 |
| 204612_at | NM_006823 | PKIA | protein kinase (cAMP-dependent, catalytic) inhibitor alpha | 0.0429 | 0.6572 | −1.3 |
| 208541_x_at | NM_012251 | TFAM | transcription factor A, mitochondrial | 0.0101 | 0.1028 | −1.3 |
| 209219_at | L03411 | RDBP | RD RNA binding protein | 0.0081 | 0.4823 | −1.3 |
| 200687_s_at | NM_012426 | SF3B3 | splicing factor 3b, subunit 3, 130 kDa | 0.0053 | 0.1142 | −1.3 |
| 209080_x_at | AF118652 | TXNL2 | thioredoxin-like 2 | 0.0060 | 0.3555 | −1.3 |
| 202415_s_at | NM_012267 | HSPBP1 | hsp70-interacting protein | 0.0110 | 0.1066 | −1.3 |
| 210527_x_at | L11645 | TUBA2 | tubulin, alpha 2 | 0.0299 | 0.5806 | −1.3 |
| 213944_x_at | BG236220 | NCLN | Nicalin homolog (zebrafish) | 0.0265 | 0.9908 | −1.3 |
| 216080_s_at | AC004770 | FADS3 | fatty acid desaturase 3 | 0.0429 | 0.6339 | −1.3 |
| 214679_x_at | AL110227 | GNA11 | guanine nucleotide binding protein (G protein), alpha 11 (Gq class) | 0.0066 | 0.0675 | −1.3 |
| 218632_at | NM_024602 | HECTD3 | HECT domain containing 3 | 0.0079 | 0.0819 | −1.3 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 203410_at | NM_006803 | AP3M2 | adaptor-related protein complex 3, mu 2 subunit | 0.0084 | 0.6490 | −1.3 |
| 212714_at | AL050205 | LARP4 | La ribonucleoprotein domain family, member 4 | 0.0259 | 0.5696 | −1.3 |
| 203733_at | NM_014015 | DEXI | dexamethasone-induced transcript | 0.0096 | 0.0775 | −1.3 |
| 204599_s_at | NM_006428 | MRPL28 | mitochondrial ribosomal protein L28 | 0.0235 | 0.7391 | −1.3 |
| 213793_s_at | BE550452 | HOMER1 | homer homolog 1 (Drosophila) | 0.0186 | 0.0395 | −1.3 |
| 218331_s_at | NM_017782 | C10orf18 | chromosome 10 open reading frame 18 | 0.0356 | 0.2221 | −1.3 |
| 204241_at | BF055171 | ACOX3 | acyl-Coenzyme A oxidase 3, pristanoyl | 0.0303 | 0.3147 | −1.2 |
| 212165_at | AF070537 | TMEM183A | transmembrane protein 183A | 0.0012 | 0.2139 | −1.2 |
| 202296_s_at | NM_007033 | RER1 | RER1 retention in endoplasmic reticulum 1 homolog (S. cerevisiae) | 0.0061 | 0.7824 | −1.2 |
| 201481_s_at | NM_002862 | PYGB | phosphorylase, glycogen; brain | 0.0064 | 0.1309 | −1.2 |
| 34868_at | AB029012 | SMG5 | Smg-5 homolog, nonsense mediated mRNA decay factor (C. elegans) | 0.0054 | 0.3627 | −1.2 |
| 212564_at | AA523921 | KCTD2 | potassium channel tetramerisation domain containing 2 | 0.0215 | 0.0579 | −1.2 |
| 204117_at | NM_002726 | PREP | prolyl endopeptidase | 0.0277 | 0.4656 | −1.2 |
| 211052_s_at | BC006364 | TBCD | tubulin folding cofactor D /// tubulin folding cofactor D | 0.0091 | 0.0783 | −1.2 |
| 202440_s_at | NM_005418 | ST5 | suppression of tumorigenicity 5 | 0.0080 | 0.0861 | −1.2 |
| 202670_at | AI571419 | MAP2K1 | mitogen-activated protein kinase kinase 1 | 0.0255 | 0.3612 | −1.2 |
| 203452_at | NM_012200 | B3GAT3 | beta-1,3-glucuronyltransferase 3 (glucuronosyltransferase I) | 0.0172 | 0.0662 | −1.2 |
| 200837_at | NM_005745 | BCAP31 | B-cell receptor-associated protein 31 | 0.0100 | 0.4385 | −1.2 |
| 219611_s_at | NM_022778 | CCDC21 | coiled-coil domain containing 21 | 0.0094 | 0.0843 | −1.2 |
| 213535_s_at | AA910614 | UBE2I | ubiquitin-conjugating enzyme E2I (UBC9 homolog, yeast) | 0.0011 | 0.1305 | −1.2 |
| 200852_x_at | NM_005273 | GNB2 | guanine nucleotide binding protein (G protein), beta polypeptide 2 | 0.0007 | 0.0274 | −1.2 |
| 201578_at | NM_005397 | PODXL | podocalyxin-like | 0.0269 | 0.7420 | −1.2 |
| 212696_s_at | BF968633 | RNF4 | ring finger protein 4 | 0.0135 | 0.5482 | −1.2 |
| 210869_s_at | M29277 | MCAM | melanoma cell adhesion molecule | 0.0197 | 0.3612 | −1.2 |
| 217787_s_at | AL525086 | GALNT2 | UDP-N-acetyl-alpha-D-galactosamine:polypeptide N-acetylgalactosaminyltransferase 2 (GalNAc-T2) | 0.0500 | 0.1670 | −1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 200774_at | BE963765 | FAM120A | family with sequence similarity 120A | 0.0219 | 0.2718 | −1.2 |
| 211037_s_at | BC006309 | LENG4 | leukocyte receptor cluster (LRC) member 4 /// leukocyte receptor cluster (LRC) member 4 | 0.0266 | 0.1880 | −1.2 |
| 204976_s_at | AK023637 | AMMECR1 | Alport syndrome, mental retardation, midface hypoplasia and elliptocytosis chromosomal region, gene 1 | 0.0193 | 0.3064 | −1.2 |
| 212978_at | AU146004 | LRRC8B | Leucine rich repeat containing 8 family, member B | 0.0233 | 0.0532 | −1.2 |
| 218058_at | NM_014593 | CXXC1 | CXXC finger 1 (PHD domain) | 0.0304 | 0.1699 | −1.2 |
| 212861_at | BF690150 | MFSD5 | major facilitator superfamily domain containing 5 | 0.0294 | 0.2091 | −1.2 |
| 218112_at | NM_023936 | MRPS34 | mitochondrial ribosomal protein S34 | 0.0079 | 0.5000 | −1.2 |
| 221828_s_at | AK024432 | FAM125B | family with sequence similarity 125, member B | 0.0057 | 0.1233 | −1.2 |
| 201397_at | NM_006623 | PHGDH | phosphoglycerate dehydrogenase | 0.0026 | 0.0935 | −1.2 |
| 202039_at | NM_004740 | TIAF1 /// MYO18A | TGFB1-induced anti-apoptotic factor 1 /// myosin XVIIIA | 0.0138 | 0.5359 | −1.2 |
| 204518_s_at | NM_000943 | PPIC | peptidylprolyl isomerase C (cyclophilin C) | 0.0138 | 0.6379 | −1.2 |
| 211804_s_at | AB012305 | CDK2 /// BCDO2 | cyclin-dependent kinase 2 /// beta-carotene dioxygenase 2 | 0.0372 | 0.1019 | −1.2 |
| 208767_s_at | AW149681 | LAPTM4B | lysosomal associated protein transmembrane 4 beta | 0.0287 | 0.7180 | −1.2 |
| 201912_s_at | NM_002094 | GSPT1 | G1 to S phase transition 1 /// G1 to S phase transition 1 | 0.0415 | 0.9318 | −1.2 |
| 201272_at | NM_001628 | AKR1B1 | aldo-keto reductase family 1, member B1 (aldose reductase) | 0.0052 | 0.0958 | −1.2 |
| 201144_s_at | NM_004094 | EIF2S1 | eukaryotic translation initiation factor 2, subunit 1 alpha, 35 kDa | 0.0018 | 0.0260 | −1.2 |
| 208999_at | D86957 | 8-Sep | septin 8 | 0.0370 | 0.3680 | −1.2 |
| 202848_s_at | BG423052 | GRK6 | G protein-coupled receptor kinase 6 | 0.0124 | 0.2148 | −1.2 |
| 218653_at | NM_014252 | SLC25A15 | solute carrier family 25 (mitochondrial carrier; ornithine transporter) member 15 | 0.0290 | 0.9035 | −1.2 |
| 202640_s_at | NM_003624 | RANBP3 | RAN binding protein 3 | 0.0202 | 0.3932 | −1.2 |
| 201559_s_at | AF109196 | CLIC4 | chloride intracellular channel 4 | 0.0481 | 0.5454 | −1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 201414_s_at | NM_005969 | NAP1L4 | nucleosome assembly protein 1-like 4 | 0.0127 | 0.0843 | −1.2 |
| 200790_at | NM_002539 | ODC1 | ornithine decarboxylase 1 | 0.0076 | 0.7147 | −1.2 |
| 219076_s_at | NM_018663 | PXMP2 | peroxisomal membrane protein 2, 22 kDa | 0.0101 | 0.0783 | −1.2 |
| 204123_at | NM_013975 | LIG3 | ligase III, DNA, ATP-dependent | 0.0209 | 0.5066 | −1.2 |
| 209208_at | AF059752 | MPDU1 | mannose-P-dolichol utilization defect 1 | 0.0105 | 0.1514 | −1.2 |
| 202348_s_at | BC000674 | TOR1A | torsin family 1, member A (torsin A) | 0.0155 | 0.9365 | −1.2 |
| 212115_at | AK023154 | HN1L | hematological and neurological expressed 1-like | 0.0039 | 0.8034 | −1.2 |
| 201851_at | NM_003025 | SH3GL1 | SH3-domain GRB2-like 1 | 0.0389 | 0.8279 | −1.2 |
| 211714_x_at | BC005838 | TUBB | tubulin, beta /// tubulin, beta | 0.0210 | 0.4381 | −1.2 |
| 209094_at | AL078459 | DDAH1 | dimethylarginine dimethylaminohydrolase 1 | 0.0015 | 0.0447 | −1.2 |
| 201715_s_at | NM_014977 | ACIN1 | apoptotic chromatin condensation inducer 1 | 0.0426 | 0.1405 | −1.2 |
| 218774_at | NM_014026 | DCPS | decapping enzyme, scavenger | 0.0055 | 0.0571 | −1.2 |
| 218629_at | NM_005631 | SMO | smoothened homolog (*Drosophila*) | 0.0234 | 0.1969 | −1.2 |
| 218016_s_at | NM_018119 | POLR3E | polymerase (RNA) III (DNA directed) polypeptide E (80 kD) | 0.0244 | 0.4851 | −1.2 |
| 218741_at | NM_024053 | CENPM | centromere protein M | 0.0144 | 0.4422 | −1.2 |
| 218586_at | NM_018270 | C20orf20 | chromosome 20 open reading frame 20 | 0.0036 | 0.3145 | −1.2 |
| 219260_s_at | NM_015362 | C17orf81 | chromosome 17 open reading frame 81 | 0.0105 | 0.2294 | −1.2 |
| 220094_s_at | NM_022102 | CCDC90A | coiled-coil domain containing 90A | 0.0461 | 0.2205 | −1.2 |
| 208831_x_at | D79984 | SUPT6H | suppressor of Ty 6 homolog (*S. cerevisiae*) | 0.0222 | 0.1216 | −1.2 |
| 214828_s_at | AL157851 | dJ222E13.2 | similar to CGI-96 | 0.0105 | 0.1409 | −1.2 |
| 209014_at | AF217963 | MAGED1 | melanoma antigen family D, 1 | 0.0008 | 0.0299 | −1.2 |
| 212766_s_at | AW294587 | ISG20L2 | interferon stimulated exonuclease gene 20 kDa-like 2 | 0.0111 | 0.8419 | −1.2 |
| 204266_s_at | NM_001277 | CHKA /// LOC650122 | choline kinase alpha /// similar to choline kinase alpha isoform a | 0.0249 | 0.3418 | −1.2 |
| 214869_x_at | AK021533 | GAPVD1 | GTPase activating protein and VPS9 domains 1 | 0.0205 | 0.7717 | −1.2 |
| 221877_at | BF508835 | — | CDNA FLJ38849 fis, clone MESAN2008936 | 0.0086 | 0.5431 | −1.2 |
| 200697_at | NM_000188 | HK1 | hexokinase 1 | 0.0416 | 0.6041 | −1.2 |
| 211750_x_at | BC005946 | TUBA6 | tubulin, alpha 6 /// tubulin, alpha 6 | 0.0011 | 0.0549 | −1.2 |
| 201587_s_at | NM_001569 | IRAK1 | interleukin-1 receptor-associated kinase 1 | 0.0035 | 0.2935 | −1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 209663_s_at | AF072132 | ITGA7 | integrin, alpha 7 | 0.0417 | 0.0631 | −1.2 |
| 221247_s_at | NM_030798 | WBSCR16 | Williams-Beuren syndrome chromosome region 16 /// Williams-Beuren syndrome chromosome region 16 | 0.0295 | 0.1278 | −1.2 |
| 201271_s_at | NM_016732 | RALY | RNA binding protein, autoantigenic (hnRNP-associated with lethal yellow homolog (mouse)) | 0.0275 | 0.2379 | −1.2 |
| 217754_at | NM_019082 | DDX56 | DEAD (Asp-Glu-Ala-Asp) box polypeptide 56 | 0.0050 | 0.1143 | −1.2 |
| 217838_s_at | NM_016337 | EVL | Enah/Vasp-like | 0.0362 | 0.0971 | −1.2 |
| 200762_at | NM_001386 | DPYSL2 | dihydropyrimidinase-like 2 | 0.0078 | 0.2899 | −1.2 |
| 218156_s_at | NM_018128 | TSR1 | TSR1, 20S rRNA accumulation, homolog (S. cerevisiae) | 0.0411 | 0.6879 | −1.2 |
| 219420_s_at | NM_023077 | C1orf163 | chromosome 1 open reading frame 163 | 0.0357 | 0.0712 | −1.2 |
| 202945_at | NM_004957 | FPGS | folylpolyglutamate synthase | 0.0044 | 0.0987 | −1.2 |
| 203795_s_at | NM_020993 | BCL7A | B-cell CLL/lymphoma 7A | 0.0366 | 0.0812 | −1.2 |
| 203550_s_at | NM_006589 | C1orf2 | chromosome 1 open reading frame 2 | 0.0123 | 0.4067 | −1.2 |
| 220244_at | NM_013343 | LOH3CR2A | loss of heterozygosity, 3, chromosomal region 2, gene A | 0.0430 | 0.3328 | −1.2 |
| 201135_at | NM_004092 | ECHS1 | enoyl Coenzyme A hydratase, short chain, 1, mitochondrial | 0.0051 | 0.1455 | −1.2 |
| 218099_at | NM_018469 | TEX2 | testis expressed sequence 2 | 0.0413 | 0.2203 | −1.2 |
| 214501_s_at | AF044286 | TLR4 /// H2AFY | toll-like receptor 4 /// H2A histone family, member Y | 0.0108 | 0.4608 | −1.2 |
| 217729_s_at | NM_001130 | AES | amino-terminal enhancer of split | 0.0049 | 0.0782 | −1.2 |
| 212871_at | NM_003668 | MAPKAPK5 | mitogen-activated protein kinase-activated protein kinase 5 | 0.0160 | 0.1840 | −1.2 |
| 219496_at | NM_023016 | ANKRD57 | ankyrin repeat domain 57 | 0.0463 | 0.1807 | −1.2 |
| 219330_at | NM_024062 | VANGL1 | vang-like 1 (van gogh, Drosophila) | 0.0128 | 0.1514 | −1.2 |
| 219806_s_at | NM_020179 | C11orf75 | chromosome 11 open reading frame 75 | 0.0311 | 0.2261 | −1.2 |
| 201460_at | AI141802 | MAPKAPK2 | mitogen-activated protein kinase-activated protein kinase 2 | 0.0147 | 0.5934 | −1.2 |
| 201763_s_at | NM_001350 | DAXX | death-associated protein 6 | 0.0012 | 0.0157 | −1.2 |
| 211432_s_at | U05682 | TYRO3 | TYRO3 protein tyrosine kinase | 0.0329 | 0.2586 | −1.2 |
| 204493_at | NM_001196 | BID | BH3 interacting domain death agonist | 0.0129 | 0.1146 | −1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 221267_s_at | NM_031213 | FAM108A1 | family with sequence similarity 108, member A1 /// family with sequence similarity 108, member A1 | 0.0178 | 0.3019 | −1.2 |
| 212333_at | AL049943 | FAM98A | family with sequence similarity 98, member A | 0.0206 | 0.0310 | −1.2 |
| 206633_at | NM_000079 | CHRNA1 | cholinergic receptor, nicotinic, alpha 1 (muscle) | 0.0127 | 0.2332 | −1.2 |
| 201841_s_at | NM_001540 | HSPB1 /// MEIS3 | heat shock 27 kDa protein 1 /// Meis1, myeloid ecotropic viral integration site 1 homolog 3 (mouse) | 0.0034 | 0.2235 | −1.2 |
| 204044_at | NM_014298 | QPRT | quinolinate phosphoribosyltransferase (nicotinate-nucleotide pyrophosphorylase (carboxylating)) | 0.0416 | 0.8129 | −1.2 |
| 210011_s_at | BC000527 | EWSR1 | Ewing sarcoma breakpoint region 1 | 0.0070 | 0.0721 | −1.2 |
| 218898_at | NM_024792 | FAM57A | family with sequence similarity 57, member A | 0.0471 | 0.7205 | −1.2 |
| 202518_at | NM_001707 | BCL7B | B-cell CLL/lymphoma 7B | 0.0264 | 0.2789 | −1.2 |
| 202069_s_at | AI826060 | IDH3A | isocitrate dehydrogenase 3 (NAD+) alpha | 0.0224 | 0.4380 | −1.2 |
| 220258_s_at | NM_018081 | WDR79 | WD repeat domain 79 | 0.0225 | 0.2213 | −1.2 |
| 201194_at | NM_003009 | SEPW1 | selenoprotein W, 1 | 0.0162 | 0.1636 | −1.2 |
| 201792_at | NM_001129 | AEBP1 | AE binding protein 1 | 0.0193 | 0.1129 | −1.2 |
| 204126_s_at | NM_003504 | CDC45L | CDC45 cell division cycle 45-like (S. cerevisiae) | 0.0253 | 0.5416 | −1.2 |
| 218961_s_at | NM_007254 | PNKP | polynucleotide kinase 3'-phosphatase | 0.0225 | 0.1313 | −1.2 |
| 209044_x_at | BC004273 | SF3B4 | splicing factor 3b, subunit 4, 49 kDa | 0.0014 | 0.3838 | −1.2 |
| 210415_s_at | AF053970 | ODF2 | outer dense fiber of sperm tails 2 | 0.0260 | 0.5497 | −1.2 |
| 203210_s_at | NM_007370 | RFC5 | replication factor C (activator 1) 5, 36.5 kDa | 0.0375 | 0.1357 | −1.2 |
| 212271_at | AA195999 | MAPK1 | mitogen-activated protein kinase 1 | 0.0470 | 0.6623 | −1.2 |
| 208696_at | AF275798 | CCT5 | chaperonin containing TCP1, subunit 5 (epsilon) | 0.0242 | 0.9588 | −1.2 |
| 218365_s_at | AI765051 | DARS2 | aspartyl-tRNA synthetase 2 (mitochondrial) | 0.0157 | 0.2829 | −1.2 |
| 218848_at | NM_024339 | THOC6 | THO complex 6 homolog (Drosophila) | 0.0396 | 0.4185 | −1.2 |
| 218542_at | NM_018131 | CEP55 | centrosomal protein 55 kDa | 0.0061 | 0.5899 | −1.2 |
| 206845_s_at | NM_014771 | RNF40 | ring finger protein 40 | 0.0244 | 0.1693 | −1.2 |
| 202592_at | NM_001487 | BLOC1S1 | biogenesis of lysosome-related organelles complex-1, subunit 1 | 0.0112 | 0.6525 | −1.2 |
| 218566_s_at | NM_012124 | CHORDC1 | cysteine and histidine-rich domain (CHORD)-containing 1 | 0.0484 | 0.3010 | −1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 200691_s_at | BC000478 | HSPA9 | heat shock 70 kDa protein 9 (mortalin) | 0.0155 | 0.4830 | −1.2 |
| 218187_s_at | NM_023080 | C8orf33 | chromosome 8 open reading frame 33 | 0.0483 | 0.5066 | −1.2 |
| 218120_s_at | D21243 | HMOX2 | heme oxygenase (decycling) 2 | 0.0440 | 0.6657 | −1.2 |
| 221737_at | AK024696 | GNA12 | guanine nucleotide binding protein (G protein) alpha 12 | 0.0258 | 0.4334 | −1.2 |
| 202828_s_at | NM_004995 | MMP14 | matrix metallopeptidase 14 (membrane-inserted) | 0.0202 | 0.5070 | −1.2 |
| 201357_s_at | NM_005877 | SF3A1 | splicing factor 3a, subunit 1, 120 kDa | 0.0267 | 0.0877 | −1.2 |
| 213696_s_at | AA421957 | MED8 | mediator of RNA polymerase II transcription, subunit 8 homolog (*S. cerevisiae*) | 0.0487 | 0.2629 | −1.2 |
| 204928_s_at | NM_019848 | SLC10A3 | solute carrier family 10 (sodium/bile acid cotransporter family), member 3 | 0.0039 | 0.2235 | −1.2 |
| 217932_at | NM_015971 | MRPS7 | mitochondrial ribosomal protein S7 | 0.0014 | 0.1160 | −1.2 |
| 201263_at | NM_003191 | TARS | threonyl-tRNA synthetase | 0.0302 | 0.0907 | −1.2 |
| 207121_s_at | NM_002748 | MAPK6 | mitogen-activated protein kinase 6 | 0.0064 | 0.1007 | −1.2 |
| 217221_x_at | AL137421 | RBM10 | RNA binding motif protein 10 | 0.0188 | 0.0866 | −1.2 |
| 202816_s_at | AW292882 | SS18 | synovial sarcoma translocation, chromosome 18 | 0.0084 | 0.0541 | −1.2 |
| 1861_at | U66879 | BAD | BCL2-antagonist of cell death | 0.0380 | 0.5209 | −1.2 |
| 202108_at | NM_000285 | PEPD | peptidase D | 0.0178 | 0.2205 | −1.2 |
| 204993_at | NM_002073 | GNAZ | guanine nucleotide binding protein (G protein), alpha z polypeptide | 0.0293 | 0.4344 | −1.2 |
| 201229_s_at | BC000422 | ARIH2 | ariadne homolog 2 (*Drosophila*) | 0.0395 | 0.3941 | −1.2 |
| 213812_s_at | AK024748 | CAMKK2 | calcium/calmodulin-dependent protein kinase kinase 2, beta | 0.0294 | 0.3375 | −1.2 |
| 201298_s_at | BC003398 | MOBK1B | MOB1, Mps One Binder kinase activator-like 1B (yeast) | 0.0077 | 0.0700 | −1.2 |
| 213270_at | AW450911 | MPP2 | membrane protein, palmitoylated 2 (MAGUK p55 subfamily member 2) | 0.0039 | 0.0933 | −1.2 |
| 220688_s_at | NM_016183 | MRT4 | mRNA turnover 4 homolog (*S. cerevisiae*) | 0.0046 | 0.0441 | −1.2 |
| 51176_at | AA131335 | CRSP8 | cofactor required for Sp1 transcriptional activation, subunit 8, 34 kDa | 0.0015 | 0.2747 | −1.2 |
| 201761_at | NM_006636 | MTHFD2 | methylenetetrahydrofolate dehydrogenase (NADP+ dependent) 2, methenyltetrahydrofolate cyclohydrolase | 0.0124 | 0.6250 | −1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 208682_s_at | AF126181 | MAGED2 | melanoma antigen family D, 2 | 0.0172 | 0.3256 | −1.2 |
| 41160_at | AC005943 | MBD3 | methyl-CpG binding domain protein 3 | 0.0031 | 0.0383 | −1.2 |
| 205661_s_at | NM_025207 | FLAD1 | FAD1 flavin adenine dinucleotide synthetase homolog (S. cerevisiae) | 0.0063 | 0.8074 | −1.2 |
| 208821_at | J04564 | SNRPB | small nuclear ribonucleoprotein polypeptides B and B1 | 0.0050 | 0.0642 | −1.2 |
| 201303_at | NM_014740 | EIF4A3 | eukaryotic translation initiation factor 4A, isoform 3 | 0.0079 | 0.9084 | −1.2 |
| 209581_at | BC001387 | HRASLS3 | HRAS-like suppressor 3 | 0.0335 | 0.1759 | −1.2 |
| 48531_at | AA522816 | TNIP2 | TNFAIP3 interacting protein 2 | 0.0131 | 0.4345 | −1.2 |
| 201697_s_at | NM_001379 | DNMT1 | DNA (cytosine-5-)-methyltransferase 1 | 0.0193 | 0.1580 | −1.2 |
| 218019_s_at | NM_021941 | PDXK | pyridoxal (pyridoxine, vitamin B6) kinase | 0.0044 | 0.0638 | −1.2 |
| 202338_at | NM_003258 | TK1 | thymidine kinase 1, soluble | 0.0295 | 0.0858 | −1.2 |
| 216232_s_at | AI697055 | GCN1L1 | GCN1 general control of amino-acid synthesis 1-like 1 (yeast) | 0.0066 | 0.1082 | −1.2 |
| 212250_at | AV700332 | MTDH | metadherin | 0.0380 | 0.1082 | −1.2 |
| 214771_x_at | AK025604 | M-RIP | myosin phosphatase-Rho interacting protein | 0.0146 | 0.3146 | −1.2 |
| 200683_s_at | BE964689 | UBE2L3 | ubiquitin-conjugating enzyme E2L 3 | 0.0214 | 0.9367 | −1.2 |
| 208152_s_at | NM_004728 | DDX21 | DEAD (Asp-Glu-Ala-Asp) box polypeptide 21 /// DEAD (Asp-Glu-Ala-Asp) box polypeptide 21 | 0.0325 | 0.1335 | −1.2 |
| 203828_s_at | NM_004221 | IL32 | interleukin 32 /// interleukin 32 | 0.0114 | 0.0452 | −1.2 |
| 208777_s_at | AF001212 | PSMD11 | proteasome (prosome, macropain) 26S subunit, non-ATPase, 11 | 0.0066 | 0.2440 | −1.2 |
| 219862_s_at | NM_012336 | NARF | nuclear prelamin A recognition factor | 0.0278 | 0.9051 | −1.2 |
| 203827_at | NM_017983 | WIPI1 | WD repeat domain, phosphoinositide interacting 1 | 0.0081 | 0.4544 | −1.2 |
| 219491_at | NM_024036 | LRFN4 | leucine rich repeat and fibronectin type III domain containing 4 | 0.0160 | 0.3821 | −1.2 |
| 202115_s_at | NM_015658 | NOC2L | nucleolar complex associated 2 homolog (S. cerevisiae) | 0.0326 | 0.6859 | −1.2 |
| 212098_at | AL134724 | LOC151162 | hypothetical protein LOC151162 | 0.0094 | 0.4141 | −1.2 |
| 203570_at | NM_005576 | LOXL1 | lysyl oxidase-like 1 | 0.0023 | 0.0499 | −1.2 |
| 210213_s_at | AF022229 | ITGB4BP | integrin beta 4 binding protein | 0.0097 | 0.2297 | −1.2 |
| 32836_at | U56417 | AGPAT1 | 1-acylglycerol-3-phosphate O-acyltransferase 1 | 0.0161 | 0.0474 | −1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| | | | (lysophosphatidic acid acyltransferase, alpha) | | | |
| 201284_s_at | NM_001640 | APEH | N-acylaminoacyl-peptide hydrolase | 0.0120 | 0.0383 | −1.2 |
| 208689_s_at | BC003560 | RPN2 | ribophorin II | 0.0060 | 0.0452 | −1.2 |
| 201307_at | AL534972 | 11-Sep | septin 11 | 0.0200 | 0.7860 | −1.2 |
| 202757_at | NM_015456 | COBRA1 | cofactor of BRCA1 | 0.0030 | 0.0278 | −1.2 |
| 212480_at | AB002374 | SPECC1L | SPECC1-like | 0.0411 | 0.1914 | −1.2 |
| 203233_at | NM_000418 | IL4R | interleukin 4 receptor | 0.0148 | 0.4358 | −1.2 |
| 211630_s_at | L42531 | GSS | glutathione synthetase /// glutathione synthetase | 0.0411 | 0.1844 | −1.2 |
| 212400_at | AL043266 | FAM102A | family with sequence similarity 102, member A | 0.0194 | 0.2054 | −1.2 |
| 221704_s_at | BC005882 | VPS37B | vacuolar protein sorting 37 homolog B (*S. cerevisiae*) /// vacuolar protein sorting 37 homolog B (*S. cerevisiae*) | 0.0045 | 0.6051 | −1.2 |
| 209452_s_at | AF035824 | VTI1B | vesicle transport through interaction with t-SNAREs homolog 1B (yeast) | 0.0357 | 0.4069 | −1.2 |
| 218758_s_at | NM_003683 | D21S2056E | DNA segment on chromosome 21 (unique) 2056 expressed sequence | 0.0362 | 0.3701 | −1.2 |
| 201361_at | NM_024092 | TMEM109 | transmembrane protein 109 | 0.0256 | 0.2193 | −1.2 |
| 209323_at | AF081567 | PRKRIR | protein-kinase, interferon-inducible double stranded RNA dependent inhibitor, repressor of (P58 repressor) | 0.0063 | 0.0537 | −1.2 |
| 204080_at | NM_025077 | TOE1 | target of EGR1, member 1 (nuclear) | 0.0179 | 0.7025 | −1.2 |
| 200708_at | NM_002080 | GOT2 | glutamic-oxaloacetic transaminase 2, mitochondrial (aspartate aminotransferase 2) | 0.0021 | 0.6983 | −1.2 |
| 220155_s_at | NM_023924 | BRD9 | bromodomain containing 9 | 0.0014 | 0.0804 | −1.2 |
| 211456_x_at | AF333388 | LOC645745 | metallothionein 1H-like protein | 0.0037 | 0.0589 | −1.2 |
| 218460_at | NM_017802 | HEATR2 | HEAT repeat containing 2 | 0.0180 | 0.7292 | −1.2 |
| 200793_s_at | NM_001098 | ACO2 | aconitase 2, mitochondrial | 0.0358 | 0.1897 | −1.2 |
| 203149_at | NM_002856 | PVRL2 | poliovirus receptor-related 2 (herpesvirus entry mediator B) | 0.0356 | 0.5506 | −1.2 |
| 201066_at | NM_001916 | CYC1 | cytochrome c-1 | 0.0069 | 0.7513 | −1.2 |
| 207707_s_at | NM_030673 | SEC13 | SEC13 homolog (*S. cerevisiae*) | 0.0025 | 0.4694 | −1.2 |
| 205351_at | NM_000821 | GGCX | gamma-glutamyl carboxylase | 0.0093 | 0.8819 | −1.2 |
| 214437_s_at | NM_005412 | SHMT2 | serine hydroxymethyltransferase 2 (mitochondrial) | 0.0054 | 0.2573 | −1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 208863_s_at | M72709 | SFRS1 | splicing factor, arginine/serine-rich 1 (splicing factor 2, alternate splicing factor) | 0.0136 | 0.1920 | −1.2 |
| 209501_at | AL582414 | CDR2 | cerebellar degeneration-related protein 2, 62 kDa | 0.0186 | 0.1069 | −1.2 |
| 206809_s_at | NM_005758 | HNRPA3P1 /// HNRPA3 | heterogeneous nuclear ribonucleoprotein A3 pseudogene 1 /// heterogeneous nuclear ribonucleoprotein A3 | 0.0275 | 0.1782 | −1.2 |
| 205055_at | NM_002208 | ITGAE | integrin, alpha E (antigen CD103, human mucosal lymphocyte antigen 1; alpha polypeptide) | 0.0225 | 0.0929 | −1.2 |
| 216977_x_at | AJ130972 | SNRPA1 | small nuclear ribonucleoprotein polypeptide A' | 0.0159 | 0.2202 | −1.2 |
| 35617_at | U29725 | MAPK7 | mitogen-activated protein kinase 7 | 0.0203 | 0.2536 | −1.2 |
| 205546_s_at | NM_003331 | TYK2 | tyrosine kinase 2 | 0.0369 | 0.1604 | −1.2 |
| 212953_x_at | BE251303 | CALR | calreticulin | 0.0294 | 0.1004 | −1.2 |
| 211168_s_at | D86988 | UPF1 | UPF1 regulator of nonsense transcripts homolog (yeast) | 0.0155 | 0.0625 | −1.2 |
| 210046_s_at | U52144 | IDH2 | isocitrate dehydrogenase 2 (NADP+), mitochondrial | 0.0035 | 0.0383 | −1.2 |
| 219933_at | NM_016066 | GLRX2 | glutaredoxin 2 | 0.0255 | 0.1890 | −1.2 |
| 219081_at | NM_024668 | ANKHD1 | ankyrin repeat and KH domain containing 1 | 0.0196 | 0.4240 | −1.2 |
| 200614_at | NM_004859 | CLTC | clathrin, heavy chain (Hc) | 0.0237 | 0.4039 | −1.2 |
| 209394_at | BC002508 | ASMTL | acetylserotonin O-methyltransferase-like | 0.0416 | 0.4632 | −1.2 |
| 49077_at | AL040538 | PPME1 | protein phosphatase methylesterase 1 | 0.0049 | 0.8306 | −1.2 |
| 217933_s_at | NM_015907 | LAP3 | leucine aminopeptidase 3 | 0.0034 | 0.0252 | −1.2 |
| 215411_s_at | AL008730 | TRAF3IP2 | TRAF3 interacting protein 2 | 0.0099 | 0.0383 | −1.2 |
| 221904_at | AI141670 | C3orf40 | chromosome 3 open reading frame 40 | 0.0459 | 0.2865 | −1.2 |
| 206445_s_at | NM_001536 | PRMT1 | protein arginine methyltransferase 1 | 0.0019 | 0.0740 | −1.2 |
| 207071_s_at | NM_002197 | ACO1 /// ANKRD15 | aconitase 1, soluble /// ankyrin repeat domain 15 | 0.0173 | 0.8523 | −1.2 |
| 213205_s_at | AU159543 | RAD54L2 | RAD54-like 2 (S. cerevisiae) | 0.0124 | 0.1547 | −1.2 |
| 207614_s_at | NM_003592 | CUL1 | cullin 1 | 0.0268 | 0.9630 | −1.2 |
| 208712_at | M73554 | CCND1 | cyclin D1 | 0.0440 | 0.1233 | −1.2 |
| 205224_at | NM_017503 | SURF2 | surfeit 2 | 0.0311 | 0.9687 | −1.2 |
| 202655_at | NM_006010 | ARMET | arginine-rich, mutated in early stage tumors | 0.0067 | 0.2238 | −1.2 |
| 201463_s_at | NM_006755 | TALDO1 | transaldolase 1 | 0.0043 | 0.6019 | −1.2 |
| 205588_s_at | NM_007045 | FGFR1OP /// C9orf4 | FGFR1 oncogene partner /// chromosome 9 open reading frame 4 | 0.0246 | 0.0856 | −1.2 |

TABLE 6-continued

Genes modulated by compound 1 treatment in Rh41 cells.

| probe | Accession # | Gene Symbol | Gene Title | fdr p value for treatment | fdr p value for treatment_Time | fold_change (compound 1 vs DMSO) |
|---|---|---|---|---|---|---|
| 203746_s_at | NM_005333 | HCCS | holocytochrome c synthase (cytochrome c heme-lyase) | 0.0080 | 0.3313 | −1.2 |
| 202240_at | NM_005030 | PLK1 | polo-like kinase 1 (*Drosophila*) | 0.0224 | 0.0274 | −1.2 |
| 207939_x_at | NM_006711 | RNPS1 | RNA binding protein S1, serine-rich domain | 0.0112 | 0.2149 | −1.2 |
| 202991_at | NM_006804 | STARD3 | START domain containing 3 | 0.0198 | 0.5816 | −1.2 |
| 218337_at | NM_022749 | RAI16 | retinoic acid induced 16 | 0.0370 | 0.4464 | −1.2 |
| 210821_x_at | BC002703 | CENPA | centromere protein A | 0.0221 | 0.0915 | −1.2 |
| 200853_at | NM_002106 | H2AFZ | H2A histone family, member Z | 0.0135 | 0.7942 | −1.2 |
| 209464_at | AB011446 | AURKB | aurora kinase B | 0.0121 | 0.0981 | −1.2 |

Cells were treated with 0.35 μM compound 1 for 6, 36 and 72 hours before harvest and subject to Affymetrix gene microarray analysis.
Each sample was run in duplicates.
A two-way ANOVA mixed model: (Intensity ~ Treatment + Time + Treatment x Time + Error) was utilized to identify drug treatment effect as well as treatment and time interaction on the expression of genes.
The genes identified as modulated by the drug are those with FDR p value < 0.05 in either the Treatment effect or Treatment x Time interaction and the fold change between treatment group and DMSO control group is greater than 1.2 fold or less than −1.2 fold and total of 2056 probe sets were selected and only 1697 representative unique genes are listed in this Table with redundant probe sets removed.

TABLE 7

Proteins modulated by compound 1 treatment in Rh41 cells.

| Peptide | FirstOfdescription | International Protein Index | Swiss-protein ID |
|---|---|---|---|
| AFTGREFDELNPSAQR (SEQ ID NO: 146) | SWISS-PROT: P16615-1 REFSEQ_NP: NP_733765 ENSEMBL: ENSP00000324892 Tax_Id = 9606 Splice isoform SERCA2B of P16615 Sarcoplasmic/endoplasmic reticulum calcium ATPase 2 | IPI00219078.1 | P16615-1 |
| AHEGEIEDLALGPDGK LVTVGR (SEQ ID NO: 147) | REFSEQ_NP: NP_037520 TREMBL: Q9UH94 ENSEMBL: ENSP00000260643 Tax_Id = 9606 Prolactin regulatory element-binding protein | IPI00033349.1 | |
| AHIAQLCEK (SEQ ID NO: 148) | SWISS-PROT: Q00610 REFSEQ_NP: NP_004850 ENSEMBL: ENSP00000269122 Tax_Id = 9606 Clathrin heavy chain 1 | IPI00024067.1 | Q00610 |
| AITGASLADIMAK (SEQ ID NO: 149) | SWISS-PROT: P38663 REFSEQ_NP: NP_000977 ENSEMBL: ENSP00000265264 Tax_Id = 9606 60S ribosomal protein L24 | IPI00220397.1 | P38663 |
| ALGTEVIQLFPEK (SEQ ID NO: 150) | SWISS-PROT: O95831-2 REFSEQ_NP: NP_665812 ENSEMBL: ENSP00000316320 Tax_Id = 9606 Splice isoform 2 of O95831 Programmed cell death protein 8 mitochondrial precursor | IPI00186214.1 | O95831-2 |
| ALMAAEDK (SEQ ID NO: 151) | TREMBL: Q9Y427; Q07414 ENSEMBL: ENSP00000267996 Tax_Id = 9606 Hypothetical protein | IPI00000230.1 | Q9Y427; Q07414 |

TABLE 7-continued

Proteins modulated by compound 1 treatment in Rh41 cells.

| Peptide | FirstOfdescription | International Protein Index | Swiss-protein ID |
|---|---|---|---|
| AMINLHIQK (SEQ ID NO: 152) | SWISS-PROT: Q9NZ45 REFSEQ_NP: NP_060934 ENSEMBL: ENSP00000242476 Tax_Id = 9606 Uncharacterized hematopoietic stem/progenitor cells protein MDS029 Uncharacterized hematopoietic stem/progenitor cells protein MDS029 | IPI00020510.1 | Q9NZ45 |
| AQSEAEKLAKERQEAEEAKEALLQASR (SEQ ID NO: 153) | SWISS-PROT: P35240-7 ENSEMBL: ENSP00000314630 Tax_Id = 9606 Splice isoform 7 of P35240 Merlin | IPI00220313.1 | P35240-7 |
| ASGDSARPVLLQVAESAYR (SEQ ID NO: 154) | SWISS-PROT: Q9UJS0 REFSEQ_NP: NP_055066 ENSEMBL: ENSP00000265631 Tax_Id = 9606 Calcium-binding mitochondrial carrier protein Aralar2 | IPI00007084.1 | Q9UJS0 |
| ASITALEAK (SEQ ID NO: 155) | SWISS-PROT: P35579 REFSEQ_NP: NP_002464 TREMBL: Q99529; Q9UMJ0 ENSEMBL: ENSP00000216181 Tax_Id = 9606 Myosin heavy chain nonmuscle type A | IPI00019502.1 | P35579 |
| AVTSANIQEFAGCKK (SEQ ID NO: 156) | SWISS-PROT: P04626 REFSEQ_NP: NP_004439 TREMBL: Q9UMK4; Q14256; Q9NP09 ENSEMBL: ENSP00000269571 Tax_Id = 9606 Receptor protein-tyrosine kinase erbB-2 precursor | IPI00025072.1 | P04626 |
| DDTIYEDEDVKEAIR (SEQ ID NO: 157) | SWISS-PROT: P14927 REFSEQ_NP: NP_006285 ENSEMBL: ENSP00000287022 Tax_Id = 9606 ubiquinol-cytochrome c reductase binding protein | IPI00220416.1 | P14927 |
| DGGQEYVVK (SEQ ID NO: 158) | SWISS-PROT: O60437 REFSEQ_NP: NP_002696 ENSEMBL: ENSP00000262369 Tax_Id = 9606 Periplakin | IPI00216295.1 | O60437 |
| DKQMELLENK (SEQ ID NO: 159) | REFSEQ_NP: NP_006401 TREMBL: O60520; Q9BUP3 ENSEMBL: ENSP00000227259 Tax_Id = 9606 Tat-interacting protein | IPI00107873.1 | NP_006401 |
| DLKPENLLLASK (SEQ ID NO: 160) | REFSEQ_NP: NP_751909 TREMBL: Q8N4I3 ENSEMBL: ENSP00000315599 Tax_Id = 9606 Calcium/calmodulin-dependent protein kinase | IPI00166707.1 | NP_751909 |
| DPIYFTGLASEPGAR (SEQ ID NO: 161) | SWISS-PROT: Q99523 Tax_Id = 9606 Sortilin precursor | IPI00016022.1 | Q99523 |
| DSIVHQAGMLK (SEQ ID NO: 162) | SWISS-PROT: O15144 REFSEQ_NP: NP_005722; NP_690601 TREMBL: Q9P1D4 ENSEMBL: ENSP00000327137 Tax_Id = 9606 ARP2/3 complex 34 kDa subunit | IPI00005161.1 | O15144 |

TABLE 7-continued

Proteins modulated by compound 1 treatment in Rh41 cells.

| Peptide | FirstOfdescription | International Protein Index | Swiss-protein ID |
|---|---|---|---|
| DVSSSTPPSVTSK (SEQ ID NO: 163) | REFSEQ_NP: NP_036451 TREMBL: Q8IXR3; Q96HP5; Q13433 ENSEMBL: ENSP00000269187 Tax_Id = 9606 LIV-1 protein estrogen regulated | IPI00098365.1 | NP_036451 |
| EGVREVFETATR (SEQ ID NO: 164) | SWISS-PROT: P01121 REFSEQ_NP: NP_004031 ENSEMBL: ENSP00000272233 Tax_Id = 9606 Transforming protein RhoB | IPI00000041.1 | P01121 |
| ELASLHDK (SEQ ID NO: 165) | SWISS-PROT: O14662-2 REFSEQ_NP: NP_003754 ENSEMBL: ENSP00000287648; ENSP00000320106 Tax_Id = 9606 Splice isoform A of O14662 Syntaxin 16 | IPI00220261.1 | O14662-2 |
| ELISNSSDALDKIR (SEQ ID NO: 166) | SWISS-PROT: P07900 REFSEQ_NP: NP_005339 TREMBL: Q96HX7; Q8TBA7; O75322 ENSEMBL: ENSP00000216281 Tax_Id = 9606 heat shock 90 kDa protein 1 alpha | IPI00217479.1 | P07900 |
| ELVSLKQEQQAFKEAADTER (SEQ ID NO: 167) | REFSEQ_NP: NP_006816 TREMBL: Q07065 ENSEMBL: ENSP00000312296 Tax_Id = 9606 P63 protein P63 protein | IPI00141318.1 | |
| EMIPFAVVGSDHEYQVNGKR (SEQ ID NO: 168) | TREMBL: Q9UHD8 Tax_Id = 9606 MLL septin-like fusion protein MSF-A MLL septin-like fusion protein MSF-A | IPI00155610.1 | Q9UHD8 |
| EQHGLQLQSEINQLHSK (SEQ ID NO: 169) | REFSEQ_NP: NP_003557 TREMBL: Q14221; Q15075 ENSEMBL: ENSP00000218310; ENSP00000317955 Tax_Id = 9606 Endosome-associated protein Endosome-associated protein | IPI00020647.1 | |
| FETEKNNGAGYFLEHLAFKGTK (SEQ ID NO: 170) | SWISS-PROT: P31930 REFSEQ_NP: NP_003356 TREMBL: Q96DD2 ENSEMBL: ENSP00000203407 Tax_Id = 9606 Ubiquinol-cytochrome C reductase complex core protein I mitochondrial precursor | IPI00013847.1 | P31930 |
| FEVIEKPQA (SEQ ID NO: 171) | SWISS-PROT: P18859 REFSEQ_NP: NP_001676 ENSEMBL: ENSP00000284971; ENSP00000318330 Tax_Id = 9606 ATP synthase coupling factor 6 mitochondrial precursor | IPI00002521.1 | P18859 |
| FFDEESYSLLRK (SEQ ID NO: 172) | SWISS-PROT: P51571 REFSEQ_NP: NP_006271 TREMBL: Q96BQ0 Tax_Id = 9606 Translocon-associated protein delta subunit precursor | IPI00019385.1 | P51571 |

TABLE 7-continued

Proteins modulated by compound 1 treatment in Rh41 cells.

| Peptide | FirstOfdescription | International Protein Index | Swiss-protein ID |
|---|---|---|---|
| FHDVLGNERPSAYMR (SEQ ID NO: 173) | REFSEQ_XP: XP_086381 ENSEMBL: ENSP00000326482 Tax_Id = 9606 similar to 40S RIBOSOMAL PROTEIN P40 (C10 PROTEIN) | IPI00084819.2 | XP_086381 |
| FKMPEMHFKAPK (SEQ ID NO: 174) | SWISS-PROT: Q09666 ENSEMBL: ENSP00000244934 Tax_Id = 9606 Neuroblast differentiation associated protein AHNAK | IPI00021812.1 | Q09666 |
| FSAYIKNSNPALNDNLEK (SEQ ID NO: 175) | SWISS-PROT: O00299 REFSEQ_NP: NP_001279 ENSEMBL: ENSP00000211475 Tax_Id = 9606 Chloride intracellular channel protein 1 | IPI00010896.1 | O00299 |
| FSFKKPFK (SEQ ID NO: 176) | SWISS-PROT: P49006 REFSEQ_NP: NP_075385 ENSEMBL: ENSP00000310885 Tax_Id = 9606 MARCKS-like protein | IPI00220803.1 | P49006 |
| GADDAMESSKPGPVQVVLVQK (SEQ ID NO: 177) | TREMBL: Q9UFL1; Q9BSE0 Tax_Id = 9606 Hypothetical protein | IPI00004806.1 | Q9UFL1; Q9BSE0 |
| GALHTVSHEDIRDIR (SEQ ID NO: 178) | REFSEQ_NP: NP_003617 TREMBL: Q13136; Q8N4I2; Q14567 ENSEMBL: ENSP00000310098 Tax_Id = 9606 PTPRF interacting protein alpha 1 isoform b | IPI00164240.3 | NP_003617 |
| GFFGYK (SEQ ID NO: 179) | TREMBL: Q15693 Tax_Id = 9606 5C5 5C5 | IPI00018949.1 | Q15693 |
| GPASPLDSTFYR (SEQ ID NO: 180) | SWISS-PROT: P04626 REFSEQ_NP: NP_004439 TREMBL: Q9UMK4; Q14256; Q9NP09 ENSEMBL: ENSP00000269571 Tax_Id = 9606 Receptor protein-tyrosine kinase erbB-2 precursor | IPI00025072.1 | P04626 |
| GPVGTVSEAQLAR (SEQ ID NO: 181) | SWISS-PROT: Q9NZM1-1 REFSEQ_NP: NP_038479 ENSEMBL: ENSP00000260690 Tax_Id = 9606 Splice isoform 1 of Q9NZM1 Myoferlin | IPI00021048.1 | Q9NZM1-1 |
| GTPGPPPAHGAALQPHPR (SEQ ID NO: 182) | SWISS-PROT: Q15654 REFSEQ_NP: NP_003293 TREMBL: Q9BUE5; Q9BXP3 ENSEMBL: ENSP00000200457 Tax_Id = 9606 Thyroid receptor interacting protein 6 | IPI00018848.2 | Q15654 |
| GVGIISEGNETVEDIAARLNIPVSQVNPR (SEQ ID NO: 183) | SWISS-PROT: P05023-1 REFSEQ_NP: NP_000692 TREMBL: Q9UJ21 ENSEMBL: ENSP00000295598 Tax_Id = 9606 Splice isoform Long of P05023 Sodium/potassium-transporting ATPase alpha-1 chain precursor | IPI00006482.1 | P05023-1 |

TABLE 7-continued

Proteins modulated by compound 1 treatment in Rh41 cells.

| Peptide | FirstOfdescription | International Protein Index | Swiss-protein ID |
|---|---|---|---|
| GYSFTTTAER (SEQ ID NO: 184) | SWISS-PROT: P02570 REFSEQ_NP: NP_001092 TREMBL: Q96DE1; Q96E67; Q9BTD2; Q9UE89; Q8WVW5; Q96FU6; Q96B34; Q9UMN3 ENSEMBL: ENSP00000158302 Tax_Id = 9606 Actin cytoplasmic 1 | IPI00021439.1 | P02570 |
| HMGLFDHAAR (SEQ ID NO: 185) | SWISS-PROT: P50213 REFSEQ_NP: NP_005521 TREMBL: Q9H3X0 ENSEMBL: ENSP00000299518 Tax_Id = 9606 Isocitrate dehydrogenase [NAP] subunit alpha mitochondrial precursor | IPI00030702.1 | P50213 |
| HSTFHGEDKLISVEDL WK (SEQ ID NO: 186) | REFSEQ_NP: NP_003147 TREMBL: Q8N382 ENSEMBL: ENSP00000300737 Tax_Id = 9606 Hypothetical protein Hypothetical protein | IPI00166512.1 | NP_003147 |
| HVIPMNPNTDDLFK (SEQ ID NO: 187) | SWISS-PROT: P13797 REFSEQ_NP: NP_005023 TREMBL: Q96HI1 ENSEMBL: ENSP00000289290 Tax_Id = 9606 plastin 3 | IPI00216694.1 | P13797 |
| IAAYAYSALSQIR (SEQ ID NO: 188) | REFSEQ_NP: NP_060377 TREMBL: Q9NWT0; Q8WZ09 ENSEMBL: ENSP00000278671 Tax_Id = 9606 Hypothetical protein Hypothetical protein | IPI00016670.1 | |
| IASQVAALDLGYKPGV EAIR (SEQ ID NO: 189) | SWISS-PROT: P28331 Tax_Id = 9606 NADH-ubiquinone oxidoreductase 75 kDa subunit mitochondrial precursor | IPI00002871.1 | P28331 |
| IEVEKPFAIAKE (SEQ ID NO: 190) | SWISS-PROT: P23284 REFSEQ_NP: NP_000933 TREMBL: Q9BVK5 ENSEMBL: ENSP00000300026 Tax_Id = 9606 Peptidylprolyl isomerase B | IPI00107117.1 | P23284 |
| IFVGGIKEDTEEHHLR (SEQ ID NO: 191) | REFSEQ_XP: XP_018399 ENSEMBL: ENSP00000267149 Tax_Id = 9606 similar to helix-destabilizing protein —rat | IPI00042578.1 | XP_018399 |
| IHEKLHYYEK (SEQ ID NO: 192) | REFSEQ_NP: NP_775767 TREMBL: Q8IY28 ENSEMBL: ENSP00000315639 Tax_Id = 9606 Similar to membrane protein palmitoylated 3 | IPI00217617.1 | NP_775767 |
| IINEPTAAAIAYGLDK (SEQ ID NO: 193) | SWISS-PROT: P34931 REFSEQ_NP: NP_005518 TREMBL: Q8NE72 REFSEQ_XP: XP_166348; XP_212623 ENSEMBL: ENSP00000259871 Tax_Id = 9606 Heat shock 70 kDa protein 1-HOM | IPI00002965.2 | P34931 |

TABLE 7-continued

Proteins modulated by compound 1 treatment in Rh41 cells.

| Peptide | FirstOfdescription | International Protein Index | Swiss-protein ID |
|---|---|---|---|
| IISANGCK (SEQ ID NO: 194) | SWISS-PROT: P05023-1 REFSEQ_NP: NP_000692 TREMBL: Q9UJ21 ENSEMBL: ENSP00000295598 Tax_Id = 9606 Splice isoform Long of P05023 Sodium/potassium-transporting ATPase alpha-1 chain precursor | IPI00006482.1 | P05023-1 |
| IIYSHFTCATDTENIR (SEQ ID NO: 195) | SWISS-PROT: P50148 REFSEQ_NP: NP_002063 TREMBL: Q9BZB9 ENSEMBL: ENSP00000286548 Tax_Id = 9606 G alpha q protein | IPI00097511.1 | P50148 |
| INVYYNEATGGK (SEQ ID NO: 196) | SWISS-PROT: P05217 REFSEQ_NP: NP_006079 TREMBL: Q96HX0; Q9BUU9 Tax_Id = 9606 Tubulin beta-2 chain Tubulin beta-2 chain | IPI00007752.1 | P05217 |
| IPDVDIDSDGVFK (SEQ ID NO: 197) | SWISS-PROT: Q9NRX4 REFSEQ_NP: NP_054891 TREMBL: Q9P019 ENSEMBL: ENSP00000247665 Tax_Id = 9606 14 kDa phosphohistidine phosphatase | IPI00156269.1 | Q9NRX4 |
| ISVYYNEATGGKYVPR (SEQ ID NO: 198) | REFSEQ_NP: NP_001060 TREMBL: O43209; Q9UGA2; Q13885 ENSEMBL: ENSP00000259799 Tax_Id = 9606 Beta tubulin | IPI00013475.1 | |
| IYHTIAYLTPLPQPNR (SEQ ID NO: 199) | SWISS-PROT: P10620 REFSEQ_NP: NP_064696; NP_665707; NP_665734; NP_665735 ENSEMBL: ENSP00000010404; ENSP00000314356; ENSP00000314383; ENSP00000314466 Tax_Id = 9606 Microsomal glutathione S-transferase 1 | IPI00021805.1 | P10620 |
| KAHLTNQYMQR (SEQ ID NO: 200) | REFSEQ_XP: XP_210297 Tax_Id = 9606 similar to Polyadenylate-binding protein 4 (Poly(A) binding protein 4) (PABP 4) (Inducible poly(A)-binding protein) (iPABP) (Activated-platelet protein-1) (APP-1) | IPI00173545.1 | |
| KALELDQER (SEQ ID NO: 201) | SWISS-PROT: P35241 REFSEQ_NP: NP_002897 TREMBL: Q9NST9 ENSEMBL: ENSP00000282281; ENSP00000310481 Tax_Id = 9606 Radixin Radixin | IPI00017367.1 | P35241 |
| KEPHESLGMTVAGGR (SEQ ID NO: 202) | SWISS-PROT: Q8N448 REFSEQ_NP: NP_699202 ENSEMBL: ENSP00000266952; ENSP00000325929 Tax_Id = 9606 Numb-binding protein 2 | IPI00171047.1 | Q8N448 |

TABLE 7-continued

Proteins modulated by compound 1 treatment in Rh41 cells.

| Peptide | FirstOfdescription | International Protein Index | Swiss-protein ID |
|---|---|---|---|
| KGLDPYNVLAPK (SEQ ID NO: 203) | SWISS-PROT: P10606 REFSEQ_NP: NP_001853 TREMBL: Q99610 ENSEMBL: ENSP00000258424 Tax_Id = 9606 Cytochrome c oxidase polypeptide Vb mitochondrial precursor | IPI00021785.2 | P10606 |
| KIYEFTLQR (SEQ ID NO: 204) | SWISS-PROT: O43795 ENSEMBL: ENSP00000306382 Tax_Id = 9606 Myosin Ib | IPI00013980.2 | O43795 |
| KLMEECKR (SEQ ID NO: 205) | SWISS-PROT: Q9P0L0 REFSEQ_NP: NP_003565 ENSEMBL: ENSP00000217602 Tax_Id = 9606 Vesicle-associated membrane protein-associated protein A | IPI00170692.1 | Q9P0L0 |
| KMMLDLNKAK (SEQ ID NO: 206) | TREMBL: Q92799 Tax_Id = 9606 Mitochondrial trifunctional protein beta subunit | IPI00023349.1 | Q92799 |
| KPQYDIWGNTVNVASR (SEQ ID NO: 207) | SWISS-PROT: O95622 ENSEMBL: ENSP00000308685 Tax_Id = 9606 Adenylate cyclase type V | IPI00218608.1 | O95622 |
| KTGENVEDAFLEAAK (SEQ ID NO: 208) | SWISS-PROT: P35287 REFSEQ_NP: NP_057406 ENSEMBL: ENSP00000238339 Tax_Id = 9606 Ras-related protein Rab-14 Ras-related protein Rab-14 | IPI00017508.1 | P35287 |
| KVEEENQGALEMIKR (SEQ ID NO: 209) | TREMBL: Q8N4U4; Q8WU84 ENSEMBL: ENSP00000304043 Tax_Id = 9606 Hypothetical protein | IPI00102860.1 | Q8N4U4; Q8WU84 |
| KWESPAQNTAHLDQFER (SEQ ID NO: 210) | SWISS-PROT: P17612-1 REFSEQ_NP: NP_002721 TREMBL: Q15136 ENSEMBL: ENSP00000263389 Tax_Id = 9606 protein kinase cAMP-dependent catalytic alpha | IPI00219591.1 | P17612-1 |
| KYELGRPAANTK (SEQ ID NO: 211) | SWISS-PROT: P09058 REFSEQ_NP: NP_001003 TREMBL: Q9BS10 ENSEMBL: ENSP00000271105 Tax_Id = 9606 40S ribosomal protein S8 40S ribosomal protein S8 | IPI00216587.1 | P09058 |
| LAALQGRLEGLGSSEADQDGLASTVR (SEQ ID NO: 212) | REFSEQ_NP: NP_006816 TREMBL: Q07065 ENSEMBL: ENSP00000312296 Tax_Id = 9606 P63 protein P63 protein | IPI00141318.1 | NP_006816 |
| LDHKFDLMYAK (SEQ ID NO: 213) | SWISS-PROT: P05215 REFSEQ_NP: NP_005991 ENSEMBL: ENSP00000248437 Tax_Id = 9606 Tubulin alpha-4 chain | IPI00007750.1 | P05215 |
| LDLRDDKDTIER (SEQ ID NO: 214) | SWISS-PROT: O14658 REFSEQ_NP: NP_005043 ENSEMBL: ENSP00000304283 Tax_Id = 9606 Ras-related C3 botulinum toxin substrate 3 | IPI00023138.1 | O14658 |

TABLE 7-continued

Proteins modulated by compound 1 treatment in Rh41 cells.

| Peptide | FirstOfdescription | International Protein Index | Swiss-protein ID |
|---|---|---|---|
| LEKHELIEFR (SEQ ID NO: 215) | SWISS-PROT: Q00610 REFSEQ_NP: NP_004850 ENSEMBL: ENSP00000269122 Tax_Id = 9606 Clathrin heavy chain 1 | IPI00024067.1 | Q00610 |
| LESEGSPETLTNLR (SEQ ID NO: 216) | TREMBL: Q9NQA7 Tax_Id = 9606 B-ind1 protein B-ind1 protein | IPI00175830.1 | Q9NQA7 |
| LHSLKTAK (SEQ ID NO: 217) | SWISS-PROT: P20929 REFSEQ_NP: NP_004534 TREMBL: Q14215; Q14918; Q14214 ENSEMBL: ENSP00000172853 Tax_Id = 9606 Nebulin Nebulin | IPI00026247.2 | P20929 |
| LIVDEAINEDNSVVSLSQPK (SEQ ID NO: 218) | SWISS-PROT: P55072 REFSEQ_NP: NP_009057 TREMBL: Q9NTC4; Q96IF9; Q9HAP1; Q9HAP0 ENSEMBL: ENSP00000298001; ENSP00000312929; ENSP00000315065; ENSP00000318011 Tax_Id = 9606 Transitional endoplasmic reticulum ATPase | IPI00022774.1 | P55072 |
| LMVHTVATFNSIK (SEQ ID NO: 219) | SWISS-PROT: Q13813 REFSEQ_NP: NP_003118 TREMBL: Q15324; Q9UG16 ENSEMBL: ENSP00000238302; ENSP00000306097; ENSP00000319196 Tax_Id = 9606 Spectrin alpha chain brain | IPI00015786.1 | Q13813 |
| LNESLDENFKK (SEQ ID NO: 220) | TREMBL: Q96CV4; Q9Y2M8; Q9H5F5 ENSEMBL: ENSP00000005260 Tax_Id = 9606 Similar to RIKEN cDNA 1300006M19 gene Similar to RIKEN cDNA 1300006M19 gene | IPI00179326.1 | Q96CV4; Q9Y2M8; Q9H5F5 |
| LQQGYNAMGFSQGGQFLR (SEQ ID NO: 221) | SWISS-PROT: P50897 REFSEQ_NP: NP_000301 ENSEMBL: ENSP00000253546 Tax_Id = 9606 Palmitoyl-protein thioesterase 1 precursor | IPI00002412.1 | P50897 |
| LQVELDNVTGLLSQSDSK (SEQ ID NO: 222) | SWISS-PROT: P35579 REFSEQ_NP: NP_002464 TREMBL: Q99529; Q9UMJ0 ENSEMBL: ENSP00000216181 Tax_Id = 9606 Myosin heavy chain nonmuscle type A | IPI00019502.1 | P35579 |
| LTVMTDLEDKNEWK (SEQ ID NO: 223) | SWISS-PROT: Q12907 REFSEQ_NP: NP_006807 ENSEMBL: ENSP00000303366 Tax_Id = 9606 Vesicular integral-membrane protein VIP36 precursor | IPI00009950.1 | Q12907 |
| MASGAANVVGPK (SEQ ID NO: 224) | SWISS-PROT: Q92520 REFSEQ_NP: NP_055703 REFSEQ_XP: XP_208425 ENSEMBL: ENSP00000222764; ENSP00000310532 Tax_Id = 9606 Protein FAM3C precursor | IPI00021923.1 | Q92520 |

TABLE 7-continued

Proteins modulated by compound 1 treatment in Rh41 cells.

| Peptide | FirstOfdescription | International Protein Index | Swiss-protein ID |
|---|---|---|---|
| MKETAENYLGHTAK (SEQ ID NO: 225) | SWISS-PROT: P38646 REFSEQ_NP: NP_004125 TREMBL: Q8N1C8 ENSEMBL: ENSP00000297185 Tax_Id = 9606 Stress-70 protein mitochondrial precursor | IPI00007765.2 | P38646 |
| MNRPAPVEVTYK (SEQ ID NO: 226) | REFSEQ_NP: NP_003454 TREMBL: Q93096; O00648 ENSEMBL: ENSP00000229983 Tax_Id = 9606 Protein tyrosine phosphatase PTPCAAX1 | IPI00020164.1 | NP_003454 |
| MSQVMREWEEAERQAK (SEQ ID NO: 227) | SWISS-PROT: P05067-7 Tax_Id = 9606 Splice isoform L-APP733 of P05067 Amyloid beta A4 protein precursor | IPI00219187.1 | P05067-7 |
| NALLSLAK (SEQ ID NO: 228) | SWISS-PROT: P04083 REFSEQ_NP: NP_000691 ENSEMBL: ENSP00000257497 Tax_Id = 9606 annexin I | IPI00218918.1 | P04083 |
| NDITPLHVASK (SEQ ID NO: 229) | SWISS-PROT: Q12955 REFSEQ_NP: NP_066267 TREMBL: Q8NAK2 ENSEMBL: ENSP00000280772; ENSP00000313984 Tax_Id = 9606 Ankyrin 3 | IPI00025770.2 | Q12955 |
| NHPLHIRENR (SEQ ID NO: 230) | REFSEQ_NP: NP_006835 TREMBL: Q9UEB2; O43341; Q96F08 ENSEMBL: ENSP00000263383 Tax_Id = 9606 Acetolactate synthase Acetolactate synthase | IPI00009963.2 | NP_006835 |
| NIVHNYSEAEIK (SEQ ID NO: 231) | REFSEQ_NP: NP_060427 TREMBL: Q9NWK2; Q9H201 ENSEMBL: ENSP00000268933 Tax_Id = 9606 Epsin 3 Epsin 3 | IPI00100282.1 | NP_060427 |
| NLDSTTVAVHGEEIYCK (SEQ ID NO: 232) | SWISS-PROT: P21291 REFSEQ_NP: NP_004069 TREMBL: Q9BTA4 ENSEMBL: ENSP00000290286 Tax_Id = 9606 cysteine and glycine-rich protein 1 | IPI00219674.1 | P21291 |
| NLGSINTELQDVQR (SEQ ID NO: 233) | REFSEQ_NP: NP_004883 TREMBL: O75396 ENSEMBL: ENSP00000286336 Tax_Id = 9606 Vesicle trafficking protein SEC22B Vesicle trafficking protein SEC22B | IPI00006865.1 | NP_004883 |
| NVLSLTNK (SEQ ID NO: 234) | SWISS-PROT: P05556-2 REFSEQ_NP: NP_389647 Tax_Id = 9606 integrin beta 1 isoform 1B precursor | IPI00107778.1 | P05556-2 |
| PAVSKGDGMR (SEQ ID NO: 235) | SWISS-PROT: O94973 REFSEQ_NP: NP_036437 TREMBL: Q9UFK5 Tax_Id = 9606 Adapter-related protein complex 2 alpha 2 subunit | IPI00016621.1 | O94973 |

TABLE 7-continued

Proteins modulated by compound 1 treatment in Rh41 cells.

| Peptide | FirstOfdescription | International Protein Index | Swiss-protein ID |
|---|---|---|---|
| PGTEPLGTTK (SEQ ID NO: 236) | SWISS-PROT: Q9Y6I9 REFSEQ_NP: NP_057010 ENSEMBL: ENSP00000296478 Tax_Id = 9606 Putative secreted protein ZSIG11 precursor Putative secreted protein ZSIG11 precursor | IPI00006372.1 | Q9Y6I9 |
| PIHPVGGLR (SEQ ID NO: 237) | SWISS-PROT: Q9HCU4 REFSEQ_NP: NP_001399 ENSEMBL: ENSP00000271332; ENSP00000319010 Tax_Id = 9606 Cadherin EGF LAG seven-pass G-type receptor 2 precursor | IPI00015346.1 | Q9HCU4 |
| QVLLAQAEAEK (SEQ ID NO: 238) | SWISS-PROT: Q14254 REFSEQ_NP: NP_004466 ENSEMBL: ENSP00000254926 Tax_Id = 9606 Flotillin-2 | IPI00029625.1 | Q14254 |
| QVTPDGESDEVGVIPSKR (SEQ ID NO: 239) | SWISS-PROT: Q15700 REFSEQ_NP: NP_001355 ENSEMBL: ENSP00000280241 Tax_Id = 9606 Channel associated protein of synapse-110 | IPI00019328.1 | Q15700 |
| RKVDWLTEK (SEQ ID NO: 240) | SWISS-PROT: P04765 REFSEQ_NP: NP_001407 TREMBL: Q9BRK6; Q9NZR9 ENSEMBL: ENSP00000293831 Tax_Id = 9606 Eukaryotic initiation factor 4A-I | IPI00025491.1 | P04765 |
| RLYWDDLKR (SEQ ID NO: 241) | SWISS-PROT: P02786 REFSEQ_NP: NP_003225 ENSEMBL: ENSP00000265238 Tax_Id = 9606 Transferrin receptor protein 1 | IPI00022462.1 | P02786 |
| RNELVIR (SEQ ID NO: 242) | SWISS-PROT: P11413-2 Tax_Id = 9606 Splice isoform Long of P11413 Glucose-6-phosphate 1-dehydrogenase | IPI00216008.1 | P11413-2 |
| RSNTENLSQHFR (SEQ ID NO: 243) | SWISS-PROT: Q9UHB6-1 REFSEQ_NP: NP_057441 ENSEMBL: ENSP00000293615 Tax_Id = 9606 Splice isoform Beta of Q9UHB6 Epithelial protein lost in neoplasm | IPI00008918.1 | Q9UHB6-1 |
| RTPVQPNPIVYMMK (SEQ ID NO: 244) | SWISS-PROT: O96000 REFSEQ_NP: NP_004539 TREMBL: Q96RX5 ENSEMBL: ENSP00000268668 Tax_Id = 9606 NADH dehydrogenase (ubiquinone) 1 beta subcomplex 10 22 kDa | IPI00220060.1 | O96000 |
| SALLAEMDKVEGHVAIK (SEQ ID NO: 245) | SWISS-PROT: P33527-6 Tax_Id = 9606 Splice isoform Delexon-17-30 of P33527 Multidrug resistance-associated protein 1 | IPI00216265.1 | P33527-6 |
| SAVTTVVNPK (SEQ ID NO: 246) | SWISS-PROT: P05556-2 REFSEQ_NP: NP_389647 Tax_Id = 9606 integrin beta 1 isoform 1B precursor | IPI00107778.1 | P05556-2 |

TABLE 7-continued

Proteins modulated by compound 1 treatment in Rh41 cells.

| Peptide | FirstOfdescription | International Protein Index | Swiss-protein ID |
|---|---|---|---|
| SEESVSRLPEEIR (SEQ ID NO: 247) | REFSEQ_NP: NP_006816<br>TREMBL: Q07065<br>ENSEMBL: ENSP00000312296<br>Tax_Id = 9606<br>P63 protein P63 protein | IPI00141318.1 | NP_006816 |
| SEHKVWSPLVTEEGKR (SEQ ID NO: 248) | SWISS-PROT: O00151<br>REFSEQ_NP: NP_066272<br>ENSEMBL: ENSP00000265995<br>Tax_Id = 9606<br>PDZ and LIM domain protein 1 | IPI00010414.2 | O00151 |
| SHEAEVLK (SEQ ID NO: 249) | SWISS-PROT: P16949<br>REFSEQ_NP: NP_005554<br>TREMBL: Q96CE4<br>ENSEMBL: ENSP00000236291<br>Tax_Id = 9606<br>Stathmin | IPI00031736.1 | P16949 |
| SKEPQLIAFYHK (SEQ ID NO: 250) | SWISS-PROT: P19634<br>REFSEQ_NP: NP_003038<br>REFSEQ_XP: XP_046881<br>ENSEMBL: ENSP00000263980<br>Tax_Id = 9606<br>Sodium/hydrogen exchanger 1 | IPI00020060.1 | P19634 |
| SLSLSKLEDPHVDIIR (SEQ ID NO: 251) | TREMBL: Q8TEP9<br>Tax_Id = 9606 FLJ00144 protein | IPI00152791.1 | Q8TEP9 |
| SLVNQQSFQDIKPMR (SEQ ID NO: 252) | SWISS-PROT: P17964<br>REFSEQ_XP: XP_209564<br>ENSEMBL: ENSP00000319096<br>Tax_Id = 9606<br>Ras-related protein RAP-2b Ras-related protein RAP-2b | IPI00018364.2 | P17964 |
| SQVLDDEDSNNITVGSLVTVLVK (SEQ ID NO: 253) | SWISS-PROT: Q9UGP8<br>REFSEQ_NP: NP_009145<br>TREMBL: Q8IWL0<br>ENSEMBL: ENSP00000027474; ENSP00000317581<br>Tax_Id = 9606<br>SEC63 endoplasmic reticulum translocon component (S. cerevisiae) like | IPI00218922.1 | Q9UGP8 |
| SRKESYSVYVYK (SEQ ID NO: 254) | REFSEQ_XP: XP_169343<br>Tax_Id = 9606 similar to H2B histone family member S | IPI00147570.1 | |
| SSSLDDTEVKK (SEQ ID NO: 255) | SWISS-PROT: O95292-1<br>REFSEQ_NP: NP_004729<br>ENSEMBL: ENSP00000265619<br>Tax_Id = 9606<br>Splice isoform 1 of O95292 Vesicle-associated membrane protein-associated protein B/C | IPI00006211.1 | O95292-1 |
| STGPGASLGTGYDRK (SEQ ID NO: 256) | SWISS-PROT: O15551<br>REFSEQ_NP: NP_001297<br>ENSEMBL: ENSP00000297926<br>Tax_Id = 9606<br>Claudin-3 | IPI00007364.1 | O15551 |
| SWEQKLEEMR (SEQ ID NO: 257) | SWISS-PROT: Q16543<br>REFSEQ_NP: NP_008996<br>ENSEMBL: ENSP00000222005<br>Tax_Id = 9606<br>Hsp90 co-chaperone Cdc37 | IPI00013122.1 | Q16543 |
| TAPYKNVNIQNFHISWK (SEQ ID NO: 258) | SWISS-PROT: P12814<br>Tax_Id = 9606 Alpha-actinin 1 | IPI00025845.1 | P12814 |

TABLE 7-continued

Proteins modulated by compound 1 treatment in Rh41 cells.

| Peptide | FirstOfdescription | International Protein Index | Swiss-protein ID |
|---|---|---|---|
| TAVVVGTITDDVR (SEQ ID NO: 259) | SWISS-PROT: Q07020 REFSEQ_NP: NP_000970 ENSEMBL: ENSP00000084795 Tax_Id = 9606 60S ribosomal protein L18 60S ribosomal protein L18 | IPI00215719.1 | Q07020 |
| TDLEKDIISDTSGDFRK (SEQ ID NO: 260) | SWISS-PROT: P07355 REFSEQ_NP: NP_004030 TREMBL: Q8TBV2 ENSEMBL: ENSP00000316276 Tax_Id = 9606 Annexin A2 Annexin A2 | IPI00216240.1 | P07355 |
| TDPVDIYK (SEQ ID NO: 261) | SWISS-PROT: P46940 REFSEQ_NP: NP_003861 TREMBL: Q96PA3 ENSEMBL: ENSP00000268182 Tax_Id = 9606 Ras GTPase-activating-like protein IQGAP1 | IPI00009342.1 | P46940 |
| TKTEISEMNR (SEQ ID NO: 262) | REFSEQ_NP: NP_778238 ENSEMBL: ENSP00000307014 Tax_Id = 9606 keratin 6 irs3 | IPI00174775.1 | NP_778238 |
| TVFDEAIR (SEQ ID NO: 263) | SWISS-PROT: P15154-2 REFSEQ_NP: NP_061485 ENSEMBL: ENSP00000258736 Tax_Id = 9606 Splice isoform B of P15154 Ras-related C3 botulinum toxin substrate 1 | IPI00219675.1 | P15154-2 |
| TVNMTWNK (SEQ ID NO: 264) | SWISS-PROT: P46939 REFSEQ_NP: NP_009055 TREMBL: Q9UJA7; Q8WYB8; Q8WYB7 ENSEMBL: ENSP00000282749 Tax_Id = 9606 Utrophin | IPI00009329.1 | P46939 |
| TVYSHLFDHVVNR (SEQ ID NO: 265) | SWISS-PROT: Q9UM54 ENSEMBL: ENSP00000265377 Tax_Id = 9606 Myosin VI Myosin VI | IPI00008455.1 | Q9UM54 |
| VKANLEK (SEQ ID NO: 266) | SWISS-PROT: P35579 REFSEQ_NP: NP_002464 TREMBL: Q99529; Q9UMJ0 ENSEMBL: ENSP00000216181 Tax_Id = 9606 Myosin heavy chain nonmuscle type A | IPI00019502.1 | P35579 |
| VKDASPNQVAEK (SEQ ID NO: 267) | SWISS-PROT: O43402 REFSEQ_NP: NP_006058 ENSEMBL: ENSP00000253457 Tax_Id = 9606 Neighbor of COX4 Neighbor of COX4 | IPI00005740.1 | O43402 |
| VKDRDDFPVVLVGNK (SEQ ID NO: 268) | SWISS-PROT: P10301 REFSEQ_NP: NP_006261 ENSEMBL: ENSP00000246792 Tax_Id = 9606 Ras-related protein R-Ras | IPI00020418.1 | P10301 |
| VKKEWEEAELQAK (SEQ ID NO: 269) | SWISS-PROT: Q06481-3 ENSEMBL: ENSP00000263575 Tax_Id = 9606 Splice isoform 3 of Q06481 Amyloid-like protein 2 precursor | IPI00220978.1 | Q06481-3 |

TABLE 7-continued

Proteins modulated by compound 1 treatment in Rh41 cells.

| Peptide | FirstOfdescription | International Protein Index | Swiss-protein ID |
|---|---|---|---|
| VKLFYLDPDAQKLDFS SAEPEVK (SEQ ID NO: 270) | SWISS-PROT: Q9BZ29-1 REFSEQ_NP: NP_056111 TREMBL: Q9BZ26 ENSEMBL: ENSP00000304814 Tax_Id = 9606 Splice isoform 1 of Q9BZ29 Cdc42 guanine nucleotide exchange factor zizimin 1 | IPI00151888.2 | Q9BZ29-1 |
| VLAFTAVGDGPPSPTIQ VK (SEQ ID NO: 271) | REFSEQ_NP: NP_569707 ENSEMBL: ENSP00000318349 Tax_Id = 9606 protein tyrosine phosphatase receptor type F isoform 2 precursor | IPI00107831.1 | |
| VNGRPLEMIEPR (SEQ ID NO: 272) | SWISS-PROT: P17008 REFSEQ_NP: NP_001011 ENSEMBL: ENSP00000251453 Tax_Id = 9606 ribosomal protein S16 | IPI00221092.1 | P17008 |
| VPTSMVLTK (SEQ ID NO: 273) | TREMBL: Q9H1H3; Q9ULE9 REFSEQ_XP: XP_045472 ENSEMBL: ENSP00000319445 Tax_Id = 9606 Hypothetical protein KIAA1271 | IPI00020719.1 | Q9H1H3; Q9ULE9 |
| VSSLGKDWHK (SEQ ID NO: 274) | SWISS-PROT: P52943 REFSEQ_NP: NP_001303 Tax_Id = 9606 Cysteine-rich protein 2 | IPI00006034.1 | P52943 |
| WEVEEMKESK (SEQ ID NO: 275) | SWISS-PROT: P27824 REFSEQ_NP: NP_001737 ENSEMBL: ENSP00000247461 Tax_Id = 9606 Calnexin precursor | IPI00020984.1 | P27824 |
| WGKPHVASLSFR (SEQ ID NO: 276) | SWISS-PROT: P04920-1 Tax_Id = 9606 Splice isoform A of P04920 Anion exchange protein 2 | IPI00026298.2 | P04920-1 |
| WILSQTHNIFTQAGVR (SEQ ID NO: 277) | REFSEQ_NP: NP_598003 TREMBL: Q8TCH2; Q8NEW0 ENSEMBL: ENSP00000294731 Tax_Id = 9606 Zinc transporter ZnT-7 Zinc transporter ZnT-7 | IPI00171632.1 | |
| WKAGLYGLPRR (SEQ ID NO: 278) | REFSEQ_NP: NP_004095 TREMBL: Q96IT0; Q969R1; Q16702; Q96C68; Q13479; Q13587 ENSEMBL: ENSP00000304592; ENSP00000304718 Tax_Id = 9606 Fatty acid synthase | IPI00107774.1 | |
| YGPSLMPGGNKEAWP HIK (SEQ ID NO: 279) | SWISS-PROT: P52209 REFSEQ_NP: NP_002622 ENSEMBL: ENSP00000322397 Tax_Id = 9606 phosphogluconate dehydrogenase | IPI00219525.1 | P52209 |
| YKVEGFPTIYFAPSGD KK (SEQ ID NO: 280) | SWISS-PROT: P13667 REFSEQ_NP: NP_004902 ENSEMBL: ENSP00000286091 Tax_Id = 9606 Protein disulfide isomerase A4 precursor | IPI00009904.1 | P13667 |
| YMGDLSGGQVLKK (SEQ ID NO: 281) | SWISS-PROT: P30519 REFSEQ_NP: NP_002125 ENSEMBL: ENSP00000219700 Tax_Id = 9606 Heme oxygenase 2 | IPI00026824.1 | P30519 |

TABLE 7-continued

Proteins modulated by compound 1 treatment in Rh41 cells.

| Peptide | FirstOfdescription | International Protein Index | Swiss-protein ID |
|---|---|---|---|
| YNGLIHRK (SEQ ID NO: 282) | SWISS-PROT: P46779 ENSEMBL: ENSP00000311213 Tax_Id = 9606 60S ribosomal protein L28 60S ribosomal protein L28 | IPI00008411.2 | P46779 |
| YQLSSEAAK (SEQ ID NO: 283) | SWISS-PROT: Q9NRW7 REFSEQ_NP: NP_009190 ENSEMBL: ENSP00000259149 Tax_Id = 9606 Vacuolar protein sorting-associated protein 45 | IPI00090327.1 | Q9NRW7 |
| YSALNVQHQMLK (SEQ ID NO: 284) | REFSEQ_NP: NP_055313 TREMBL: O00461 ENSEMBL: ENSP00000309893 Tax_Id = 9606 130 kDa golgi-localized phosphoprotein | IPI00004962.1 | |
| YSQVLANGLDNK (SEQ ID NO: 285) | SWISS-PROT: P25232 REFSEQ_NP: NP_072045 ENSEMBL: ENSP00000211372; ENSP00000313640 Tax_Id = 9606 40S ribosomal protein S18 | IPI00013296.1 | P25232 |
| YYPTEDVPRK (SEQ ID NO: 286) | SWISS-PROT: Q02878 REFSEQ_NP: NP_000961 TREMBL: Q8N5Z7; Q9HBB3; Q8TBK5; Q8WW97 ENSEMBL: ENSP00000202773 Tax_Id = 9606 60S ribosomal protein L6 | IPI00027271.1 | Q02878 |

Cells were treated with 0.35 µM compound 1 for 6, 36 and 72 hours before harvest and subject to LC/MS based protein profiling.
There are biological duplicates and technique duplicates.
A two-way ANOVA mixed model was utilized to identify drug treatment effect as well as treatment and time interaction on the expression of peptide ions.
The peptide ions identified as modulated by the drug are those with p value < 0.05 in either the Treatment effect or Treatment x Time interaction.
FDR correction was not applied to the protein profiling data.

Remarkably, these genes are mainly involved in apoptosis (AIFM1, ACIN1, BIRC2, BIRC5, BAD, BAG3, BAX, CARD10, CIAPIN1, DAP, DAXX, DAPK1, PDCD11 and PDCD4), cell growth and proliferation (Ki67, BOP1, GAS1 and ING3), cell cycles (cyclin family members of B, D, E, G, H, I, K, L; CDK 2 and 7; centromere protein A, B, M, N; CDKN3 and CDKN1B) and multiple tyrosine kinases such as ERBB3, PDGFR, FGFR1, 2 and 4, MET, EPH as well as the down-stream IGF1R signaling pathways: MAPK, PI3K and AKT. Interestingly, contrary to what was reported with IGF1R antibody (R. Baserga, Expert Opin. Ther. Targets; 9:753-68 (2005)), inhibition of kinase activity by compound 1 did not result in the receptor down-regulation, but rather induced the expression of IGF1R, insulin receptor substrate 2 (IRS2) and insulin-like growth factor binding protein 3 (IGFBP3). This could be one of the mechanisms by which cells attempt to compensate the reduced activity of the IGF1R caused by the inhibitor, and the feedback loop then restores the inhibited pathway activity.

Genes Related to Acquired Resistance to IGF1R Inhibitor Compound 1:

Acquired resistance to anti-cancer agents is a major clinical problem. To study the mechanism of acquired resistance to IGF1R inhibitor, we derived resistance cells by culturing a compound 1 sensitive RMS cell line RD-1($IC_{50}$=0.238 µM) in the presence of a gradually increased concentration of compound 1 in every other passage to reach the resistance level of plateau. The resulted resistant RD1 cells had $IC_{50}$=1.999 µM to compound 1, which is 8 fold higher than the $IC_{50}$ of the parent RD1. In order to identify markers that may contribute to acquired resistance to the IGF1R inhibitor, global gene expression profiles for both parental RD1 and resistant RD1 were analyzed using Affymetrix gene chip. A statistical analysis was conducted using GeneChip® Expression Analysis software MAS 5.0 to identify the genes differentially expressed between the sensitive and acquired resistant cells (Table 8).

TABLE 8

Genes related to acquired resistance to compound 1.

Genes higher expressed in acquired resistant RD-1 cells

| | | | | |
|---|---|---|---|---|
| 209278_s_at | L27624 | tissue factor pathway inhibitor 2 | TFPI2 | 194 |
| 202820_at | NM_001621 | aryl hydrocarbon receptor | AHR | 157.6 |
| 216598_s_at | S69738 | chemokine (C-C motif) ligand 2 | CCL2 | 104 |

TABLE 8-continued

Genes related to acquired resistance to compound 1.

| | | | | |
|---|---|---|---|---|
| 209875_s_at | M83248 | secreted phosphoprotein 1 (osteopontin, bone sialoprotein I, early T-lymphocyte activation 1) | SPP1 | 104 |
| 201301_s_at | BC000182 | annexin A4 | ANXA4 | 97 |
| 206785_s_at | NM_002260 | killer cell lectin-like receptor subfamily C, member 1 /// killer cell lectin-like receptor subfamily C, member 2 | KLRC1 /// KLRC2 | 84.4 |
| 201427_s_at | NM_005410 | selenoprotein P, plasma, 1 | SEPP1 | 84.4 |
| 213156_at | BG251521 | *Homo sapiens*, clone IMAGE: 4214654, mRNA | — | 64 |
| 201005_at | NM_001769 | CD9 molecule | CD9 | 59.7 |
| 220038_at | NM_013257 | serum/glucocorticoid regulated kinase family, member 3 | SGK3 | 48.5 |
| 212681_at | AI770004 | erythrocyte membrane protein band 4.1-like 3 | EPB41L3 | 45.3 |
| 220014_at | NM_016644 | proline rich 16 | PRR16 | 45.3 |
| 205563_at | NM_002256 | KiSS-1 metastasis-suppressor | KISS1 | 42.2 |
| 211343_s_at | M33653 | collagen, type XIII, alpha 1 | COL13A1 | 34.3 |
| 202555_s_at | NM_005965 | myosin, light chain kinase /// myosin, light chain kinase | MYLK | 32 |
| 212909_at | AL567376 | LY6/PLAUR domain containing 1 | LYPD1 | 29.9 |
| 206363_at | NM_005360 | v-maf musculoaponeurotic fibrosarcoma oncogene homolog (avian) | MAF | 29.9 |
| 217967_s_at | AF288391 | family with sequence similarity 129, member A | FAM129A | 27.9 |
| 209789_at | BF939649 | coronin, actin binding protein, 2B | CORO2B | 26 |
| 206693_at | NM_000880 | interleukin 7 | IL7 | 26 |
| 206157_at | NM_002852 | pentraxin-related gene, rapidly induced by IL-1 beta | PTX3 | 26 |
| 206315_at | NM_004750 | cytokine receptor-like factor 1 | CRLF1 | 24.3 |
| 222020_s_at | AW117456 | neurotrimin | HNT | 24.3 |
| 221884_at | BE466525 | ecotropic viral integration site 1 | EVI1 | 22.6 |
| 205691_at | NM_004209 | synaptogyrin 3 | SYNGR3 | 22.6 |
| 203888_at | NM_000361 | thrombomodulin | THBD | 21.1 |
| 214841_at | AF070524 | cornichon homolog 3 (*Drosophila*) | CNIH3 | 17.1 |
| 210809_s_at | D13665 | periostin, osteoblast specific factor | POSTN | 17.1 |
| 203910_at | NM_004815 | Rho GTPase activating protein 29 | ARHGAP29 | 16 |
| 214587_at | BE877796 | collagen, type VIII, alpha 1 | COL8A1 | 14.9 |
| 214297_at | BE857703 | Chondroitin sulfate proteoglycan 4 (melanoma-associated) | CSPG4 | 14.9 |
| 204014_at | NM_001394 | dual specificity phosphatase 4 | DUSP4 | 14.9 |
| 201163_s_at | NM_001553 | insulin-like growth factor binding protein 7 | IGFBP7 | 14.9 |
| 221986_s_at | AW006750 | kelch-like 24 (*Drosophila*) | KLHL24 | 14.9 |
| 204249_s_at | NM_005574 | LIM domain only 2 (rhombotin-like 1) | LMO2 | 14.9 |
| 217901_at | BF031829 | Desmoglein 2 | DSG2 | 13.9 |
| 204836_at | NM_000170 | glycine dehydrogenase (decarboxylating) | GLDC | 13.9 |
| 204475_at | NM_002421 | matrix metallopeptidase 1 (interstitial collagenase) | MMP1 | 13.9 |
| 205858_at | NM_002507 | nerve growth factor receptor (TNFR superfamily, member 16) | NGFR | 13.9 |
| 213716_s_at | BF939675 | secreted and transmembrane 1 | SECTM1 | 13.9 |
| 214954_at | BF977837 | sushi domain containing 5 | SUSD5 | 13.9 |
| 205110_s_at | NM_004114 | fibroblast growth factor 13 | FGF13 | 13 |
| 207018_s_at | NM_004163 | RAB27B, member RAS oncogene family /// SH3 domain binding glutamic acid-rich protein | RAB27B /// SH3BGR | 13 |
| 212912_at | AI992251 | ribosomal protein S6 kinase, 90 kDa, polypeptide 2 | RPS6KA2 | 13 |
| 205862_at | NM_014668 | GREB1 protein | GREB1 | 12.1 |
| 209870_s_at | AW571582 | amyloid beta (A4) precursor protein-binding, family A, member 2 (X11-like) | APBA2 | 11.3 |
| 212062_at | AB014511 | ATPase, Class II, type 9A | ATP9A | 11.3 |
| 213865_at | AI378788 | discoidin, CUB and LCCL domain containing 2 | DCBLD2 | 11.3 |
| 205884_at | NM_000885 | integrin, alpha 4 (antigen CD49D, alpha 4 subunit of VLA-4 receptor) | ITGA4 | 11.3 |
| 212188_at | AA551075 | potassium channel tetramerisation domain containing 12 /// potassium channel tetramerisation domain containing 12 | KCTD12 | 11.3 |
| 202625_at | AI356412 | v-yes-1 Yamaguchi sarcoma viral related oncogene homolog /// v-yes-1 Yamaguchi sarcoma viral related oncogene homolog | LYN | 11.3 |

TABLE 8-continued

Genes related to acquired resistance to compound 1.

| | | | | |
|---|---|---|---|---|
| 205538_at | NM_003389 | coronin, actin binding protein, 2A | CORO2A | 10.6 |
| 206638_at | NM_000867 | 5-hydroxytryptamine (serotonin) receptor 2B | HTR2B | 10.6 |
| 202718_at | NM_000597 | insulin-like growth factor binding protein 2, 36 kDa | IGFBP2 | 10.6 |
| 219181_at | NM_006033 | lipase, endothelial | LIPG | 10.6 |
| 209610_s_at | BF340083 | solute carrier family 1 (glutamate/neutral amino acid transporter), member 4 | SLC1A4 | 10.6 |
| 214930_at | AW449813 | SLIT and NTRK-like family, member 5 | SLITRK5 | 10.6 |
| 210095_s_at | M31159 | insulin-like growth factor binding protein 3 | IGFBP3 | 9.8 |
| 209598_at | AB020690 | paraneoplastic antigen MA2 | PNMA2 | 9.8 |
| 209859_at | AF220036 | tripartite motif-containing 9 | TRIM9 | 9.8 |
| 213712_at | BF508639 | elongation of very long chain fatty acids (FEN1/Elo2, SUR4/Elo3, yeast)-like 2 | ELOVL2 | 9.2 |
| 219093_at | NM_017933 | hypothetical protein FLJ20701 /// hypothetical protein FLJ20701 | FLJ20701 | 8 |
| 202350_s_at | NM_002380 | matrilin 2 | MATN2 | 8 |
| 204048_s_at | AA551142 | phosphatase and actin regulator 2 | PHACTR2 | 8 |
| 206893_at | NM_002968 | sal-like 1 (*Drosophila*) | SALL1 | 8 |
| 209591_s_at | M60316 | bone morphogenetic protein 7 (osteogenic protein 1) | BMP7 | 7.5 |
| 209167_at | AI419030 | glycoprotein M6B | GPM6B | 7.5 |
| 211959_at | AW007532 | insulin-like growth factor binding protein 5 | IGFBP5 | 7.5 |
| 205825_at | NM_000439 | proprotein convertase subtilisin/kexin type 1 | PCSK1 | 7.5 |
| 215856_at | AK025833 | CD33 molecule-like 3 | CD33L3 | 7 |
| 205816_at | NM_002214 | integrin, beta 8 | ITGB8 | 7 |
| 212092_at | BE858180 | paternally expressed 10 | PEG10 | 7 |
| 207426_s_at | NM_003326 | tumor necrosis factor (ligand) superfamily, member 4 (tax-transcriptionally activated glycoprotein 1, 34 kDa) | TNFSF4 | 7 |
| 203940_s_at | NM_014909 | vasohibin 1 | VASH1 | 7 |
| 221019_s_at | NM_030781 | collectin sub-family member 12 /// collectin sub-family member 12 | COLEC12 | 6.5 |
| 206669_at | NM_013445 | glutamate decarboxylase 1 (brain, 67 kDa) /// LAG1 homolog, ceramide synthase 6 (*S. cerevisiae*) | GAD1 /// LASS6 | 6.5 |
| 202755_s_at | AI354864 | glypican 1 | GPC1 | 6.5 |
| 212314_at | AB018289 | KIAA0746 protein | KIAA0746 | 6.5 |
| 215446_s_at | L16895 | lysyl oxidase | LOX | 6.5 |
| 202729_s_at | NM_000627 | latent transforming growth factor beta binding protein 1 | LTBP1 | 6.5 |
| 207808_s_at | NM_000313 | protein S (alpha) | PROS1 | 6.5 |
| 204198_s_at | AA541630 | runt-related transcription factor 3 | RUNX3 | 6.5 |
| 212812_at | AI700633 | Serine incorporator 5 | SERINC5 | 6.5 |
| 202935_s_at | AI382146 | SRY (sex determining region Y)-box 9 (campomelic dysplasia, autosomal sex-reversal) | SOX9 | 6.5 |
| 201925_s_at | NM_000574 | CD55 molecule, decay accelerating factor for complement (Cromer blood group) | CD55 | 6.1 |
| 221760_at | BG287153 | Mannosidase, alpha, class 1A, member 1 | MAN1A1 | 6.1 |
| 211026_s_at | BC006230 | monoglyceride lipase /// monoglyceride lipase | MGLL | 6.1 |
| 213906_at | AW592266 | v-myb myeloblastosis viral oncogene homolog (avian)-like 1 | MYBL1 | 6.1 |
| 201110_s_at | NM_003246 | thrombospondin 1 | THBS1 | 6.1 |
| 215034_s_at | AI189753 | transmembrane 4 L six family member 1 | TM4SF1 | 6.1 |
| 44790_s_at | AI129310 | chromosome 13 open reading frame 18 | C13orf18 | 5.7 |
| 219619_at | NM_017594 | DIRAS family, GTP-binding RAS-like 2 | DIRAS2 | 5.7 |
| 202149_at | AL136139 | neural precursor cell expressed, developmentally down-regulated 9 | NEDD9 | 5.7 |
| 204671_s_at | BE677131 | ankyrin repeat domain 6 | ANKRD6 | 5.3 |
| 204456_s_at | AW611727 | growth arrest-specific 1 | GAS1 | 5.3 |
| 209631_s_at | U87460 | G protein-coupled receptor 37 (endothelin receptor type B-like) | GPR37 | 5.3 |
| 213954_at | AB020695 | KIAA0888 protein | KIAA0888 | 5.3 |
| 212298_at | BE620457 | neuropilin 1 | NRP1 | 5.3 |
| 205593_s_at | NM_002606 | phosphodiesterase 9A | PDE9A | 5.3 |
| 204908_s_at | NM_005178 | B-cell CLL/lymphoma 3 | BCL3 | 4.9 |
| 206932_at | NM_003956 | cholesterol 25-hydroxylase | CH25H | 4.9 |
| 218031_s_at | NM_018589 | checkpoint suppressor 1 | CHES1 | 4.9 |
| 204072_s_at | NM_023037 | furry homolog (*Drosophila*) | FRY | 4.9 |

TABLE 8-continued

Genes related to acquired resistance to compound 1.

| | | | | |
|---|---|---|---|---|
| 39549_at | AI743090 | neuronal PAS domain protein 2 | NPAS2 | 4.9 |
| 218736_s_at | NM_017734 | palmdelphin | PALMD | 4.9 |
| 203708_at | NM_002600 | phosphodiesterase 4B, cAMP-specific (phosphodiesterase E4 dunce homolog, Drosophila) | PDE4B | 4.9 |
| 214660_at | X68742 | Pelota homolog (Drosophila) | PELO | 4.9 |
| 221524_s_at | AF272036 | Ras-related GTP binding D | RRAGD | 4.9 |
| 208608_s_at | NM_021021 | syntrophin, beta 1 (dystrophin-associated protein A1, 59 kDa, basic component 1) | SNTB1 | 4.9 |
| 203476_at | NM_006670 | trophoblast glycoprotein | TPBG | 4.9 |
| 221156_x_at | NM_004748 | cell cycle progression 1 | CCPG1 | 4.6 |
| 213230_at | AI422335 | cerebellar degeneration-related protein 2-like | CDR2L | 4.6 |
| 205100_at | NM_005110 | glutamine-fructose-6-phosphate transaminase 2 | GFPT2 | 4.6 |
| 201141_at | NM_002510 | glycoprotein (transmembrane) nmb | GPNMB | 4.6 |
| 201656_at | NM_000210 | integrin, alpha 6 | ITGA6 | 4.6 |
| 221584_s_at | U11058 | potassium large conductance calcium-activated channel, subfamily M, alpha member 1 | KCNMA1 | 4.6 |
| 212190_at | AL541302 | serpin peptidase inhibitor, clade E (nexin, plasminogen activator inhibitor type 1), member 2 | SERPINE2 | 4.6 |
| 201147_s_at | BF347089 | TIMP metallopeptidase inhibitor 3 (Sorsby fundus dystrophy, pseudoinflammatory) | TIMP3 | 4.6 |
| 213943_at | X99268 | twist homolog 1 (acrocephalosyndactyly 3; Saethre-Chotzen syndrome) (Drosophila) | TWIST1 | 4.6 |
| 221973_at | AI983904 | CDNA clone IMAGE: 5217021, with apparent retained intron | — | 4.3 |
| 220658_s_at | NM_020183 | aryl hydrocarbon receptor nuclear translocator-like 2 | ARNTL2 | 4.3 |
| 212992_at | AI935123 | chromosome 14 open reading frame 78 | C14orf78 | 4.3 |
| 205379_at | NM_001236 | carbonyl reductase 3 | CBR3 | 4.3 |
| 203139_at | NM_004938 | death-associated protein kinase 1 | DAPK1 | 4.3 |
| 212641_at | AL023584 | human immunodeficiency virus type I enhancer binding protein 2 | HIVEP2 | 4.3 |
| 205559_s_at | NM_006200 | proprotein convertase subtilisin/kexin type 5 | PCSK5 | 4.3 |
| 212646_at | D42043 | raftlin, lipid raft linker 1 | RFTN1 | 4.3 |
| 205383_s_at | NM_015642 | zinc finger and BTB domain containing 20 | ZBTB20 | 4.3 |
| 205390_s_at | NM_000037 | ankyrin 1, erythrocytic /// ankyrin 1, erythrocytic | ANK1 | 4 |
| 202888_s_at | NM_001150 | alanyl (membrane) aminopeptidase (aminopeptidase N, aminopeptidase M, microsomal aminopeptidase, CD13, p150) | ANPEP | 4 |
| 209962_at | M34986 | erythropoietin receptor | EPOR | 4 |
| 221245_s_at | NM_030804 | frizzled homolog 5 (Drosophila) /// frizzled homolog 5 (Drosophila) | FZD5 | 4 |
| 201125_s_at | NM_002213 | integrin, beta 5 | ITGB5 | 4 |
| 211470_s_at | AF186255 | sulfotransferase family, cytosolic, 1C, member 1 | SULT1C1 | 4 |
| 210512_s_at | AF022375 | vascular endothelial growth factor A | VEGFA | 4 |
| 202222_s_at | NM_001927 | desmin | DES | 3.7 |
| 205366_s_at | NM_018952 | homeobox B6 | HOXB6 | 3.7 |
| 213424_at | AB020702 | KIAA0895 protein | KIAA0895 | 3.7 |
| 209888_s_at | M20643 | myosin, light chain 1, alkali; skeletal, fast | MYL1 | 3.7 |
| 218162_at | NM_020190 | olfactomedin-like 3 | OLFML3 | 3.7 |
| 202074_s_at | NM_021980 | optineurin | OPTN | 3.7 |
| 219304_s_at | NM_025208 | platelet derived growth factor D | PDGFD | 3.7 |
| 201739_at | NM_005627 | serum/glucocorticoid regulated kinase | SGK | 3.7 |
| 205856_at | NM_015865 | solute carrier family 14 (urea transporter), member 1 (Kidd blood group) | SLC14A1 | 3.7 |
| 202363_at | AF231124 | sparc/osteonectin, cwcv and kazal-like domains proteoglycan (testican) 1 | SPOCK1 | 3.7 |
| 204236_at | NM_002017 | Friend leukemia virus integration 1 | FLI1 | 3.5 |
| 202794_at | NM_002194 | inositol polyphosphate-1-phosphatase | INPP1 | 3.5 |
| 205876_at | NM_002310 | leukemia inhibitory factor receptor alpha | LIFR | 3.5 |

TABLE 8-continued

Genes related to acquired resistance to compound 1.

| | | | | |
|---|---|---|---|---|
| 202161_at | NM_002741 | protein kinase N1 | PKN1 | 3.5 |
| 218640_s_at | NM_024613 | pleckstrin homology domain containing, family F (with FYVE domain) member 2 | PLEKHF2 | 3.5 |
| 203680_at | NM_002736 | protein kinase, cAMP-dependent, regulatory, type II, beta | PRKAR2B | 3.5 |
| 204897_at | AA897516 | prostaglandin E receptor 4 (subtype EP4) | PTGER4 | 3.5 |
| 213325_at | AA129716 | poliovirus receptor-related 3 | PVRL3 | 3.5 |
| 203217_s_at | NM_003896 | ST3 beta-galactoside alpha-2,3-sialyltransferase 5 | ST3GAL5 | 3.5 |
| 215440_s_at | AL523320 | brain expressed X-linked-like 1 | BEXL1 | 3.2 |
| 209081_s_at | NM_030582 | collagen, type XVIII, alpha 1 | COL18A1 | 3.2 |
| 204036_at | AW269335 | endothelial differentiation, lysophosphatidic acid G-protein-coupled receptor, 2 | EDG2 | 3.2 |
| 200878_at | AF052094 | endothelial PAS domain protein 1 | EPAS1 | 3.2 |
| 213526_s_at | BF215644 | protein F25965 | F25965 | 3.2 |
| 201631_s_at | NM_003897 | immediate early response 3 | IER3 | 3.2 |
| 203474_at | NM_006633 | IQ motif containing GTPase activating protein 2 | IQGAP2 | 3.2 |
| 201015_s_at | NM_021991 | junction plakoglobin | JUP | 3.2 |
| 203939_at | NM_002526 | 5'-nucleotidase, ecto (CD73) | NT5E | 3.2 |
| 213075_at | AL050002 | olfactomedin-like 2A | OLFML2A | 3.2 |
| 205226_at | NM_006207 | platelet-derived growth factor receptor-like | PDGFRL | 3.2 |
| 200986_at | NM_000062 | serpin peptidase inhibitor, clade G (C1 inhibitor), member 1, (angioedema, hereditary) | SERPING1 | 3.2 |
| 203167_at | NM_003255 | TIMP metallopeptidase inhibitor 2 | TIMP2 | 3.2 |
| 215783_s_at | X14174 | alkaline phosphatase, liver/bone/kidney | ALPL | 3 |
| 213004_at | AI074333 | angiopoietin-like 2 | ANGPTL2 | 3 |
| 212614_at | BG285011 | AT rich interactive domain 5B (MRF1-like) | ARID5B | 3 |
| 221211_s_at | NM_020152 | chromosome 21 open reading frame 7 | C21orf7 | 3 |
| 209906_at | U62027 | complement component 3a receptor 1 | C3AR1 | 3 |
| 210026_s_at | AY028896 | caspase recruitment domain family, member 10 | CARD10 | 3 |
| 201360_at | NM_000099 | cystatin C (amyloid angiopathy and cerebral hemorrhage) | CST3 | 3 |
| 217889_s_at | NM_024843 | cytochrome b reductase 1 | CYBRD1 | 3 |
| 203791_at | NM_005509 | Dmx-like 1 | DMXL1 | 3 |
| 202500_at | NM_006736 | DnaJ (Hsp40) homolog, subfamily B, member 2 | DNAJB2 | 3 |
| 209343_at | BC002449 | EF-hand domain family, member D1 | EFHD1 | 3 |
| 206307_s_at | NM_004472 | forkhead box D1 | FOXD1 | 3 |
| 216033_s_at | S74774 | FYN oncogene related to SRC, FGR, YES | FYN | 3 |
| 204115_at | NM_004126 | guanine nucleotide binding protein (G protein), gamma 11 | GNG11 | 3 |
| 214104_at | AI703188 | G protein-coupled receptor 161 | GPR161 | 3 |
| 203108_at | NM_003979 | G protein-coupled receptor, family C, group 5, member A | GPRC5A | 3 |
| 218469_at | NM_013372 | gremlin 1, cysteine knot superfamily, homolog (Xenopus laevis) | GREM1 | 3 |
| 215933_s_at | Z21533 | homeobox, hematopoietically expressed | HHEX | 3 |
| 209185_s_at | AF073310 | insulin receptor substrate 2 | IRS2 | 3 |
| 221011_s_at | NM_030915 | limb bud and heart development homolog (mouse) /// limb bud and heart development homolog (mouse) | LBH | 3 |
| 201069_at | NM_004530 | matrix metallopeptidase 2 (gelatinase A, 72 kDa gelatinase, 72 kDa type IV collagenase) | MMP2 | 3 |
| 212096_s_at | AL096842 | mitochondrial tumor suppressor 1 | MTUS1 | 3 |
| 205880_at | NM_002742 | protein kinase D1 | PRKD1 | 3 |
| 217983_s_at | NM_003730 | ribonuclease T2 | RNASET2 | 3 |
| 202636_at | NM_005667 | ring finger protein 103 | RNF103 | 3 |
| 201286_at | Z48199 | syndecan 1 | SDC1 | 3 |
| 216997_x_at | AL358975 | transducin-like enhancer of split 4 (E(sp1) homolog, Drosophila) | TLE4 | 3 |
| 213338_at | BF062629 | transmembrane protein 158 | TMEM158 | 3 |
| 219296_at | NM_019028 | zinc finger, DHHC-type containing 13 | ZDHHC13 | 3 |
| 209765_at | Y13786 | ADAM metallopeptidase domain 19 (meltrin beta) | ADAM19 | 2.8 |

TABLE 8-continued

Genes related to acquired resistance to compound 1.

| | | | | |
|---|---|---|---|---|
| 212560_at | AV728268 | chromosome 11 open reading frame 32 | C11orf32 | 2.8 |
| 218546_at | NM_024709 | chromosome 1 open reading frame 115 | C1orf115 | 2.8 |
| 213492_at | X06268 | collagen, type II, alpha 1 (primary osteoarthritis, spondyloepiphyseal dysplasia, congenital) | COL2A1 | 2.8 |
| 218995_s_at | NM_001955 | endothelin 1 | EDN1 | 2.8 |
| 201809_s_at | NM_000118 | endoglin (Osler-Rendu-Weber syndrome 1) | ENG | 2.8 |
| 219683_at | NM_017412 | frizzled homolog 3 (*Drosophila*) | FZD3 | 2.8 |
| 205462_s_at | NM_002149 | hippocalcin-like 1 | HPCAL1 | 2.8 |
| 212830_at | W68084 | multiple EGF-like-domains 9 | MEGF9 | 2.8 |
| 205054_at | NM_004543 | nebulin | NEB | 2.8 |
| 209324_s_at | BF304996 | regulator of G-protein signalling 16 | RGS16 | 2.8 |
| 210365_at | D43967 | runt-related transcription factor 1 (acute myeloid leukemia 1; aml1 oncogene) | RUNX1 | 2.8 |
| 207413_s_at | NM_000335 | sodium channel, voltage-gated, type V, alpha (long QT syndrome 3) | SCN5A | 2.8 |
| 201920_at | NM_005415 | solute carrier family 20 (phosphate transporter), member 1 | SLC20A1 | 2.8 |
| 204981_at | NM_002555 | solute carrier family 22 (organic cation transporter), member 18 | SLC22A18 | 2.8 |
| 204466_s_at | BG260394 | synuclein, alpha (non A4 component of amyloid precursor) /// synuclein, alpha (non A4 component of amyloid precursor) | SNCA | 2.8 |
| 206258_at | NM_013305 | ST8 alpha-N-acetyl-neuraminide alpha-2,8-sialyltransferase 5 | ST8SIA5 | 2.8 |
| 218424_s_at | NM_018234 | STEAP family member 3 | STEAP3 | 2.8 |
| 214378_at | BF109662 | tissue factor pathway inhibitor (lipoprotein-associated coagulation inhibitor) | TFPI | 2.8 |
| 212665_at | AL556438 | TCDD-inducible poly(ADP-ribose) polymerase | TIPARP | 2.8 |
| 219736_at | NM_018700 | tripartite motif-containing 36 | TRIM36 | 2.8 |
| 217823_s_at | AL562528 | ubiquitin-conjugating enzyme E2, J1 (UBC6 homolog, yeast) | UBE2J1 | 2.8 |
| 213429_at | AW025579 | CDNA FLJ26539 fis, clone KDN09310 | — | 2.6 |
| 215617_at | AU145711 | CDNA FLJ11754 fis, clone HEMBA1005588 | — | 2.6 |
| 60474_at | AA469071 | chromosome 20 open reading frame 42 | C20orf42 | 2.6 |
| 202403_s_at | AA788711 | collagen, type I, alpha 2 | COL1A2 | 2.6 |
| 201200_at | NM_003851 | cellular repressor of E1A-stimulated genes 1 | CREG1 | 2.6 |
| 202481_at | NM_004753 | dehydrogenase/reductase (SDR family) member 3 | DHRS3 | 2.6 |
| 218532_s_at | NM_019000 | hypothetical protein FLJ20152 | FLJ20152 | 2.6 |
| 210220_at | L37882 | frizzled homolog 2 (*Drosophila*) | FZD2 | 2.6 |
| 204137_at | NM_003272 | G protein-coupled receptor 137B | GPR137B | 2.6 |
| 205240_at | NM_013296 | G-protein signalling modulator 2 (AGS3-like, *C. elegans*) | GPSM2 | 2.6 |
| 212942_s_at | AB033025 | KIAA1199 | KIAA1199 | 2.6 |
| 220940_at | NM_025190 | KIAA1641 | KIAA1641 | 2.6 |
| 213248_at | AL577024 | hypothetical protein LOC221362 /// similar to heterogeneous nuclear ribonucleoprotein A/B | LOC221362 /// LOC730101 | 2.6 |
| 40016_g_at | AB002301 | microtubule associated serine/threonine kinase family member 4 | MAST4 | 2.6 |
| 208047_s_at | NM_005966 | NGFI-A binding protein 1 (EGR1 binding protein 1) | NAB1 | 2.6 |
| 217765_at | NM_013392 | nuclear receptor binding protein 1 | NRBP1 | 2.6 |
| 209034_at | AF279899 | proline-rich nuclear receptor coactivator 1 | PNRC1 | 2.6 |
| 209282_at | AF309082 | protein kinase D2 | PRKD2 | 2.6 |
| 201481_s_at | NM_002862 | phosphorylase, glycogen; brain | PYGB | 2.6 |
| 219610_at | NM_022448 | Rho-guanine nucleotide exchange factor | RGNEF | 2.6 |
| 219457_s_at | NM_024832 | Ras and Rab interactor 3 | RIN3 | 2.6 |
| 206558_at | NM_005069 | single-minded homolog 2 (*Drosophila*) | SIM2 | 2.6 |
| 215223_s_at | W46388 | superoxide dismutase 2, mitochondrial | SOD2 | 2.6 |
| 204955_at | NM_006307 | sushi-repeat-containing protein, X-linked | SRPX | 2.6 |
| 210612_s_at | AF318616 | synaptojanin 2 | SYNJ2 | 2.6 |
| 209198_s_at | BC004291 | synaptotagmin XI | SYT11 | 2.6 |
| 205122_at | BF439316 | transmembrane protein with EGF-like and two follistatin-like domains 1 | TMEFF1 | 2.6 |

TABLE 8-continued

Genes related to acquired resistance to compound 1.

| | | | | |
|---|---|---|---|---|
| 201690_s_at | AA524023 | tumor protein D52 | TPD52 | 2.6 |
| 202893_at | NM_006377 | unc-13 homolog B (*C. elegans*) | UNC13B | 2.6 |
| 204254_s_at | NM_000376 | vitamin D (1,25-dihydroxyvitamin D3) receptor | VDR | 2.6 |
| 208622_s_at | AA670344 | villin 2 (ezrin) | VIL2 | 2.6 |
| 212993_at | AA114166 | MRNA; cDNA DKFZp667B1718 (from clone DKFZp667B1718) | — | 2.5 |
| 221881_s_at | AI638420 | adducin 3 (gamma) /// chloride intracellular channel 4 | ADD3 /// CLIC4 | 2.5 |
| 220092_s_at | NM_018153 | anthrax toxin receptor 1 | ANTXR1 | 2.5 |
| 40148_at | U62325 | amyloid beta (A4) precursor protein-binding, family B, member 2 (Fe65-like) | APBB2 | 2.5 |
| 203576_at | NM_001190 | branched chain aminotransferase 2, mitochondrial | BCAT2 | 2.5 |
| 215509_s_at | AL137654 | BUB1 budding uninhibited by benzimidazoles 1 homolog (yeast) | BUB1 | 2.5 |
| 220975_s_at | NM_030968 | C1q and tumor necrosis factor related protein 1 /// C1q and tumor necrosis factor related protein 1 | C1QTNF1 | 2.5 |
| 220918_at | NM_025143 | chromosome 21 open reading frame 96 | C21orf96 | 2.5 |
| 208908_s_at | AF327443 | calpastatin | CAST | 2.5 |
| 204154_at | NM_001801 | cysteine dioxygenase, type I | CDO1 | 2.5 |
| 212091_s_at | AI141603 | collagen, type VI, alpha 1 | COL6A1 | 2.5 |
| 202517_at | NM_001313 | collapsin response mediator protein 1 | CRMP1 | 2.5 |
| 201487_at | NM_001814 | cathepsin C | CTSC | 2.5 |
| 201279_s_at | BC003064 | disabled homolog 2, mitogen-responsive phosphoprotein (*Drosophila*) | DAB2 | 2.5 |
| 222101_s_at | BF222893 | dachsous 1 (*Drosophila*) | DCHS1 | 2.5 |
| 202929_s_at | NM_001355 | D-dopachrome tautomerase | DDT | 2.5 |
| 203881_s_at | NM_004010 | dystrophin (muscular dystrophy, Duchenne and Becker types) | DMD | 2.5 |
| 218225_at | NM_016581 | ECSIT homolog (*Drosophila*) | ECSIT | 2.5 |
| 217154_s_at | AL035250 | endothelin 3 | EDN3 | 2.5 |
| 205738_s_at | NM_004102 | fatty acid binding protein 3, muscle and heart (mammary-derived growth inhibitor) | FABP3 | 2.5 |
| 201910_at | BF213279 | FERM, RhoGEF (ARHGEF) and pleckstrin domain protein 1 (chondrocyte-derived) | FARP1 | 2.5 |
| 207357_s_at | NM_017540 | UDP-N-acetyl-alpha-D-galactosamine:polypeptide N-acetylgalactosaminyltransferase 10 (GalNAc-T10) | GALNT10 | 2.5 |
| 216733_s_at | X86401 | glycine amidinotransferase (L-arginine:glycine amidinotransferase) | GATM | 2.5 |
| 221577_x_at | AF003934 | growth differentiation factor 15 | GDF15 | 2.5 |
| 203390_s_at | NM_002254 | kinesin family member 3C | KIF3C | 2.5 |
| 203130_s_at | NM_004522 | kinesin family member 5C | KIF5C | 2.5 |
| 204682_at | NM_000428 | latent transforming growth factor beta binding protein 2 | LTBP2 | 2.5 |
| 219278_at | NM_004672 | mitogen-activated protein kinase kinase kinase 6 | MAP3K6 | 2.5 |
| 206571_s_at | NM_004834 | mitogen-activated protein kinase kinase kinase kinase 4 | MAP4K4 | 2.5 |
| 218890_x_at | NM_016622 | mitochondrial ribosomal protein L35 | MRPL35 | 2.5 |
| 212365_at | BF215996 | myosin IB | MYO1B | 2.5 |
| 215073_s_at | AL554245 | nuclear receptor subfamily 2, group F, member 2 | NR2F2 | 2.5 |
| 204622_x_at | NM_006186 | nuclear receptor subfamily 4, group A, member 2 | NR4A2 | 2.5 |
| 210448_s_at | U49396 | purinergic receptor P2X, ligand-gated ion channel, 5 | P2RX5 | 2.5 |
| 210139_s_at | L03203 | peripheral myelin protein 22 | PMP22 | 2.5 |
| 209158_s_at | BC004361 | pleckstrin homology, Sec7 and coiled-coil domains 2 (cytohesin-2) | PSCD2 | 2.5 |
| 49306_at | AI890191 | Ras association (RalGDS/AF-6) domain family 4 | RASSF4 | 2.5 |
| 204364_s_at | BE535746 | receptor accessory protein 1 | REEP1 | 2.5 |
| 209568_s_at | AF186779 | ral guanine nucleotide dissociation stimulator-like 1 | RGL1 | 2.5 |
| 209306_s_at | AI139569 | SWAP-70 protein | SWAP70 | 2.5 |
| 209890_at | AF065389 | tetraspanin 5 /// tetraspanin 5 | TSPAN5 | 2.5 |
| 213996_at | NM_013313 | yippee-like 1 (*Drosophila*) | YPEL1 | 2.5 |

TABLE 8-continued

Genes related to acquired resistance to compound 1.

| | | | | |
|---|---|---|---|---|
| 217783_s_at | NM_016061 | yippee-like 5 (*Drosophila*) | YPEL5 | 2.5 |
| 212985_at | BF115739 | Full-length cDNA clone CS0DC015YK09 of Neuroblastoma Cot 25-normalized of *Homo sapiens* (human) | — | 2.3 |
| 218795_at | NM_016361 | acid phosphatase 6, lysophosphatidic | ACP6 | 2.3 |
| 205401_at | NM_003659 | alkylglycerone phosphate synthase | AGPS | 2.3 |
| 202587_s_at | BC001116 | adenylate kinase 1 | AK1 | 2.3 |
| 202920_at | BF726212 | ankyrin 2, neuronal | ANK2 | 2.3 |
| 210202_s_at | U87558 | bridging integrator 1 | BIN1 | 2.3 |
| 200921_s_at | NM_001731 | B-cell translocation gene 1, anti-proliferative | BTG1 | 2.3 |
| 205308_at | NM_016010 | chromosome 8 open reading frame 70 | C8orf70 | 2.3 |
| 200622_x_at | AV685208 | calmodulin 3 (phosphorylase kinase, delta) | CALM3 | 2.3 |
| 201850_at | NM_001747 | capping protein (actin filament), gelsolin-like | CAPG | 2.3 |
| 220004_at | NM_018665 | DEAD (Asp-Glu-Ala-Asp) box polypeptide 43 | DDX43 | 2.3 |
| 215482_s_at | AJ011307 | eukaryotic translation initiation factor 2B, subunit 4 delta, 67 kDa | EIF2B4 | 2.3 |
| 219253_at | NM_024121 | family with sequence similarity 11, member B | FAM11B | 2.3 |
| 209576_at | AL049933 | guanine nucleotide binding protein (G protein), alpha inhibiting activity polypeptide 1 | GNAI1 | 2.3 |
| 221902_at | AL567940 | G protein-coupled receptor 153 | GPR153 | 2.3 |
| 218603_at | NM_016217 | headcase homolog (*Drosophila*) | HECA | 2.3 |
| 221004_s_at | NM_030926 | integral membrane protein 2C /// integral membrane protein 2C | ITM2C | 2.3 |
| 212492_s_at | AW237172 | jumonji domain containing 2B | JMJD2B | 2.3 |
| 219287_at | NM_014505 | potassium large conductance calcium-activated channel, subfamily M, beta member 4 | KCNMB4 | 2.3 |
| 204334_at | AA488672 | Kruppel-like factor 7 (ubiquitous) | KLF7 | 2.3 |
| 204584_at | AI653981 | L1 cell adhesion molecule | L1CAM | 2.3 |
| 203041_s_at | J04183 | lysosomal-associated membrane protein 2 | LAMP2 | 2.3 |
| 208949_s_at | BC001120 | lectin, galactoside-binding, soluble, 3 (galectin 3) | LGALS3 | 2.3 |
| 204091_at | NM_002601 | phosphodiesterase 6D, cGMP-specific, rod, delta | PDE6D | 2.3 |
| 211924_s_at | AY029180 | plasminogen activator, urokinase receptor /// plasminogen activator, urokinase receptor | PLAUR | 2.3 |
| 206574_s_at | NM_007079 | protein tyrosine phosphatase type IVA, member 3 | PTP4A3 | 2.3 |
| 207836_s_at | NM_006867 | RNA binding protein with multiple splicing | RBPMS | 2.3 |
| 202898_at | NM_014654 | syndecan 3 (N-syndecan) | SDC3 | 2.3 |
| 208127_s_at | NM_014011 | suppressor of cytokine signaling 5 | SOCS5 | 2.3 |
| 212780_at | AA700167 | son of sevenless homolog 1 (*Drosophila*) | SOS1 | 2.3 |
| 216941_s_at | AK026521 | TATA box binding protein (TBP)-associated factor, RNA polymerase I, B, 63 kDa | TAF1B | 2.3 |
| 203083_at | NM_003247 | thrombospondin 2 | THBS2 | 2.3 |
| 212989_at | AI377497 | transmembrane protein 23 | TMEM23 | 2.3 |
| 211300_s_at | K03199 | tumor protein p53 (Li-Fraumeni syndrome) | TP53 | 2.3 |
| 210609_s_at | BC000474 | tumor protein p53 inducible protein 3 | TP53I3 | 2.3 |
| 202368_s_at | AI986461 | translocation associated membrane protein 2 | TRAM2 | 2.3 |
| 202478_at | NM_021643 | tribbles homolog 2 (*Drosophila*) | TRIB2 | 2.3 |
| 214023_x_at | AL533838 | tubulin, beta 2B | TUBB2B | 2.3 |
| 208998_at | U94592 | uncoupling protein 2 (mitochondrial, proton carrier) | UCP2 | 2.3 |
| 218807_at | NM_006113 | vav 3 oncogene | VAV3 | 2.3 |
| 203855_at | NM_014969 | WD repeat domain 47 | WDR47 | 2.3 |
| 221646_s_at | AF267859 | zinc finger, DHHC-type containing 11 | ZDHHC11 | 2.3 |
| 215447_at | AL080215 | — | — | 2.1 |
| 205434_s_at | AW451954 | AP2 associated kinase 1 /// hypothetical protein LOC647217 | AAK1 /// LOC647217 | 2.1 |
| 210517_s_at | AB003476 | A kinase (PRKA) anchor protein (gravin) 12 | AKAP12 | 2.1 |
| 214073_at | BG475299 | Aldehyde dehydrogenase 1 family, member A3 | ALDH1A3 | 2.1 |

TABLE 8-continued

Genes related to acquired resistance to compound 1.

| | | | | |
|---|---|---|---|---|
| 219637_at | NM_025139 | armadillo repeat containing 9 | ARMC9 | 2.1 |
| 200070_at | BC001393 | chromosome 2 open reading frame 24 /// chromosome 2 open reading frame 24 | C2orf24 | 2.1 |
| 209829_at | AB002384 | chromosome 6 open reading frame 32 | C6orf32 | 2.1 |
| 204392_at | NM_003656 | calcium/calmodulin-dependent protein kinase I | CAMK1 | 2.1 |
| 209956_s_at | U23460 | calcium/calmodulin-dependent protein kinase (CaM kinase) II beta | CAMK2B | 2.1 |
| 218309_at | NM_018584 | calcium/calmodulin-dependent protein kinase II inhibitor 1 | CAMK2N1 | 2.1 |
| 212624_s_at | BF339445 | chimerin (chimaerin) 1 | CHN1 | 2.1 |
| 206414_s_at | NM_003887 | development and differentiation enhancing factor 2 | DDEF2 | 2.1 |
| 212503_s_at | N22859 | DIP2 disco-interacting protein 2 homolog C (Drosophila) | DIP2C | 2.1 |
| 202196_s_at | NM_013253 | dickkopf homolog 3 (Xenopus laevis) | DKK3 | 2.1 |
| 209365_s_at | U65932 | extracellular matrix protein 1 | ECM1 | 2.1 |
| 220161_s_at | NM_019114 | erythrocyte membrane protein band 4.1 like 4B | EPB41L4B | 2.1 |
| 221766_s_at | AW246673 | family with sequence similarity 46, member A | FAM46A | 2.1 |
| 202949_s_at | NM_001450 | four and a half LIM domains 2 | FHL2 | 2.1 |
| 218610_s_at | NM_018340 | hypothetical protein FLJ11151 | FLJ11151 | 2.1 |
| 218880_at | N36408 | FOS-like antigen 2 | FOSL2 | 2.1 |
| 219170_at | NM_024333 | fibronectin type III and SPRY domain containing 1 /// similar to fibronectin type III and SPRY domain containing 1 | FSD1 /// LOC731565 | 2.1 |
| 218204_s_at | NM_024513 | FYVE and coiled-coil domain containing 1 | FYCO1 | 2.1 |
| 218070_s_at | NM_013335 | GDP-mannose pyrophosphorylase A | GMPPA | 2.1 |
| 214438_at | M60721 | H2.0-like homeobox 1 (Drosophila) | HLX1 | 2.1 |
| 213150_at | BF792917 | homeobox A10 | HOXA10 | 2.1 |
| 214434_at | AB007877 | heat shock 70 kDa protein 12A | HSPA12A | 2.1 |
| 201565_s_at | NM_002166 | inhibitor of DNA binding 2, dominant negative helix-loop-helix protein | ID2 | 2.1 |
| 201888_s_at | U81379 | interleukin 13 receptor, alpha 1 | IL13RA1 | 2.1 |
| 204465_s_at | NM_004692 | internexin neuronal intermediate filament protein, alpha | INA | 2.1 |
| 201189_s_at | NM_002224 | inositol 1,4,5-triphosphate receptor, type 3 | ITPR3 | 2.1 |
| 212689_s_at | AA524505 | jumonji domain containing 1A | JMJD1A | 2.1 |
| 201776_s_at | AK001487 | KIAA0494 | KIAA0494 | 2.1 |
| 213157_s_at | BF115148 | KIAA0523 protein | KIAA0523 | 2.1 |
| 201596_x_at | NM_000224 | keratin 18 | KRT18 | 2.1 |
| 204527_at | NM_000259 | myosin VA (heavy chain 12, myoxin) | MYO5A | 2.1 |
| 218231_at | NM_017567 | N-acetylglucosamine kinase /// N-acetylglucosamine kinase | NAGK | 2.1 |
| 213568_at | AI811298 | odd-skipped related 2 (Drosophila) | OSR2 | 2.1 |
| 203803_at | N45309 | prenylcysteine oxidase 1 | PCYOX1 | 2.1 |
| 219126_at | NM_018288 | PHD finger protein 10 | PHF10 | 2.1 |
| 209625_at | BC004100 | phosphatidylinositol glycan anchor biosynthesis, class H | PIGH | 2.1 |
| 202732_at | NM_007066 | protein kinase (cAMP-dependent, catalytic) inhibitor gamma | PKIG | 2.1 |
| 203896_s_at | NM_000933 | phospholipase C, beta 4 | PLCB4 | 2.1 |
| 205934_at | NM_006226 | phospholipase C-like 1 | PLCL1 | 2.1 |
| 203718_at | NM_006702 | patatin-like phospholipase domain containing 6 | PNPLA6 | 2.1 |
| 205933_at | NM_015559 | SET binding protein 1 | SETBP1 | 2.1 |
| 218720_x_at | NM_012410 | seizure related 6 homolog (mouse)-like 2 | SEZ6L2 | 2.1 |
| 204362_at | NM_003930 | src kinase associated phosphoprotein 2 | SKAP2 | 2.1 |
| 202855_s_at | AL513917 | solute carrier family 16, member 3 (monocarboxylic acid transporter 4) | SLC16A3 | 2.1 |
| 221041_s_at | NM_012434 | solute carrier family 17 (anion/sugar transporter), member 5 | SLC17A5 | 2.1 |
| 220123_at | NM_025181 | solute carrier family 35, member F5 | SLC35F5 | 2.1 |
| 209748_at | AB029006 | spastin | SPAST | 2.1 |
| 202786_at | NM_013233 | serine threonine kinase 39 (STE20/SPS1 homolog, yeast) | STK39 | 2.1 |
| 212625_at | NM_003765 | syntaxin 10 | STX10 | 2.1 |
| 203310_at | NM_007269 | syntaxin binding protein 3 | STXBP3 | 2.1 |
| 201079_at | NM_004710 | synaptogyrin 2 | SYNGR2 | 2.1 |
| 215273_s_at | AK024982 | transcriptional adaptor 3 (NGG1 homolog, yeast)-like | TADA3L | 2.1 |
| 205993_s_at | NM_005994 | T-box 2 | TBX2 | 2.1 |
| 218996_at | NM_013342 | TCF3 (E2A) fusion partner (in childhood Leukemia) | TFPT | 2.1 |

TABLE 8-continued

Genes related to acquired resistance to compound 1.

| | | | | |
|---|---|---|---|---|
| 209118_s_at | AF141347 | tubulin, alpha 3 | TUBA3 | 2.1 |
| 204141_at | NM_001069 | tubulin, beta 2A | TUBB2A | 2.1 |
| 219201_s_at | NM_020648 | twisted gastrulation homolog 1 (*Drosophila*) | TWSG1 | 2.1 |
| 214755_at | AK022632 | UDP-N-acteylglucosamine pyrophosphorylase 1-like 1 | UAP1L1 | 2.1 |
| 210024_s_at | AB017644 | ubiquitin-conjugating enzyme E2E 3 (UBC4/5 homolog, yeast) | UBE2E3 | 2.1 |
| 209551_at | BC004875 | Yip1 domain family, member 4 | YIPF4 | 2.1 |
| 201662_s_at | D89053 | acyl-CoA synthetase long-chain family member 3 | ACSL3 | 2 |
| 201753_s_at | NM_019903 | adducin 3 (gamma) | ADD3 | 2 |
| 201952_at | AA156721 | activated leukocyte cell adhesion molecule | ALCAM | 2 |
| 212747_at | AI990523 | ankyrin repeat and sterile alpha motif domain containing 1A | ANKS1A | 2 |
| 207076_s_at | NM_000050 | argininosuccinate synthetase 1 | ASS1 | 2 |
| 213587_s_at | AI884867 | ATPase, H+ transporting V0 subunit e2 | ATP6V0E2 | 2 |
| 202685_s_at | AI467916 | AXL receptor tyrosine kinase | AXL | 2 |
| 40093_at | X83425 | basal cell adhesion molecule (Lutheran blood group) | BCAM | 2 |
| 219506_at | NM_024579 | chromosome 1 open reading frame 54 | C1orf54 | 2 |
| 205575_at | NM_006688 | complement component 1, q subcomponent-like 1 | C1QL1 | 2 |
| 204489_s_at | NM_000610 | CD44 molecule (Indian blood group) | CD44 | 2 |
| 202910_s_at | NM_001784 | CD97 molecule | CD97 | 2 |
| 204039_at | NM_004364 | CCAAT/enhancer binding protein (C/EBP), alpha | CEBPA | 2 |
| 203973_s_at | NM_005195 | CCAAT/enhancer binding protein (C/EBP), delta | CEBPD | 2 |
| 209357_at | AF109161 | Cbp/p300-interacting transactivator, with Glu/Asp-rich carboxy-terminal domain, 2 | CITED2 | 2 |
| 211141_s_at | AF180474 | CCR4-NOT transcription complex, subunit 3 | CNOT3 | 2 |
| 205229_s_at | AA669336 | coagulation factor C homolog, cochlin (*Limulus polyphemus*) | COCH | 2 |
| 37892_at | J04177 | collagen, type XI, alpha 1 | COL11A1 | 2 |
| 206100_at | NM_001874 | carboxypeptidase M | CPM | 2 |
| 221988_at | AA463853 | Cofactor required for Sp1 transcriptional activation, subunit 7, 70 kDa | CRSP7 | 2 |
| 215785_s_at | AL161999 | cytoplasmic FMR1 interacting protein 2 | CYFIP2 | 2 |
| 215537_x_at | AJ012008 | dimethylarginine dimethylaminohydrolase 2 | DDAH2 | 2 |
| 214027_x_at | AA889653 | desmin /// family with sequence similarity 48, member A | DES /// FAM48A | 2 |
| 213420_at | AA100250 | DEAH (Asp-Glu-Ala-Asp/His) box polypeptide 57 | DHX57 | 2 |
| 200664_s_at | BG537255 | DnaJ (Hsp40) homolog, subfamily B, member 1 | DNAJB1 | 2 |
| 205248_at | NM_005128 | dopey family member 2 | DOPEY2 | 2 |
| 204034_at | NM_014297 | ethylmalonic encephalopathy 1 | ETHE1 | 2 |
| 219377_at | NM_022751 | family with sequence similarity 59, member A | FAM59A | 2 |
| 213249_at | AU145127 | F-box and leucine-rich repeat protein 7 | FBXL7 | 2 |
| 219208_at | NM_025133 | F-box protein 11 | FBXO11 | 2 |
| 208378_x_at | NM_004464 | fibroblast growth factor 5 | FGF5 | 2 |
| 208476_s_at | NM_018027 | FERM domain containing 4A | FRMD4A | 2 |
| 218084_x_at | NM_014164 | FXYD domain containing ion transport regulator 5 | FXYD5 | 2 |
| 212891_s_at | BF972185 | growth arrest and DNA-damage-inducible, gamma interacting protein 1 | GADD45GIP1 | 2 |
| 214510_at | NM_005293 | G protein-coupled receptor 20 | GPR20 | 2 |
| 212822_at | AA121502 | HEG homolog 1 (zebrafish) | HEG1 | 2 |
| 205453_at | NM_002145 | homeobox B2 | HOXB2 | 2 |
| 204779_s_at | NM_004502 | homeobox B7 | HOXB7 | 2 |
| 201841_s_at | NM_001540 | heat shock 27 kDa protein 1 /// Meis1, myeloid ecotropic viral integration site 1 homolog 3 (mouse) | HSPB1 /// MEIS3 | 2 |
| 211152_s_at | AF184911 | HtrA serine peptidase 2 | HTRA2 | 2 |
| 201566_x_at | D13891 | inhibitor of DNA binding 2, dominant negative helix-loop-helix protein /// inhibitor of DNA binding 2B, dominant negative helix-loop-helix protein | ID2 /// ID2B | 2 |
| 201315_x_at | NM_006435 | interferon induced transmembrane protein 2 (1-8D) | IFITM2 | 2 |

TABLE 8-continued

Genes related to acquired resistance to compound 1.

| | | | | |
|---|---|---|---|---|
| 203336_s_at | AL548363 | integrin beta 1 binding protein 1 | ITGB1BP1 | 2 |
| 202962_at | NM_015254 | kinesin family member 13B | KIF13B | 2 |
| 209234_at | BF939474 | kinesin family member 1B | KIF1B | 2 |
| 220253_s_at | NM_013437 | low density lipoprotein-related protein 12 | LRP12 | 2 |
| 201862_s_at | NM_004735 | leucine rich repeat (in FLII) interacting protein 1 | LRRFIP1 | 2 |
| 212246_at | BE880828 | multiple coagulation factor deficiency 2 | MCFD2 | 2 |
| 210087_s_at | AF095727 | myelin protein zero-like 1 | MPZL1 | 2 |
| 202180_s_at | NM_017458 | major vault protein | MVP | 2 |
| 220319_s_at | NM_013262 | myosin regulatory light chain interacting protein | MYLIP | 2 |
| 212843_at | AA126505 | neural cell adhesion molecule 1 | NCAM1 | 2 |
| 212949_at | D38553 | non-SMC condensin I complex, subunit H | NCAPH | 2 |
| 203315_at | BC000103 | NCK adaptor protein 2 /// similar to NCK adaptor protein 2 | NCK2 /// LOC729030 | 2 |
| 200701_at | NM_006432 | Niemann-Pick disease, type C2 | NPC2 | 2 |
| 219789_at | AI628360 | natriuretic peptide receptor C/guanylate cyclase C (atrionatriuretic peptide receptor C) | NPR3 | 2 |
| 209262_s_at | BC002669 | nuclear receptor subfamily 2, group F, member 6 | NR2F6 | 2 |
| 214130_s_at | AI821791 | phosphodiesterase 4D interacting protein (myomegalin) /// similar to phosphodiesterase 4D interacting protein isoform 2 | PDE4DIP /// LOC727942 | 2 |
| 210041_s_at | BC001258 | phosphoglucomutase 3 | PGM3 | 2 |
| 209803_s_at | AF001294 | pleckstrin homology-like domain, family A, member 2 | PHLDA2 | 2 |
| 201860_s_at | NM_000930 | plasminogen activator, tissue | PLAT | 2 |
| 211668_s_at | K03226 | plasminogen activator, urokinase /// plasminogen activator, urokinase | PLAU | 2 |
| 203467_at | NM_002676 | phosphomannomutase 1 | PMM1 | 2 |
| 204284_at | N26005 | protein phosphatase 1, regulatory (inhibitor) subunit 3C | PPP1R3C | 2 |
| 213093_at | AI471375 | protein kinase C, alpha | PRKCA | 2 |
| 219729_at | NM_016307 | paired related homeobox 2 | PRRX2 | 2 |
| 202458_at | NM_007173 | protease, serine, 23 | PRSS23 | 2 |
| 205128_x_at | NM_000962 | prostaglandin-endoperoxide synthase 1 (prostaglandin G/H synthase and cyclooxygenase) | PTGS1 | 2 |
| 205503_at | NM_005401 | protein tyrosine phosphatase, non-receptor type 14 | PTPN14 | 2 |
| 34478_at | X79780 | RAB11B, member RAS oncogene family | RAB11B | 2 |
| 210138_at | AF074979 | regulator of G-protein signalling 20 | RGS20 | 2 |
| 221770_at | BE964473 | ribulose-5-phosphate-3-epimerase | RPE | 2 |
| 202497_x_at | AI631159 | solute carrier family 2 (facilitated glucose transporter), member 3 | SLC2A3 | 2 |
| 209712_at | AI769637 | solute carrier family 35 (UDP-glucuronic acid/UDP-N-acetylgalactosamine dual transporter), member D1 | SLC35D1 | 2 |
| 210001_s_at | AB005043 | suppressor of cytokine signaling 1 | SOCS1 | 2 |
| 203509_at | NM_003105 | sortilin-related receptor, L (DLR class) A repeats-containing | SORL1 | 2 |
| 210218_s_at | U36501 | SP100 nuclear antigen | SP100 | 2 |
| 202506_at | NM_006751 | sperm specific antigen 2 | SSFA2 | 2 |
| 208992_s_at | BC000627 | signal transducer and activator of transcription 3 (acute-phase response factor) | STAT3 | 2 |
| 220761_s_at | NM_016281 | TAO kinase 3 | TAOK3 | 2 |
| 219169_s_at | NM_016020 | transcription factor B1, mitochondrial | TFB1M | 2 |
| 202011_at | NM_003257 | tight junction protein 1 (zona occludens 1) | TJP1 | 2 |
| 217730_at | NM_022152 | transmembrane BAX inhibitor motif containing 1 | TMBIM1 | 2 |
| 208296_x_at | NM_014350 | tumor necrosis factor, alpha-induced protein 8 | TNFAIP8 | 2 |
| 202704_at | AA675892 | transducer of ERBB2, 1 | TOB1 | 2 |
| 212481_s_at | AI214061 | tropomyosin 4 | TPM4 | 2 |
| 202124_s_at | AV705253 | trafficking protein, kinesin binding 2 | TRAK2 | 2 |
| 215047_at | AL080170 | tripartite motif-containing 58 | TRIM58 | 2 |
| 211701_s_at | AF349720 | trophinin /// trophinin | TRO | 2 |
| 213174_at | BE675549 | tetratricopeptide repeat domain 9 | TTC9 | 2 |
| 209372_x_at | BF971587 | tubulin, beta 2A /// tubulin, beta 2B | TUBB2A /// TUBB2B | 2 |

TABLE 8-continued

Genes related to acquired resistance to compound 1.

| | | | | |
|---|---|---|---|---|
| 202663_at | AI005043 | WAS/WASL interacting protein family, member 1 | WIPF1 | 2 |
| 218110_at | NM_020196 | XPA binding protein 2 | XAB2 | 2 |
| 220748_s_at | NM_016202 | zinc finger protein 580 | ZNF580 | 2 |

Genes higher expressed in the sensitive RD-1 cells:

| | | | | |
|---|---|---|---|---|
| 204239_s_at | NM_005386 | neuronatin | NNAT | −29.9 |
| 202942_at | NM_001985 | electron-transfer-flavoprotein, beta polypeptide | ETFB | −26 |
| 215731_s_at | X98258 | M-phase phosphoprotein 9 | MPHOSPH9 | −26 |
| 219271_at | NM_024572 | UDP-N-acetyl-alpha-D-galactosamine:polypeptide N-acetylgalactosaminyltransferase 14 (GalNAc-T14) | GALNT14 | −22.6 |
| 219274_at | NM_012338 | tetraspanin 12 | TSPAN12 | −21.1 |
| 209656_s_at | AL136550 | transmembrane protein 47 | TMEM47 | −19.7 |
| 204439_at | NM_006820 | interferon-induced protein 44-like | IFI44L | −18.4 |
| 203510_at | BG170541 | met proto-oncogene (hepatocyte growth factor receptor) | MET | −18.4 |
| 206228_at | AW769732 | paired box gene 2 | PAX2 | −18.4 |
| 207173_x_at | D21254 | cadherin 11, type 2, OB-cadherin (osteoblast) | CDH11 | −17.1 |
| 206440_at | NM_004664 | lin-7 homolog A (*C. elegans*) | LIN7A | −17.1 |
| 205352_at | NM_005025 | serpin peptidase inhibitor, clade I (neuroserpin), member 1 | SERPINI1 | −17.1 |
| 218541_s_at | NM_020130 | chromosome 8 open reading frame 4 | C8orf4 | −14.9 |
| 206432_at | NM_005328 | hyaluronan synthase 2 | HAS2 | −13.9 |
| 202508_s_at | NM_003081 | synaptosomal-associated protein, 25 kDa | SNAP25 | −13 |
| 216005_at | BF434846 | Tenascin C (hexabrachion) | TNC | −13 |
| 220586_at | NM_025134 | chromodomain helicase DNA binding protein 9 | CHD9 | −12.1 |
| 219908_at | NM_014421 | dickkopf homolog 2 (*Xenopus laevis*) | DKK2 | −12.1 |
| 47560_at | AI525402 | latrophilin 1 | LPHN1 | −10.6 |
| 206459_s_at | AB045117 | wingless-type MMTV integration site family, member 2B | WNT2B | −10.6 |
| 206385_s_at | NM_020987 | ankyrin 3, node of Ranvier (ankyrin G) | ANK3 | −9.8 |
| 207039_at | NM_000077 | cyclin-dependent kinase inhibitor 2A (melanoma, p16, inhibits CDK4) | CDKN2A | −9.8 |
| 205003_at | NM_014705 | dedicator of cytokinesis 4 | DOCK4 | −9.8 |
| 214829_at | AK023446 | aminoadipate-semialdehyde synthase | AASS | −9.2 |
| 218775_s_at | NM_024949 | WW and C2 domain containing 2 | WWC2 | −9.2 |
| 209732_at | BC005254 | C-type lectin domain family 2, member B /// CMT1A duplicated region transcript 15 pseudogene | CLEC2B /// CDRT15P | −8.6 |
| 202310_s_at | K01228 | collagen, type I, alpha 1 | COL1A1 | −8.6 |
| 36830_at | U80034 | mitochondrial intermediate peptidase | MIPEP | −8.6 |
| 215008_at | AA582404 | tolloid-like 2 | TLL2 | −8.6 |
| 200953_s_at | NM_001759 | cyclin D2 | CCND2 | −8 |
| 211155_s_at | D32047 | thrombopoietin (myeloproliferative leukemia virus oncogene ligand, megakaryocyte growth and development factor) | THPO | −8 |
| 204470_at | NM_001511 | chemokine (C—X—C motif) ligand 1 (melanoma growth stimulating activity, alpha) | CXCL1 | −7.5 |
| 215231_at | AU144309 | Protein kinase, AMP-activated, gamma 2 non-catalytic subunit | PRKAG2 | −7 |
| 214331_at | AI796813 | Ts translation elongation factor, mitochondrial | TSFM | −7 |
| 206001_at | NM_000905 | neuropeptide Y | NPY | −6.5 |
| 213718_at | BE222257 | RNA binding motif protein 4 | RBM4 | −6.5 |
| 205498_at | NM_000163 | growth hormone receptor | GHR | −6.1 |
| 218717_s_at | NM_018192 | leprecan-like 1 | LEPREL1 | −6.1 |
| 205113_at | NM_005382 | neurofilament, medium polypeptide 150 kDa | NEFM | −6.1 |
| 204081_at | NM_006176 | neurogranin (protein kinase C substrate, RC3) | NRGN | −6.1 |
| 207558_s_at | NM_000325 | paired-like homeodomain transcription factor 2 | PITX2 | −6.1 |
| 202659_at | NM_002801 | proteasome (prosome, macropain) subunit, beta type, 10 | PSMB10 | −6.1 |
| 205433_at | NM_000055 | butyrylcholinesterase | BCHE | −5.7 |
| 214045_at | BF056778 | lipoic acid synthetase | LIAS | −5.7 |
| 209267_s_at | AB040120 | solute carrier family 39 (zinc transporter), member 8 | SLC39A8 | −5.7 |
| 207850_at | NM_002090 | chemokine (C—X—C motif) ligand 3 | CXCL3 | −5.3 |
| 205132_at | NM_005159 | actin, alpha, cardiac muscle 1 | ACTC1 | −4.9 |

TABLE 8-continued

Genes related to acquired resistance to compound 1.

| | | | | |
|---|---|---|---|---|
| 200897_s_at | NM_016081 | palladin, cytoskeletal associated protein | PALLD | −4.9 |
| 207119_at | NM_006258 | protein kinase, cGMP-dependent, type I | PRKG1 | −4.9 |
| 219498_s_at | NM_018014 | B-cell CLL/lymphoma 11A (zinc finger protein) | BCL11A | −4.6 |
| 1405_i_at | M21121 | chemokine (C-C motif) ligand 5 | CCL5 | −4.6 |
| 217028_at | AJ224869 | chemokine (C—X—C motif) receptor 4 | CXCR4 | −4.6 |
| 219118_at | NM_016594 | FK506 binding protein 11, 19 kDa | FKBP11 | −4.6 |
| 213797_at | AI337069 | radical S-adenosyl methionine domain containing 2 | RSAD2 | −4.6 |
| 204268_at | NM_005978 | S100 calcium binding protein A2 | S100A2 | −4.6 |
| 213500_at | AI307760 | Coatomer protein complex, subunit beta 2 (beta prime) | COPB2 | −4.3 |
| 218676_s_at | NM_021213 | phosphatidylcholine transfer protein | PCTP | −4.3 |
| 211570_s_at | BC004196 | receptor-associated protein of the synapse, 43 kD | RAPSN | −4.3 |
| 213591_at | AU149534 | Aldehyde dehydrogenase 7 family, member A1 | ALDH7A1 | −4 |
| 209774_x_at | M57731 | chemokine (C—X—C motif) ligand 2 | CXCL2 | −4 |
| 221667_s_at | AF133207 | heat shock 22 kDa protein 8 | HSPB8 | −4 |
| 205992_s_at | NM_000585 | interleukin 15 | IL15 | −4 |
| 220145_at | NM_024826 | microtubule-associated protein 9 | MAP9 | −4 |
| 220346_at | NM_025001 | methylenetetrahydrofolate dehydrogenase (NADP+ dependent) 2-like | MTHFD2L | −4 |
| 210556_at | U85430 | nuclear factor of activated T-cells, cytoplasmic, calcineurin-dependent 3 | NFATC3 | −4 |
| 204589_at | NM_014840 | NUAK family, SNF1-like kinase, 1 | NUAK1 | −4 |
| 213817_at | AL049435 | CDNA FLJ13601 fis, clone PLACE1010069 | — | −3.7 |
| 219973_at | NM_024590 | arylsulfatase family, member J | ARSJ | −3.7 |
| 213880_at | AL524520 | leucine-rich repeat-containing G protein-coupled receptor 5 | LGR5 | −3.7 |
| 204597_x_at | NM_003155 | stanniocalcin 1 | STC1 | −3.7 |
| 208847_s_at | M29872 | alcohol dehydrogenase 5 (class III), chi polypeptide | ADH5 | −3.5 |
| 212384_at | AI282485 | HLA-B associated transcript 1 | BAT1 | −3.5 |
| 211237_s_at | AF202063 | fibroblast growth factor receptor 4 | FGFR4 | −3.5 |
| 214604_at | NM_021192 | homeobox D11 | HOXD11 | −3.5 |
| 209099_x_at | U73936 | jagged 1 (Alagille syndrome) | JAG1 | −3.5 |
| 219582_at | NM_024576 | opioid growth factor receptor-like 1 | OGFRL1 | −3.5 |
| 207943_x_at | NM_006718 | pleiomorphic adenoma gene-like 1 | PLAGL1 | −3.5 |
| 202457_s_at | AA911231 | protein phosphatase 3 (formerly 2B), catalytic subunit, alpha isoform (calcineurin A alpha) | PPP3CA | −3.5 |
| 212749_s_at | AI096477 | ring finger and CHY zinc finger domain containing 1 | RCHY1 | −3.5 |
| 215591_at | AK025127 | SATB family member 2 | SATB2 | −3.5 |
| 205609_at | NM_001146 | angiopoietin 1 | ANGPT1 | −3.2 |
| 202370_s_at | NM_001755 | core-binding factor, beta subunit | CBFB | −3.2 |
| 221521_s_at | BC003186 | GINS complex subunit 2 (Psf2 homolog) | GINS2 | −3.2 |
| 201036_s_at | NM_005327 | hydroxyacyl-Coenzyme A dehydrogenase | HADH | −3.2 |
| 213032_at | AI186739 | nuclear factor I/B | NFIB | −3.2 |
| 206653_at | BF062139 | polymerase (RNA) III (DNA directed) polypeptide G (32 kD) | POLR3G | −3.2 |
| 213852_at | BG289199 | RNA binding motif protein 8A | RBM8A | −3.2 |
| 210432_s_at | AF225986 | sodium channel, voltage-gated, type III, alpha | SCN3A | −3.2 |
| 221495_s_at | AF322111 | transcription factor 25 (basic helix-loop-helix) /// matrix-remodelling associated 7 | TCF25 /// MXRA7 | −3.2 |
| 220104_at | NM_020119 | zinc finger CCCH-type, antiviral 1 | ZC3HAV1 | −3.2 |
| 201067_at | BF215487 | — | — | −3 |
| 212126_at | BG391282 | CDNA clone IMAGE: 4842353 | — | −3 |
| 211148_s_at | AF187858 | angiopoietin 2 | ANGPT2 | −3 |
| 203264_s_at | NM_015185 | Cdc42 guanine nucleotide exchange factor (GEF) 9 | ARHGEF9 | −3 |
| 219023_at | NM_018569 | chromosome 4 open reading frame 16 | C4orf16 | −3 |
| 206070_s_at | AF213459 | EPH receptor A3 | EPHA3 | −3 |
| 214240_at | AL556409 | galanin | GAL | −3 |
| 220085_at | NM_018063 | helicase, lymphoid-specific | HELLS | −3 |
| 213359_at | W74620 | Heterogeneous nuclear ribonucleoprotein D (AU-rich element RNA binding protein 1, 37 kDa) | HNRPD | −3 |

TABLE 8-continued

Genes related to acquired resistance to compound 1.

| | | | | |
|---|---|---|---|---|
| 210112_at | U96721 | Hermansky-Pudlak syndrome 1 | HPS1 | −3 |
| 219213_at | NM_021219 | junctional adhesion molecule 2 | JAM2 | −3 |
| 222018_at | AI992187 | nascent-polypeptide-associated complex alpha polypeptide /// nascent-polypeptide-associated complex alpha polypeptide pseudogene 1 /// similar to nascent polypeptide-associated complex alpha polypeptide | NACA /// NACAP1 /// LOC389240 | −3 |
| 219368_at | NM_021963 | nucleosome assembly protein 1-like 2 | NAP1L2 | −3 |
| 220741_s_at | NM_006903 | pyrophosphatase (inorganic) 2 /// tripartite motif-containing 69 | PPA2 /// TRIM69 | −3 |
| 203789_s_at | NM_006379 | sema domain, immunoglobulin domain (Ig), short basic domain, secreted, (semaphorin) 3C | SEMA3C | −3 |
| 215389_s_at | X79857 | troponin T type 2 (cardiac) | TNNT2 | −3 |
| 203869_at | AK024318 | ubiquitin specific peptidase 46 | USP46 | −3 |
| 213790_at | W46291 | CDNA FLJ31066 fis, clone HSYRA2001153 | — | −2.8 |
| 219474_at | NM_024616 | chromosome 3 open reading frame 52 | C3orf52 | −2.8 |
| 209446_s_at | BC001743 | chromosome 7 open reading frame 44 | C7orf44 | −2.8 |
| 219555_s_at | NM_018455 | centromere protein N | CENPN | −2.8 |
| 208968_s_at | BC002568 | cytokine induced apoptosis inhibitor 1 | CIAPIN1 | −2.8 |
| 201733_at | AA902971 | chloride channel 3 | CLCN3 | −2.8 |
| 203498_at | NM_005822 | Down syndrome critical region gene 1-like 1 | DSCR1L1 | −2.8 |
| 222104_x_at | AI569458 | general transcription factor IIH, polypeptide 3, 34 kDa | GTF2H3 | −2.8 |
| 209256_s_at | AF277177 | KIAA0265 protein | KIAA0265 | −2.8 |
| 209211_at | AF132818 | Kruppel-like factor 5 (intestinal) | KLF5 | −2.8 |
| 211042_x_at | BC006329 | melanoma cell adhesion molecule /// melanoma cell adhesion molecule | MCAM | −2.8 |
| 208754_s_at | AL162068 | nucleosome assembly protein 1-like 1 | NAP1L1 | −2.8 |
| 219158_s_at | NM_025085 | NMDA receptor regulated 1 | NARG1 | −2.8 |
| 204105_s_at | NM_005010 | neuronal cell adhesion molecule | NRCAM | −2.8 |
| 201831_s_at | BE875592 | p21/Cdc42/Rac1-activated kinase 1 (STE20 homolog, yeast) /// vesicle docking protein p115 | PAK1 /// VDP | −2.8 |
| 209486_at | BC004546 | disrupter of silencing 10 | SAS10 | −2.8 |
| 219772_s_at | NM_014332 | small muscle protein, X-linked | SMPX | −2.8 |
| 205444_at | NM_004320 | ATPase, Ca++ transporting, cardiac muscle, fast twitch 1 | ATP2A1 | −2.6 |
| 212189_s_at | AK022874 | component of oligomeric golgi complex 4 | COG4 | −2.6 |
| 213546_at | AL050378 | hypothetical protein DKFZp586I1420 | DKFZp586I1420 | −2.6 |
| 212327_at | AK026815 | hypothetical protein | DKFZP686A01247 | −2.6 |
| 219237_s_at | NM_024920 | DnaJ (Hsp40) homolog, subfamily B, member 14 | DNAJB14 | −2.6 |
| 205061_s_at | NM_005033 | exosome component 9 | EXOSC9 | −2.6 |
| 207327_at | NM_004100 | eyes absent homolog 4 (Drosophila) | EYA4 | −2.6 |
| 202771_at | NM_014745 | family with sequence similarity 38, member A | FAM38A | −2.6 |
| 219646_at | NM_017702 | hypothetical protein FLJ20186 | FLJ20186 | −2.6 |
| 205280_at | NM_000824 | glycine receptor, beta | GLRB | −2.6 |
| 200853_at | NM_002106 | H2A histone family, member Z | H2AFZ | −2.6 |
| 219863_at | NM_016323 | hect domain and RLD 5 | HERC5 | −2.6 |
| 218604_at | NM_014319 | LEM domain containing 3 | LEMD3 | −2.6 |
| 203740_at | NM_005792 | M-phase phosphoprotein 6 | MPHOSPH6 | −2.6 |
| 209519_at | BG108193 | nuclear cap binding protein subunit 1, 80 kDa | NCBP1 | −2.6 |
| 201939_at | NM_006622 | polo-like kinase 2 (Drosophila) | PLK2 | −2.6 |
| 212037_at | BF508848 | pinin, desmosome associated protein | PNN | −2.6 |
| 202541_at | BF589679 | small inducible cytokine subfamily E, member 1 (endothelial monocyte-activating) | SCYE1 | −2.6 |
| 206529_x_at | NM_000441 | solute carrier family 26, member 4 | SLC26A4 | −2.6 |
| 201996_s_at | AL524033 | spen homolog, transcriptional regulator (Drosophila) | SPEN | −2.6 |
| 209989_at | AF317549 | zinc finger protein 268 | ZNF268 | −2.6 |
| 201307_at | AL534972 | septin 11 | 11-Sep | −2.5 |
| 221727_at | AA456973 | — | — | −2.5 |
| 221844_x_at | AV756161 | CDNA clone IMAGE: 6208446 | — | −2.5 |
| 221217_s_at | NM_018723 | ataxin 2-binding protein 1 | A2BP1 | −2.5 |
| 37577_at | U79256 | Rho GTPase activating protein 19 | ARHGAP19 | −2.5 |
| 203482_at | AL133215 | chromosome 10 open reading frame 6 | C10orf6 | −2.5 |
| 204521_at | NM_013300 | chromosome 12 open reading frame 24 | C12orf24 | −2.5 |
| 218447_at | NM_020188 | chromosome 16 open reading frame 61 | C16orf61 | −2.5 |

TABLE 8-continued

Genes related to acquired resistance to compound 1.

| | | | | |
|---|---|---|---|---|
| 213436_at | U73304 | cannabinoid receptor 1 (brain) | CNR1 | −2.5 |
| 205931_s_at | NM_004904 | cAMP responsive element binding protein 5 | CREB5 | −2.5 |
| 201018_at | AL079283 | eukaryotic translation initiation factor 1A, X-linked | EIF1AX | −2.5 |
| 217820_s_at | NM_018212 | enabled homolog (Drosophila) | ENAH | −2.5 |
| 204422_s_at | NM_002006 | fibroblast growth factor 2 (basic) | FGF2 | −2.5 |
| 64900_at | AA401703 | hypothetical protein FLJ22167 | FLJ22167 | −2.5 |
| 213094_at | AL033377 | G protein-coupled receptor 126 | GPR126 | −2.5 |
| 215030_at | AK023187 | G-rich RNA sequence binding factor 1 | GRSF1 | −2.5 |
| 202934_at | AI761561 | hexokinase 2 | HK2 | −2.5 |
| 222040_at | AI144007 | heterogeneous nuclear ribonucleoprotein A1 /// hypothetical protein LOC728844 /// hypothetical protein LOC731172 | HNRPA1 /// LOC728844 /// LOC731172 | −2.5 |
| 212859_x_at | BF217861 | metallothionein 1E (functional) | MT1E | −2.5 |
| 221916_at | BF055311 | neurofilament, light polypeptide 68 kDa | NEFL | −2.5 |
| 218375_at | NM_024047 | nudix (nucleoside diphosphate linked moiety X)-type motif 9 | NUDT9 | −2.5 |
| 203060_s_at | AF074331 | 3'-phosphoadenosine 5'-phosphosulfate synthase 2 | PAPSS2 | −2.5 |
| 214239_x_at | AI560455 | polycomb group ring finger 2 | PCGF2 | −2.5 |
| 213302_at | AL044326 | phosphoribosylformylglycinamidine synthase (FGAR amidotransferase) | PFAS | −2.5 |
| 207469_s_at | NM_003662 | pirin (iron-binding nuclear protein) | PIR | −2.5 |
| 203737_s_at | NM_015062 | peroxisome proliferator-activated receptor gamma, coactivator-related 1 | PPRC1 | −2.5 |
| 218564_at | BC002574 | ring finger and WD repeat domain 3 | RFWD3 | −2.5 |
| 215009_s_at | U92014 | SEC31 homolog A (S. cerevisiae) | SEC31A | −2.5 |
| 219751_at | NM_024860 | SET domain containing 6 | SETD6 | −2.5 |
| 202524_s_at | NM_014767 | sparc/osteonectin, cwcv and kazal-like domains proteoglycan (testican) 2 | SPOCK2 | −2.5 |
| 206415_at | AI769310 | tolloid-like 1 | TLL1 | −2.5 |
| 213201_s_at | AJ011712 | troponin T type 1 (skeletal, slow) | TNNT1 | −2.5 |
| 212654_at | AL566786 | tropomyosin 2 (beta) /// peptidylprolyl isomerase (cyclophilin)-like 5 | TPM2 /// PPIL5 | −2.5 |
| 218505_at | NM_024673 | WD repeat domain 59 | WDR59 | −2.5 |
| 214714_at | AK022360 | zinc finger protein 394 | ZNF394 | −2.5 |
| 218981_at | NM_020186 | ACN9 homolog (S. cerevisiae) | ACN9 | −2.3 |
| 218868_at | NM_020445 | ARP3 actin-related protein 3 homolog B (yeast) | ACTR3B | −2.3 |
| 219384_s_at | NM_012091 | adenosine deaminase, tRNA-specific 1 | ADAT1 | −2.3 |
| 201272_at | NM_001628 | aldo-keto reductase family 1, member B1 (aldose reductase) | AKR1B1 | −2.3 |
| 202268_s_at | NM_003905 | amyloid beta precursor protein binding protein 1 | APPBP1 | −2.3 |
| 213892_s_at | AA927724 | adenine phosphoribosyltransferase | APRT | −2.3 |
| 209539_at | D25304 | Rac/Cdc42 guanine nucleotide exchange factor (GEF) 6 | ARHGEF6 | −2.3 |
| 212599_at | AK025298 | autism susceptibility candidate 2 | AUTS2 | −2.3 |
| 218264_at | NM_016567 | BRCA2 and CDKN1A interacting protein | BCCIP | −2.3 |
| 208656_s_at | AF135162 | cyclin I | CCNI | −2.3 |
| 218803_at | NM_018223 | checkpoint with forkhead and ring finger domains | CHFR | −2.3 |
| 200861_at | NM_016284 | CCR4-NOT transcription complex, subunit 1 | CNOT1 | −2.3 |
| 217726_at | NM_016057 | coatomer protein complex, subunit zeta 1 | COPZ1 | −2.3 |
| 203880_at | NM_005694 | COX17 cytochrome c oxidase assembly homolog (S. cerevisiae) | COX17 | −2.3 |
| 220230_s_at | NM_016229 | cytochrome b5 reductase 2 | CYB5R2 | −2.3 |
| 204076_at | AB002390 | ectonucleoside triphosphate diphosphohydrolase 4 | ENTPD4 | −2.3 |
| 203806_s_at | NM_000135 | Fanconi anemia, complementation group A /// Fanconi anemia, complementation group A | FANCA | −2.3 |
| 219901_at | NM_018351 | FYVE, RhoGEF and PH domain containing 6 | FGD6 | −2.3 |
| 205848_at | NM_005256 | growth arrest-specific 2 | GAS2 | −2.3 |
| 213129_s_at | AI970157 | glycine cleavage system protein H (aminomethyl carrier) /// similar to Glycine cleavage system H protein, mitochondrial precursor /// similar to Glycine cleavage system H protein, mitochondrial precursor | GCSH /// LOC654085 /// LOC730107 | −2.3 |

TABLE 8-continued

Genes related to acquired resistance to compound 1.

| | | | | |
|---|---|---|---|---|
| 214730_s_at | AK025457 | golgi apparatus protein 1 /// sema domain, transmembrane domain (TM), and cytoplasmic domain, (semaphorin) 6C /// CDC42 small effector 1 | GLG1 /// SEMA6C /// CDC42SE1 | −2.3 |
| 201348_at | NM_002084 | glutathione peroxidase 3 (plasma) | GPX3 | −2.3 |
| 211998_at | AW138159 | H3 histone, family 3B (H3.3B) | H3F3B | −2.3 |
| 214059_at | BE049439 | Interferon-induced protein 44 | IFI44 | −2.3 |
| 209760_at | AL136932 | KIAA0922 | KIAA0922 | −2.3 |
| 221219_s_at | NM_017566 | kelch domain containing 4 | KLHDC4 | −2.3 |
| 209840_s_at | AI221950 | leucine rich repeat neuronal 3 | LRRN3 | −2.3 |
| 203478_at | NM_002494 | NADH dehydrogenase (ubiquinone) 1, subcomplex unknown, 1, 6 kDa | NDUFC1 | −2.3 |
| 218888_s_at | NM_018092 | neuropilin (NRP) and tolloid (TLL)-like 2 | NETO2 | −2.3 |
| 202432_at | NM_021132 | protein phosphatase 3 (formerly 2B), catalytic subunit, beta isoform (calcineurin A beta) | PPP3CB | −2.3 |
| 221919_at | AW450929 | Protein tyrosine phosphatase, receptor type, U | PTPRU | −2.3 |
| 206950_at | NM_002977 | sodium channel, voltage-gated, type IX, alpha | SCN9A | −2.3 |
| 209897_s_at | AF055585 | slit homolog 2 (*Drosophila*) | SLIT2 | −2.3 |
| 213139_at | AI572079 | snail homolog 2 (*Drosophila*) | SNAI2 | −2.3 |
| 205406_s_at | NM_017425 | sperm autoantigenic protein 17 | SPA17 | −2.3 |
| 203046_s_at | NM_003920 | timeless homolog (*Drosophila*) | TIMELESS | −2.3 |
| 201377_at | NM_014847 | ubiquitin associated protein 2-like | UBAP2L | −2.3 |
| 209096_at | U62136 | ubiquitin-conjugating enzyme E2 variant 2 | UBE2V2 | −2.3 |
| 201760_s_at | NM_018639 | WD repeat and SOCS box-containing 2 | WSB2 | −2.3 |
| 209814_at | BC004421 | zinc finger protein 330 | ZNF330 | −2.3 |
| 220709_at | NM_024967 | zinc finger protein 556 | ZNF556 | −2.3 |
| 201425_at | NM_000690 | aldehyde dehydrogenase 2 family (mitochondrial) | ALDH2 | −2.1 |
| 219649_at | NM_013339 | asparagine-linked glycosylation 6 homolog (*S. cerevisiae*, alpha-1,3-glucosyltransferase) | ALG6 | −2.1 |
| 213905_x_at | AA845258 | biglycan /// teashirt family zinc finger 1 | BGN /// TSHZ1 | −2.1 |
| 218954_s_at | AF298153 | BRF2, subunit of RNA polymerase III transcription initiation factor, BRF1-like | BRF2 | −2.1 |
| 202763_at | NM_004346 | caspase 3, apoptosis-related cysteine peptidase | CASP3 | −2.1 |
| 221107_at | NM_017581 | cholinergic receptor, nicotinic, alpha 9 | CHRNA9 | −2.1 |
| 221139_s_at | NM_015989 | cysteine sulfinic acid decarboxylase | CSAD | −2.1 |
| 218970_s_at | NM_015960 | cutC copper transporter homolog (*E. coli*) | CUTC | −2.1 |
| 218102_at | NM_015954 | 2-deoxyribose-5-phosphate aldolase homolog (*C. elegans*) | DERA | −2.1 |
| 208810_at | AF080569 | DnaJ (Hsp40) homolog, subfamily B, member 6 /// similar to DnaJ (Hsp40) homolog, subfamily B, member 6 isoform a | DNAJB6 /// LOC387820 | −2.1 |
| 212792_at | AB020684 | dpy-19-like 1 (*C. elegans*) | DPY19L1 | −2.1 |
| 205741_s_at | NM_001392 | dystrobrevin, alpha | DTNA | −2.1 |
| 201632_at | NM_001414 | eukaryotic translation initiation factor 2B, subunit 1 alpha, 26 kDa | EIF2B1 | −2.1 |
| 201437_s_at | NM_001968 | eukaryotic translation initiation factor 4E | EIF4E | −2.1 |
| 202973_x_at | NM_014883 | family with sequence similarity 13, member A1 | FAM13A1 | −2.1 |
| 218986_s_at | NM_017631 | hypothetical protein FLJ20035 | FLJ20035 | −2.1 |
| 53071_s_at | AI885411 | hypothetical protein FLJ22222 | FLJ22222 | −2.1 |
| 215143_at | AL049437 | Hypothetical protein FLJ36166 | FLJ36166 | −2.1 |
| 208841_s_at | AB014560 | GTPase activating protein (SH3 domain) binding protein 2 | G3BP2 | −2.1 |
| 205527_s_at | NM_015487 | gem (nuclear organelle) associated protein 4 | GEMIN4 | −2.1 |
| 206104_at | NM_002202 | ISL1 transcription factor, LIM/homeodomain, (islet-1) | ISL1 | −2.1 |
| 203162_s_at | NM_005886 | katanin p80 (WD repeat containing) subunit B 1 | KATNB1 | −2.1 |
| 217956_s_at | NM_021204 | E-1 enzyme | MASA | −2.1 |
| 209585_s_at | AF084943 | multiple inositol polyphosphate histidine phosphatase, 1 | MINPP1 | −2.1 |
| 220615_s_at | NM_018099 | male sterility domain containing 1 | MLSTD1 | −2.1 |
| 204326_x_at | NM_002450 | metallothionein 1X | MT1X | −2.1 |
| 203212_s_at | NM_016156 | myotubularin related protein 2 | MTMR2 | −2.1 |
| 218568_at | NM_018238 | multiple substrate lipid kinase | MULK | −2.1 |
| 202431_s_at | NM_002467 | v-myc myelocytomatosis viral oncogene homolog (avian) | MYC | −2.1 |

TABLE 8-continued

Genes related to acquired resistance to compound 1.

| | | | | |
|---|---|---|---|---|
| 201304_at | NM_005000 | NADH dehydrogenase (ubiquinone) 1 alpha subcomplex, 5, 13 kDa | NDUFA5 | −2.1 |
| 212808_at | AI884627 | nuclear factor of activated T-cells, cytoplasmic, calcineurin-dependent 2 interacting protein | NFATC2IP | −2.1 |
| 219031_s_at | NM_016101 | nuclear import 7 homolog (S. cerevisiae) | NIP7 | −2.1 |
| 202188_at | NM_014669 | nucleoporin 93 kDa | NUP93 | −2.1 |
| 201013_s_at | AA902652 | phosphoribosylaminoimidazole carboxylase, phosphoribosylaminoimidazole succinocarboxamide synthetase | PAICS | −2.1 |
| 204873_at | NM_000466 | peroxisome biogenesis factor 1 | PEX1 | −2.1 |
| 213700_s_at | AA554945 | Pyruvate kinase, muscle | PKM2 | −2.1 |
| 204887_s_at | NM_014264 | polo-like kinase 4 (Drosophila) | PLK4 | −2.1 |
| 209434_s_at | U00238 | phosphoribosyl pyrophosphate amidotransferase | PPAT | −2.1 |
| 201489_at | BC005020 | peptidylprolyl isomerase F (cyclophilin F) | PPIF | −2.1 |
| 211737_x_at | BC005916 | pleiotrophin (heparin binding growth factor 8, neurite growth-promoting factor 1) /// pleiotrophin (heparin binding growth factor 8, neurite growth-promoting factor 1) | PTN | |
| 206290_s_at | NM_002924 | regulator of G-protein signalling 7 | RGS7 | −2.1 |
| 219154_at | NM_024714 | Ras homolog gene family, member F (in filopodia) | RHOF | −2.1 |
| 214967_at | AU146983 | Sterile alpha motif domain containing 4A | SAMD4A | −2.1 |
| 221768_at | AV705803 | Splicing factor proline/glutamine-rich (polypyrimidine tract binding protein associated) | SFPQ | −2.1 |
| 213505_s_at | BG252853 | splicing factor, arginine/serine-rich 14 | SFRS14 | −2.1 |
| 217289_s_at | AF097831 | solute carrier family 37 (glycerol-6-phosphate transporter), member 4 | SLC37A4 | −2.1 |
| 203580_s_at | NM_003983 | solute carrier family 7 (cationic amino acid transporter, y+ system), member 6 | SLC7A6 | −2.1 |
| 208920_at | AV752215 | sorcin | SRI | −2.1 |
| 208095_s_at | NM_001222 | signal recognition particle 72 kDa | SRP72 | −2.1 |
| 214597_at | BC000256 | somatostatin receptor 2 | SSTR2 | −2.1 |
| 207871_s_at | NM_018412 | suppression of tumorigenicity 7 | ST7 | −2.1 |
| 217914_at | NM_017901 | two pore segment channel 1 | TPCN1 | −2.1 |
| 218354_at | NM_016209 | trafficking protein particle complex 2-like | TRAPPC2L | −2.1 |
| 205300_s_at | NM_022717 | U11/U12 snRNP 35K | U1SNRNPBP | −2.1 |
| 200667_at | BF448062 | ubiquitin-conjugating enzyme E2D 3 (UBC4/5 homolog, yeast) | UBE2D3 | −2.1 |
| 209137_s_at | BC000263 | ubiquitin specific peptidase 10 | USP10 | −2.1 |
| 213256_at | AW593996 | membrane-associated ring finger (C3HC4) 3 | 3-Mar | −2 |
| 208838_at | AB020636 | — | — | −2 |
| 201872_s_at | AI002002 | ATP-binding cassette, sub-family E (OABP), member 1 | ABCE1 | −2 |
| 202422_s_at | NM_022977 | acyl-CoA synthetase long-chain family member 4 | ACSL4 | −2 |
| 214846_s_at | AB037751 | alpha-kinase 3 | ALPK3 | −2 |
| 219437_s_at | NM_013275 | ankyrin repeat domain 11 | ANKRD11 | −2 |
| 212211_at | AI986295 | ankyrin repeat domain 17 | ANKRD17 | −2 |
| 203350_at | NM_001128 | adaptor-related protein complex 1, gamma 1 subunit | AP1G1 | −2 |
| 212536_at | AB023173 | ATPase, Class VI, type 11B | ATP11B | −2 |
| 208764_s_at | D13119 | ATP synthase, H+ transporting, mitochondrial F0 complex, subunit C2 (subunit 9) | ATP5G2 | −2 |
| 208445_s_at | NM_023005 | bromodomain adjacent to zinc finger domain, 1B | BAZ1B | −2 |
| 203796_s_at | AI950380 | B-cell CLL/lymphoma 7A | BCL7A | −2 |
| 201261_x_at | BC002416 | biglycan | BGN | −2 |
| 201032_at | NM_006698 | bladder cancer associated protein | BLCAP | −2 |
| 221776_s_at | AI885109 | bromodomain containing 7 | BRD7 | −2 |
| 64432_at | W05463 | chromosome 12 open reading frame 47 | C12orf47 | −2 |
| 204215_at | NM_024315 | chromosome 7 open reading frame 23 | C7orf23 | −2 |
| 218187_s_at | NM_023080 | chromosome 8 open reading frame 33 | C8orf33 | −2 |
| 219644_at | NM_016122 | coiled-coil domain containing 41 | CCDC41 | −2 |
| 203166_at | NM_006324 | craniofacial development protein 1 | CFDP1 | −2 |
| 218057_x_at | NM_006067 | COX4 neighbor | COX4NB | −2 |
| 202521_at | NM_006565 | CCCTC-binding factor (zinc finger protein) | CTCF | −2 |

TABLE 8-continued

Genes related to acquired resistance to compound 1.

| | | | | |
|---|---|---|---|---|
| 214743_at | BE046521 | cut-like 1, CCAAT displacement protein (*Drosophila*) | CUTL1 | −2 |
| 201572_x_at | NM_001921 | dCMP deaminase | DCTD | −2 |
| 202577_s_at | BC005162 | DEAD (Asp-Glu-Ala-As) box polypeptide 19A | DDX19A | −2 |
| 202534_x_at | NM_000791 | dihydrofolate reductase | DHFR | −2 |
| 205762_s_at | NM_007016 | dihydrouridine synthase 4-like (*S. cerevisiae*) | DUS4L | −2 |
| 201540_at | NM_001449 | four and a half LIM domains 1 | FHL1 | −2 |
| 218894_s_at | NM_018048 | mago-nashi homolog 2 | FLJ10292 | −2 |
| 209702_at | U79260 | fatso | FTO | −2 |
| 212847_at | AL036840 | Far upstream element (FUSE) binding protein 1 | FUBP1 | −2 |
| 209710_at | AL563460 | GATA binding protein 2 | GATA2 | −2 |
| 221028_s_at | NM_030819 | glucose-fructose oxidoreductase domain containing 2 /// glucose-fructose oxidoreductase domain containing 2 | GFOD2 | −2 |
| 200708_at | NM_002080 | glutamic-oxaloacetic transaminase 2, mitochondrial (aspartate aminotransferase 2) | GOT2 | −2 |
| 214280_x_at | X79536 | heterogeneous nuclear ribonucleoprotein A1 | HNRPA1 | −2 |
| 215513_at | AF241534 | hydatidiform mole associated and imprinted | HYMAI | −2 |
| 208937_s_at | D13889 | inhibitor of DNA binding 1, dominant negative helix-loop-helix protein | ID1 | −2 |
| 203327_at | N22903 | insulin-degrading enzyme | IDE | −2 |
| 210881_s_at | M17863 | insulin-like growth factor 2 (somatomedin A) /// insulin-insulin-like growth factor 2 | IGF2 /// INS-IGF2 | −2 |
| 205070_at | NM_019071 | inhibitor of growth family, member 3 | ING3 | −2 |
| 203607_at | NM_014937 | inositol polyphosphate-5-phosphatase F | INPP5F | −2 |
| 200079_s_at | AF285758 | lysyl-tRNA synthetase /// lysyl-tRNA synthetase | KARS | −2 |
| 213478_at | AB028949 | kazrin | KIAA1026 | −2 |
| 212714_at | AL050205 | La ribonucleoprotein domain family, member 4 | LARP4 | −2 |
| 217506_at | H49382 | Hypothetical protein LOC339290 | LOC339290 | −2 |
| 214109_at | AI659561 | LPS-responsive vesicle trafficking, beach and anchor containing | LRBA | −2 |
| 204059_s_at | NM_002395 | malic enzyme 1, NADP(+)-dependent, cytosolic | ME1 | −2 |
| 218654_s_at | NM_016071 | mitochondrial ribosomal protein S33 | MRPS33 | −2 |
| 203359_s_at | AL525412 | c-myc binding protein | MYCBP | −2 |
| 201468_s_at | NM_000903 | NAD(P)H dehydrogenase, quinone 1 | NQO1 | −2 |
| 210797_s_at | AF063612 | 2'-5'-oligoadenylate synthetase-like | OASL | −2 |
| 219105_x_at | NM_014321 | origin recognition complex, subunit 6 like (yeast) | ORC6L | −2 |
| 204004_at | AI336206 | PRKC, apoptosis, WT1, regulator | PAWR | −2 |
| 213227_at | BE879873 | progesterone receptor membrane component 2 | PGRMC2 | −2 |
| 219459_at | NM_018082 | polymerase (RNA) III (DNA directed) polypeptide B | POLR3B | −2 |
| 202313_at | NM_002717 | protein phosphatase 2 (formerly 2A), regulatory subunit B (PR 52), alpha isoform | PPP2R2A | −2 |
| 209049_s_at | BC001004 | protein kinase C binding protein 1 | PRKCBP1 | −2 |
| 212610_at | U79291 | protein tyrosine phosphatase, non-receptor type 11 (Noonan syndrome 1) | PTPN11 | −2 |
| 203831_at | NM_014925 | R3H domain containing 2 | R3HDM2 | −2 |
| 218430_s_at | NM_022841 | regulatory factor X domain containing 2 | RFXDC2 | −2 |
| 204337_at | AL514445 | regulator of G-protein signalling 4 | RGS4 | −2 |
| 212191_x_at | AW574664 | ribosomal protein L13 | RPL13 | −2 |
| 213939_s_at | AI871641 | RUN and FYVE domain containing 3 | RUFY3 | −2 |
| 209127_s_at | AW173076 | squamous cell carcinoma antigen recognized by T cells 3 | SART3 | −2 |
| 204019_s_at | NM_015677 | SH3 domain containing, Ysc84-like 1 (*S. cerevisiae*) | SH3YL1 | −2 |
| 202980_s_at | AI953523 | seven in absentia homolog 1 (*Drosophila*) | SIAH1 | −2 |
| 221543_s_at | AL442077 | SPFH domain family, member 2 | SPFH2 | −2 |
| 212061_at | AB002330 | U2-associated SR140 protein | SR140 | −2 |
| 215772_x_at | AL050226 | succinate-CoA ligase, GDP-forming, beta subunit | SUCLG2 | −2 |
| 222116_s_at | AL157485 | TBC1 domain family, member 16 | TBC1D16 | −2 |
| 212282_at | BF038366 | transmembrane protein 97 | TMEM97 | −2 |
| 214948_s_at | AL050136 | TATA element modulatory factor 1 | TMF1 | −2 |
| 202330_s_at | NM_003362 | uracil-DNA glycosylase | UNG | −2 |

TABLE 8-continued

Genes related to acquired resistance to compound 1.

| 213480_at | AF052100 | vesicle-associated membrane protein 4 | VAMP4 | −2 |
| 220917_s_at | NM_025132 | WD repeat domain 19 | WDR19 | −2 |
| 216350_s_at | X52332 | zinc finger protein 10 | ZNF10 | −2 |
| 209538_at | U69645 | zinc finger protein 32 | ZNF32 | −2 |
| 214761_at | AW149417 | zinc finger protein 423 | ZNF423 | −2 |
| 205739_x_at | NM_016220 | zinc finger protein 588 | ZNF588 | −2 |
| 206583_at | NM_017776 | zinc finger protein 673 | ZNF673 | −2 |

Gene expression profiles of compound 1 sensitive RMS cell line RD-1 ($IC_{50}$ = 0.238 μM) and the acquired resistant RD-1 cells has ($IC_{50}$ = 1.999 μM) which is more than 8 fold of the parental RD1 was compared and analyzed using using GeneChip ® Expression Analysis software MAS 5.0 to identify genes differentially expressed between these cells.
A change call of "increase" or "decrease" in gene expression level was assigned for each probe set and the fold change between the resistant RD-1 cells and the parental sensitive cells was calculated.
The redundant probes were removed and left one as the representative for the gene.
The fold change is listed, the positive indicates higher expression in the resistant RD-1, and the negative indicates the higher expression in the sensitive parental RD-1.

These genes may reflect the mechanism of acquired resistance to IGF1R inhibitor. Interestingly, several insulin-like growth factor binding proteins were expressed at higher level in the acquired resistant cells compared to the sensitive parent RD-1, such as IGFBP2 (10.6 fold), IGFBP3 (6.4 fold), IGFBP5 (4.8 fold), IGFBP7 (15 fold), whereas, IGF2 had conversely expression pattern. SRC family members FYN and LYN also had increased expression levels in the acquired resistant cells. Comparison of the genes correlated with the intrinsic (de novo) resistance (Table 3) to the ones related to acquired resistance (Table 8), there are common genes, such as CAST, CD44, PLAUR, SP100, STK10, TFPI2 and THBS1 with higher expression in both de novo and acquired resistant cells, suggesting there may be some common mechanisms for both types of drug resistance. Thrombospondin 1 (THBS1) was reported to prevent camptothecin- and doxorubicin-induced apoptosis in human thyroid carcinoma cells, this shed new light on a possible role for THBS 1 in drug resistance (G. Rath, et al., Biochim. Biophys. Acta., October;1763(10): 1125-34 (2006)). THBS1 was up regulated by IGF stimulation to promote cell survival (data not shown) and over expressed in the resistant cells, and thus may involved in both de novo and acquired resistance to IGF1R inhibitors.

Significant Differences in Multiple Pathways Between the Sensitive and Resistant Cell Lines at Basal Level:

Global pathway analysis on the basal gene expression of 28 cell lines using globaltest indicated that 75 out 183 tested pathways were significantly associated with the sensitive/resistant classification to compound 1 (FEW adjusted p value<0.05). Several interesting pathways including apoptosis pathway, and signaling pathways of MAPK, TGFβ, Jak-STAT, insulin, VEGF and natural killer cell mediated cytotoxicity were among those significant pathways that were different between the sensitive and resistant cell lines, while mTOR signaling pathway is different (p value=0.0005) yet slightly higher than the the significance cutoff (FWE adjusted p value=0.0559). Pathway analysis of expression data for the compound 1 treated Rh41 cell compared to that for the untreated control cells, above mentioned pathways are also different between the cells treated with or without the drug with p value all less than 0.01 but not reach the statistical significant cutoff based on the FWE adjusted p values.

Ingenuity pathway analysis on the 497 probe sets that significantly correlated with the sensitivity of compound 1 in the 28-cell line panel were performed, over expression of multiple kinases (e.g., EGFR, MET, TGFβR2) in the compound 1 resistant cell lines was observed in the most significant network. This may explain why these cell lines are still proliferating and surviving even in presence of the drug, since they use alternative growth signal pathways instead of IGF1R. In this specific situation, targeting multiple pathways may be necessary to sufficiently inhibit the growth of these cells and synergistic effects with the combination of inhibitors targeting these kinases could be possible.

Synergistic Activity Between Inhibitors of IGF1R and Other Kinases:

IGF signaling through IGF1R has also been shown to protect cancer cells from the cytotoxic effects of chemotherapy and radiation, and this may be an important factor in tumor cell drug resistance (J. Gooch, et al., Breast Cancer Res. Treat., 56(1): 1-10 (1999), B. Turner, et al., Cancer Res, 57(15):3079-83 (1997)). Recent evidence suggests that resistance to Herceptin® in some forms of breast cancer may be due to activation of IGF1R signaling in those cancers (Y. Lu, et al., J. Natl. Cancer Inst., 93(24):1852-7 (2001)). Tumor cells rely on alternative receptors for activation of critical signaling pathways, therefore, strategies designed to block signaling from multiple receptors may be advantageous. Due to the wide expression of IGF1R and the potential cross-talk between the IGF1R pathway and the other signaling pathways implicated in oncogenesis (EGFR, Her2 and mTOR), IGF1R inhibitors may have potential to be combined with other therapies in a wide range of tumors to increase the overall survival of patients. Through ingenuity pathway analysis, the overexpression of multiple kniases (EGFR, MET, TGFR) in the compound 1 resistant cell lines was observed to be within the top network. Given the important roles of IGF1R, EGFR and Her2 in cell cycle progression, we carried out combination studies to investigate whether inhibition of multiple targets might result in enhanced inhibition of tumor growth. Table 9 summarizes the data for in vitro combination studies in multiple types of tumor cell lines and indicated that the drug combinations resulted in synergistic effects between IGF1R inhibitor compound 1 and various inhibitors of EGFR, including both Her 1 and/or Her2 inhibitors in the forms of either antibody (cetuximab) or small molecules (gefitnib, erlotinib and lapatinib).

TABLE 9

In vitro combination study of compound 1 with other anti-tumor agents in multiple cell lines: IGF1R-sal, Colo205, RD1, HT-29, WiDr, GEO, MDA-PCa-2b, MCF-7, H3396, N-87, BT474, and SKBR3 cell lines.

| Class/Compound | Combination Result |
|---|---|
| HER1/HER2 Inhibitor | |
| cetuximab | Synergy |
| gefitnib | Synergy |
| erlotinib | Synergy |
| lapatinib | Synergy |

TABLE 9-continued

In vitro combination study of compound 1 with other anti-tumor agents in multiple cell lines: IGF1R-sal, Colo205, RD1, HT-29, WiDr, GEO, MDA-PCa-2b, MCF-7, H3396, N-87, BT474, and SKBR3 cell lines.

| Class/Compound | Combination Result |
|---|---|
| Other targets | |
| dasatinib | Synergy |
| Cytotoxic | |
| paclitaxel | Additive |
| cisplatin | Additive |
| VP-16 | Additive |
| ADR | Additive |
| vincristine | Additive |

The combination results were analyzed by Isobolograms.

These results confirmed our hypothesis based on the pathway analysis. In vivo synergistic effects were also observed in selected xenograft models (data not shown). In addition, combination between multiple cytotoxic agents and compound 1 also resulted in additive activity.

Increased expression level of SRC family members FYN (3 fold) and LYN (11 fold) in the compound 1 acquired resistant RD-1 cells may suggest SRC family members act as an alternative signal pathway to play an important role in growth and survival of the acquired resistant cells, and targeting IGF1R in this case is not sufficient enough. Targeting multiple pathways could be one of ways to prevent the acquired resistance. The results in Table 9 also demonstrated that synergistic effect observed between IGF1R inhibitor compound 1 and dasatinib, a novel, oral, multi-targeted kinase inhibitor that targets important oncogenic pathways, including SRC family kinases, BCR-ABL, PDGFR, c-KIT and EPHA2 (L. Lombardo, et al., J. Med. Chem.;47:6658-61 (2004), A. Todd, et al., PNAS; 102;11011-11016 (2005)).

Discussion

The development of trastuzumab and EGFR tyrosine kinase inhibitors have demonstrated that careful measurement of biomarkers is necessary when only a small percentage of patients have receptor-driven tumors. Identification of molecular markers predictive of response to IGF1R inhibitors could assist in clinical development by selecting patients most likely to derive clinical benefit. In the present study, by utilizing both microarray gene expression profiling and LC/MS based "bottom-up" protein profiling technologies and a panel of 29 sarcoma and neuroblastoma cell lines, we identified genes and proteins that differentially expressed between the sensitive and resistant cell lines to IGF1R inhibitors compound 2 and compound 1. Realizing the sensitivity/resistance demarcation in the panel of the cell lines is arbitrarily defined and its relevance to the peak range of the drug concentrations in plasma of patients treated with the clinical achievable dose is unclear, we applied Pearson correlation analysis of expression levels with $IC_{50}$ values to identify genes/protein correlated with the sensitivity of the drugs in combination with two-sample t-test.

There is a correlation between sensitive/resistant classification to IGF1R inhibitors and different sub-types of cell lines. Notably, most of neuroblastoma, Ewing's and RMS cell lines are sensitive to the inhibitors, making these cell types as the preferred targeting population for IGF1R inhibitors. However, it may create potential possibility of the markers identified are the ones reflecting the specific cell types rather than reflecting the sensitivity of cells to the IGF1R inhibitors. This is not the case for two reasons: first, the sensitive cell lines are consisted of three cell types rather than a single one, and vise visa for the resistant cell llines; second, comparing the drug sensitivity markers identified in this study with the signatures for specific subtypes of sarcomas further excluded the possibility.

A number of gene expression profiling studies of soft tissue tumors have identified the signatures for specific subtypes of sarcomas (C. Baer, et al., Int. J. Cancer,110(5):687-94 (2004), K. Baird, et al., Cancer Res., 65: (20)9226-35 (2005), T. Nielsen, et al., Lancet, 359(9314):1301-7 (2002)). For example, the top discriminators for Ewing's sarcoma include FVT1, DCC, DKK2, PAX3 and JAK1; for fibrosarcoma are PMP22, PTPRZ1, FN1; for RMS are MYL4, FGFR4, TNN11, ACTC, FLNC, and CDH15; for liposarcoma are PPARG, FABP4, FALCS, SH3KBP1, HOXAS and AIM1, for leiomyosarcoma MYLK, CCN1, PBX1 and SLMAP. The comparison results indicated that none of the subtype specific markers are among the intrinsic sensitivity markers we identified.

Since IGF1R plays a role in cell survival and in resistance to the anti-HER2 monoclonal antibody trastuzumab, the expression patterns of the components of IGFs/IGF1R system were evaluated in this study to see if they have any correlation with the intrinsic sensitivity/resistance to IGF1R inhibitors in the panel of cell lines. The results showed that IGF1R expression level was not significantly correlated to the sensitivity of compound 2 and/or compound 1 in the 29 sarcoma cell lines even through some of the sensitive cell lines had higher IGF1R expression, this does not exclude the possibility that the sensitive cell lines have elevated activity of IGF1R or IGF1R is the major player for the growth of these cell lines. On the other hand, one member of the IGF-binding proteins (IGFBPs), IGFBP6, was significantly higher (>10 fold) in the group of resistant cell lines at basal level. Intriguingly, in the compound 1 acquired resistant RD-1 cells, IRS2 was 2 fold and IGFBP2, IGFBP 3, IGFBP 5 and IGFBP 7 were 7 to 15 fold elevated compared to the parent sensitive cells. IRS2 is the substrate for IGF1R and can enhance the IGF1R activity associated with a metastatic phenotype which correlated with increased migration and motility (J. Jackson, et al., Oncogene, 20(50): 7318-25 (2001)). IGFBPs influenced IGF signaling by modulate the bioavailability and bioactivity of the IGFs. Several IGFBPs are implicated in drug resistance. IGFBP3 and IGFBP5 were reported to be significantly higher from ovarian cancer non-response patients to aromatase inhibitor letrozole compared with responders (G. Walker, et al., Clin. Cancer Res., 13(5):1438-44 (2007)). IGFBP-2 mRNA and protein level were found to be overexpressed in resistant cell lines to antiestrogen Faslodex/Fulvestrant, tamoxifen or RU 58,668 (A. Juncker-Jensen, et al., Growth Horm. IGF. Res., 16(4):224-39 (2006)). IGFBPs' actions can be modulated by IGFBP proteases, such as cathepsins that cleave IGFBPs. Higher basal expression level (4 to 12 fold) of lysosomal cysteine protease cathepsin B, L and Z and lysosomal aspartyl protease cathepsin D were observed in the resistant cell lines. In cancer patients, elevated cathepsin B activity correlates to poor therapy outcome. Several studies have shown that levels of cathepsin B and/or cathepsin L are correlated with drug-resistance (e.g., adriamycin) (M. Osmak, et al., Anticancer Res., 21(1A):481-3 (2001), P. Scaddan, et al., Invasion Metastasis., 13(6):301-13 (1993)). Cathepsin L acts as a cell survival molecule responsible for initiation of resistance to chemotherapy, inhibition of cathepsin L with siRNA facilitates induction of senescence and reversal of drug resistance (A. Juncker-Jensen, et al., Growth Horm. IGF Res., 16(4):224-39 (2006)). The association between drug-resistance and cathepsin D was also studied in nine cervical and laryngeal carcinoma cell lines resistant to different cytostatics, and all drug resistant cell lines had increased concentration of cathepsin D (M. Osmak, et al., Anticancer Res., July-August;19(4B):3193-7 (1999)).

Another group of genes involved in the intrinsic (de novo) drug resistance to IGF1R inhibitors was metallothionein family members (1F, G, H, M, X, 2A), with over-expression (4 to 9 fold) in resistant cell lines. Metallothionein family members are cysteine-rich proteins that involved in many pathophysiological processes such as metal ion homeostasis and detoxification, protection against oxidative damage, cell proliferation and apoptosis, chemo-resistance (platinum agents, tamoxifen) and radiotherapy resistance (M. Ebadi, et al., Gen Pharmacol., 25(7):1297-310 (1994)). The basal level overexpression of these family members was also observed in a group of colon cancer lines that are resistant to compound 1 compared to the sensitive cell lines, suggesting the role of metallothionein family members in IGF1R inhibitor drug resistance.

Inhibition of oncogenic protein kinases by small molecule inhibitors has proven to be a valuable strategy for the directed and target-specific treatment of an ever-increasing number of cancer types. Unfortunately, initially successful therapy is often hampered by relatively rapid onset of resistance to the drug and subsequent relapse, particularly in patients with advanced disease. In addition to deriving mutations, loss of target dependence due to the activation of parallel signaling pathways has been also reported as cause for acquired drug resistance. Therefore, novel therapeutic approaches are based on concepts to prevent or circumvent drug resistance, e.g., with target-specific novel drugs interfering with signaling and apoptotic pathways. Revelation of mechanistic details of drug resistance also provides the basis for the development of therapies with novel or conventional antitumor drugs in combination with specific inhibitors to re-establish chemosensitivity. From the present study, it is noteworthy that in the cell lines with de novo resistant to IGF1R inhibitors, other tyrosine kinases such as Met and EGFR were overexpressed. Furthermore, SRC family members FYN and LYN also increased expression levels in the compound 1 acquired resistant cells. These observations may suggest that loss of IGF1R dependence due to overexpression of other kinases and activation of different signal pathways plays an important role as one of the possible mechanisms in the de novo and acquired resistances to IGF1R inhibitors. It is possible that in the IGF1R inhibitor resistant cell lines, MET and EGFR pathways are presumably more activated and are major factors for the growth signaling, so targeting only IGF1R is not sufficient enough to inhibit growth of these cells.

The same hypothesis could be applied to the IGF1R inhibitor acquired resistant cells because SRC family members FYN and LYN elevated their expression level after the IGF1R inhibitor treatment. Based on these observations, we hypothesize that there should be a potential sensitize activity between IGF1R inhibitors and inhibitors for Met, EGFR or SRC pathways. The combination studies in several tumor cell lines (Table 9) actually demonstrated the synergy effects between IGF1R inhibitor compound 1 and multiple HER1/HER2 inhibitors or dasatinib, a multi-targeted kinase inhibitor that targets important oncogenic pathways including SRC family kinases. The same synergy effects were also observed for IGF1R inhibitor compound 2 (data not show). The results further support the observation that co-inhibition of IGF1R and EGFR synergistically sensitizes cancer cells to induce apoptosis (A. Camirand, et al., Breast Cancer Res., 7(4): R570-9 (2005), J. Steinbach, et al., Biochem. Biophys. Res. Commun., 321(3):524-30 (2004)).

Because the mutations in tyrosine receptor kinases have been linked to the efficacy of the inhibitors targeting these kinases, it is reasonable to ask whether mutations or/and single nucleotide polymorphisms (SNPs) in IGF1R would correlate with the response to the IGF1R inhibitors, compound 2 and compound 1. Sequencing of the IGF1R in Rh41 and RD-1 (sensitive lines), Rh36 (primary resistant line) and resistant RD-1 (acquired resistant line) has shown no mutations or/and SNPs exist that might cause resistance to the IGF1R inhibitors. Interestingly, no specific mutations in IGF receptors or ligands have been identified in human cancers, but there is clear evidence of epigenetic alterations such as the loss of imprinting (LOI) of IGF-II in a variety of human tumors (S. Ranier, et al., Hum. Mol. Genet., 3(2):386 (1994), S. Zhan, et al., Clin. Invest., 94(1): 445-8 (1994)). Furthermore, no SNPs that cause amino acid changes in the IGF1R protein have been reported in the NCBI dbSNP database, the Japanese SNP database or the Incyte Foundation database. In addition, no human inherited disorders are attributed to mutations in IGF1R. In order to further evaluate potential IGF1R mutations in human cancers, we sequenced the human IGF1R gene from a panel of genomic DNA derived from 24 tumor-derived cell lines and from 48 human primary lung tumors and no germline variations or somatic mutations were identified in these tumor/cell line samples during tumorigenesis, although amplification of the IGF1R locus has been reported in a small number of breast cancer and melanoma specimens (A. Almeida, et al., Genes Chromosomes Cancer, 11(1): 63-5 (1994)).

From protein profiles of the baseline expression in 29 cell lines, a strikingly large number of the proteins identified are involved in cell adhesion and cell motility and extracellular signaling regulated processes. Most actin binding proteins found were present in lower levels in the IGF1R sensitive cell lines. The overall goal of this study is to understand the difference in the proteomic signatures of resistant and sensitive cell lines. The pattern emerging from these data is a profile of sensitive cell lines with lower levels of cytoskeleton binding proteins, and overall higher levels of DNA and RNA binding proteins found in the nucleus. The open question is how these features confer the sensitivity to IGF1R inhibitors on the sarcoma cell lines studied here.

There is differential sensitivity of compound 2 and compound 1 in a pair of human RMS cells that are sensitive (Rh41) or resistant (Rh36) to the drugs in a cellular proliferation assay (Table 1). These two cell lines have different chromosomal translocations: Rh41 cells harbor a PAX3-FKHR translocation, t(2;13)(q35;q14), whereas Rh36 cells harbor a EWS-FLI-1 translocation, t(11;22)(q24;q12). Gene expression revealed that Rh41 cells have a significant higher level of IGF1R but limited expression of IR, the results were confirmed by RT-PCR measurements (IGF1R/IR ratio=445) and by FACS analysis (data not shown). No mutations in the IGF1R were apparent in both cell lines. In general, the level of IGF1R expression has not been correlated with increased sensitivity in multiple cell lines, thus the sensitivity might be due to differential signaling pathways in these cells. In order to better understand the mechanism of the differential sensitivity, the two cell lines were evaluated by drug treatment and global gene/protein profiling to monitor the differential changes in gene/protein expression. Overall, in Rh36 cells the drug had little, to no effect especially at later time points, 36 and 72 hrs. This makes sense considering the drug concentration of compound 1 used in the study, Rh36 is highly resistant. However, in the sensitive cell Rh41, 30% of genes have significant expression changes upon the drug treatment. These genes are mainly involved in apoptosis, cell growth and proliferation, cell cycles and multiple tyrosine kinases pathways as well as the down-stream IGF1R signaling pathways: MAPK, PI3K and AKT. The expression level of survivin was significantly reduced especially at 36 and 72 hours and programmed cell death 4 (PDCD4) was up-regulated by compound 1 treatment in the sensitive Rh41 cells, but not in resistant Rh36 cells. PDCD4 is a tumor suppressor protein and its expression is strongly induced during apoptosis in a number of cell types (0. Afonja, et al., Oncogene, 23(49): 8135-45 (2004)). Thus, up-regulation of PDCD4 expression may suggest apoptosis induced by compound 1 in sensitive cell lines only. This is in agreement with Western blot analysis showed both Rh41 and Rh36 cell lines have high expression of pBad, but only Rh41 cells showed significant reduction in pBad activity by 6 hrs of drug treatment. The reduction in pBad activity was accompanied by an increase in apoptosis when cells were exposed to the drugs for 24-48 hrs, followed by a G1 arrest. Remarkable but not complete decrease of Ki-67 in compound 1 treated cells may suggest the inhibitor with the cytostatic rather than cytotoxic effect. The inhibitor may induce apoptosis and lower the survival threshold of cancer cells thereby augmenting a second apoptotic stimulus by another agent in a combination therapy.

There are 41% of 183 total tested KEGG pathways significantly different between the sensitive and resistant cell lines to IGF1R inhibitor. This provides a general clue on what are the main differences conferring the cell's sensitivity to IGF1R inhibitor. For example, apoptosis pathway is one of the differences, many genes promoting apoptosis have higher expression levels in the resistant cell lines. Detailed dissection of the pathway is needed to get insights for whether resistant cell lines have higher threshold to be apoptotic due to presence of other growth signaling pathways (e.g., EGFR, MET) in addition to IGF1R pathway, whereas in the sensitive cell lines, IGF1R is probably the dominant growth and survival driver.

In conclusion, molecular characterization of a panel of soft tissue sarcoma cell lines lead to identified signatures or candidate markers correlating with the intrinsic sensitivity in vitro to IGF1R inhibitors, compound 1 and compound 2. Whether these signatures or markers have the utility in predicting the response to IGF1R inhibitors in the patients with sarcoma needs to be tested in clinic. The possible mechanisms for both intrinsic and acquired drug resistances were explored and could be due to the alternative activation of other parallel signaling pathways besides IGF1R. Based on these possible mechanisms, the combination strategies to target multiple pathways was proposed and tested, synergistic activity of inhibitors for IGF1-R and EGFR, or SRC was observed. This provides some clues on the strategies for developing IGF1R inhibitor and possible combination therapies in clinical trials to achieve synergy between inhibitors for IGF1R and other kinases.

Example 2

Production of Antibodies Against the Biomarkers

Antibodies against the biomarkers can be prepared by a variety of methods. For example, cells expressing an biomarker polypeptide can be administered to an animal to induce the production of sera containing polyclonal antibodies directed to the expressed polypeptides. In one aspect, the biomarker protein is prepared and isolated or otherwise purified to render it substantially free of natural contaminants, using techniques commonly practiced in the art. Such a preparation is then introduced into an animal in order to produce polyclonal antisera of greater specific activity for the expressed and isolated polypeptide.

In one aspect, the antibodies of the invention are monoclonal antibodies (or protein binding fragments thereof). Cells expressing the biomarker polypeptide can be cultured in any suitable tissue culture medium, however, it is preferable to culture cells in Earle's modified Eagle's medium supplemented to contain 10% fetal bovine serum (inactivated at about 56° C.), and supplemented to contain about 10 g/l nonessential amino acids, about 1,00 U/ml penicillin, and about 100 µg/ml streptomycin.

The splenocytes of immunized (and boosted) mice can be extracted and fused with a suitable myeloma cell line. Any suitable myeloma cell line can be employed in accordance with the invention, however, it is preferable to employ the parent myeloma cell line (SP2/0), available from the ATCC. After fusion, the resulting hybridoma cells are selectively maintained in HAT medium, and then cloned by limiting dilution as described by Wands et al. (1981, Gastroenterology, 80:225-232). The hybridoma cells obtained through such a selection are then assayed to identify those cell clones that secrete antibodies capable of binding to the polypeptide immunogen, or a portion thereof.

Alternatively, additional antibodies capable of binding to the biomarker polypeptide can be produced in a two-step procedure using anti-idiotypic antibodies. Such a method makes use of the fact that antibodies are themselves antigens and, therefore, it is possible to obtain an antibody that binds to a second antibody. In accordance with this method, protein specific antibodies can be used to immunize an animal, preferably a mouse. The splenocytes of such an immunized animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce the formation of further protein-specific antibodies.

Example 3

Immunofluorescence Assays

The following immunofluorescence protocol may be used, for example, to verify IGF1R biomarker protein expression on cells or, for example, to check for the presence of one or more antibodies that bind IGF1R biomarkers expressed on the surface of cells. Briefly, Lab-Tek II chamber slides are coated overnight at 4° C. with 10 micrograms/milliliter (µg/ml) of bovine collagen Type II in DPBS containing calcium and magnesium (DPBS++). The slides are then washed twice with cold DPBS++ and seeded with 8000 CHO-CCR5 or CHO pC4 transfected cells in a total volume of 125 µl and incubated at 37° C. in the presence of 95% oxygen/5% carbon dioxide.

The culture medium is gently removed by aspiration and the adherent cells are washed twice with DPBS++ at ambient temperature. The slides are blocked with DPBS++ containing 0.2% BSA (blocker) at 0-4° C. for one hour. The blocking solution is gently removed by aspiration, and 125 µl of antibody containing solution (an antibody containing solution may be, for example, a hybridoma culture supernatant which is usually used undiluted, or serum/plasma which is usually diluted, e.g., a dilution of about 1/100 dilution). The slides are incubated for 1 hour at 0-4° C. Antibody solutions are then gently removed by aspiration and the cells are washed five times with 400 µl of ice cold blocking solution. Next, 125 µl of 1 μg/ml rhodamine labeled secondary antibody (e.g., anti-human IgG) in blocker solution is added to the cells. Again, cells are incubated for 1 hour at 0-4° C.

The secondary antibody solution is then gently removed by aspiration and the cells are washed three times with 400 μl of ice cold blocking solution, and five times with cold DPBS++. The cells are then fixed with 125 μl of 3.7% formaldehyde in DPBS++ for 15 minutes at ambient temperature. Thereafter, the cells are washed five times with 400 μl of DPBS++ at ambient temperature. Finally, the cells are mounted in 50% aqueous glycerol and viewed in a fluorescence microscope using rhodamine filters.

What is claimed is:

1. A method for predicting the likelihood a patient will respond therapeutically to a method of treating cancer comprising administering an IGF1R inhibitor, said method comprises:
   (a) measuring the expression level of the IGFBP6 biomarker in a biological cancer sample of said patient;
   (b) determining whether said sample has an increased level of said biomarker in said cancer sample that is at least 2-fold higher relative to a predetermined level of said biomarker,
   (c) classifying said patient as having an increased likelihood of responding therapeutically to said method of treating cancer if said patient has a decreased level of said biomarker,
   and
   (d) administering (2S)-1-(4-(5-cyclopropyl-1H-pyrazol-3-yl)amino)pyrrolo[2,1-f][1,2,4]triazin-2-yl)-N-(6-fluoro-3-pyridinyl)-2-methyl-2-pyrrolidinecarboxamide to said patient.

2. The method of claim 1 further comprising the measurement of at least one additional biomarker selected from Table 2.

3. The method of claim 1 wherein said biological sample is a tissue sample comprising cancer cells and said tissue is fixed, paraffin-embedded, fresh, or frozen.

4. A method for predicting the likelihood a patient will respond therapeutically to a method of treating cancer comprising administering an IGF1R inhibitor, said method comprises:
   (a) measuring the expression level of the IGFBP6 biomarker in a cancer sample of said patient;
   (b) administering an IGF1R inhibitor to said patient;
   (c) following the administering step (b), measuring in said sample of said patient the expression level of said biomarker, and
   (d) classifying said patient as having a decreased likelihood of responding therapeutically to said method of treating cancer if said patient has an increased level of said biomarker measured in step (c) that is at least 2-fold higher than the level of said biomarker measured in step (a), wherein said IGF1R inhibitor is (2S)-1-(4-((5-cyclopropyl-1H-pyrazol-3-yl)amino)pyrrolo[2,1-f][1,2,4]triazin-2-yl)-N-(6-fluoro-3-pyridinyl)-2-methyl-2-pyrrolidinecarboxamide.

5. The method according to claim 4, further comprising the step of selecting the optimal dose of said IGF1R inhibitor to achieve a therapeutic response.

6. The method according to claim 4, further comprising the step of administering said IGF1R inhibitor in combination with another agent to achieve a therapeutic response.

7. The method according to claim 6, wherein said other agent is an EGFR inhibitor.

* * * * *

UNITED STATES PATENT AND TRADEMARK OFFICE
CERTIFICATE OF CORRECTION

| | |
|---|---|
| PATENT NO. | : 8,492,328 B2 |
| APPLICATION NO. | : 12/600504 |
| DATED | : July 23, 2013 |
| INVENTOR(S) | : Fei Huang et al. |

It is certified that error appears in the above-identified patent and that said Letters Patent is hereby corrected as shown below:

In the Claims:

Claim 1:

Column 381, line 18, change "(d) administering (2S)-1-(4-(5-cyclopropyl-1H-pyrazol-3-" to -- (d) administering (2S)-1-(4-((5-cyclopropyl-1H-pyrazol-3- --.

Signed and Sealed this
Fourth Day of February, 2014

Michelle K. Lee
*Deputy Director of the United States Patent and Trademark Office*

SEQUENCE LISTING

```
<160> NUMBER OF SEQ ID NOS: 286

<210> SEQ ID NO 1
<211> LENGTH: 12
<212> TYPE: PRT
<213> ORGANISM: Homo Sapiens

<400> SEQUENCE: 1

Val Gly Trp Glu Gln Leu Leu Thr Thr Ile Ala Arg
1               5                   10

<210> SEQ ID NO 2
<211> LENGTH: 14
<212> TYPE: PRT
<213> ORGANISM: Homo Sapiens

<400> SEQUENCE: 2

Phe Ala Ile Gln Asp Ile Ser Val Glu Glu Thr Ser Ala Lys
1               5                   10

<210> SEQ ID NO 3
<211> LENGTH: 12
<212> TYPE: PRT
<213> ORGANISM: Homo Sapiens

<400> SEQUENCE: 3

Thr Ile Asn Glu Val Glu Asn Gln Ile Leu Thr Arg
1               5                   10

<210> SEQ ID NO 4
<211> LENGTH: 11
<212> TYPE: PRT
<213> ORGANISM: Homo Sapiens

<400> SEQUENCE: 4

Asp Tyr Glu Thr Ala Thr Leu Ser Asp Ile Lys
1               5                   10

<210> SEQ ID NO 5
<211> LENGTH: 9
<212> TYPE: PRT
<213> ORGANISM: Homo Sapiens

<400> SEQUENCE: 5

Val Pro Gly Ile Asp Ala Thr Thr Lys
1               5

<210> SEQ ID NO 6
<211> LENGTH: 12
<212> TYPE: PRT
<213> ORGANISM: Homo Sapiens

<400> SEQUENCE: 6

Gly Glu Gly Pro Glu Val Asp Val Asn Leu Pro Lys
1               5                   10

<210> SEQ ID NO 7
```

```
<211> LENGTH: 7
<212> TYPE: PRT
<213> ORGANISM: Homo Sapiens

<400> SEQUENCE: 7

Phe Ser Met Pro Gly Phe Lys
1               5

<210> SEQ ID NO 8
<211> LENGTH: 19
<212> TYPE: PRT
<213> ORGANISM: Homo Sapiens

<400> SEQUENCE: 8

Ile Gly Phe Ser Gly Pro Lys Leu Glu Gly Gly Glu Val Asp Leu Lys
1               5                   10                  15

Gly Pro Lys

<210> SEQ ID NO 9
<211> LENGTH: 11
<212> TYPE: PRT
<213> ORGANISM: Homo Sapiens

<400> SEQUENCE: 9

Ile Ser Met Pro Asp Phe Asp Leu His Leu Lys
1               5                   10

<210> SEQ ID NO 10
<211> LENGTH: 11
<212> TYPE: PRT
<213> ORGANISM: Homo Sapiens

<400> SEQUENCE: 10

Ile Ser Met Pro Asp Ile Asp Leu Asn Leu Lys
1               5                   10

<210> SEQ ID NO 11
<211> LENGTH: 21
<212> TYPE: PRT
<213> ORGANISM: Homo Sapiens

<400> SEQUENCE: 11

Gly Glu Gly Pro Asp Val His Met Thr Leu Pro Lys Gly Asp Ile Ser
1               5                   10                  15

Ile Ser Gly Pro Lys
            20

<210> SEQ ID NO 12
<211> LENGTH: 14
<212> TYPE: PRT
<213> ORGANISM: Homo Sapiens

<400> SEQUENCE: 12

Ser Met Ser Thr Val Ile Arg Asn Pro Asn Gly Gly Phe Arg
1               5                   10

<210> SEQ ID NO 13
<211> LENGTH: 16
<212> TYPE: PRT
<213> ORGANISM: Homo Sapiens

<400> SEQUENCE: 13

Thr Ser Pro Val Glu Gly Leu Ser Gly Asn Pro Ala Asp Leu Glu Lys
1               5                   10                  15
```

```
<210> SEQ ID NO 14
<211> LENGTH: 13
<212> TYPE: PRT
<213> ORGANISM: Homo Sapiens

<400> SEQUENCE: 14

Pro Ala Asp Gly Ile Leu Ile Gln Gly Asn Asp Leu Lys
1               5                   10

<210> SEQ ID NO 15
<211> LENGTH: 12
<212> TYPE: PRT
<213> ORGANISM: Homo Sapiens

<400> SEQUENCE: 15

Thr Ile Ala Met Asp Gly Thr Glu Gly Leu Val Arg
1               5                   10

<210> SEQ ID NO 16
<211> LENGTH: 13
<212> TYPE: PRT
<213> ORGANISM: Homo Sapiens

<400> SEQUENCE: 16

Ser Met Val Ala Val Met Asp Ser Asp Thr Thr Gly Lys
1               5                   10

<210> SEQ ID NO 17
<211> LENGTH: 13
<212> TYPE: PRT
<213> ORGANISM: Homo Sapiens

<400> SEQUENCE: 17

Phe Cys Thr Gly Leu Thr Gln Ile Glu Thr Leu Phe Lys
1               5                   10

<210> SEQ ID NO 18
<211> LENGTH: 12
<212> TYPE: PRT
<213> ORGANISM: Homo Sapiens

<400> SEQUENCE: 18

Gly Val Thr Phe Asn Val Thr Thr Val Asp Thr Lys
1               5                   10

<210> SEQ ID NO 19
<211> LENGTH: 8
<212> TYPE: PRT
<213> ORGANISM: Homo Sapiens

<400> SEQUENCE: 19

Val Gly Glu Val Ile Val Thr Lys
1               5

<210> SEQ ID NO 20
<211> LENGTH: 6
<212> TYPE: PRT
<213> ORGANISM: Homo Sapiens

<400> SEQUENCE: 20

Thr Leu Ala Val Glu Arg
1               5

<210> SEQ ID NO 21
<211> LENGTH: 12
```

```
<212> TYPE: PRT
<213> ORGANISM: Homo Sapiens

<400> SEQUENCE: 21

His Val Asn Pro Val Gln Ala Leu Ser Glu Phe Lys
1               5                   10

<210> SEQ ID NO 22
<211> LENGTH: 11
<212> TYPE: PRT
<213> ORGANISM: Homo Sapiens

<400> SEQUENCE: 22

Tyr Ala Leu Tyr Asp Ala Ser Phe Glu Thr Lys
1               5                   10

<210> SEQ ID NO 23
<211> LENGTH: 11
<212> TYPE: PRT
<213> ORGANISM: Homo Sapiens

<400> SEQUENCE: 23

Val Gly Glu Thr Ile Ile Asp Leu Glu Asn Arg
1               5                   10

<210> SEQ ID NO 24
<211> LENGTH: 8
<212> TYPE: PRT
<213> ORGANISM: Homo Sapiens

<400> SEQUENCE: 24

Gly Asp Tyr Val Leu Ala Val Lys
1               5

<210> SEQ ID NO 25
<211> LENGTH: 12
<212> TYPE: PRT
<213> ORGANISM: Homo Sapiens

<400> SEQUENCE: 25

Ser Ser Leu His Tyr Lys Pro Thr Pro Asp Leu Arg
1               5                   10

<210> SEQ ID NO 26
<211> LENGTH: 7
<212> TYPE: PRT
<213> ORGANISM: Homo Sapiens

<400> SEQUENCE: 26

Glu Ile Gln Thr Ala Val Arg
1               5

<210> SEQ ID NO 27
<211> LENGTH: 7
<212> TYPE: PRT
<213> ORGANISM: Homo Sapiens

<400> SEQUENCE: 27

Glu Ile Ala Gln Asp Phe Lys
1               5

<210> SEQ ID NO 28
<211> LENGTH: 7
<212> TYPE: PRT
<213> ORGANISM: Homo Sapiens
```

```
<400> SEQUENCE: 28

Thr Leu Tyr Gly Phe Gly Gly
1               5

<210> SEQ ID NO 29
<211> LENGTH: 10
<212> TYPE: PRT
<213> ORGANISM: Homo Sapiens

<400> SEQUENCE: 29

Asp Ala Val Thr Tyr Thr Glu His Ala Lys
1               5                   10

<210> SEQ ID NO 30
<211> LENGTH: 9
<212> TYPE: PRT
<213> ORGANISM: Homo Sapiens

<400> SEQUENCE: 30

Tyr Arg Pro Gly Thr Val Ala Leu Arg
1               5

<210> SEQ ID NO 31
<211> LENGTH: 14
<212> TYPE: PRT
<213> ORGANISM: Homo Sapiens

<400> SEQUENCE: 31

Lys His Pro Asp Ala Ser Val Asn Phe Ser Glu Phe Ser Lys
1               5                   10

<210> SEQ ID NO 32
<211> LENGTH: 11
<212> TYPE: PRT
<213> ORGANISM: Homo Sapiens

<400> SEQUENCE: 32

Leu Gly Glu Met Trp Ser Glu Gln Ser Ala Lys
1               5                   10

<210> SEQ ID NO 33
<211> LENGTH: 12
<212> TYPE: PRT
<213> ORGANISM: Homo Sapiens

<400> SEQUENCE: 33

Met Ser Ser Tyr Ala Phe Phe Val Gln Thr Cys Arg
1               5                   10

<210> SEQ ID NO 34
<211> LENGTH: 10
<212> TYPE: PRT
<213> ORGANISM: Homo Sapiens

<400> SEQUENCE: 34

Ile Asp Thr Ile Glu Ile Ile Thr Asp Arg
1               5                   10

<210> SEQ ID NO 35
<211> LENGTH: 8
<212> TYPE: PRT
<213> ORGANISM: Homo Sapiens

<400> SEQUENCE: 35

Leu Thr Asp Cys Val Val Met Arg
```

```
1               5

<210> SEQ ID NO 36
<211> LENGTH: 14
<212> TYPE: PRT
<213> ORGANISM: Homo Sapiens

<400> SEQUENCE: 36

Ile Phe Val Gly Gly Leu Ser Pro Asp Thr Pro Glu Glu Lys
1               5                   10

<210> SEQ ID NO 37
<211> LENGTH: 18
<212> TYPE: PRT
<213> ORGANISM: Homo Sapiens

<400> SEQUENCE: 37

Asn Gln Gly Gly Tyr Gly Gly Ser Ser Ser Ser Ser Tyr Gly Ser
1               5                   10                  15

Gly Arg

<210> SEQ ID NO 38
<211> LENGTH: 13
<212> TYPE: PRT
<213> ORGANISM: Homo Sapiens

<400> SEQUENCE: 38

Glu Asp Ser Gln Arg Pro Gly Ala His Leu Thr Val Lys
1               5                   10

<210> SEQ ID NO 39
<211> LENGTH: 15
<212> TYPE: PRT
<213> ORGANISM: Homo Sapiens

<400> SEQUENCE: 39

Gly Phe Gly Phe Val Thr Phe Asp Asp His Asp Pro Val Asp Lys
1               5                   10                  15

<210> SEQ ID NO 40
<211> LENGTH: 12
<212> TYPE: PRT
<213> ORGANISM: Homo Sapiens

<400> SEQUENCE: 40

Met Phe Ile Gly Gly Leu Ser Trp Asp Thr Thr Lys
1               5                   10

<210> SEQ ID NO 41
<211> LENGTH: 8
<212> TYPE: PRT
<213> ORGANISM: Homo Sapiens

<400> SEQUENCE: 41

Gly Phe Gly Phe Val Leu Phe Lys
1               5

<210> SEQ ID NO 42
<211> LENGTH: 12
<212> TYPE: PRT
<213> ORGANISM: Homo Sapiens

<400> SEQUENCE: 42

Ile Ile Leu Asp Leu Ile Ser Glu Ser Pro Ile Lys
1               5                   10
```

```
<210> SEQ ID NO 43
<211> LENGTH: 11
<212> TYPE: PRT
<213> ORGANISM: Homo Sapiens

<400> SEQUENCE: 43

Ala Phe Ile Thr Asn Ile Pro Phe Asp Val Lys
1               5                   10

<210> SEQ ID NO 44
<211> LENGTH: 20
<212> TYPE: PRT
<213> ORGANISM: Homo Sapiens

<400> SEQUENCE: 44

Asp Ser Leu Asp Pro Ser Phe Thr His Ala Met Gln Leu Leu Thr Ala
1               5                   10                  15

Glu Ile Glu Lys
            20

<210> SEQ ID NO 45
<211> LENGTH: 11
<212> TYPE: PRT
<213> ORGANISM: Homo Sapiens

<400> SEQUENCE: 45

Tyr Pro His Ile Lys Asp Gly Glu Asp Leu Lys
1               5                   10

<210> SEQ ID NO 46
<211> LENGTH: 11
<212> TYPE: PRT
<213> ORGANISM: Homo Sapiens

<400> SEQUENCE: 46

Ser Asn Thr Glu Asn Leu Ser Gln His Phe Arg
1               5                   10

<210> SEQ ID NO 47
<211> LENGTH: 12
<212> TYPE: PRT
<213> ORGANISM: Homo Sapiens

<400> SEQUENCE: 47

Met Lys Ser Gln Ala Phe Ile Glu Met Glu Thr Arg
1               5                   10

<210> SEQ ID NO 48
<211> LENGTH: 21
<212> TYPE: PRT
<213> ORGANISM: Homo Sapiens

<400> SEQUENCE: 48

Tyr Gln Leu Leu Gln Leu Val Glu Pro Phe Gly Val Ile Ser Asn His
1               5                   10                  15

Leu Ile Leu Asn Lys
            20

<210> SEQ ID NO 49
<211> LENGTH: 25
<212> TYPE: PRT
<213> ORGANISM: Homo Sapiens

<400> SEQUENCE: 49
```

```
Asp Leu Ser Ala Ala Gly Ile Gly Leu Leu Ala Ala Ala Thr Gln Ser
1               5                   10                  15

Leu Ser Met Pro Ala Ser Leu Gly Arg
            20                  25

<210> SEQ ID NO 50
<211> LENGTH: 7
<212> TYPE: PRT
<213> ORGANISM: Homo Sapiens

<400> SEQUENCE: 50

Val Val Phe Gln Glu Phe Arg
1               5

<210> SEQ ID NO 51
<211> LENGTH: 16
<212> TYPE: PRT
<213> ORGANISM: Homo Sapiens

<400> SEQUENCE: 51

Leu Gln Gln Glu Leu Asp Asp Leu Leu Val Asp Leu Asp His Gln Arg
1               5                   10                  15

<210> SEQ ID NO 52
<211> LENGTH: 14
<212> TYPE: PRT
<213> ORGANISM: Homo Sapiens

<400> SEQUENCE: 52

Val Ile Ser Gly Val Leu Gln Leu Gly Asn Ile Val Phe Lys
1               5                   10

<210> SEQ ID NO 53
<211> LENGTH: 11
<212> TYPE: PRT
<213> ORGANISM: Homo Sapiens

<400> SEQUENCE: 53

Leu Asp Pro His Leu Val Leu Asp Gln Leu Arg
1               5                   10

<210> SEQ ID NO 54
<211> LENGTH: 9
<212> TYPE: PRT
<213> ORGANISM: Homo Sapiens

<400> SEQUENCE: 54

His Val Leu Val Thr Leu Gly Glu Lys
1               5

<210> SEQ ID NO 55
<211> LENGTH: 9
<212> TYPE: PRT
<213> ORGANISM: Homo Sapiens

<400> SEQUENCE: 55

Glu Leu Leu Thr Thr Met Gly Asp Arg
1               5

<210> SEQ ID NO 56
<211> LENGTH: 8
<212> TYPE: PRT
<213> ORGANISM: Homo Sapiens

<400> SEQUENCE: 56
```

```
Glu Ala Phe Gln Leu Phe Asp Arg
1               5
```

<210> SEQ ID NO 57
<211> LENGTH: 18
<212> TYPE: PRT
<213> ORGANISM: Homo Sapiens

<400> SEQUENCE: 57

```
Asp Gly Phe Ile Asp Lys Glu Asp Leu His Asp Met Leu Ala Ser Leu
1               5                   10                  15

Gly Lys
```

<210> SEQ ID NO 58
<211> LENGTH: 14
<212> TYPE: PRT
<213> ORGANISM: Homo Sapiens

<400> SEQUENCE: 58

```
Ile Ala Glu Phe Thr Thr Asn Leu Thr Glu Glu Glu Glu Lys
1               5                   10
```

<210> SEQ ID NO 59
<211> LENGTH: 16
<212> TYPE: PRT
<213> ORGANISM: Homo Sapiens

<400> SEQUENCE: 59

```
Val Leu Asp Phe Glu His Phe Leu Pro Met Leu Gln Thr Val Ala Lys
1               5                   10                  15
```

<210> SEQ ID NO 60
<211> LENGTH: 9
<212> TYPE: PRT
<213> ORGANISM: Homo Sapiens

<400> SEQUENCE: 60

```
Ile Val Val Val Thr Ala Gly Val Arg
1               5
```

<210> SEQ ID NO 61
<211> LENGTH: 15
<212> TYPE: PRT
<213> ORGANISM: Homo Sapiens

<400> SEQUENCE: 61

```
Ala Met Gly Ile Met Asn Ser Phe Val Asn Asp Ile Phe Glu Arg
1               5                   10                  15
```

<210> SEQ ID NO 62
<211> LENGTH: 7
<212> TYPE: PRT
<213> ORGANISM: Homo Sapiens

<400> SEQUENCE: 62

```
Phe Asp Leu Met Tyr Ala Lys
1               5
```

<210> SEQ ID NO 63
<211> LENGTH: 6
<212> TYPE: PRT
<213> ORGANISM: Homo Sapiens

<400> SEQUENCE: 63

```
Met Tyr Ala Val Tyr Lys
1               5

<210> SEQ ID NO 64
<211> LENGTH: 13
<212> TYPE: PRT
<213> ORGANISM: Homo Sapiens

<400> SEQUENCE: 64

Ile Ile Thr Leu Thr Gly Pro Thr Asn Ala Ile Phe Lys
1               5                   10

<210> SEQ ID NO 65
<211> LENGTH: 9
<212> TYPE: PRT
<213> ORGANISM: Homo Sapiens

<400> SEQUENCE: 65

Leu Pro Phe Pro Ile Ile Asp Asp Arg
1               5

<210> SEQ ID NO 66
<211> LENGTH: 6
<212> TYPE: PRT
<213> ORGANISM: Homo Sapiens

<400> SEQUENCE: 66

Thr Phe Ala Leu His Lys
1               5

<210> SEQ ID NO 67
<211> LENGTH: 11
<212> TYPE: PRT
<213> ORGANISM: Homo Sapiens

<400> SEQUENCE: 67

Tyr Ala Asn Val Ile Ala Tyr Asp His Ser Arg
1               5                   10

<210> SEQ ID NO 68
<211> LENGTH: 9
<212> TYPE: PRT
<213> ORGANISM: Homo Sapiens

<400> SEQUENCE: 68

Lys Ala Leu Glu Leu Asp Gln Glu Arg
1               5

<210> SEQ ID NO 69
<211> LENGTH: 10
<212> TYPE: PRT
<213> ORGANISM: Homo Sapiens

<400> SEQUENCE: 69

Lys Glu Asn Pro Leu Gln Phe Lys Phe Arg
1               5                   10

<210> SEQ ID NO 70
<211> LENGTH: 17
<212> TYPE: PRT
<213> ORGANISM: Homo Sapiens

<400> SEQUENCE: 70

Leu Phe Val Gly Asn Leu Pro Ala Asp Ile Thr Glu Asp Glu Phe Lys
1               5                   10                  15
```

Arg

<210> SEQ ID NO 71
<211> LENGTH: 7
<212> TYPE: PRT
<213> ORGANISM: Homo Sapiens

<400> SEQUENCE: 71

Ala Leu Ala Val Glu Gly Lys
1               5

<210> SEQ ID NO 72
<211> LENGTH: 13
<212> TYPE: PRT
<213> ORGANISM: Homo Sapiens

<400> SEQUENCE: 72

Ala Ala Met Arg Glu Thr Trp Leu Ser Glu Asn Gln Arg
1               5                   10

<210> SEQ ID NO 73
<211> LENGTH: 9
<212> TYPE: PRT
<213> ORGANISM: Homo Sapiens

<400> SEQUENCE: 73

Asp Leu Ser Leu Glu Glu Ile Gln Lys
1               5

<210> SEQ ID NO 74
<211> LENGTH: 15
<212> TYPE: PRT
<213> ORGANISM: Homo Sapiens

<400> SEQUENCE: 74

Thr Leu Asn Gln Leu Gly Thr Pro Gln Asp Ser Pro Glu Leu Arg
1               5                   10                  15

<210> SEQ ID NO 75
<211> LENGTH: 13
<212> TYPE: PRT
<213> ORGANISM: Homo Sapiens

<400> SEQUENCE: 75

Tyr Gly Val Asn Pro Gly Pro Ile Val Gly Thr Thr Arg
1               5                   10

<210> SEQ ID NO 76
<211> LENGTH: 19
<212> TYPE: PRT
<213> ORGANISM: Homo Sapiens

<400> SEQUENCE: 76

Ile Lys Ile Tyr Glu Phe Pro Glu Thr Asp Asp Glu Glu Glu Asn Lys
1               5                   10                  15

Leu Val Lys

<210> SEQ ID NO 77
<211> LENGTH: 12
<212> TYPE: PRT
<213> ORGANISM: Homo Sapiens

<400> SEQUENCE: 77

Val Gly Trp Glu Gln Leu Leu Thr Thr Ile Ala Arg
1               5                   10

<210> SEQ ID NO 78
<211> LENGTH: 14
<212> TYPE: PRT
<213> ORGANISM: Homo Sapiens

<400> SEQUENCE: 78

Phe Ala Ile Gln Asp Ile Ser Val Glu Glu Thr Ser Ala Lys
1               5                   10

<210> SEQ ID NO 79
<211> LENGTH: 12
<212> TYPE: PRT
<213> ORGANISM: Homo Sapiens

<400> SEQUENCE: 79

Thr Ile Asn Glu Val Glu Asn Gln Ile Leu Thr Arg
1               5                   10

<210> SEQ ID NO 80
<211> LENGTH: 11
<212> TYPE: PRT
<213> ORGANISM: Homo Sapiens

<400> SEQUENCE: 80

Arg Asp Gln Ala Leu Thr Glu Glu His Ala Arg
1               5                   10

<210> SEQ ID NO 81
<211> LENGTH: 11
<212> TYPE: PRT
<213> ORGANISM: Homo Sapiens

<400> SEQUENCE: 81

Asp Tyr Glu Thr Ala Thr Leu Ser Asp Ile Lys
1               5                   10

<210> SEQ ID NO 82
<211> LENGTH: 13
<212> TYPE: PRT
<213> ORGANISM: Homo Sapiens

<400> SEQUENCE: 82

Ile Ser Asn Arg Pro Ala Phe Met Pro Ser Glu Gly Lys
1               5                   10

<210> SEQ ID NO 83
<211> LENGTH: 9
<212> TYPE: PRT
<213> ORGANISM: Homo Sapiens

<400> SEQUENCE: 83

Val Pro Gly Ile Asp Ala Thr Thr Lys
1               5

<210> SEQ ID NO 84
<211> LENGTH: 12
<212> TYPE: PRT
<213> ORGANISM: Homo Sapiens

<400> SEQUENCE: 84

Gly Glu Gly Pro Glu Val Asp Val Asn Leu Pro Lys
1               5                   10

<210> SEQ ID NO 85

```
<211> LENGTH: 7
<212> TYPE: PRT
<213> ORGANISM: Homo Sapiens

<400> SEQUENCE: 85

Phe Ser Met Pro Gly Phe Lys
1               5

<210> SEQ ID NO 86
<211> LENGTH: 19
<212> TYPE: PRT
<213> ORGANISM: Homo Sapiens

<400> SEQUENCE: 86

Ile Gly Phe Ser Gly Pro Lys Leu Glu Gly Glu Val Asp Leu Lys
1               5                   10                  15

Gly Pro Lys

<210> SEQ ID NO 87
<211> LENGTH: 11
<212> TYPE: PRT
<213> ORGANISM: Homo Sapiens

<400> SEQUENCE: 87

Ile Ser Met Pro Asp Phe Asp Leu His Leu Lys
1               5                   10

<210> SEQ ID NO 88
<211> LENGTH: 11
<212> TYPE: PRT
<213> ORGANISM: Homo Sapiens

<400> SEQUENCE: 88

Ile Ser Met Pro Asp Ile Asp Leu Asn Leu Lys
1               5                   10

<210> SEQ ID NO 89
<211> LENGTH: 21
<212> TYPE: PRT
<213> ORGANISM: Homo Sapiens

<400> SEQUENCE: 89

Gly Glu Gly Pro Asp Val His Met Thr Leu Pro Lys Gly Asp Ile Ser
1               5                   10                  15

Ile Ser Gly Pro Lys
            20

<210> SEQ ID NO 90
<211> LENGTH: 11
<212> TYPE: PRT
<213> ORGANISM: Homo Sapiens

<400> SEQUENCE: 90

Gly Asp Leu Asp Ala Ser Val Pro Ser Met Lys
1               5                   10

<210> SEQ ID NO 91
<211> LENGTH: 16
<212> TYPE: PRT
<213> ORGANISM: Homo Sapiens

<400> SEQUENCE: 91

Thr Ser Pro Val Glu Gly Leu Ser Gly Asn Pro Ala Asp Leu Glu Lys
1               5                   10                  15
```

-continued

<210> SEQ ID NO 92
<211> LENGTH: 13
<212> TYPE: PRT
<213> ORGANISM: Homo Sapiens

<400> SEQUENCE: 92

Pro Ala Asp Gly Ile Leu Ile Gln Gly Asn Asp Leu Lys
1               5                   10

<210> SEQ ID NO 93
<211> LENGTH: 12
<212> TYPE: PRT
<213> ORGANISM: Homo Sapiens

<400> SEQUENCE: 93

Thr Ile Ala Met Asp Gly Thr Glu Gly Leu Val Arg
1               5                   10

<210> SEQ ID NO 94
<211> LENGTH: 13
<212> TYPE: PRT
<213> ORGANISM: Homo Sapiens

<400> SEQUENCE: 94

Phe Cys Thr Gly Leu Thr Gln Ile Glu Thr Leu Phe Lys
1               5                   10

<210> SEQ ID NO 95
<211> LENGTH: 12
<212> TYPE: PRT
<213> ORGANISM: Homo Sapiens

<400> SEQUENCE: 95

Gly Val Thr Phe Asn Val Thr Val Asp Thr Lys
1               5                   10

<210> SEQ ID NO 96
<211> LENGTH: 12
<212> TYPE: PRT
<213> ORGANISM: Homo Sapiens

<400> SEQUENCE: 96

His Val Asn Pro Val Gln Ala Leu Ser Glu Phe Lys
1               5                   10

<210> SEQ ID NO 97
<211> LENGTH: 11
<212> TYPE: PRT
<213> ORGANISM: Homo Sapiens

<400> SEQUENCE: 97

Tyr Ala Leu Tyr Asp Ala Ser Phe Glu Thr Lys
1               5                   10

<210> SEQ ID NO 98
<211> LENGTH: 11
<212> TYPE: PRT
<213> ORGANISM: Homo Sapiens

<400> SEQUENCE: 98

Val Gly Glu Thr Ile Ile Asp Leu Glu Asn Arg
1               5                   10

<210> SEQ ID NO 99
<211> LENGTH: 8

```
<212> TYPE: PRT
<213> ORGANISM: Homo Sapiens

<400> SEQUENCE: 99

Gly Asp Tyr Val Leu Ala Val Lys
1               5

<210> SEQ ID NO 100
<211> LENGTH: 12
<212> TYPE: PRT
<213> ORGANISM: Homo Sapiens

<400> SEQUENCE: 100

Ser Ser Leu His Tyr Lys Pro Thr Pro Asp Leu Arg
1               5                   10

<210> SEQ ID NO 101
<211> LENGTH: 9
<212> TYPE: PRT
<213> ORGANISM: Homo Sapiens

<400> SEQUENCE: 101

Glu Ser Tyr Ser Val Tyr Val Tyr Lys
1               5

<210> SEQ ID NO 102
<211> LENGTH: 9
<212> TYPE: PRT
<213> ORGANISM: Homo Sapiens

<400> SEQUENCE: 102

Tyr Arg Pro Gly Thr Val Ala Leu Arg
1               5

<210> SEQ ID NO 103
<211> LENGTH: 14
<212> TYPE: PRT
<213> ORGANISM: Homo Sapiens

<400> SEQUENCE: 103

Lys His Pro Asp Ala Ser Val Asn Phe Ser Glu Phe Ser Lys
1               5                   10

<210> SEQ ID NO 104
<211> LENGTH: 12
<212> TYPE: PRT
<213> ORGANISM: Homo Sapiens

<400> SEQUENCE: 104

Met Ser Ser Tyr Ala Phe Phe Val Gln Thr Cys Arg
1               5                   10

<210> SEQ ID NO 105
<211> LENGTH: 8
<212> TYPE: PRT
<213> ORGANISM: Homo Sapiens

<400> SEQUENCE: 105

Leu Thr Asp Cys Val Val Met Arg
1               5

<210> SEQ ID NO 106
<211> LENGTH: 18
<212> TYPE: PRT
<213> ORGANISM: Homo Sapiens
```

```
<400> SEQUENCE: 106

Asn Gln Gly Gly Tyr Gly Gly Ser Ser Ser Ser Ser Tyr Gly Ser
1               5                   10                  15

Gly Arg

<210> SEQ ID NO 107
<211> LENGTH: 13
<212> TYPE: PRT
<213> ORGANISM: Homo Sapiens

<400> SEQUENCE: 107

Glu Asp Ser Gln Arg Pro Gly Ala His Leu Thr Val Lys
1               5                   10

<210> SEQ ID NO 108
<211> LENGTH: 15
<212> TYPE: PRT
<213> ORGANISM: Homo Sapiens

<400> SEQUENCE: 108

Gly Phe Gly Phe Val Thr Phe Asp Asp His Asp Pro Val Asp Lys
1               5                   10                  15

<210> SEQ ID NO 109
<211> LENGTH: 8
<212> TYPE: PRT
<213> ORGANISM: Homo Sapiens

<400> SEQUENCE: 109

Gly Phe Gly Phe Val Leu Phe Lys
1               5

<210> SEQ ID NO 110
<211> LENGTH: 12
<212> TYPE: PRT
<213> ORGANISM: Homo Sapiens

<400> SEQUENCE: 110

Ile Ile Leu Asp Leu Ile Ser Glu Ser Pro Ile Lys
1               5                   10

<210> SEQ ID NO 111
<211> LENGTH: 11
<212> TYPE: PRT
<213> ORGANISM: Homo Sapiens

<400> SEQUENCE: 111

Ala Phe Ile Thr Asn Ile Pro Phe Asp Val Lys
1               5                   10

<210> SEQ ID NO 112
<211> LENGTH: 20
<212> TYPE: PRT
<213> ORGANISM: Homo Sapiens

<400> SEQUENCE: 112

Asp Ser Leu Asp Pro Ser Phe Thr His Ala Met Gln Leu Leu Thr Ala
1               5                   10                  15

Glu Ile Glu Lys
            20

<210> SEQ ID NO 113
<211> LENGTH: 11
<212> TYPE: PRT
```

<213> ORGANISM: Homo Sapiens

<400> SEQUENCE: 113

Tyr Pro His Ile Lys Asp Gly Glu Asp Leu Lys
1               5                   10

<210> SEQ ID NO 114
<211> LENGTH: 11
<212> TYPE: PRT
<213> ORGANISM: Homo Sapiens

<400> SEQUENCE: 114

Ser Asn Thr Glu Asn Leu Ser Gln His Phe Arg
1               5                   10

<210> SEQ ID NO 115
<211> LENGTH: 12
<212> TYPE: PRT
<213> ORGANISM: Homo Sapiens

<400> SEQUENCE: 115

Met Lys Ser Gln Ala Phe Ile Glu Met Glu Thr Arg
1               5                   10

<210> SEQ ID NO 116
<211> LENGTH: 21
<212> TYPE: PRT
<213> ORGANISM: Homo Sapiens

<400> SEQUENCE: 116

Tyr Gln Leu Leu Gln Leu Val Glu Pro Phe Gly Val Ile Ser Asn His
1               5                   10                  15

Leu Ile Leu Asn Lys
            20

<210> SEQ ID NO 117
<211> LENGTH: 25
<212> TYPE: PRT
<213> ORGANISM: Homo Sapiens

<400> SEQUENCE: 117

Asp Leu Ser Ala Ala Gly Ile Gly Leu Leu Ala Ala Ala Thr Gln Ser
1               5                   10                  15

Leu Ser Met Pro Ala Ser Leu Gly Arg
            20                  25

<210> SEQ ID NO 118
<211> LENGTH: 7
<212> TYPE: PRT
<213> ORGANISM: Homo Sapiens

<400> SEQUENCE: 118

Val Val Phe Gln Glu Phe Arg
1               5

<210> SEQ ID NO 119
<211> LENGTH: 16
<212> TYPE: PRT
<213> ORGANISM: Homo Sapiens

<400> SEQUENCE: 119

Leu Gln Gln Glu Leu Asp Asp Leu Leu Val Asp Leu Asp His Gln Arg
1               5                   10                  15

```
<210> SEQ ID NO 120
<211> LENGTH: 14
<212> TYPE: PRT
<213> ORGANISM: Homo Sapiens

<400> SEQUENCE: 120

Val Ile Ser Gly Val Leu Gln Leu Gly Asn Ile Val Phe Lys
1               5                   10

<210> SEQ ID NO 121
<211> LENGTH: 11
<212> TYPE: PRT
<213> ORGANISM: Homo Sapiens

<400> SEQUENCE: 121

Leu Asp Pro His Leu Val Leu Asp Gln Leu Arg
1               5                   10

<210> SEQ ID NO 122
<211> LENGTH: 20
<212> TYPE: PRT
<213> ORGANISM: Homo Sapiens

<400> SEQUENCE: 122

Ile Val Gly Leu Asp Gln Val Thr Gly Met Thr Glu Thr Ala Phe Gly
1               5                   10                  15

Ser Ala Tyr Lys
            20

<210> SEQ ID NO 123
<211> LENGTH: 9
<212> TYPE: PRT
<213> ORGANISM: Homo Sapiens

<400> SEQUENCE: 123

His Val Leu Val Thr Leu Gly Glu Lys
1               5

<210> SEQ ID NO 124
<211> LENGTH: 8
<212> TYPE: PRT
<213> ORGANISM: Homo Sapiens

<400> SEQUENCE: 124

Glu Ala Phe Gln Leu Phe Asp Arg
1               5

<210> SEQ ID NO 125
<211> LENGTH: 9
<212> TYPE: PRT
<213> ORGANISM: Homo Sapiens

<400> SEQUENCE: 125

Ile Val Val Val Thr Ala Gly Val Arg
1               5

<210> SEQ ID NO 126
<211> LENGTH: 15
<212> TYPE: PRT
<213> ORGANISM: Homo Sapiens

<400> SEQUENCE: 126

Ala Met Gly Ile Met Asn Ser Phe Val Asn Asp Ile Phe Glu Arg
1               5                   10                  15
```

```
<210> SEQ ID NO 127
<211> LENGTH: 11
<212> TYPE: PRT
<213> ORGANISM: Homo Sapiens

<400> SEQUENCE: 127

Thr Pro Ala Gln Tyr Asp Ala Ser Glu Leu Lys
1               5                   10

<210> SEQ ID NO 128
<211> LENGTH: 12
<212> TYPE: PRT
<213> ORGANISM: Homo Sapiens

<400> SEQUENCE: 128

Ile Val Leu Asp Asn Ser Val Phe Ser Glu His Arg
1               5                   10

<210> SEQ ID NO 129
<211> LENGTH: 7
<212> TYPE: PRT
<213> ORGANISM: Homo Sapiens

<400> SEQUENCE: 129

Phe Asp Leu Met Tyr Ala Lys
1               5

<210> SEQ ID NO 130
<211> LENGTH: 11
<212> TYPE: PRT
<213> ORGANISM: Homo Sapiens

<400> SEQUENCE: 130

Leu Asp His Lys Phe Asp Leu Met Tyr Ala Lys
1               5                   10

<210> SEQ ID NO 131
<211> LENGTH: 11
<212> TYPE: PRT
<213> ORGANISM: Homo Sapiens

<400> SEQUENCE: 131

Glu Thr Gly Phe Ser His Ser Gln Ile Thr Arg
1               5                   10

<210> SEQ ID NO 132
<211> LENGTH: 11
<212> TYPE: PRT
<213> ORGANISM: Homo Sapiens

<400> SEQUENCE: 132

Ile Ser Arg Asp Glu Leu Leu Gln Val Leu Arg
1               5                   10

<210> SEQ ID NO 133
<211> LENGTH: 6
<212> TYPE: PRT
<213> ORGANISM: Homo Sapiens

<400> SEQUENCE: 133

Met Tyr Ala Val Tyr Lys
1               5

<210> SEQ ID NO 134
<211> LENGTH: 13
<212> TYPE: PRT
```

<213> ORGANISM: Homo Sapiens

<400> SEQUENCE: 134

Ile Ile Thr Leu Thr Gly Pro Thr Asn Ala Ile Phe Lys
1               5                   10

<210> SEQ ID NO 135
<211> LENGTH: 9
<212> TYPE: PRT
<213> ORGANISM: Homo Sapiens

<400> SEQUENCE: 135

Leu Pro Phe Pro Ile Ile Asp Asp Arg
1               5

<210> SEQ ID NO 136
<211> LENGTH: 11
<212> TYPE: PRT
<213> ORGANISM: Homo Sapiens

<400> SEQUENCE: 136

Tyr Ala Asn Val Ile Ala Tyr Asp His Ser Arg
1               5                   10

<210> SEQ ID NO 137
<211> LENGTH: 9
<212> TYPE: PRT
<213> ORGANISM: Homo Sapiens

<400> SEQUENCE: 137

Lys Ala Leu Glu Leu Asp Gln Glu Arg
1               5

<210> SEQ ID NO 138
<211> LENGTH: 8
<212> TYPE: PRT
<213> ORGANISM: Homo Sapiens

<400> SEQUENCE: 138

Lys Glu Asn Pro Leu Gln Phe Lys
1               5

<210> SEQ ID NO 139
<211> LENGTH: 17
<212> TYPE: PRT
<213> ORGANISM: Homo Sapiens

<400> SEQUENCE: 139

Leu Phe Val Gly Asn Leu Pro Ala Asp Ile Thr Glu Asp Glu Phe Lys
1               5                   10                  15

Arg

<210> SEQ ID NO 140
<211> LENGTH: 12
<212> TYPE: PRT
<213> ORGANISM: Homo Sapiens

<400> SEQUENCE: 140

Val Gly Asp Leu Tyr Ser Asp Leu Arg Asp Gly Arg
1               5                   10

<210> SEQ ID NO 141
<211> LENGTH: 13
<212> TYPE: PRT
<213> ORGANISM: Homo Sapiens

<400> SEQUENCE: 141

Ala Ala Met Arg Glu Thr Trp Leu Ser Glu Asn Gln Arg
1               5                   10

<210> SEQ ID NO 142
<211> LENGTH: 9
<212> TYPE: PRT
<213> ORGANISM: Homo Sapiens

<400> SEQUENCE: 142

Asp Leu Ser Leu Glu Glu Ile Gln Lys
1               5

<210> SEQ ID NO 143
<211> LENGTH: 15
<212> TYPE: PRT
<213> ORGANISM: Homo Sapiens

<400> SEQUENCE: 143

Thr Leu Asn Gln Leu Gly Thr Pro Gln Asp Ser Pro Glu Leu Arg
1               5                   10                  15

<210> SEQ ID NO 144
<211> LENGTH: 13
<212> TYPE: PRT
<213> ORGANISM: Homo Sapiens

<400> SEQUENCE: 144

Tyr Gly Val Asn Pro Gly Pro Ile Val Gly Thr Thr Arg
1               5                   10

<210> SEQ ID NO 145
<211> LENGTH: 17
<212> TYPE: PRT
<213> ORGANISM: Homo Sapiens

<400> SEQUENCE: 145

Glu Ile Val His Ile Gln Ala Gly Gln Cys Gly Asn Gln Ile Gly Ala
1               5                   10                  15

Lys

<210> SEQ ID NO 146
<211> LENGTH: 16
<212> TYPE: PRT
<213> ORGANISM: Homo Sapiens

<400> SEQUENCE: 146

Ala Phe Thr Gly Arg Glu Phe Asp Glu Leu Asn Pro Ser Ala Gln Arg
1               5                   10                  15

<210> SEQ ID NO 147
<211> LENGTH: 22
<212> TYPE: PRT
<213> ORGANISM: Homo Sapiens

<400> SEQUENCE: 147

Ala His Glu Gly Glu Ile Glu Asp Leu Ala Leu Gly Pro Asp Gly Lys
1               5                   10                  15

Leu Val Thr Val Gly Arg
            20

<210> SEQ ID NO 148
<211> LENGTH: 9

```
<212> TYPE: PRT
<213> ORGANISM: Homo Sapiens

<400> SEQUENCE: 148

Ala His Ile Ala Gln Leu Cys Glu Lys
1               5

<210> SEQ ID NO 149
<211> LENGTH: 13
<212> TYPE: PRT
<213> ORGANISM: Homo Sapiens

<400> SEQUENCE: 149

Ala Ile Thr Gly Ala Ser Leu Ala Asp Ile Met Ala Lys
1               5                   10

<210> SEQ ID NO 150
<211> LENGTH: 13
<212> TYPE: PRT
<213> ORGANISM: Homo Sapiens

<400> SEQUENCE: 150

Ala Leu Gly Thr Glu Val Ile Gln Leu Phe Pro Glu Lys
1               5                   10

<210> SEQ ID NO 151
<211> LENGTH: 8
<212> TYPE: PRT
<213> ORGANISM: Homo Sapiens

<400> SEQUENCE: 151

Ala Leu Met Ala Ala Glu Asp Lys
1               5

<210> SEQ ID NO 152
<211> LENGTH: 9
<212> TYPE: PRT
<213> ORGANISM: Homo Sapiens

<400> SEQUENCE: 152

Ala Met Ile Asn Leu His Ile Gln Lys
1               5

<210> SEQ ID NO 153
<211> LENGTH: 27
<212> TYPE: PRT
<213> ORGANISM: Homo Sapiens

<400> SEQUENCE: 153

Ala Gln Ser Glu Ala Glu Lys Leu Ala Lys Glu Arg Gln Glu Ala Glu
1               5                   10                  15

Glu Ala Lys Glu Ala Leu Leu Gln Ala Ser Arg
            20                  25

<210> SEQ ID NO 154
<211> LENGTH: 19
<212> TYPE: PRT
<213> ORGANISM: Homo Sapiens

<400> SEQUENCE: 154

Ala Ser Gly Asp Ser Ala Arg Pro Val Leu Leu Gln Val Ala Glu Ser
1               5                   10                  15

Ala Tyr Arg
```

```
<210> SEQ ID NO 155
<211> LENGTH: 9
<212> TYPE: PRT
<213> ORGANISM: Homo Sapiens

<400> SEQUENCE: 155

Ala Ser Ile Thr Ala Leu Glu Ala Lys
1               5

<210> SEQ ID NO 156
<211> LENGTH: 15
<212> TYPE: PRT
<213> ORGANISM: Homo Sapiens

<400> SEQUENCE: 156

Ala Val Thr Ser Ala Asn Ile Gln Glu Phe Ala Gly Cys Lys Lys
1               5                   10                  15

<210> SEQ ID NO 157
<211> LENGTH: 15
<212> TYPE: PRT
<213> ORGANISM: Homo Sapiens

<400> SEQUENCE: 157

Asp Asp Thr Ile Tyr Glu Asp Glu Asp Val Lys Glu Ala Ile Arg
1               5                   10                  15

<210> SEQ ID NO 158
<211> LENGTH: 9
<212> TYPE: PRT
<213> ORGANISM: Homo Sapiens

<400> SEQUENCE: 158

Asp Gly Gly Gln Glu Tyr Val Val Lys
1               5

<210> SEQ ID NO 159
<211> LENGTH: 10
<212> TYPE: PRT
<213> ORGANISM: Homo Sapiens

<400> SEQUENCE: 159

Asp Lys Gln Met Glu Leu Leu Glu Asn Lys
1               5                   10

<210> SEQ ID NO 160
<211> LENGTH: 12
<212> TYPE: PRT
<213> ORGANISM: Homo Sapiens

<400> SEQUENCE: 160

Asp Leu Lys Pro Glu Asn Leu Leu Leu Ala Ser Lys
1               5                   10

<210> SEQ ID NO 161
<211> LENGTH: 15
<212> TYPE: PRT
<213> ORGANISM: Homo Sapiens

<400> SEQUENCE: 161

Asp Pro Ile Tyr Phe Thr Gly Leu Ala Ser Glu Pro Gly Ala Arg
1               5                   10                  15

<210> SEQ ID NO 162
<211> LENGTH: 11
<212> TYPE: PRT
```

<213> ORGANISM: Homo Sapiens

<400> SEQUENCE: 162

Asp Ser Ile Val His Gln Ala Gly Met Leu Lys
1               5                   10

<210> SEQ ID NO 163
<211> LENGTH: 13
<212> TYPE: PRT
<213> ORGANISM: Homo Sapiens

<400> SEQUENCE: 163

Asp Val Ser Ser Ser Thr Pro Pro Ser Val Thr Ser Lys
1               5                   10

<210> SEQ ID NO 164
<211> LENGTH: 12
<212> TYPE: PRT
<213> ORGANISM: Homo Sapiens

<400> SEQUENCE: 164

Glu Gly Val Arg Glu Val Phe Glu Thr Ala Thr Arg
1               5                   10

<210> SEQ ID NO 165
<211> LENGTH: 8
<212> TYPE: PRT
<213> ORGANISM: Homo Sapiens

<400> SEQUENCE: 165

Glu Leu Ala Ser Leu His Asp Lys
1               5

<210> SEQ ID NO 166
<211> LENGTH: 14
<212> TYPE: PRT
<213> ORGANISM: Homo Sapiens

<400> SEQUENCE: 166

Glu Leu Ile Ser Asn Ser Ser Asp Ala Leu Asp Lys Ile Arg
1               5                   10

<210> SEQ ID NO 167
<211> LENGTH: 20
<212> TYPE: PRT
<213> ORGANISM: Homo Sapiens

<400> SEQUENCE: 167

Glu Leu Val Ser Leu Lys Gln Glu Gln Gln Ala Phe Lys Glu Ala Ala
1               5                   10                  15

Asp Thr Glu Arg
            20

<210> SEQ ID NO 168
<211> LENGTH: 20
<212> TYPE: PRT
<213> ORGANISM: Homo Sapiens

<400> SEQUENCE: 168

Glu Met Ile Pro Phe Ala Val Val Gly Ser Asp His Glu Tyr Gln Val
1               5                   10                  15

Asn Gly Lys Arg
            20

<210> SEQ ID NO 169
<211> LENGTH: 17
<212> TYPE: PRT
<213> ORGANISM: Homo Sapiens

<400> SEQUENCE: 169

Glu Gln His Gly Leu Gln Leu Gln Ser Glu Ile Asn Gln Leu His Ser
1               5                   10                  15

Lys

<210> SEQ ID NO 170
<211> LENGTH: 22
<212> TYPE: PRT
<213> ORGANISM: Homo Sapiens

<400> SEQUENCE: 170

Phe Glu Thr Glu Lys Asn Asn Gly Ala Gly Tyr Phe Leu Glu His Leu
1               5                   10                  15

Ala Phe Lys Gly Thr Lys
            20

<210> SEQ ID NO 171
<211> LENGTH: 9
<212> TYPE: PRT
<213> ORGANISM: Homo Sapiens

<400> SEQUENCE: 171

Phe Glu Val Ile Glu Lys Pro Gln Ala
1               5

<210> SEQ ID NO 172
<211> LENGTH: 12
<212> TYPE: PRT
<213> ORGANISM: Homo Sapiens

<400> SEQUENCE: 172

Phe Phe Asp Glu Glu Ser Tyr Ser Leu Leu Arg Lys
1               5                   10

<210> SEQ ID NO 173
<211> LENGTH: 15
<212> TYPE: PRT
<213> ORGANISM: Homo Sapiens

<400> SEQUENCE: 173

Phe His Asp Val Leu Gly Asn Glu Arg Pro Ser Ala Tyr Met Arg
1               5                   10                  15

<210> SEQ ID NO 174
<211> LENGTH: 12
<212> TYPE: PRT
<213> ORGANISM: Homo Sapiens

<400> SEQUENCE: 174

Phe Lys Met Pro Glu Met His Phe Lys Ala Pro Lys
1               5                   10

<210> SEQ ID NO 175
<211> LENGTH: 18
<212> TYPE: PRT
<213> ORGANISM: Homo Sapiens

<400> SEQUENCE: 175

Phe Ser Ala Tyr Ile Lys Asn Ser Asn Pro Ala Leu Asn Asp Asn Leu
1               5                   10                  15

Glu Lys

<210> SEQ ID NO 176
<211> LENGTH: 8
<212> TYPE: PRT
<213> ORGANISM: Homo Sapiens

<400> SEQUENCE: 176

Phe Ser Phe Lys Lys Pro Phe Lys
1               5

<210> SEQ ID NO 177
<211> LENGTH: 21
<212> TYPE: PRT
<213> ORGANISM: Homo Sapiens

<400> SEQUENCE: 177

Gly Ala Asp Asp Ala Met Glu Ser Ser Lys Pro Gly Pro Val Gln Val
1               5                   10                  15

Val Leu Val Gln Lys
            20

<210> SEQ ID NO 178
<211> LENGTH: 15
<212> TYPE: PRT
<213> ORGANISM: Homo Sapiens

<400> SEQUENCE: 178

Gly Ala Leu His Thr Val Ser His Glu Asp Ile Arg Asp Ile Arg
1               5                   10                  15

<210> SEQ ID NO 179
<211> LENGTH: 6
<212> TYPE: PRT
<213> ORGANISM: Homo Sapiens

<400> SEQUENCE: 179

Gly Phe Phe Gly Tyr Lys
1               5

<210> SEQ ID NO 180
<211> LENGTH: 12
<212> TYPE: PRT
<213> ORGANISM: Homo Sapiens

<400> SEQUENCE: 180

Gly Pro Ala Ser Pro Leu Asp Ser Thr Phe Tyr Arg
1               5                   10

<210> SEQ ID NO 181
<211> LENGTH: 13
<212> TYPE: PRT
<213> ORGANISM: Homo Sapiens

<400> SEQUENCE: 181

Gly Pro Val Gly Thr Val Ser Glu Ala Gln Leu Ala Arg
1               5                   10

<210> SEQ ID NO 182
<211> LENGTH: 18
<212> TYPE: PRT
<213> ORGANISM: Homo Sapiens

<400> SEQUENCE: 182

Gly Thr Pro Gly Pro Pro Ala His Gly Ala Ala Leu Gln Pro His
1               5                   10                  15

Pro Arg

<210> SEQ ID NO 183
<211> LENGTH: 29
<212> TYPE: PRT
<213> ORGANISM: Homo Sapiens

<400> SEQUENCE: 183

Gly Val Gly Ile Ile Ser Glu Gly Asn Glu Thr Val Glu Asp Ile Ala
1               5                   10                  15

Ala Arg Leu Asn Ile Pro Val Ser Gln Val Asn Pro Arg
            20                  25

<210> SEQ ID NO 184
<211> LENGTH: 10
<212> TYPE: PRT
<213> ORGANISM: Homo Sapiens

<400> SEQUENCE: 184

Gly Tyr Ser Phe Thr Thr Thr Ala Glu Arg
1               5                   10

<210> SEQ ID NO 185
<211> LENGTH: 10
<212> TYPE: PRT
<213> ORGANISM: Homo Sapiens

<400> SEQUENCE: 185

His Met Gly Leu Phe Asp His Ala Ala Arg
1               5                   10

<210> SEQ ID NO 186
<211> LENGTH: 18
<212> TYPE: PRT
<213> ORGANISM: Homo Sapiens

<400> SEQUENCE: 186

His Ser Thr Phe His Gly Glu Asp Lys Leu Ile Ser Val Glu Asp Leu
1               5                   10                  15

Trp Lys

<210> SEQ ID NO 187
<211> LENGTH: 14
<212> TYPE: PRT
<213> ORGANISM: Homo Sapiens

<400> SEQUENCE: 187

His Val Ile Pro Met Asn Pro Asn Thr Asp Asp Leu Phe Lys
1               5                   10

<210> SEQ ID NO 188
<211> LENGTH: 13
<212> TYPE: PRT
<213> ORGANISM: Homo Sapiens

<400> SEQUENCE: 188

Ile Ala Ala Tyr Ala Tyr Ser Ala Leu Ser Gln Ile Arg
1               5                   10

<210> SEQ ID NO 189
<211> LENGTH: 20
<212> TYPE: PRT

```
<213> ORGANISM: Homo Sapiens

<400> SEQUENCE: 189

Ile Ala Ser Gln Val Ala Ala Leu Asp Leu Gly Tyr Lys Pro Gly Val
1               5                   10                  15

Glu Ala Ile Arg
            20

<210> SEQ ID NO 190
<211> LENGTH: 12
<212> TYPE: PRT
<213> ORGANISM: Homo Sapiens

<400> SEQUENCE: 190

Ile Glu Val Glu Lys Pro Phe Ala Ile Ala Lys Glu
1               5                   10

<210> SEQ ID NO 191
<211> LENGTH: 16
<212> TYPE: PRT
<213> ORGANISM: Homo Sapiens

<400> SEQUENCE: 191

Ile Phe Val Gly Gly Ile Lys Glu Asp Thr Glu Glu His His Leu Arg
1               5                   10                  15

<210> SEQ ID NO 192
<211> LENGTH: 10
<212> TYPE: PRT
<213> ORGANISM: Homo Sapiens

<400> SEQUENCE: 192

Ile His Glu Lys Leu His Tyr Tyr Glu Lys
1               5                   10

<210> SEQ ID NO 193
<211> LENGTH: 16
<212> TYPE: PRT
<213> ORGANISM: Homo Sapiens

<400> SEQUENCE: 193

Ile Ile Asn Glu Pro Thr Ala Ala Ala Ile Ala Tyr Gly Leu Asp Lys
1               5                   10                  15

<210> SEQ ID NO 194
<211> LENGTH: 8
<212> TYPE: PRT
<213> ORGANISM: Homo Sapiens

<400> SEQUENCE: 194

Ile Ile Ser Ala Asn Gly Cys Lys
1               5

<210> SEQ ID NO 195
<211> LENGTH: 16
<212> TYPE: PRT
<213> ORGANISM: Homo Sapiens

<400> SEQUENCE: 195

Ile Ile Tyr Ser His Phe Thr Cys Ala Thr Asp Thr Glu Asn Ile Arg
1               5                   10                  15

<210> SEQ ID NO 196
<211> LENGTH: 12
<212> TYPE: PRT
```

-continued

<213> ORGANISM: Homo Sapiens

<400> SEQUENCE: 196

Ile Asn Val Tyr Tyr Asn Glu Ala Thr Gly Gly Lys
1               5                   10

<210> SEQ ID NO 197
<211> LENGTH: 13
<212> TYPE: PRT
<213> ORGANISM: Homo Sapiens

<400> SEQUENCE: 197

Ile Pro Asp Val Asp Ile Asp Ser Asp Gly Val Phe Lys
1               5                   10

<210> SEQ ID NO 198
<211> LENGTH: 16
<212> TYPE: PRT
<213> ORGANISM: Homo Sapiens

<400> SEQUENCE: 198

Ile Ser Val Tyr Tyr Asn Glu Ala Thr Gly Gly Lys Tyr Val Pro Arg
1               5                   10                  15

<210> SEQ ID NO 199
<211> LENGTH: 16
<212> TYPE: PRT
<213> ORGANISM: Homo Sapiens

<400> SEQUENCE: 199

Ile Tyr His Thr Ile Ala Tyr Leu Thr Pro Leu Pro Gln Pro Asn Arg
1               5                   10                  15

<210> SEQ ID NO 200
<211> LENGTH: 11
<212> TYPE: PRT
<213> ORGANISM: Homo Sapiens

<400> SEQUENCE: 200

Lys Ala His Leu Thr Asn Gln Tyr Met Gln Arg
1               5                   10

<210> SEQ ID NO 201
<211> LENGTH: 9
<212> TYPE: PRT
<213> ORGANISM: Homo Sapiens

<400> SEQUENCE: 201

Lys Ala Leu Glu Leu Asp Gln Glu Arg
1               5

<210> SEQ ID NO 202
<211> LENGTH: 15
<212> TYPE: PRT
<213> ORGANISM: Homo Sapiens

<400> SEQUENCE: 202

Lys Glu Pro His Glu Ser Leu Gly Met Thr Val Ala Gly Gly Arg
1               5                   10                  15

<210> SEQ ID NO 203
<211> LENGTH: 12
<212> TYPE: PRT
<213> ORGANISM: Homo Sapiens

<400> SEQUENCE: 203

```
Lys Gly Leu Asp Pro Tyr Asn Val Leu Ala Pro Lys
1               5                   10
```

<210> SEQ ID NO 204
<211> LENGTH: 9
<212> TYPE: PRT
<213> ORGANISM: Homo Sapiens

<400> SEQUENCE: 204

```
Lys Ile Tyr Glu Phe Thr Leu Gln Arg
1               5
```

<210> SEQ ID NO 205
<211> LENGTH: 8
<212> TYPE: PRT
<213> ORGANISM: Homo Sapiens

<400> SEQUENCE: 205

```
Lys Leu Met Glu Glu Cys Lys Arg
1               5
```

<210> SEQ ID NO 206
<211> LENGTH: 10
<212> TYPE: PRT
<213> ORGANISM: Homo Sapiens

<400> SEQUENCE: 206

```
Lys Met Met Leu Asp Leu Asn Lys Ala Lys
1               5                   10
```

<210> SEQ ID NO 207
<211> LENGTH: 16
<212> TYPE: PRT
<213> ORGANISM: Homo Sapiens

<400> SEQUENCE: 207

```
Lys Pro Gln Tyr Asp Ile Trp Gly Asn Thr Val Asn Val Ala Ser Arg
1               5                   10                  15
```

<210> SEQ ID NO 208
<211> LENGTH: 15
<212> TYPE: PRT
<213> ORGANISM: Homo Sapiens

<400> SEQUENCE: 208

```
Lys Thr Gly Glu Asn Val Glu Asp Ala Phe Leu Glu Ala Ala Lys
1               5                   10                  15
```

<210> SEQ ID NO 209
<211> LENGTH: 15
<212> TYPE: PRT
<213> ORGANISM: Homo Sapiens

<400> SEQUENCE: 209

```
Lys Val Glu Glu Glu Asn Gln Gly Ala Leu Glu Met Ile Lys Arg
1               5                   10                  15
```

<210> SEQ ID NO 210
<211> LENGTH: 17
<212> TYPE: PRT
<213> ORGANISM: Homo Sapiens

<400> SEQUENCE: 210

```
Lys Trp Glu Ser Pro Ala Gln Asn Thr Ala His Leu Asp Gln Phe Glu
1               5                   10                  15
```

Arg

<210> SEQ ID NO 211
<211> LENGTH: 12
<212> TYPE: PRT
<213> ORGANISM: Homo Sapiens

<400> SEQUENCE: 211

Lys Tyr Glu Leu Gly Arg Pro Ala Ala Asn Thr Lys
1               5                   10

<210> SEQ ID NO 212
<211> LENGTH: 26
<212> TYPE: PRT
<213> ORGANISM: Homo Sapiens

<400> SEQUENCE: 212

Leu Ala Ala Leu Gln Gly Arg Leu Glu Gly Leu Gly Ser Ser Glu Ala
1               5                   10                  15

Asp Gln Asp Gly Leu Ala Ser Thr Val Arg
            20                  25

<210> SEQ ID NO 213
<211> LENGTH: 11
<212> TYPE: PRT
<213> ORGANISM: Homo Sapiens

<400> SEQUENCE: 213

Leu Asp His Lys Phe Asp Leu Met Tyr Ala Lys
1               5                   10

<210> SEQ ID NO 214
<211> LENGTH: 12
<212> TYPE: PRT
<213> ORGANISM: Homo Sapiens

<400> SEQUENCE: 214

Leu Asp Leu Arg Asp Asp Lys Asp Thr Ile Glu Arg
1               5                   10

<210> SEQ ID NO 215
<211> LENGTH: 10
<212> TYPE: PRT
<213> ORGANISM: Homo Sapiens

<400> SEQUENCE: 215

Leu Glu Lys His Glu Leu Ile Glu Phe Arg
1               5                   10

<210> SEQ ID NO 216
<211> LENGTH: 14
<212> TYPE: PRT
<213> ORGANISM: Homo Sapiens

<400> SEQUENCE: 216

Leu Glu Ser Glu Gly Ser Pro Glu Thr Leu Thr Asn Leu Arg
1               5                   10

<210> SEQ ID NO 217
<211> LENGTH: 8
<212> TYPE: PRT
<213> ORGANISM: Homo Sapiens

<400> SEQUENCE: 217

```
Leu His Ser Leu Lys Thr Ala Lys
1               5

<210> SEQ ID NO 218
<211> LENGTH: 20
<212> TYPE: PRT
<213> ORGANISM: Homo Sapiens

<400> SEQUENCE: 218

Leu Ile Val Asp Glu Ala Ile Asn Glu Asp Asn Ser Val Val Ser Leu
1               5                   10                  15

Ser Gln Pro Lys
            20

<210> SEQ ID NO 219
<211> LENGTH: 13
<212> TYPE: PRT
<213> ORGANISM: Homo Sapiens

<400> SEQUENCE: 219

Leu Met Val His Thr Val Ala Thr Phe Asn Ser Ile Lys
1               5                   10

<210> SEQ ID NO 220
<211> LENGTH: 11
<212> TYPE: PRT
<213> ORGANISM: Homo Sapiens

<400> SEQUENCE: 220

Leu Asn Glu Ser Leu Asp Glu Asn Phe Lys Lys
1               5                   10

<210> SEQ ID NO 221
<211> LENGTH: 18
<212> TYPE: PRT
<213> ORGANISM: Homo Sapiens

<400> SEQUENCE: 221

Leu Gln Gln Gly Tyr Asn Ala Met Gly Phe Ser Gln Gly Gly Gln Phe
1               5                   10                  15

Leu Arg

<210> SEQ ID NO 222
<211> LENGTH: 18
<212> TYPE: PRT
<213> ORGANISM: Homo Sapiens

<400> SEQUENCE: 222

Leu Gln Val Glu Leu Asp Asn Val Thr Gly Leu Leu Ser Gln Ser Asp
1               5                   10                  15

Ser Lys

<210> SEQ ID NO 223
<211> LENGTH: 14
<212> TYPE: PRT
<213> ORGANISM: Homo Sapiens

<400> SEQUENCE: 223

Leu Thr Val Met Thr Asp Leu Glu Asp Lys Asn Glu Trp Lys
1               5                   10

<210> SEQ ID NO 224
<211> LENGTH: 12
<212> TYPE: PRT
```

<213> ORGANISM: Homo Sapiens

<400> SEQUENCE: 224

Met Ala Ser Gly Ala Ala Asn Val Val Gly Pro Lys
1               5                   10

<210> SEQ ID NO 225
<211> LENGTH: 14
<212> TYPE: PRT
<213> ORGANISM: Homo Sapiens

<400> SEQUENCE: 225

Met Lys Glu Thr Ala Glu Asn Tyr Leu Gly His Thr Ala Lys
1               5                   10

<210> SEQ ID NO 226
<211> LENGTH: 12
<212> TYPE: PRT
<213> ORGANISM: Homo Sapiens

<400> SEQUENCE: 226

Met Asn Arg Pro Ala Pro Val Glu Val Thr Tyr Lys
1               5                   10

<210> SEQ ID NO 227
<211> LENGTH: 16
<212> TYPE: PRT
<213> ORGANISM: Homo Sapiens

<400> SEQUENCE: 227

Met Ser Gln Val Met Arg Glu Trp Glu Ala Glu Arg Gln Ala Lys
1               5                   10                  15

<210> SEQ ID NO 228
<211> LENGTH: 8
<212> TYPE: PRT
<213> ORGANISM: Homo Sapiens

<400> SEQUENCE: 228

Asn Ala Leu Leu Ser Leu Ala Lys
1               5

<210> SEQ ID NO 229
<211> LENGTH: 11
<212> TYPE: PRT
<213> ORGANISM: Homo Sapiens

<400> SEQUENCE: 229

Asn Asp Ile Thr Pro Leu His Val Ala Ser Lys
1               5                   10

<210> SEQ ID NO 230
<211> LENGTH: 10
<212> TYPE: PRT
<213> ORGANISM: Homo Sapiens

<400> SEQUENCE: 230

Asn His Pro Leu His Ile Arg Glu Asn Arg
1               5                   10

<210> SEQ ID NO 231
<211> LENGTH: 12
<212> TYPE: PRT
<213> ORGANISM: Homo Sapiens

<400> SEQUENCE: 231

Asn Ile Val His Asn Tyr Ser Glu Ala Glu Ile Lys
1               5                   10

<210> SEQ ID NO 232
<211> LENGTH: 17
<212> TYPE: PRT
<213> ORGANISM: Homo Sapiens

<400> SEQUENCE: 232

Asn Leu Asp Ser Thr Thr Val Ala Val His Gly Glu Glu Ile Tyr Cys
1               5                   10                  15
Lys

<210> SEQ ID NO 233
<211> LENGTH: 14
<212> TYPE: PRT
<213> ORGANISM: Homo Sapiens

<400> SEQUENCE: 233

Asn Leu Gly Ser Ile Asn Thr Glu Leu Gln Asp Val Gln Arg
1               5                   10

<210> SEQ ID NO 234
<211> LENGTH: 8
<212> TYPE: PRT
<213> ORGANISM: Homo Sapiens

<400> SEQUENCE: 234

Asn Val Leu Ser Leu Thr Asn Lys
1               5

<210> SEQ ID NO 235
<211> LENGTH: 10
<212> TYPE: PRT
<213> ORGANISM: Homo Sapiens

<400> SEQUENCE: 235

Pro Ala Val Ser Lys Gly Asp Gly Met Arg
1               5                   10

<210> SEQ ID NO 236
<211> LENGTH: 10
<212> TYPE: PRT
<213> ORGANISM: Homo Sapiens

<400> SEQUENCE: 236

Pro Gly Thr Glu Pro Leu Gly Thr Thr Lys
1               5                   10

<210> SEQ ID NO 237
<211> LENGTH: 9
<212> TYPE: PRT
<213> ORGANISM: Homo Sapiens

<400> SEQUENCE: 237

Pro Ile His Pro Val Gly Gly Leu Arg
1               5

<210> SEQ ID NO 238
<211> LENGTH: 11
<212> TYPE: PRT
<213> ORGANISM: Homo Sapiens

<400> SEQUENCE: 238

```
Gln Val Leu Leu Ala Gln Ala Glu Ala Glu Lys
1               5                   10
```

<210> SEQ ID NO 239
<211> LENGTH: 18
<212> TYPE: PRT
<213> ORGANISM: Homo Sapiens

<400> SEQUENCE: 239

```
Gln Val Thr Pro Asp Gly Glu Ser Asp Glu Val Gly Val Ile Pro Ser
1               5                   10                  15

Lys Arg
```

<210> SEQ ID NO 240
<211> LENGTH: 9
<212> TYPE: PRT
<213> ORGANISM: Homo Sapiens

<400> SEQUENCE: 240

```
Arg Lys Val Asp Trp Leu Thr Glu Lys
1               5
```

<210> SEQ ID NO 241
<211> LENGTH: 9
<212> TYPE: PRT
<213> ORGANISM: Homo Sapiens

<400> SEQUENCE: 241

```
Arg Leu Tyr Trp Asp Asp Leu Lys Arg
1               5
```

<210> SEQ ID NO 242
<211> LENGTH: 7
<212> TYPE: PRT
<213> ORGANISM: Homo Sapiens

<400> SEQUENCE: 242

```
Arg Asn Glu Leu Val Ile Arg
1               5
```

<210> SEQ ID NO 243
<211> LENGTH: 12
<212> TYPE: PRT
<213> ORGANISM: Homo Sapiens

<400> SEQUENCE: 243

```
Arg Ser Asn Thr Glu Asn Leu Ser Gln His Phe Arg
1               5                   10
```

<210> SEQ ID NO 244
<211> LENGTH: 14
<212> TYPE: PRT
<213> ORGANISM: Homo Sapiens

<400> SEQUENCE: 244

```
Arg Thr Pro Val Gln Pro Asn Pro Ile Val Tyr Met Met Lys
1               5                   10
```

<210> SEQ ID NO 245
<211> LENGTH: 17
<212> TYPE: PRT
<213> ORGANISM: Homo Sapiens

<400> SEQUENCE: 245

```
Ser Ala Leu Leu Ala Glu Met Asp Lys Val Glu Gly His Val Ala Ile
```

```
                1               5                  10                 15

Lys

<210> SEQ ID NO 246
<211> LENGTH: 10
<212> TYPE: PRT
<213> ORGANISM: Homo Sapiens

<400> SEQUENCE: 246

Ser Ala Val Thr Thr Val Val Asn Pro Lys
1               5                  10

<210> SEQ ID NO 247
<211> LENGTH: 13
<212> TYPE: PRT
<213> ORGANISM: Homo Sapiens

<400> SEQUENCE: 247

Ser Glu Glu Ser Val Ser Arg Leu Pro Glu Glu Ile Arg
1               5                  10

<210> SEQ ID NO 248
<211> LENGTH: 16
<212> TYPE: PRT
<213> ORGANISM: Homo Sapiens

<400> SEQUENCE: 248

Ser Glu His Lys Val Trp Ser Pro Leu Val Thr Glu Glu Gly Lys Arg
1               5                  10                 15

<210> SEQ ID NO 249
<211> LENGTH: 8
<212> TYPE: PRT
<213> ORGANISM: Homo Sapiens

<400> SEQUENCE: 249

Ser His Glu Ala Glu Val Leu Lys
1               5

<210> SEQ ID NO 250
<211> LENGTH: 12
<212> TYPE: PRT
<213> ORGANISM: Homo Sapiens

<400> SEQUENCE: 250

Ser Lys Glu Pro Gln Leu Ile Ala Phe Tyr His Lys
1               5                  10

<210> SEQ ID NO 251
<211> LENGTH: 16
<212> TYPE: PRT
<213> ORGANISM: Homo Sapiens

<400> SEQUENCE: 251

Ser Leu Ser Leu Ser Lys Leu Glu Asp Pro His Val Asp Ile Ile Arg
1               5                  10                 15

<210> SEQ ID NO 252
<211> LENGTH: 15
<212> TYPE: PRT
<213> ORGANISM: Homo Sapiens

<400> SEQUENCE: 252

Ser Leu Val Asn Gln Gln Ser Phe Gln Asp Ile Lys Pro Met Arg
1               5                  10                 15
```

<210> SEQ ID NO 253
<211> LENGTH: 23
<212> TYPE: PRT
<213> ORGANISM: Homo Sapiens

<400> SEQUENCE: 253

Ser Gln Val Leu Asp Asp Glu Asp Ser Asn Asn Ile Thr Val Gly Ser
1               5                   10                  15

Leu Val Thr Val Leu Val Lys
            20

<210> SEQ ID NO 254
<211> LENGTH: 12
<212> TYPE: PRT
<213> ORGANISM: Homo Sapiens

<400> SEQUENCE: 254

Ser Arg Lys Glu Ser Tyr Ser Val Tyr Val Tyr Lys
1               5                   10

<210> SEQ ID NO 255
<211> LENGTH: 11
<212> TYPE: PRT
<213> ORGANISM: Homo Sapiens

<400> SEQUENCE: 255

Ser Ser Ser Leu Asp Asp Thr Glu Val Lys Lys
1               5                   10

<210> SEQ ID NO 256
<211> LENGTH: 15
<212> TYPE: PRT
<213> ORGANISM: Homo Sapiens

<400> SEQUENCE: 256

Ser Thr Gly Pro Gly Ala Ser Leu Gly Thr Gly Tyr Asp Arg Lys
1               5                   10                  15

<210> SEQ ID NO 257
<211> LENGTH: 10
<212> TYPE: PRT
<213> ORGANISM: Homo Sapiens

<400> SEQUENCE: 257

Ser Trp Glu Gln Lys Leu Glu Glu Met Arg
1               5                   10

<210> SEQ ID NO 258
<211> LENGTH: 17
<212> TYPE: PRT
<213> ORGANISM: Homo Sapiens

<400> SEQUENCE: 258

Thr Ala Pro Tyr Lys Asn Val Asn Ile Gln Asn Phe His Ile Ser Trp
1               5                   10                  15

Lys

<210> SEQ ID NO 259
<211> LENGTH: 13
<212> TYPE: PRT
<213> ORGANISM: Homo Sapiens

<400> SEQUENCE: 259

```
Thr Ala Val Val Val Gly Thr Ile Thr Asp Asp Val Arg
1               5                   10
```

<210> SEQ ID NO 260
<211> LENGTH: 17
<212> TYPE: PRT
<213> ORGANISM: Homo Sapiens

<400> SEQUENCE: 260

```
Thr Asp Leu Glu Lys Asp Ile Ile Ser Asp Thr Ser Gly Asp Phe Arg
1               5                   10                  15
Lys
```

<210> SEQ ID NO 261
<211> LENGTH: 8
<212> TYPE: PRT
<213> ORGANISM: Homo Sapiens

<400> SEQUENCE: 261

```
Thr Asp Pro Val Asp Ile Tyr Lys
1               5
```

<210> SEQ ID NO 262
<211> LENGTH: 10
<212> TYPE: PRT
<213> ORGANISM: Homo Sapiens

<400> SEQUENCE: 262

```
Thr Lys Thr Glu Ile Ser Glu Met Asn Arg
1               5                   10
```

<210> SEQ ID NO 263
<211> LENGTH: 8
<212> TYPE: PRT
<213> ORGANISM: Homo Sapiens

<400> SEQUENCE: 263

```
Thr Val Phe Asp Glu Ala Ile Arg
1               5
```

<210> SEQ ID NO 264
<211> LENGTH: 8
<212> TYPE: PRT
<213> ORGANISM: Homo Sapiens

<400> SEQUENCE: 264

```
Thr Val Asn Met Thr Trp Asn Lys
1               5
```

<210> SEQ ID NO 265
<211> LENGTH: 13
<212> TYPE: PRT
<213> ORGANISM: Homo Sapiens

<400> SEQUENCE: 265

```
Thr Val Tyr Ser His Leu Phe Asp His Val Val Asn Arg
1               5                   10
```

<210> SEQ ID NO 266
<211> LENGTH: 7
<212> TYPE: PRT
<213> ORGANISM: Homo Sapiens

<400> SEQUENCE: 266

```
Val Lys Ala Asn Leu Glu Lys
```

-continued

```
<210> SEQ ID NO 267
<211> LENGTH: 12
<212> TYPE: PRT
<213> ORGANISM: Homo Sapiens

<400> SEQUENCE: 267

Val Lys Asp Ala Ser Pro Asn Gln Val Ala Glu Lys
1               5                   10

<210> SEQ ID NO 268
<211> LENGTH: 15
<212> TYPE: PRT
<213> ORGANISM: Homo Sapiens

<400> SEQUENCE: 268

Val Lys Asp Arg Asp Asp Phe Pro Val Val Leu Val Gly Asn Lys
1               5                   10                  15

<210> SEQ ID NO 269
<211> LENGTH: 13
<212> TYPE: PRT
<213> ORGANISM: Homo Sapiens

<400> SEQUENCE: 269

Val Lys Lys Glu Trp Glu Glu Ala Glu Leu Gln Ala Lys
1               5                   10

<210> SEQ ID NO 270
<211> LENGTH: 23
<212> TYPE: PRT
<213> ORGANISM: Homo Sapiens

<400> SEQUENCE: 270

Val Lys Leu Phe Tyr Leu Asp Pro Asp Ala Gln Lys Leu Asp Phe Ser
1               5                   10                  15

Ser Ala Glu Pro Glu Val Lys
            20

<210> SEQ ID NO 271
<211> LENGTH: 19
<212> TYPE: PRT
<213> ORGANISM: Homo Sapiens

<400> SEQUENCE: 271

Val Leu Ala Phe Thr Ala Val Gly Asp Gly Pro Pro Ser Pro Thr Ile
1               5                   10                  15

Gln Val Lys

<210> SEQ ID NO 272
<211> LENGTH: 12
<212> TYPE: PRT
<213> ORGANISM: Homo Sapiens

<400> SEQUENCE: 272

Val Asn Gly Arg Pro Leu Glu Met Ile Glu Pro Arg
1               5                   10

<210> SEQ ID NO 273
<211> LENGTH: 9
<212> TYPE: PRT
<213> ORGANISM: Homo Sapiens

<400> SEQUENCE: 273
```

```
Val Pro Thr Ser Met Val Leu Thr Lys
1               5
```

<210> SEQ ID NO 274
<211> LENGTH: 10
<212> TYPE: PRT
<213> ORGANISM: Homo Sapiens

<400> SEQUENCE: 274

```
Val Ser Ser Leu Gly Lys Asp Trp His Lys
1               5                   10
```

<210> SEQ ID NO 275
<211> LENGTH: 10
<212> TYPE: PRT
<213> ORGANISM: Homo Sapiens

<400> SEQUENCE: 275

```
Trp Glu Val Glu Glu Met Lys Glu Ser Lys
1               5                   10
```

<210> SEQ ID NO 276
<211> LENGTH: 12
<212> TYPE: PRT
<213> ORGANISM: Homo Sapiens

<400> SEQUENCE: 276

```
Trp Gly Lys Pro His Val Ala Ser Leu Ser Phe Arg
1               5                   10
```

<210> SEQ ID NO 277
<211> LENGTH: 16
<212> TYPE: PRT
<213> ORGANISM: Homo Sapiens

<400> SEQUENCE: 277

```
Trp Ile Leu Ser Gln Thr His Asn Ile Phe Thr Gln Ala Gly Val Arg
1               5                   10                  15
```

<210> SEQ ID NO 278
<211> LENGTH: 11
<212> TYPE: PRT
<213> ORGANISM: Homo Sapiens

<400> SEQUENCE: 278

```
Trp Lys Ala Gly Leu Tyr Gly Leu Pro Arg Arg
1               5                   10
```

<210> SEQ ID NO 279
<211> LENGTH: 18
<212> TYPE: PRT
<213> ORGANISM: Homo Sapiens

<400> SEQUENCE: 279

```
Tyr Gly Pro Ser Leu Met Pro Gly Gly Asn Lys Glu Ala Trp Pro His
1               5                   10                  15

Ile Lys
```

<210> SEQ ID NO 280
<211> LENGTH: 18
<212> TYPE: PRT
<213> ORGANISM: Homo Sapiens

<400> SEQUENCE: 280

```
Tyr Lys Val Glu Gly Phe Pro Thr Ile Tyr Phe Ala Pro Ser Gly Asp
1               5                   10                  15

Lys Lys

<210> SEQ ID NO 281
<211> LENGTH: 13
<212> TYPE: PRT
<213> ORGANISM: Homo Sapiens

<400> SEQUENCE: 281

Tyr Met Gly Asp Leu Ser Gly Gly Gln Val Leu Lys Lys
1               5                   10

<210> SEQ ID NO 282
<211> LENGTH: 8
<212> TYPE: PRT
<213> ORGANISM: Homo Sapiens

<400> SEQUENCE: 282

Tyr Asn Gly Leu Ile His Arg Lys
1               5

<210> SEQ ID NO 283
<211> LENGTH: 9
<212> TYPE: PRT
<213> ORGANISM: Homo Sapiens

<400> SEQUENCE: 283

Tyr Gln Leu Ser Ser Glu Ala Ala Lys
1               5

<210> SEQ ID NO 284
<211> LENGTH: 12
<212> TYPE: PRT
<213> ORGANISM: Homo Sapiens

<400> SEQUENCE: 284

Tyr Ser Ala Leu Asn Val Gln His Gln Met Leu Lys
1               5                   10

<210> SEQ ID NO 285
<211> LENGTH: 12
<212> TYPE: PRT
<213> ORGANISM: Homo Sapiens

<400> SEQUENCE: 285

Tyr Ser Gln Val Leu Ala Asn Gly Leu Asp Asn Lys
1               5                   10

<210> SEQ ID NO 286
<211> LENGTH: 10
<212> TYPE: PRT
<213> ORGANISM: Homo Sapiens

<400> SEQUENCE: 286

Tyr Tyr Pro Thr Glu Asp Val Pro Arg Lys
1               5                   10
```